United States Patent
Khan et al.

(10) Patent No.: US 7,175,679 B2
(45) Date of Patent: *Feb. 13, 2007

(54) OLIGOPEPTIDE TREATMENT OF NF-κB MEDIATED INFLAMMATION

(75) Inventors: Nisar Asmed Khan, Rotterdam (NL); Robert Benner, Barendrecht (NL)

(73) Assignee: Biotempt B.V., Koekange (NL)

( * ) Notice: Subject to any disclaimer, the term of this patent is extended or adjusted under 35 U.S.C. 154(b) by 300 days.

This patent is subject to a terminal disclaimer.

(21) Appl. No.: 10/029,206

(22) Filed: Dec. 21, 2001

(65) Prior Publication Data

US 2003/0119720 A1 Jun. 26, 2003

Related U.S. Application Data

(63) Continuation-in-part of application No. 09/821,380, filed on Mar. 29, 2001, now Pat. No. 6,844,315.

(51) Int. Cl.
A61K 38/04 (2006.01)
A61K 38/07 (2006.01)

(52) U.S. Cl. ............................................. 51/2; 514/21
(58) Field of Classification Search .................. 514/2, 514/21
See application file for complete search history.

(56) References Cited

U.S. PATENT DOCUMENTS

| | | | |
|---|---|---|---|
| 4,977,244 A | 12/1990 | Muchmore et al. | |
| 5,380,668 A | 1/1995 | Herron | |
| 5,677,275 A | 10/1997 | Lunardi-Iskandar et al. | |
| 5,851,997 A | 12/1998 | Harris | |
| 5,854,004 A | 12/1998 | Czernilofsky et al. | |
| 5,877,148 A | 3/1999 | Lunardi-Iskandar et al. | |
| 5,958,413 A | 9/1999 | Anagnostopulos et al. | |
| 5,968,513 A | 10/1999 | Gallo et al. | |
| 5,997,871 A | 12/1999 | Gallo et al. | |
| 6,150,500 A * | 11/2000 | Salerno .................. 530/300 | |
| 6,319,504 B1 | 11/2001 | Gallo et al. | |
| 6,361,992 B1 | 3/2002 | Szkudlinski et al. | |
| 6,489,296 B1 | 12/2002 | Grinnell et al. | |
| 6,583,109 B1 | 6/2003 | Gallo et al. | |
| 6,596,688 B1 | 7/2003 | Gallo et al. | |
| 6,620,416 B1 | 9/2003 | Gallo et al. | |
| 6,727,227 B1 | 4/2004 | Khavinson | |
| 6,844,315 B2 * | 1/2005 | Khan et al. .................. 514/2 | |
| 2002/0041871 A1 | 4/2002 | Brudnak | |
| 2002/0064501 A1 | 5/2002 | Khan et al. | |
| 2003/0049273 A1 | 3/2003 | Gallo et al. | |
| 2003/0113733 A1 | 6/2003 | Khan et al. | |
| 2003/0119720 A1 | 6/2003 | Khan et al. | |
| 2003/0166556 A1 | 9/2003 | Khan et al. | |
| 2003/0186244 A1 | 10/2003 | Margus et al. | |
| 2003/0215434 A1 | 11/2003 | Khan et al. | |
| 2003/0219425 A1 | 11/2003 | Khan et al. | |
| 2003/0220257 A1 | 11/2003 | Benner et al. | |
| 2003/0220258 A1 | 11/2003 | Benner et al. | |
| 2003/0220259 A1 | 11/2003 | Benner et al. | |
| 2003/0220260 A1 | 11/2003 | Khan et al. | |
| 2003/0220261 A1 | 11/2003 | Khan et al. | |
| 2003/0224995 A1 | 12/2003 | Khan et al. | |
| 2004/0013661 A1 | 1/2004 | Wensvoort et al. | |

FOREIGN PATENT DOCUMENTS

| | | |
|---|---|---|
| DE | 3715662 | 11/1987 |
| DE | 19953339 | 5/2001 |
| EP | 1 138 692 A1 | 10/2001 |
| EP | 1 300 418 | 4/2003 |
| FR | 2 706 772 | 12/1994 |
| WO | 96/04008 | 2/1996 |
| WO | 97/49373 | 12/1997 |
| WO | 97/49418 | 12/1997 |
| WO | 97/49432 | 12/1997 |
| WO | WO 97/49721 | 12/1997 |
| WO | WO 98/35691 | 8/1998 |
| WO | WO 99/59617 | 11/1999 |
| WO | WO 01/10907 A2 | 2/2001 |
| WO | WO 01/11048 A2 | 2/2001 |
| WO | WO 01/29067 | 4/2001 |
| WO | WO 01/72831 | 10/2001 |
| WO | WO 02/085117 | 10/2002 |
| WO | WO 03/029292 A2 | 4/2003 |

OTHER PUBLICATIONS

Cui et al., Am. J. Physiol. Integr. Comp. Physiol. 286: R699-R709 (2004).*
Moayeri et al., Journal of Clinical Investigation 112(5): 670-682 (Sep. 2003).*
Kalns et al., Biochem. Biophys. Res. Comm. 297: 506-509 (2002).*
Kalns et al., Biochem. Biophys. Res. Comm. 292: 41-44 (2002).*
Pellizzari et al., FEBS Letters 462: 199-204 (1999).*
PCT International Search Report, PCT/NL01/00259, dated Dec. 18, 2001, 3 pages.
PCT International Preliminary Examination Report, PCT/NL99/00313, dated Jul. 21, 2000, 6 pages.
PCT International Search Report, PCT/EP99/00313, dated Nov. 29, 1999, 3 pages.
Lang et al., "Induction of apoptosis in Kaposi's sarcoma spindle cell cultures by the subunits of human chorionic gonadotropin", *AIDS* 1997, vol. 11, No. 11, pp. 1333-1340.
Iskandar et al., "Effects of a urinary factor from women in early pregnancy on HIV-1. SIV and associated disease", *Nature Medicine*, Apr. 1998, vol. 4, No. 4, pp. 428-434.
International Search Report, International Application No. PCT/NL02/00639, mailed Aug. 4, 2003 (8 pages).

(Continued)

Primary Examiner—Jean C. Witz
(74) Attorney, Agent, or Firm—TraskBritt

(57) ABSTRACT

The invention relates to the modulation of gene expression in a cell, also called gene control, in particular in relation to the treatment of anthrax. The invention provides a method for modulating expression of a gene in a cell comprising providing the cell with a signaling molecule comprising a peptide or functional analogue thereof.

17 Claims, 39 Drawing Sheets

OTHER PUBLICATIONS

Christman et al., Nuclear factor kappaB: a pivotal role in the systemic inflammatory response syndrome and new target for therapy, Intens Care Med, 1998, pp. 1131-1138, vol. 24.

Jyonouchi et al., Proinflammatory and regulatory cytokine production associated with innate and adaptive immune responses in children with autism spectrum disorders and developmental regression, J Neuroim., 2001, pp. 170-179, vol. 120.

Kanungo et al., Advanced Maturation of Heteropneustes Fossilis (Bloch) by Oral Administration of Human Chorionic Gonadotropin, J. Adv. Zool., 1999, pp. 1-5, vol. 20.

Rohrig et al., Growth-stimulating Influence of Human Chorionic Gonadotropin (hCG) on Plasmodium falciparum in vitro, Zentralblatt Bakt, 1999, pp. 89-99, vol. 289.

Tak et al., NF-kappaB: a key role in inflammatory diseases, J Clin Invest., 2001, pp. 7-11, vol. 107.

Tan et al., The role of activation of nuclear factor-kappa B of rat brain in the pathogenesis of experimental allergic encephalomyelitis, Acta Physiol Sinica, 2003, pp. 58-64, vol. 55.

Tovey et al., Mucosal Cytokine Therapy: Marked Antiviral and Antitumor Activity, J. Interferon Cytokine Res., 1999, pp. 911-921, vol. 19.

Albini, A., et al., "Old drugs as novel angiogenesis inhibitors: Preclinical studies with NAC, hCG, EGCG and somatostatin," 17 Clinical & Experimental Metastasis 739 (1999).

Blackwell, Timothy S., et al., "The Role of Nuclear Factor-kB in Cytokine Gene Regulation," 17 Am. J. Respir. Cell Mol. Biol. 3-9 (1997).

Keller, S., et al., "Human Chorionic Gonadotropin (hCG) Is a Potent Angiogenic Factor for Uterine Endothelial Cells in Vitro," 20(5-6) PLACENTA, p. A37 (Jul. 1999).

Khan, Nisar A., et al., "Inhibition of Diabetes in NOD Mice by Human Pregnancy Factor," 62(12) Human Immunology 1315-1323 (Dec. 2001).

Khan, Nisar A., et al., "Inhibition of Septic Shock in Mice by an Oligopeptide From the β-Chain of Human Chorionic Gonadotrophin Hormone," 63(1) Human Immunology 1-7 (Jan. 2002).

Muchmore et al., Immunoregulatory Properties of Fractions from Human Pregnancy Urine: Evidence that Human Chorionic Gonadotropin is not Responsible, The Journal of Immunology, Mar. 1997, pp. 881-886, vol. 118, No. 3.

Muchmore et al., Purification and Characterization of a Mannose-Containing Disaccharide Obtained from Human Pregnancy Urine, Journal of Experimental Medicine, Dec. 1984, pp. 1672-1685, vol. 160.

Patil, A., et al., "The Study of the Effect of Human Chorionic Gonadotrophic (HCG) Hormone on the Survival of Adrenal Medulla Transplant in Brain. Preliminary Study," 87 ACTA Neurochir (WIEN) 76-78 (1987).

Slater, Lewis M., et al., "Decreased Mortality of Murine Graft-Versus-Host Disease by Human Chorionic gonadotropin," 23(1) Transplantation 103-104 (Jan. 1977).

Wulczyn, F. Gregory, et al., "The NF-kB/Rel and IkB gene families: mediators of immune response and inflammation," 74(12) J. Mol. Med. 749-769 (1996).

Yamamoto, Y., et al., "Role of the NF-kB Pathway in the Pathogenesis of Human Disease States," 1(3) Current Molecular Medicine 287-296 (Jul. 2001).

Connelly et al., Biphasic Regulation of NF-kB Activity Underties the Pro- and Anti-Inflammatory Actions of Nitric Oxide, The Journal of Immunology, 2001, pp. 3873-3881, 166, The American Association of Immunologists, USA.

Friedlander, Tackling anthrax, Nature, Nov. 8, 2001, pp. 160-161, vol. 414.

Medzhitov, Toll-like Receptors and Innate Immunity, Nature Reviews/Immunology, Nov. 2001, pp. 135-145, vol. 1.

Kachra et al., "Low Molecular Weight Components but Not Dimeric HCG Inhibit Growth and Down-Regulate AP-1 Transcription Factor in Kaposi's Sarcoma Cells," Endocrinology, 1997, pp. 4038-4041, vol. 138, No. 9.

Khavinson et al., "Mechanisms Underlying Geroprotective Effects of Peptides," Bulletin of Experimental Biology and Medicine, Jan. 2002, pp. 1-5, vol. 133, No. 1.

Khavinson et al., "Peptide Promotes Overcoming of the Division Limit in Human Somatic Cell," Bulletin of Experimental Biology and Medicine, May 2004, pp. 503-506, vol. 137, No. 5.

Morozov et al., "Natural and Synthetic Thymic Peptides as Therapeutics for Immune Dysfunction," Int. J. Immunopharmac., 1997, pp. 501-505, vol. 19, No. 9/10.

Khavinson et al., "Inductive Activity of Retinal Peptides," Bulletin of Experimental Biology and Medicine, Nov. 2002, pp. 482-484, vol. 134, No. 5.

Khavinson et al., "Effects of Short Peptides on Lymphocyte Chromatin in Senile Subjects," Bulletin of Experimental Biology and Medicine, Jan. 2004, pp. 78-81, vol. 137, No. 1.

Khavinson et al., "Effects of Livagen Peptide on Chromatin Activation in Lymphocytes from Old People," Bulletin of Experimental Biology and Medicine, Oct. 2002, pp. 389-392, vol. 134, No. 4.

Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.

Ivanov et al., "Hemoglobin as a Source of Endogenous Bioactive Peptides: The Concept of TissueSpecific Peptide Pool," Biopolymers, 1997, pp. 171-188, vol. 39.

Khavinson et al, Gerontological Aspects of Genome Peptide Regulation, 2005, S. Karger AG, Basel, Switzerland.

* cited by examiner

OLIGOPEPTIDE TREATMENT OF NF-κB MEDIATED INFLAMMATION

CROSS-REFERENCE TO RELATED APPLICATION

This application is a continuation in part of U.S. Ser. No. 09/821,380 filed on Mar. 29, 2001, now U.S. Pat. No. 6,844,315 the contents of which are incorporated herein by this reference.

TECHNICAL FIELD

The invention relates to a method of treating disease, particularly anthrax.

BACKGROUND

Anthrax, the disease caused by the spore-forming *Bacillus anthracis* (*B. anthracis*), continues to be a worldwide problem among domesticated and wild herbivores in Asia and Africa and poses a worldwide threat when being used as a biological weapon for biological warfare or bioterrorism. Human infections occur after contact with infected animals or contaminated animal products. Outbreaks or epidemics are a constant threat for endemic regions because spores can persist in the soil for long periods of time. Importation controls on certain animal products are necessary to prevent the establishment of anthrax where the disease is not endemic. Human anthrax is usually classified by the portal of entry into the host. Cutaneous anthrax, which accounts for the vast majority of human anthrax cases, is a localized infection with generally mild systemic symptoms and characterized by a painless papule that is surrounded by edema which can be quite extensive. The papule ulcerates by day 5 or 6 and develops into the characteristic black eschar of cutaneous anthrax. Inhalation anthrax, which occurs after inhaling airborne spores, gastrointestinal anthrax, resulting from ingestion of contaminated food, and, in some instances, untreated cutaneous anthrax are characterized by dissemination of the bacteria from the initial site of infection with development of a massive septicemia and toxemia. In inhalation anthrax, phagocytic cells transport the spores from the lung alveoli to the regional lymph nodes, where the spores germinate and bacteria multiply. The bacilli then spread into the bloodstream, where they are temporarily removed by the reticuloendothelial system. Prior to death, which occurs 2 to 5 days after infection, there is a sudden onset of acute symptoms characterized by hypotension, edema, and fatal shock due to an extensive septicemia and toxemia. Therapeutic intervention, in general, must be initiated early, as septicemic infections are nearly always fatal.

The invention relates to the modulation of gene expression in a cell, also called gene control, in relation to the treatment of a variety of diseases such as anthrax. As said, anthrax is a disease of animals and humans that poses a significant threat as an agent of biological warfare and terrorism. Inhalational anthrax, in which spores of *B. anthracis* are inhaled, is almost always fatal, as diagnosis is rarely possible before the disease has progressed to a point where antibiotic treatment is ineffective. The major virulence factors of *B. anthracis* are a poly-D-glutamic acid capsule and anthrax toxin. Anthrax toxin consists of three distinct proteins that act in concert: two enzymes, lethal factor (LF) and edema factor (EF; an adenylate cyclase); and protective antigen (PA). The PA is a four-domain protein that binds a host cell-surface receptor by its carboxy-terminal domain; cleavage of its N-terminal domain by a furin-like protease allows PA to form heptamers that bind the toxic enzymes with high affinity through homologous N-terminal domains. The complex is endocytosed; acidification of the endosome leads to membrane insertion of the PA heptamer by forming a 14-stranded beta-barrel, followed by translocation of the toxic enzymes into the cytosol by an unknown mechanism. The binary combination of PA and LF is sufficient to induce rapid death in animals when given intravenously, and certain metalloprotease inhibitors block the effects of the toxin in vitro. Thus, LF is a potential target for therapeutic agents that would inhibit its catalytic activity or block its association with PA. LF is a protein (relative molecular mass 90,000) that is critical in the pathogenesis of anthrax. It comprises four domains: domain I binds the membrane-translocating component of anthrax toxin, the PA; domains II, III and IV together create a long deep groove that holds the 16-residue N-terminal tail of mitogen-activated protein kinase kinase-2 (MAPKK-2) before cleavage. Domain II resembles the ADP-ribosylating toxin from *Bacillus cereus*, but the active site has been mutated and recruited to augment substrate recognition. Domain III is inserted into domain II and seems to have arisen from a repeated duplication of a structural element of domain II. Domain IV is distantly related to the zinc metalloprotease family and contains the catalytic center; it also resembles domain I. The structure thus reveals a protein that has evolved through a process of gene duplication, mutation and fusion into an enzyme with high and unusual specificity.

The MAPKK family of proteins is the only known cellular substrates of LF. Cleavage by LF near to its N-terminal removes the docking sequence for the downstream cognate MAP kinase. The effect of lethal toxin on tumor cells, for example, is to inhibit tumor growth and angiogenesis, most probably by inhibiting the MAPKK-1 and MAPKK-2 pathways. However, the primary cell type affected in anthrax pathogenesis is the macrophage. LF has been shown to cleave short N-terminal fragments from mitogen or extracellular signal-regulated MAPKK-1, MAPKK-2, MAPKK-3, and MAPKK-6, the upstream activators of extracellular signal-regulated kinase 1 (ERK1), ERK2, and p38. Recent data show that this results in inhibiting release, but not production, of the pro-inflammatory mediators, NO and tumor necrosis factor-alpha (TNF-alpha). In addition, high levels of lethal toxin lead to lysis of macrophages within a few hours by an unknown mechanism. Recent data suggests that this happens due to inhibition of growth-factor pathways leading to macrophage death. These observations suggest that at an early stage in infection, lethal toxin may reduce (or delay) the immune response, whereas at a late stage in infection, high titers of the bacterium in the bloodstream trigger macrophage lysis and the sudden release of high levels of NO and TNF-alpha. This may explain the symptoms before death which are characterized by the hyperstimulation of host macrophage inflammatory pathways, leading to dramatic hypotension and shock. These symptoms resemble those of LPS-induced septic shock, whereby it is of note that LPS-nonresponder mice such as C3H/HeJ are also quite resistant against anthrax toxin.

The recognition sites for LF require the presence of the proline (P) residue followed by a hydrophobic residue or a glycine (G) residue, between which LF cleaves. The recognition sites further require an uncharged amino acid following the hydrophobic residue and at least one positively charged amino acid (and no negatively charged amino acid, such as Asp and Glu) within the 5 amino acids to the N-terminal side of the proline residue. Other residues in the sequence provide appropriate spacing between the critical residues or between the donor and acceptor, and thus their composition is not critical and can include any natural or unnatural amino acid.

Gene control is generally thought to occur at four levels: 1) transcription (either initiation or termination), 2) processing of primary transcripts, 3) stabilization or destabilization of mRNAs, and 4) mRNA translation. The primary function of gene control in cells is to adjust the enzymatic machinery of the cell to its nutritional, chemical and physical environment.

It is generally thought that gene expression is regulated at both the level of transcription and translation. Modulation or regulation of gene expression requires factors called transcriptional factors. The term "gene control or regulation" also refers to the formation and use of mRNA. Although control can be exerted at a number of different molecular steps, differential transcription probably most frequently underlies the differential rate of protein synthesis in prokaryotes as well as eukaryotes. It is generally thought that activator proteins (also called transcription factors or transcriptional activators) bind to DNA and recruit the transcriptional machinery in a cell to a promotor, thereby stimulating gene expression. Further, differential processing of RNA transcripts in the cell nucleus, differential stabilization of mRNA in the cytoplasm, and differential translation of mRNA into protein are also important in eukaryotic gene control. These steps define the regulatory decisions in a transcriptional circuit and misregulation at any stage can result in a variety of diseases.

Where in unicellular organisms, be it of prokaryotic or eukaryotic origin, a cell's response to its environment is influenced by many stimuli from the outside world, reflecting the often widely variable environment of the single cell, most cells in multicellular organisms experience a fairly constant environment. Perhaps for this reason, genes that are devoted to responses to environmental changes constitute a much smaller fraction of the total number of genes in multicellular organisms than in single-cell organisms.

As said above, cells react to environmental changes, which they perceive through extracellular signals. These signals can be either physical (e.g., light, temperature, pressure and electricity) or chemical (e.g., food, hormones and neurotransmitters). Cells can both sense and produce signals. This makes it possible that they communicate with each other. In order to achieve this, there are complex signal-sensing and -producing mechanisms in uni- and multi-cellular organisms.

Two groups of chemical signals can be distinguished: membrane-permeable and membrane-impermeable signals. The membrane-permeable signal molecules comprise the large family of steroid hormones, such as estrogens, progesterone and androgens. Steroids pass the plasma membrane and bind to specific receptors, which are localized in the cytoplasm or nucleus of the cell. After binding of the hormone, the receptor undergoes a conformational change. The receptor is then able to bind to DNA itself or to proteins which can in turn interact with DNA. In general, steroid hormones can directly regulate gene expression by means of this process. The membrane-impermeable signal molecules include acetylcholine, growth factors, extracellular matrix components, thrombin, lysophosphatidic acid, the yeast mating factors and, for the social amoeba *Dictyostellium discoideum*, folic acid and cyclic AMP. They are recognized by receptors, which are localized on the plasma membrane of the cell. The receptors are specific for one particular signal molecule or a family of closely related signal molecules. Upon binding of their ligands, these receptors transduce the signals by several mechanisms.

The most characteristic and exacting requirement of gene control on multicellular organisms is the execution of precise developmental decisions so that the right gene is activated in the right cell at the right time. These developmental decisions include not only those related to the development of an organism per se, as, for example, can be seen during embryogenesis and organogenesis, or in response to disease but also relate to the differentiation or proliferation or apoptosis of those cells that merely carry out their genetic program essentially without leaving progeny behind.

Such cells, such as skin cells, precursors of red blood cells, lens cells of the eye, and antibody-producing cells, are also often regulated by patterns of gene control that serve the need of the whole organism and not the survival of an individual cell.

It is generally reasoned that there are at least three components of gene control: molecular signals, levels and mechanisms. First, it is reasoned that specific signaling molecules exist to which a specific gene can respond. Second, control is exerted on one or more levels (i.e., the step or steps) in the chain of events leading from the transcription of DNA to the use of mRNA in protein synthesis. Third, at each of those levels, specific molecular mechanisms are employed to finally exert the control over the gene to be expressed.

Many genes are regulated not by a signaling molecule that enters the cells but by molecules that bind to specific receptors on the surface of cells. Interaction between cell-surface receptors and their ligands can be followed by a cascade of intracellular events including variations in the intracellular levels of so-called second messengers (diacylglycerol, $Ca^{2+}$, cyclic nucleotides). The second messengers in turn lead to changes in protein phosphorylation through the action of cyclic AMP, cyclic GMP, calcium-activated protein kinases, or protein kinase C, which is activated by diaglycerol.

Many of the responses to binding of ligands to cell-surface receptors are cytoplasmatic and do not involve immediate gene activation in the nucleus. Some receptor-ligand interactions, however, are known to cause prompt nuclear transcriptional activation of a specific and limited set of genes. For example, one proto-oncogene, c-fos, is known to be activated in some cell types by elevation of almost every one of the known second messengers and also by at least two growth factors, platelet-derived growth factor and epidermal growth factor. However, progress has been slow in determining exactly how such activation is achieved. In a few cases, the transcriptional proteins that respond to cell-surface signals have been characterized.

One of the clearest examples of activation of a pre-existing inactive transcription factor following a cell-surface interaction is the nuclear factor (NF)-κB, which was originally detected because it stimulates the transcription of genes encoding immunoglobulins of the kappa (κ) class in B-lymphocytes. The binding site for NK-κB in the kappa gene is well defined (see, for example, P. A. Baeuerle and D. Baltimore, 1988, Science 242:540), providing an assay for the presence of the active factor. This factor exists in the cytoplasm of lymphocytes complexed with an inhibitor. Treatment of the isolated complex in vitro with mild denaturing conditions dissociates the complex, thus freeing NK-κB to bind to its DNA site. Release of active NF-κB in cells is now known to occur after a variety of stimuli including treating cells with bacterial lipopolysaccharide (LPS) and extracellular polypeptides as well as chemical molecules (e.g., phobol esters) that stimulate intracellular phosphokinases. Thus, a phosphorylation event triggered by many possible stimuli may account for NF-KB conversion to the active state. The active factor is then translocated to the cell nucleus to stimulate transcription only of genes with a binding site for active NF-κB.

The inflammatory response involves the sequential release of mediators and the recruitment of circulating leukocytes, which become activated at the inflammatory site and release further mediators (Nat. Med. 7:1294;2001). This response is self-limiting and resolves through the release of endogenous anti-inflammatory mediators and the clearance of inflammatory cells. The persistent accumulation and activation of leukocytes is a hallmark of chronic inflammation. Current approaches to the treatment of inflammation rely on the inhibition of pro-inflammatory mediator production and of mechanisms that initiate the inflammatory response. However, the mechanisms by which the inflammatory response resolves might provide new targets in the treatment of chronic inflammation. Studies in different experimental models of resolving inflammation have identified several putative mechanisms and mediators of inflammatory resolution. We have shown that cyclopentenone prostaglandins (cyPGs) may be endogenous anti-inflammatory mediators and promote the resolution of inflammation in vivo. Others have shown a temporal shift to the production of anti-inflammatory lipoxins during the resolution of inflammation. In recent years, apoptosis has been identified as an important mechanism for the resolution of inflammation in vivo. It has been postulated that defects in leukocyte apoptosis are important in the pathogenesis of inflammatory disease. In addition, the selective induction of apoptosis in leukocytes may offer a new therapeutic approach to inflammatory disease.

Considering that NF-KB is thought by many to be a primary effector of disease (A. S. Baldwin, J. Clin. Invest., 2001, 107:3–6), numerous efforts are underway to develop safe inhibitors of NF-κB to be used in treatment of both chronic and acute disease situations. Specific inhibitors of NF-κB should reduce side effects associated with drugs such as NSAIDS and glucocorticoids and would offer significant potential for the treatment of a variety of human and animal diseases. Specific diseases or syndromes where patients would benefit from NF-κB inhibition vary widely, and range from rheumatoid arthritis, atherosclerosis, multiple sclerosis, chronic inflammatory demyelinating polyradiculoneuritis, asthma, inflammatory bowel disease, to *Helicobacter pylori*-associated gastritis and other inflammatory responses, and a variety of drugs that have effects on NF-κB activity, such as corticosteroids, sulfasalazine, 5-aminosalicylic acid, aspirin, tepoxalin, leflunomide, curcumin, antioxidants and proteasome inhibitors. These drugs are considered to be non-specific and often only applicable in high concentrations that may end up being toxic for the individual treated.

Inactive cytoplasmatic forms of transcription factors can thus be activated by removal of an inhibitor, as is the case with NF-kapppaB, or, alternatively, by association of two (or more) proteins, neither of which is active by itself as in the case of interferon-alpha-stimulated factor (D. E. Levy et al., 1989, Genes and Development 3:1362). After interferon-alpha attaches to its cell-surface receptor, one of the proteins is changed within a minute or less, and the two can combine. The active (combined) factor is then translocated to the cell nucleus to stimulate transcription only of genes with a binding site for the protein. Considering that interferon-alpha is a mediator of responses of the body directed at pathogens and self-antigens, modulating regulation of genes that are under influence of the interferon-alpha-stimulated factor would contribute to the treatment of a variety of human and animal diseases.

Other typical examples of signaling molecules that affect gene expression via cell-surface receptor interaction are polypeptide hormones such as insulin, glucagon, various growth factors such as EGF, VEGF, and so on.

The steroid hormones and their receptors represent one of the best understood cases that affect transcription. Because steroid hormones are soluble in lipid membranes, they can diffuse into cells. They affect transcription by binding to specific intracellular receptors that are site-specific DNA-binding molecules. Other examples of signaling molecules that enter the cell and act intra-cellularly are thyroid hormone ($T_3$), vitamin D and retinoic acid, other small lipid-soluble signaling molecules that enter cells and modulate gene expression. The characteristic DNA-binding sites for the receptors for these signaling molecules are also known as response elements.

Another example of a small molecule that is involved in regulation of gene expression is ethylene, a gas that, for example, induces the expression of genes involved in fruit ripening. Also, small plant hormones, known as auxins and cytokinins, regulate plant growth and differentiation directly by regulating gene expression.

Given the critical role of regulatory factors in gene regulation, the development of artificial or synthetic counterparts that could be used in methods to rectify errors in gene expression has been a long-standing goal at the interface of chemistry and biology.

DISCLOSURE OF THE INVENTION

The invention provides a method for modulating expression of a gene in a cell comprising providing the cell with a signaling molecule comprising an oligopeptide or functional analogue or derivative thereof. Such a molecule is herein also called NMPF and referenced by number. Since peptides, and functional analogues and derivatives of relatively short amino acid sequences, are easily synthesized these days, the invention provides a method to modulate gene expression with easily obtainable synthetic compounds such as synthetic peptides or functional analogues or derivatives thereof.

The invention also provides a method for the treatment of an inflammatory condition comprising administering to a subject in need of such treatment a molecule comprising an oligopeptide peptide or functional analogue or derivative thereof the molecule capable of reducing production of NO by a cell, in particular wherein the molecule additionally is capable of modulating translocation and/or activity of a gene transcription factor present in a cell, especially wherein the gene transcription factor comprises an NF-κB/Rel protein. Advantageously, the invention provides a method wherein the modulating translocation and/or activity of a gene transcription factor allows modulation of TNF-alpha production by the cell, in particular wherein the TNF-alpha production is reduced. Considering that TNF-alpha production is central to almost all, if not all, inflammatory conditions, reducing TNF-alpha production can greatly alleviate, or mitigate, a great host of inflammatory conditions that are described herein. In particular, the invention provides a method wherein the inflammatory condition comprises an acute inflammatory condition, and it is especially useful to treat anthrax-related disease, especially when considering that with anthrax, both NO and TNF-alpha reduction will greatly mitigate the course of disease. Table 6 lists oligopeptides according to the invention that have such modulatory effect. In particular, the invention provides a method of treatment wherein the treatment comprises administering to the subject a pharmaceutical composition comprising an oligopeptide or functional analogue or derivative thereof capable of reducing production of NO by a cell, preferably wherein the composition comprises at least two oligopeptides or functional analogues or derivatives thereof capable of reducing production of NO by a cell; examples of such combinations can be selected under guidance of table 6, whereby it suffices to select two, or more, with a desired effect, such as wherein the at least two oligopeptides are selected from the group LQGV (SEQ ID NO:1), AQGV (SEQ ID NO:2) and VLPALP (SEQ ID NO:3).

The invention also provides an isolated, preferably synthetic, oligopeptide or functional analogue or derivative thereof or mixture of such oligopeptides or analogues or derivatives capable of reducing production of NO by a cell. Such cell is preferably of a macrophage or DC lineage, considering the central role these cells play in the inflammatory process. The invention also provides a pharmaceutical composition comprising an oligopeptide or functional analogue or derivative according to the invention or comprising at least two oligopeptides or functional analogues or derivatives thereof capable of reducing production of NO by a cell. Furthermore, the invention provides the use of an oligopeptide or functional analogue or derivative thereof capable of reducing production of NO by a cell for the production of a pharmaceutical composition for the treatment of an inflammatory condition by the reduction of NO production by macrophages or DC in the subject to be treated.

A functional analogue or derivative of a peptide is defined as an amino acid sequence, or other sequence monomers, which has been altered such that the functional properties of the sequence are essentially the same in kind, not necessarily in amount. An analogue or derivative can be provided in many ways, for instance, through conservative amino acid substitution. Also peptidomimetic compounds can be designed that functionally or structurally resemble the original peptide taken as a starting point but that are, for example, composed of non-naturally occurring amino acids or polyamides. With conservative amino acid substitution, one amino acid residue is substituted with another residue with generally similar properties (size, hydrophobicity, etc.), such that the overall functioning is likely not to be seriously affected. However, it is often much more desirable to improve a specific function. A derivative can also be provided by systematically improving at least one desired property of an amino acid sequence. This can for instance be done by an Ala-scan and/or replacement net mapping method. With these methods, many different peptides are generated, based on an original amino acid sequence but each containing a substitution of at least one amino acid residue. The amino acid residue may either be replaced by alanine (Ala-scan) or by any other amino acid residue (replacement net mapping). This way, many positional variants of the original amino acid sequence are synthesized. Every positional variant is screened for a specific activity. The generated data are used to design improved peptide derivatives of a certain amino acid sequence.

A derivative or analogue can also for instance be generated by substitution of an L-amino acid residue with a D-amino acid residue. This substitution, leading to a peptide which does not naturally occur in nature, can improve a property of an amino acid sequence. It is, for example, useful to provide a peptide sequence of known activity of all D-amino acids in retro inversion format, thereby allowing for retained activity and increased half-life values. By generating many positional variants of an original amino acid sequence and screening for a specific activity, improved peptide derivatives comprising such D-amino acids can be designed with further improved characteristics.

A person skilled in the art is well able to generate analogous compounds of an amino acid sequence. This can for instance be done through screening of a peptide library. Such an analogue has essentially the same functional properties of the sequence in kind, not necessarily in amount. Also, peptides or analogues can be circularized (for example, by providing them with (terminal) cysteines, dimerized or multimerized, for example, by linkage to lysine or cysteine or other compounds with side-chains that allow linkage or multimerization, brought in tandem- or repeat-configuration, conjugated or otherwise linked to carriers known in the art, if only by a labile link that allows dissociation.

The invention also provides a signaling molecule for modulating expression of a gene in a cell comprising a small peptide or functional analogue or derivative thereof. Surprisingly, the inventors found that a small peptide acts as a signaling molecule that can modulate signal transduction pathways and gene expression. A functional analogue or derivative of a small peptide that acts as such a signaling molecule for modulating expression of one or more genes in a cell can be identified or obtained by at least one of various methods for finding such a signaling molecule as provided herein.

For example, one method as provided herein for identifying or obtaining a signaling molecule comprising a peptide or functional derivative or analogue thereof capable of modulating expression of a gene in a cell comprises providing the cell with a peptide or derivative or analogue thereof and determining the activity and/or nuclear translocation of one or more gene transcription factors. Such activity can be determined in various ways using means and/or methods honed to the specific transcription factor(s) under study. In the detailed description, it is provided to study NF-κB/Rel protein translocation and/or activity, but it is, of course, also easily possible to study translocation and/or activity of any other transcription factor for which such tools are available or can be designed. One such other transcription factor is, for example, the interferon-alpha-stimulated factor as discussed above. Other useful transcription factors to study in this context comprise c-Jun, ATF-2, Fos, and their complexes, ELK-1, EGR-1, IRF-1, IRF-3/7, AP-1, NF-AT, C/EBPs, Sp1, CREB, PPARgamma, and STAT proteins to name a few. Considering that many proteins are subject to proteolytic breakdown whereby oligopeptide fragments are generated, many already before the full protein even has exerted a function, it is hereby established that oligopeptide fragments of such proteins (of which a non-extensive list is given in the detailed description, but one can, for example, think of MAPKK-2 that can give rise to a peptide MLARRKPVLPALTINP (SEQ ID NO:4), and subsequently to a peptide comprising MLARRKP (SEQ ID NO:5) or MLAR (SEQ ID NO:6) or VLPALT (SEQ ID NO:7) or VLPAL (SEQ ID NO:8), but also of nitric oxide synthase that can give rise to peptides FPGC (SEQ ID NO:9) or PGCP (SEQ ID NO:10), GVLPAVP (SEQ ID NO:11), LPA, VLPAVP (SEQ ID NO:12), or PAVP (SEQ ID NO:13) after proper proteolysis) are involved in feedback mechanisms regulating gene expression, likely by the effect of transcription factors on gene expression. In addition, oligopeptide fragments of proteins (of which a non-extensive list is given in the detailed description) can also modulate the activity of extracellular components such as factor XIII (examples of oligopeptide fragments obtained from factor XIII are LQGV (SEQ ID NO:1), LQGVVPRGV (SEQ ID NO:14), GVVP (SEQ ID NO:15), VPRGV (SEQ ID NO:16), PRG, PRGV (SEQ ID NO:17)) or activated protein C (APC) and thereby eventually lead to the modulation of intracellular signal transduction pathways and gene(s) expression.

As said, the invention provides active oligopeptides acting as a signaling molecule. To allow for improved bioavailability of such a signaling molecule (which is useful as a pharmacon, especially when produced artificially), the invention also provides a method for determining whether a small peptide or derivative or analogue thereof can act as a functional signaling molecule according to the invention, the method further comprising determining whether the signaling molecule is membrane-permeable.

The invention, for example, provides a process or method for obtaining information about the capacity or tendency of an oligopeptide, or a modification or derivative thereof, to regulate expression of a gene comprising the steps of:
a) contacting the oligopeptide, or a modification or derivative thereof, with at least one cell;
b) determining the presence of at least one gene product in or derived from the cell. It is preferred that the oligopeptide comprises an amino acid sequence corresponding to a fragment of a naturally occurring polypeptide, such as hCG, or MAPKK (SEQ ID NO:18), or another kinase, be it of plant or animal cell, or of eukaryotic or prokaryotic origin, or a synthase of a regulatory protein in a cell, such as wherein the regulatory protein is a (pro-) inflammatory mediator, such as a cytokine. Several candidate proteins and peptide fragments are listed in the detailed description which are a first choice for such an analysis from the inventors' perspective, but the person skilled in the art, and working in a specific field of interest in biotechnology, shall immediately understand which protein to select for such analyses for his or her own purposes related to his or her field.

In particular, it is provided to perform a process according to the invention further comprising a step c) comprising determining the presence of the gene product in or derived from a cell which has not been contacted with the oligopeptide, or a modification or derivative thereof, and determining the ratio of gene product found in step b to gene product found in step c, as can easily be done with the present-day genechip technology (see, for example, the detailed description herein) and related methods of expression profiling known in the art.

Another method provided herein for identifying or obtaining information on a signaling molecule, (or for that matter, the signaling molecule itself, considering that the next step of synthesizing the molecule, generally being a short peptide, is whole within the art) comprising a peptide or functional derivative or analogue thereof capable of modulating expression of a gene in a cell comprises providing the cell with a peptide or derivative or analogue thereof and determining relative up-regulation and/or down-regulation of at least one gene expressed in the cell. The up-regulation can classically be studied by determining via, for example, Northern or Western blotting or nucleic acid detection by PCR or immunological detection of proteins whether a cell or cells make more (in the case of up-regulation) or less (in the case of down-regulation) of a gene expression product such as mRNA or protein after the cell or cells have been provided with the peptide or derivative or analogue thereof. Of course, various methods of the invention can be combined to better analyze the functional analogue of the peptide or derivative or analogue under study. Furthermore, relative up-regulation and/or down-regulation of a multitude or clusters of genes expressed in the cell can be easily studied as well, using libraries of positionally or spatially addressable predetermined or known relevant nucleic acid sequences or unique fragments thereof bound to an array or brought in an array format, using, for example, a nucleic acid library or so-called gene-chip expression analysis systems. Lysates of cells or preparations of cytoplasma and/or nuclei of cells that have been provided with the peptide or derivative or analogue under study are than contacted with the library, and relative binding of, for example, mRNA to individual nucleic acids of the library is then determined, as further described herein in the detailed description.

A functional analogue or derivative of a small peptide that can act as a signaling molecule for modulating expression of a gene in a cell can also be identified or obtained by a method for identifying or obtaining a signaling molecule comprising an oligopeptide or functional derivative or analogue thereof capable of modulating expression of a gene in a cell comprising providing a peptide or derivative or analogue thereof and determining binding of the peptide or derivative or analogue thereof to a factor related to gene control. Such a factor related to gene control can be any factor related to transcription (either initiation or termination), processing of primary transcripts, stabilization or destabilization of mRNAs, and mRNA translation.

Binding of a peptide or derivative or analogue thereof to such a factor can be determined by various methods known in the art. Classically, peptides or derivatives or analogues can be (radioactively) labeled and binding to the factor can be determined by detection of a labeled peptide-factor complex, such as by electrophoresis, or other separation methods known in the art. However, for determining binding to such factors, array techniques, such as used with peptide libraries, can also be employed, comprising providing a multitude of peptides or derivatives or analogues thereof and determining binding of at least one of the peptides or derivatives or analogues thereof to a factor related to gene control.

In a preferred embodiment, the factor related to gene control comprises a transcription factor, such as an NF-κB-Rel protein or another transcription factor desired to be studied. When binding of a functional analogue according to the invention to such factor has been established, it is of course possible to further analyze the analogue by providing a cell with the peptide or derivative or analogue thereof and determining the activity and/or nuclear translocation of a gene transcription factor in the cell, and/or by providing a cell with the peptide or derivative or analogue thereof and determining relative up-regulation and/or down-regulation of at least one gene expressed in the cell.

The invention thus provides a signaling molecule useful in modulating expression of a gene in a cell and/or useful for reducing NO production by a cell and identifiable or obtainable by employing a method according to the invention. Useful examples of such a signaling molecule can be selected from the group of oligopeptides LQG, AQG, LQGV (SEQ ID NO:1), AQGV (SEQ ID NO:2), LQGA (SEQ ID NO:19), VLPALPQVVC (SEQ ID NO:20), VLPALP (SEQ ID NO:3), ALPALP (SEQ ID NO:21), VAPALP (SEQ ID NO:22), ALPALPQ (SEQ ID NO:23), VLPAAPQ (SEQ ID NO:24), VLPALAQ (SEQ ID NO:25), LAGV (SEQ ID NO:26), VLAALP (SEQ ID NO:27), VLPALA (SEQ ID NO:28), VLPALPQ (SEQ ID NO:29), VLAALPQ (SEQ ID NO:30), VLPALPA (SEQ ID NO:31), GVLPALP (SEQ ID NO:32), GVLPALPQ (SEQ ID NO:33), LQGVLPALPQVVC (SEQ ID NO:34), VVCNYRDVRFESIRLPGCPRGVNPVVSYAVALSCQCAL (SEQ ID NO:35), RPRCRPINATLAVEK (SEQ ID NO:36), EGCPVCITVNTTICAGYCPT (SEQ ID NO:37), SKAPPPSLPSPSRLPGPS (SEQ ID NO:38), SIRLPGCPRGVNPVVS (SEQ ID NO:39), LPGCPRGVNPVVS (SEQ ID NO:40), LPGC (SEQ ID NO:41), MTRV (SEQ ID NO:42), MTR, VVC, QVVC (SEQ ID NO:43) and functional analogues or derivatives thereof.

A preferred size of a signaling molecule according to the invention is at most 30–40 amino acids, although much smaller molecules, in particular of oligopeptide size, have been shown to be particularly effective. Surprisingly, the invention provides here the insight that gene expression can be modulated or regulated by small peptides that are most likely breakdown products of larger polypeptides such as chorionic gonadotrophin (CG) and growth hormones or growth factors such as fibroblast growth factor, EGF, VEGF, RNA 3' terminal phosphate cyclase and CAP18. In principle, such regulating peptide sequences can be derived from a part of any protein of polypeptide molecule produced by prokaryotic and/or eukaryotic cells, and the invention provides the insight that breakdown products of polypeptides, preferably oligopeptides at about the sizes as provided herein, are naturally involved as signaling molecule in modulation of gene expression. In particular, as signaling molecule, a (synthetic) peptide is provided obtainable or derivable from beta-human chorionic gonadotrophin (beta-HCG), preferably from nicked beta-HCG. It was thought before that breakdown products of nicked-beta hCG were involved in immuno-modulation (PCT International Patent Publication WO99/59671) or in the treatment of wasting syndrome (PCT International Patent Publication WO97/49721), but a relationship with modulation of gene expression was not forwarded in these publications. Of course, such an oligopeptide or functional equivalent or derivative thereof is likely obtainable or derivable from other proteins that are subject to breakdown or proteolysis and that are close to a gene regulatory cascade. Preferably, the peptide signaling molecule is obtained from a peptide having at least 10 amino acids such as a peptide having an amino acid sequence MTRVLQGVLPALPQVVC (SEQ ID NO:44), SIRLPGCPRGVNPVVS (SEQ ID NO:39), VVCNYRDVRFESIRLPGCPRGVNPVVSYAVALSCQCAL (SEQ ID NO:35), RPRCRPINATLAVEKEGCPVCITVNTTICAGYCPT (SEQ ID NO:45), CALCRRSTFDCGGPKDHPLTC (SEQ ID NO:46), SKAPPPSLPSPSRLPGPS (SEQ ID NO:38), CRRSTTDCGGPKDHPLTC (SEQ ID NO:47), TCDDPRFQDSSSSKAPPPSLPSPSRLPGPSDTPILPQ (SEQ ID NO:48) or functional fragment (e.g., a breakdown product) or functional analogue thereof. "Functional analogue" herein relates to the signaling molecular effect or activity as, for example, can be measured by measuring nuclear translocation of a relevant transcription factor, such as NF-κB in an NF-κB assay, or AP-1 in an AP-1 assay, or by another method as provided herein. Fragments can be somewhat (i.e., 1 or 2 amino acids) smaller or larger on one or both sides, while still providing functional activity.

Not wishing to be bound by theory, it is postulated herein that an unexpected mode of gene regulation has been uncovered. Polypeptides, such as endogenous CG, EGF, etc., but also polypeptides of pathogens, such as viral, bacterial or protozoal polypeptides, are subject to breakdown into distinct oligopeptides, for example, by intracellular proteolysis. Distinct proteolytic enzymes are widely available in the cell, for example, in eukaryotes in the lysosomal or proteasomal system. Some of the resulting breakdown products are oligopeptides of 3 to 15, preferably 4 to 9, most preferably 4 to 6 amino acids long that are surprisingly not without any function or effect to the cell but, as demonstrated herein, may be involved, possibly via a feedback mechanism in the case of breakdown of endogenous polypeptides, as signaling molecules in the regulation of gene expression, as demonstrated herein by the regulation of the activity or translocation of a gene transcription factor such as NF-KB by, for example, peptide LQGV (SEQ ID NO:1), VLPALPQVVC (SEQ ID NO:20), LQGVLPALPQ (SEQ ID NO:49), LQG, GVLPALPQ (SEQ ID NO:33), VLPALP (SEQ ID NO:3), VLPALPQ (SEQ ID NO:29), GVLPALP (SEQ ID NO:32), VVC, MTRV (SEQ ID NO:42), MTR. Synthetic versions of these oligopeptides, as described above, and functional analogues or derivatives of these breakdown products are herein provided to modulate gene expression in a cell and be used in methods to rectify errors in gene expression or the treatment of disease. Oligopeptides such as LQG, AQG, LQGV (SEQ ID NO:1), AQGV (SEQ ID NO:2), LQGA (SEQ ID NO:19), VLPALP (SEQ ID NO:3), ALPALP (SEQ ID NO:21), VAPALP (SEQ ID NO:22), ALPALPQ (SEQ ID NO:23), VLPAAPQ (SEQ ID NO:24), VLPALAQ (SEQ ID NO:25), LAGV (SEQ ID NO:26), VLAALP (SEQ ID NO:27), VLPALA (SEQ ID NO:28), VLPALPQ (SEQ ID NO:29), VLAALPQ (SEQ ID NO:30), VLPALPA (SEQ ID NO:31), GVLPALP (SEQ ID NO:32), GVLPALPQ (SEQ ID NO:33), LQGVLPALPQVVC (SEQ ID NO:34), SIRLPGCPRGVNPVVS (SEQ ID NO:39), SKAPPPSLPSPSRLPGPS (SEQ ID NO:38), LPGCPRGVNPVVS (SEQ ID NO:40), LPGC (SEQ ID NO:41), MTRV (SEQ ID NO:42), MTR, VVC, or functional analogues or derivatives (including breakdown products) of the longer sequences thereof, are particularly effective.

By using the insight as expressed herein, in a preferred embodiment, the invention provides a method for modulating expression of a gene in a cell comprising providing the cell with a signaling molecule comprising an oligopeptide or functional analogue or derivative thereof wherein the signaling molecule is membrane-permeable in that it enters the cell. Most small peptides as described herein have already an inherent propensity to become intracellularly involved, but signaling molecules as provided herein can also be provided with additional peptide sequences, such as arginine- or lysine-rich stretches of amino acids, that allow for improved internalization across a lipid bilayer membrane, and may possibly be cleaved off later by internal proteolytic activity.

In a preferred embodiment, the invention provides a method for modulating expression of a gene in a cell comprising providing the cell with a signaling molecule comprising a small peptide (amino acid sequence) or functional analogue or derivative thereof, wherein the signaling molecule modulates NF-κB/Rel protein conversion or translocation. As said, NF-κB was originally identified as a gene transcription factor that bound to an enhancer element in the gene for the Igκ light chain and was believed to be B-cell-specific. However, subsequent studies revealed that NF-κB/Rel proteins are ubiquitously expressed and play a central role as transcription factor in regulating the expression of many genes, particularly those involved in immune, inflammatory, developmental and apoptotic processes. NF-KBrelated gene transcription factors can be activated by different stimuli such as microbial products, proinflammatory cytokines, T- and B-cell mitogens, and physical and chemical stresses. NF-KB in turn regulates the inducible expression of many cytokines, chemokines, adhesion molecules, acute phase proteins, and antimicrobial peptides.

NF-κB represents a group of structurally related and evolutionarily conserved gene transcription factors. So far, five mammalian NF-KB proteins named Rel (c-Rel), RelA (p65), RelB, NF-κB1 (p50 and its precursor p105), and NF-κB2 (p52 and it precursor p100) have been described. NF-κB proteins can exist as homo- or heterodimers, and although most NF-κB dimers are activators of transcription, the p50/p50 and p52/p52 homodimers often repress the transcription of their target genes. In *Drosophila*, three NF-κB homologs named Dorsal, Dif, and Relish have been identified and characterized. Structurally, all NF-κB/Rel proteins share a highly conserved $NH_2$-terminal Rel homology domain (RHD) that is responsible for DNA binding, dimerization, and association with inhibitory proteins known as IκBs. In resting cells, NF-κB/Rel dimers are bound to IκBs and retained in an inactive form in the cytoplasm. Like NF-κB, IκBs are also members of a multigene family containing seven known mammalian members including IκBα, IκBβ, IκBγ, IκBε, Bcl-3, the precursor Rel-proteins, p100, and p105, and one *Drosophila* IκB named Cactus. The IκB family is characterized by the presence of multiple copies of ankyrin repeats, which are protein—protein interaction motifs that interact with NF-κB via the RHD. Upon appropriate stimulation, IκB is phosphorylated by IκB kinases (IKKs), polyubiquitinated by a ubiquitin ligase complex, and degraded by the 26S proteosome. Consequently, NF-κB is released and translocates into the nucleus to initiate gene expression.

NF-κB-related transcription factors regulate the expression of a wide variety of genes that play critical roles in innate immune responses. Such NF-κB target genes include those encoding cytokines (e.g., IL-1, IL-2, IL-6, IL-12, TNF-α, LTα, LTβ, and GM-CSF), adhesion molecules (e.g., ICAM, VCAM, endothelial leukocyte adhesion molecule [ELAM]), acute phase proteins (e.g., SAA), and inducible enzymes (e.g., iNOS and COX-2). In addition, it has been demonstrated recently that several evolutionary conserved antimicrobial peptides, for example, O-defensins, are also regulated by NF-κB, a situation similar to *Drosophila*. Besides regulating the expression of molecules involved in innate immunity, NF-κB also plays a role in the expression of molecules important for adaptive immunity, such as MHC proteins, and the expression of critical cytokines such as IL-2, IL-12 and IFN-γ. Finally, NF-κB plays an important role in the overall immune response by affecting the expression of genes that is critical for regulating the apoptotic process, such as c-IAP-1 and c-IAP-2, Fas ligand, c-myc, p53, and cyclin D1.

Under normal conditions, NF-κB is rapidly activated upon microbial and viral invasion, and this activation usually correlates with resistance of the host to infection. However, persistent activation of NF-κB may lead to the production of excessive amounts of pro-inflammatory mediators such as IL-12 and TNF-alpha, resulting in tissue damage, as in insulin-dependent diabetes mellitus, atherosclerosis, Crohn's disease, organ failure, and even death of the host, as in bacterial infection-induced septic shock. It is interesting to note that in order to survive in the host, certain pathogens, such as *Bordetella, Yersinia, Toxoplasma gondii* and African Swine Fever Virus, have evolved mechanisms to counteract or escape the host system by inhibiting NF-κB activation. On the other hand, some viruses, including HIV-1, CMV and SV-40, take advantage of NF-κB as a host factor that is activated at sites of infection.

Furthermore, the invention provides a method to explore alterations in gene expression in antigen-presenting cells such as dendritic cells in response to microbial exposure by analyzing a gene-expression profile of dendritic cells in response to microorganisms such as, for example, bacteria such as *Escherichia coli*, or other pathogenic bacteria, fungi or yeasts such as *Candida albicans*, viruses such as influenza virus and the effect of (simultameous) treatment of these diseases with a signaling molecule according to the invention. For example, human monocyte-derived dendritic cells are cultured with one or more pathogens for 1–36 hours, and gene expression is analyzed using an oligonucleotide array representing a (be it large or small) set of genes. When the pathogens regulate the expression of a core set of a distinct number of genes, these genes may be classified according to their kinetics of expression and function. Generally, within 4 hours of pathogen exposure, genes associated with pathogen recognition and phagocytosis will be down-regulated, whereas genes for antigen processing and presentation are up-regulated 8 hours post-exposure. Treatment of such dendritic cells with a signaling molecule according to the invention (be it simultaneous or before or after the treatment of the cells with the pathogen) allows studying the effect of a signaling molecule on the effect a pathogen has on an antigen-presenting cell.

In short, the invention surprisingly provides a signaling molecule capable of modulating expression of a gene in a cell, the molecule being a short peptide, preferably of at most 30 amino acids long or a functional analogue or derivative thereof. In a much preferred embodiment, the peptide is an oligopeptide of from about 3 to about 15 amino acids long, preferably 4 to 12, more preferably 4 to 9, most preferably 4 to 6 amino acids long, or a functional analogue or derivative thereof. Of course, such signaling molecule can be longer, for example, by extending it (N- and/or C-terminally, with more amino acids or other side groups, which can, for example, be (enzymatically) cleaved off when the molecule enters the place of final destination. Such extension may even be preferable to prevent the signaling molecule from becoming active in an untimely fashion; however, the core or active fragment of the molecule comprises the aforementioned oligopeptide or analogue or derivative thereof.

In particular, the invention provides a modulator of NF-κB/Rel protein activation comprising a signaling molecule according to the invention. Such modulators are widely searched after these days. Furthermore, the invention provides use of a signaling molecule according to the invention for the production of a pharmaceutical composition for the modulation of gene expression.

Also, the invention provides a method for the treatment of bone disease such as osteoporosis comprising administering to a subject in need of such treatment a molecule comprising an oligopeptide peptide or functional analogue thereof, the molecule capable of modulating production of NO and/or TNF-alpha by a cell. Such a method of treatment is particularly useful in post-menopausal women that do not longer experience the benefits of being provided with a natural source of several of the signaling molecules as provided herein, hCG and its breakdown products. Furthermore, the invention provides a method for the treatment of an inflammatory condition associated with TNF-alpha activity of fibroblasts, such as seen with chronic arthritis or synovitis, comprising administering to a subject in need of such treatment a molecule comprising an oligopeptide peptide or functional analogue thereof wherein the molecule is capable of modulating translocation and/or activity of a gene transcription factor present in a cell, in particular of the NF-κB factor. Such a treatment can be achieved by systemic administration of a signaling molecule according to the invention, but local administration in joints, bursae or tendon sheaths is provided as well. The molecule can be selected from table 6 or identified in a method according to the invention. It is preferred when the treatment comprises administering to the subject a pharmaceutical composition comprising an oligopeptide or functional analogue thereof also capable of reducing production of NO by a cell, for example, wherein the composition comprises at least two oligopeptides or functional analogues thereof, each capable of reducing production of NO and/or TNF-alpha by a cell, in particular wherein the at least two oligopeptides are selected from the group LQGV (SEQ ID NO:1), AQGV (SEQ ID NO:2) and VLPALP (SEQ ID NO:3).

Furthermore, the invention provides use of an oligopeptide or functional analogue thereof capable of reducing production of NO and/or TNF-alpha by a cell for the production of a pharmaceutical composition for the treatment of an inflammatory condition or a post-menopausal condition, or a bone disease such as osteoporosis, or for the induction of weight loss. The term "pharmaceutical composition" as used herein is intended to cover both the active signaling molecule alone or a composition containing the signaling molecule together with a pharmaceutically acceptable carrier, diluent or excipient. Acceptable diluents of an oligopeptide as described herein in the detailed description are, for example, physiological salt solutions or phosphate buffered salt solutions. In one embodiment of the present invention, a signal molecule is administered in an effective concentration to an animal or human systemically, for instance, by intravenous, intra-muscular or intraperitoneal administration. Another way of administration comprises perfusion of organs or tissue, be it in vivo or ex vivo, with a perfusion fluid comprising a signal molecule according to the invention. Topical administration, e.g., in ointments or sprays, may also apply, for example, in inflammations of the skin or mucosal surfaces of, for example, mouth, nose and/or genitals. Local administration can occur in joints, bursae, tendon sheaths, in or around the spinal cord at locations where nerve bundles branch off, at the location of hernias, in or around infarcted areas in brain or heart, etc. The administration may be done as a single dose, as a discontinuous sequence of various doses, or continuously for a period of time sufficient to permit substantial modulation of gene expression. In the case of a continuous administration, the duration of the administration may vary depending upon a number of factors that would readily be appreciated by those skilled in the art.

The administration dose of the active molecule may be varied over a fairly broad range. The concentrations of an active molecule that can be administered would be limited by efficacy at the lower end and the solubility of the compound at the upper end. The optimal dose or doses for a particular patient should and can be determined by the physician or medical specialist involved, taking into consideration well-known relevant factors such as the condition, weight and age of the patient, etc.

The active molecule may be administered directly in a suitable vehicle, such as, for example, phosphate-buffered saline (PBS), or as solutions in alcohol or DMSO. Pursuant to preferred embodiments of the present invention, however, the active molecule is administered through a single-dose delivery using a drug-delivery system, such as a sustained-release delivery system, which enables the maintenance of the required concentrations of the active molecule for a period of time sufficient for adequate modulation of gene expression. A suitable drug-delivery system would be pharmacologically inactive or at least tolerable. It should preferably not be immunogenic nor cause inflammatory reactions, and should permit release of the active molecule so as to maintain effective levels thereof over the desired time period. A large variety of alternatives are known in the art as suitable for purposes of sustained release and are contemplated as within the scope of the present invention. Suitable delivery vehicles include, but are not limited to, the following: microcapsules or microspheres; liposomes and other lipid-based release systems; viscous instillates; absorbable and/or biodegradable mechanical barriers and implants; and polymeric delivery materials, such as polyethylene oxide/polypropylene oxide block copolymers, polyesters, cross-linked polyvinylalcohols, polyanhydrides, polymethacrylate and polymethacrylamide hydrogels, anionic carbohydrate polymers, etc. Useful delivery systems are well known in the art.

A highly suitable formulation to achieve the active molecule release comprises injectable microcapsules or microspheres made from a biodegradable polymer, such as poly (dl-lactide), poly (dl-lactide-co-glycolide), polycaprolactone, polyglycolide, polylactic acid-co-glycolide, poly (hydroxybutyric acid), polyesters or polyacetals. Injectable systems comprising microcapsules or microspheres having a diameter of about 50 to about 500 micrometers offer advantages over other delivery systems. For example, they generally use less active molecules and may be administered by paramedical personnel. Moreover, such systems are inherently flexible in the design of the duration and rate of separate drug release by selection of microcapsule or microsphere size, drug loading and dosage administered. Further, they can be successfully sterilized by gamma irradiation.

The design, preparation and use of microcapsules and microspheres are well within the reach of persons skilled in the art and detailed information concerning these points is available in the literature. Biodegradable polymers (such as lactide, glycolide and caprolactone polymers) may also be used in formulations other than microcapsules and microspheres; for example, pre-made films and spray-on films of these polymers containing the active molecule would be suitable for use in accordance with the present invention. Fibers or filaments comprising the active molecule are also contemplated as within the scope of the present invention.

Another highly suitable formulation for a single-dose delivery of the active molecule in accordance with the present invention involves liposomes. The encapsulation of an active molecule in liposomes or multilamellar vesicles is a well-known technique for targeted drug delivery and prolonged drug residence. The preparation and use of drug-loaded liposomes is well within the reach of persons skilled in the art and well documented in the literature.

Yet another suitable approach for single dose delivery of an active molecule in accordance with the present invention involves the use of viscous instillates. In this technique, high molecular weight carriers are used in admixture with the active molecule, giving rise to a structure that produces a solution with high viscosity. Suitable high molecular weight carriers include, but are not limited to, the following: dextrans and cyclodextrans; hydrogels; (cross-linked) viscous materials, including (cross-linked) viscoelastics; carboxymethylcellulose; hyaluronic acid; and chondroitin sulfate. The preparation and use of drug-loaded viscous instillates is well known to persons skilled in the art.

Pursuant to yet another approach, the active molecule may be administered in combination with absorbable mechanical barriers such as oxidized, regenerated cellulose. The active molecule may be covalently or non-covalently (e.g., ionically) bound to such a barrier, or it may simply be dispersed therein. A pharmaceutical composition as provided herein is particularly useful for the modulation of gene expression by inhibiting NF-κB/Rel protein activation.

NF-κB/Rel proteins are a group of structurally related and evolutionarily conserved proteins (Rel). Well known are c-Rel, RelA (p65), RelB, NF-κB1 (p50 and its precursor p105), and NF-κB2 (p52 and its precursor p100). Most NF-KB dimers are activators of transcription; p50/p50 and p52/p52 homodimers repress the transcription of their target genes. All NF-κB/Rel proteins share a highly conserved NH2-terminal Rel homology domain (RHD). RHD is responsible for DNA binding, dimerization, and association with inhibitory proteins known asIκBs. In resting cells, NF-κB/Rel dimers are bound to IκBs and retained in an inactive form in the cytoplasm. IκBs are members of a multigene family (IκBα, IκBβ, IκBγ, IκBϵ, Bcl-3, the precursor Rel-proteins, p100 and p105). The presence of multiple copies of ankyrin repeats to interact with NF-κB via the RHD (protein—protein interaction). Upon appropriate stimulation, IκB is phosphorylated by IκB Kinase (IKKs), polyubiquitinated by ubiquitin ligase complex, and degraded by the 26S proteosome. NF-κB is released and translocates into the nucleus to initiate gene expression.

NF-KB regulation of gene expression includes innate immune responses: such as regulated by cytokines IL-1, IL-2, IL-6, IL-12, TNF-α, LTα, LT-β, GM-CSF; expression of adhesion molecules (ICAM, VCAM, endothelial leukocyte adhesion molecule [ELAM]), acute phase proteins (SAA), inducible enzymes (iNOS and COX-2) and antimicrobial peptides (beta-defensins). For adaptive immunity, MHC proteins, IL-2, IL-12 and IFN-α are regulated by NF-κB. Regulation of overall immune response includes the regulation of genes critical for regulation of apoptosis (c-IAP-1 and c-IAP-2, Fas Ligand, c-myc, p53 and cyclin D1.

Considering that NF-κB and related transcription factors are cardinal pro-inflammatory transcription factors, and considering that the invention provides a signaling molecule, such as an oligopeptide and functional analogues or derivatives thereof that are capable of inhibiting NF-κB and likely also other pro-inflammatory transcription factors, herein also called NF-κB inhibitors, the invention provides a method for modulating NF-κB activated gene expression, in particular for inhibiting the expression and thus inhibiting a central pro-inflammatory pathway.

The consequence of this potency to inhibit this pro-inflammatory pathway is wide and far-reaching. The invention, for example, provides a method to mitigate or treat inflammatory airway disease such as asthma. Generally, asthma patients show persistent activation of NF-κB of cells lining the respiratory tract. Providing these patients, for example, by aerosol application, with a signaling molecule according to the invention, such as LQGV (SEQ ID NO:1) or AQGV (SEQ ID NO:2) or MTRV (SEQ ID NO:3) or functional analogue or derivative thereof, will alleviate the inflammatory airway response of these individuals by inhibiting NF-KB activation of the cells. Such compositions can advantageously be made with signaling molecules that are taken up in liposomes.

As said, inflammation involves the sequential activation of signaling pathways leading to the production of both pro- and anti-inflammatory mediators. Considering that much attention has focused on pro-inflammatory pathways that initiate inflammation, relatively little is known about the mechanisms that switch off inflammation and resolve the inflammatory response. The transcription factor NF-κB is thought to have a central role in the induction of pro-inflammatory gene expression and has attracted interest as a new target for the treatment of inflammatory disease. However, NF-κB activation of leukocytes recruited during the onset of inflammation is also associated with pro-inflammatory gene expression, whereas such activation during the resolution of inflammation is associated with the expression of anti-inflammatory genes and the induction of apoptosis. Inhibition of NF-κB during the resolution of inflammation protracts the inflammatory response and prevents apoptosis. This shows that NF-κB has an anti-inflammatory role in vivo involving the regulation of inflammatory resolution. The invention provides a tool to modulate the inflammation at the end phase; a signaling molecule or modulator as provided herein allows the modulation of the NF-κB pathway at different stages of the inflammatory response in vivo. In a particular embodiment, the invention provides a modulator of NF-κB for use in the resolution of inflammation, for example, through the regulation of leukocyte apoptosis. Useful oligopeptides can be found among those that accelerate shock.

The invention also provides a method to mitigate or treat neonatal lung disease, also called chronic lung disease of prematurity, a condition often seen with premature children who develop a prolonged pulmonary inflammation or bronchopulmonary dysplasia. Treating such premature children with an NF-κB inhibitor, such as oligopeptide LQGV (SEQ ID NO:1), or functional analogue or derivative thereof, as provided herein, allows such lung conditions to be prevented or ameliorated as well.

Recent advances in bone biology provide insight into the pathogenesis of bone diseases. The invention also provides a method of treatment of a post-menopausal condition such as osteoporosis comprising modulation and inhibition of osteoclast differentiation and inhibiting TNF-alpha induced apoptosis of osteoblasts, thereby limiting the dissolution of bone structures, otherwise so prominent in post-menopausal women that no longer have a natural source of hCG and thus lack the modulatory effect of the signal molecules that are derived from hCG as shown herein. The invention thus also provides a method of treatment of a bone disease, such as osteoporosis (which is often, but not exclusively seen with post-menopausal women) Furthermore, NO and TNF-alpha modulators as provided herein inhibit the inflammatory response and bone loss in periodontitis. Furthermore, considering that there is a correlation between TNF-alpha activity and severity of clinical manifestations in ankylosing spondylitis, the invention provides the treatment of spondylitis by use of a signaling molecule as provided herein.

Furthermore, considering that an important pathogenic component in the development of insulin-dependent diabetes mellitus (type 1) comprises over-activation of the NF-κB pathway as seen in dendritic cells, treatment with an NF-κB inhibitor according to the invention will lead to reduced symptoms of diabetes, or at least to a prolonged time to onset of the disease. Particularly effective oligopeptide signaling molecules according to the invention in this context are GVLPALPQ (SEQ ID NO:33), LQGV (SEQ ID NO:1), MTRV (SEQ ID NO:42), VLPALPQVVC (SEQ ID NO:20), VLPALP (SEQ ID NO:3), VLPALPQ (SEQ ID NO:29), LPGCPRGVNPVVS (SEQ ID NO:40), LPGC (SEQ ID NO:41), VVCNYRDVRFESIRLPGCPRGVNPV-VSYAVALSCQCAL (SEQ ID NO:35), CPRGVNPVVS (SEQ ID NO:50), which were shown herein to postpone onset of diabetes in a Non-obese Diabetic Mouse (NOD). Another approach to treatment of diabetes, in particular insulin-independent diabetes (type 2), comprises inhibition of the PPARgamma cascade with an oligopeptide signaling molecule or functional analogue or derivative thereof.

Another use that is provided relates to a method for combating or treating auto-immune disease. A non-limiting list of immune diseases includes:

Hashimoto's thyroiditis, primary myxedema thyrotoxicosis, pernicious anemia, autoimmune atrophic gastritis, Addison's disease, premature menopause, insulin-dependent diabetes mellitus, stiff-man syndrome, Goodpasture's syndrome, myasthenia gravis, male infertility, pemphigus vulgaris, pemphigoid, sympathetic ophthalmia, phagocogenic uveitis, multiple sclerosis, autoimmune hemolytic anemia, idiopathic thrombocytopenic purpura, idiopathic leucopenia, primary biliary cirrhosis, active chronic hepatitis, autoimmune deafness, cryptogenic cirrhosis, ulcerative colitis, Sjögren's syndrome, rheumatoid arthritis, dermatomyositis, polymyositis, scleroderma, mixed connective tissue disease, discoid lupus erythematosus, and systemic lupus erythematosus.

Another use that is provided relates to a method for combating or treating infections caused by microorganisms, in particular those infections that are caused by microorganisms that activate the NF-κB pathway during infections.

Such microorganisms are manifold, including bacteria, viruses, fungi, protozoa, but other pathogens (e.g., worms) can have the same effect. Activation of the NFκB pathway by a microbial infection, in general, occurs via activation of the Toll-like receptor pathway. The invention provides a method to modulate and, in particular, to inhibit parts of gene expression that are related to the inflammatory responses of an organism that are generally activated through one of the Toll-like receptor pathways.

Toll-like receptor-mediated NF-κ-B activation is central in recognition of pathogens by a host. Such recognition of pathogens generally occurs through germline-encoded molecules, the so-called pattern recognition receptors (PRRs). These PRRs recognize widespread pathogen-associated molecular patterns (PAMPs). The pattern recognition receptors are expressed as either membrane-bound or soluble proteins. They include CD14, beta2-integrins (CD11/CD18), C-type lectins, macrophage scavenger receptors, complement receptors (CR11/CD35, CR2/CD21) and Toll-like receptors (TLRs). TLRs are distinguished from other PRRs by their ability to recognize and discriminate between different classes of pathogens. TLRs represent a family of transmembrane proteins that have an extracellular domain comprising multiple copies of leucine-rich repeats (LRRs) and a cytoplasmic: Toll/IL-1R (TIR) motif that has significant homology to the intracellular signaling domain of the type I IL-1 receptor (IL-1RI). Therefore, TLRs are thought to belong to the IL-1R superfamily.

Pathogen-associated molecular patterns (PAMPS) are not expressed by hosts but are components of the pathogenic microorganism. Such PAMPS comprise bacterial cell wall components such as lipopolysaccharides (LPS), lipoproteins (BLP), peptidoglycans (PGN), lipoarabinomannan (LAM), lipoteichoic acid (LTA), DNA containing unmethylated CpG motifs, yeast and fungal cell wall mannans and beta-glucans, double-stranded RNA, several unique glycosylated proteins and lipids of protozoa, and so on.

Recognition of these PAMPS foremost provides for differential recognition of pathogens by TLRs. For example, TLR2 is generally activated in response to BLPs, PGNs of gram-positive bacteria, LAM of mycobacteria, and mannans of yeasts, whereas TLR4 is often activated by LPS of gram-negative bacteria and LTA of gram-negative bacteria; also a secreted small molecule MD-2 can account for TLR4 signaling.

Several oligopeptides capable of modulating gene expression according to the invention have earlier been tested, both ex vivo and in vivo, and in small animals, but a relationship with modulation of gene expression was not brought forward. A beneficial effect of these oligopeptides on LPS-induced sepsis in mice, namely the inhibition of the effect of the sepsis, was observed. Immunomodulatory effects with these oligopeptides have been observed in vitro and in ex vivo such as in T-cell assays showing the inhibition of pathological Th1 immune responses, suppression of inflammatory cytokines (MIF), increase in production of anti-inflammatory cytokines (IL-10, TGF-beta) and immunomodulatory effects on antigen-presenting cells (APC) like dendritic cells, monocytes and macrophages.

Now that the insight has been provided that distinct synthetic oligopeptides or functional analogues or derivatives thereof, for example, those that resemble breakdown products which can be derived by proteolysis from endogenous proteins such as hCG, can be used to modulate gene expression, for example, by NF-κB inhibition, such oligopeptides find much wider application. Release of active NF-κB in cells is now known to occur after a variety of stimuli including treating cells with bacterial lipopolysaccharide (LPS) and the interaction with a Toll-like receptor (see, for example, Guha and Mackman, Cell. Sign. 2001, 13:85–94). In particular, LPS stimulation of dendritic cells, monocytes and macrophages induces many genes that are under the influence of activation by transcription factors such as NF-κB, p50, EGR-1, IRF-1 and others that can be modulated by a signaling molecule according to the invention. Considering that LPS induction of EGR-1 is required for maximal induction of TNF-alpha, it is foreseen that inhibition of EGR-1 considerably reduces the effects of sepsis seen after LPS activation. Now knowing the gene modulatory effect of the signaling molecules such as oligopeptides as provided herein allows for rational design of signal molecule mixtures that better alleviate the symptoms seen with sepsis, one such mixture, a 1:1:1 mixture of LQGV (SEQ ID NO:1), AQGV (SEQ ID NO:2) and VLPALP (SEQ ID NO:3) was administered to primates in a gram-negative induced rhesus monkey sepsis model for prevention of septic shock and found to be effective in this primate model. Accordingly, the invention provides a pharmaceutical composition for the treatment of sepsis in a primate and a method for the treatment of sepsis in a primate comprising subjecting the primate to a signaling molecule according to the invention, preferably to a mixture of such signaling molecules. Administration of such a signaling molecule or mixture preferably occurs systematically, e.g., by intravenous or intraperitoneal administration. In a further embodiment, such treatment also comprises the use of, for example, an antibiotic, however, only when such use is not contra-indicated because of the risk of generating further toxin loads because of lysis of the bacteria subject to the action of those antibiotics in an individual thus treated.

Another use that is contemplated relates to a method for combating or treating viral infections, in particular those infections that are caused by viruses that activate the NF-κB pathway during infections. Such virus infections are manifold; classical examples are hepatitis B virus-induced cell transformation by persistent activation of NF-κB. Use of a signaling molecule according to the invention is herein provided to counter or prevent this cell transformation.

Other diseases where persistent NF-κB activation is advantageously inhibited by a signaling molecule according to the invention are transplantation-related diseases such as transplantation-related immune responses, graft-versus-host-disease, in particular with bone-marrow transplants, acute or chronic xeno-transplant rejection, and post-transfusion thrombocytopenia.

Another case where persistent NF-κB activation is advantageously inhibited by a signaling molecule according to the invention is found in the prevention or mitigation of ischemia-related tissue damage seen after infarcts, seen, for example, in vivo in brain or heart, or ex vivo in organs or tissue that are being prepared or stored in preparation of further use as a transplant. Ischemia-related tissue damage can now be mitigated by perfusing the (pre)ischemic area with a signaling molecule according to the invention that inhibits NF-κB activation. An example of a condition where ischemia (also called underperfusion) plays a role is eclampsia which can be ascribed to focal cerebral ischemia resulting from vasoconstriction, consistent with the evidence of changes detected by new cerebral imaging techniques. The liver dysfunction intrinsic to the HELLP (hemolysis, elevated liver enzymes, and low platelet count) syndrome could also be attributed to the effects of acute underperfusion. Other conditions of ischemia are seen after coronary occlusion, leading to irreversible myocardial damage produced by prolonged episodes of coronary artery occlusion and reperfusion in vivo, which has already been discussed in International Patent Application PCT/NL01/00259 as well.

Now that the insight has been provided that distinct synthetic oligopeptides, for example, those that resemble breakdown products which can be derived by proteolysis from endogenous proteins such as hCG, can be used to modulate gene expression, for example, by NF-κB inhibition, the oligopeptides find much wider application. For example, the invention provides a method for perfusing a transplant with a perfusing fluid comprising at least one signaling molecule according to the invention; ischemic or pre-implantation damage due to activation of NF-κB in the transplant can then greatly be diminished, allowing a wider use of the transplants.

The invention provides a signaling molecule useful in modulating expression of a gene in a cell. Several examples of the use of such a signaling molecule for the production of a pharmaceutical composition for the treatment of medical or veterinary conditions are herewith given. In one embodiment, the invention provides such use in the treatment of an immune-mediated disorder, in particular of those cases whereby a central role of NF-κB/Rel proteins in the immune response is found. However as said, modulating gene expression via modulating activity of other transcription factors, such as AP-1 or PPARgamma, and others, is also provided, now that the gene modulating role of signaling molecules such as the oligopetides or analogues or derivatives thereof is understood. As also said, now knowing that oligopeptides, likely breakdown products, play such a central role in modulation of gene expression, the invention provides straightforward ways for identifying further gene expression modulating oligopeptides, and provides synthetic versions of these, and analogues and derivatives thereof for use in a wide variety of disorders and for use in the preparation of a wide variety of pharmaceutical compositions. Examples of such treatment and useful pharmaceutical compositions are found in relation to conditions wherein the immune-mediated disorder comprises chronic inflammation, such as diabetes, multiple sclerosis or acute or chronic transplant rejection, in particular in those cases whereby antigen-presenting cells (APC's) or dendritic cells (DCs) are enhanced by (overactive) and persistent NF-κB-expression or wherein the immune-mediated disorder comprises acute inflammation, such as septic or anaphylactic shock or acute transplant rejection. Other immune-mediated disorders that can be treated with a pharmaceutical composition comprising a signaling molecule according to the invention comprise auto-immune disease, such as systemic lupus erythematosus or rheumatoid arthritis (in particular by inhibiting IL-8 and/or IL-15 production by inhibiting NF-κB activity on the expression of these genes), allergy, such as asthma or parasitic disease, overly strong immune responses directed against an infectious agent, such as a virus or bacterium (in particular responses that include rapid hemorrhagic disease caused by infection with organisms such as *Yersinia pestis*, Ebola-virus, *Staphylococcus aureus* (e.g., in cases of tampon-disease), bacterial (such as meningococcal) or viral meningitis and/or encephalitis, and other life-threatening conditions). Such overly strong responses are seen with, for example, pre-eclampsia, recurrent spontaneous abortions (RSA) or preterm parturition or other pregnancy-related disorders. Especially with forms of eclampsia/pre-eclampsia that are associated with genetically programmed increased production of tumor-growth factor beta-1, treatment according to the invention is recommended. Also, in situations where RSA is likely attributable to increased IL-10 levels during pregnancy, or to increased TNF-alpha activity, for example, due to the presence of an unfavorable allele, in particular of a G to A polymorphism in the promoter of the gene encoding TNF-alpha, treatment with a pharmaceutical composition as provided herein is recommended. Treatment directed at such pregnancy-related immune disorders is herein also provided by inhibiting NF-κB activity directed at activating natural killer (NK) cell activity. Also, LPS-induced reduced fertility, or abortions, seen in pregnant sows, can be reduced by applying a signaling molecule or method as provided herein.

Such use in treatment of an immune-mediated disorder preferably comprises regulating relative ratios and/or cytokine activity of lymphocyte-, dendritic- or antigen-presenting cell subset-populations in a treated individual, in particular wherein the subset populations comprise Th1 or Th2, or DC1 or DC2 cells. Other embodiments of the invention comprise use of a signaling molecule according to the invention for the manufacture of a medicament for modulating a cardiovascular or circulatory disorder, such as coronary arterial occlusion, and also in a pregnancy related cardiovascular or circulatory disorder.

Furthermore, the invention provides a pharmaceutical composition for modulating a cardiovascular or circulatory disorder, in particular a pregnancy related cardiovascular or circulatory disorder, comprising a signaling molecule according to the invention or mixtures thereof. Such a composition finds use in a method for modulating a cardiovascular or circulatory disorder, in particular a pregnancy related cardiovascular or circulatory disorder, comprising subjecting an animal (in particular a mammal) to treatment with at least one signaling molecule according to the invention. Non-pregnancy related disorders, which are, for example, related to hypercholesterolemia, are susceptible to treatment with a signaling molecule according to the invention as well. For example, apolipoprotein E (apoE) deficiency is associated with a series of pathological conditions including dyslipidemia, atherosclerosis, Alzheimer's disease, increased body weight and shorter life span. Inheritance of different alleles of the polymorphic apoE gene is responsible for 10% of the variation in plasma cholesterol in most populations. Individuals homozygous for one variant, apoE2, can develop type III dysbetalipoproteinemia if an additional genetic or environmental factor is present. Some much rarer alleles of apoE produce dominant expression of this disorder in heterozygous individuals. ApoE is a ligand for the LDL receptor and its effects on plasma cholesterol are mediated by differences in the affinity of the LDL receptor for lipoproteins carrying variant apoE proteins. The factors that regulate apoE gene transcription have been investigated extensively by the expression of gene constructs in transgenic mice and involve complex interactions between factors that bind elements in the 5' promoter region, in the first intron and in 3' regions many kilobases distant from the structural gene. Deletion of the ApoE gene is associated with changes in lipoprotein metabolism (plasma total cholesterol), HDL cholesterol, HDL/TC, and HDL/LDL ratios, esterification rate in apo B-depleted plasma, plasma triglyceride, hepatic HMG-CoA reductase activity, hepatic cholesterol content, decreased plasma homocyst(e)ine and glucose levels, and severe atherosclerosis and cutaneous xanthomatosis. The invention provides a method and a signaling molecule for the treatment of conditions that are associated with dysfunctional LDL receptors such as apoE and other members of the apolipoprotein family. In particular, use of a signaling molecule comprising GVLPALPQ (SEQ ID NO:33) and/or VLPALP (SEQ ID NO:3) or a functional analogue or derivative thereof is preferred.

The invention also provides use of a signaling molecule for the preparation of a pharmaceutical composition or medicament and methods of treatment for various medical conditions that are other than use in the preparation of a pharmaceutical composition for the treatment of an immune-mediated disorder or a method of treatment of an immune-mediated-disorder. For example, the invention provides topical application in an ointment or spray comprising a signaling molecule according to the invention, for the prevention or mitigation of skin afflictions, such as eczemas, psoriasis, but also of skin damage related to over-exposure to UV-light.

Also, use is contemplated in palliative control, whereby a gene related to prostaglandin synthesis is modulated such that COX2 pathways are effected.

Furthermore, the invention also provides use of a signaling molecule for the preparation of a pharmaceutical composition or medicament and methods of treatment for various medical conditions that are other than use in the preparation of a pharmaceutical composition for the treatment of wasting syndrome, such as the treatment of particular individuals that are suffering from infection with HIV or a method of treatment of wasting syndrome of such individuals.

In one embodiment, the invention provides the use of a signaling molecule according to the invention for the preparation of a pharmaceutical composition or medicament for modulating angiogenesis or vascularization, in particular during embryonal development or after transplantation, to stimulate vascularization into the transplanted organ or inhibit it in a later phase. Signaling molecules that effect angiogenesis are disclosed herein in the detailed description.

Use as provided herein also comprises regulating TNF-alpha receptor (e.g., CD27) expression on cells, thereby modulating the relative ratios and/or cytokine activity of lymphocyte-, dendritic- or antigen-presenting cell subset populations in a treated individual. As, for example, described in the detailed description, a particular oligopeptide according to the invention is capable of down-regulating CD27 expression on cells of the T-cell lineage.

Down-regulating TNF-alpha itself is also particularly useful in septic-shock-like conditions that not only display increased TNF-alpha activity but display further release of other inflammatory compounds, such as NO. NO production is a central mediator of the vascular and inflammatory response. Our results show that inflammatory cells like macrophages stimulated with an inflammatory active compound such as LPS produce large amounts of NO. However, these cells co-stimulated with most of the NMPF peptides (NMPF peptides 1 to 14, 43 to 66 and 69), even in a very low dose (1 pg/ml), inhibited production of NO. Typical septic-shock-like conditions that can preferably be treated by down-regulating TNF-alpha and NO production comprise disease conditions such as those caused by *Bacillus anthracis* and *Yersinia pestis* toxins or infections with these microorganisms likely involved in bioterrorism. Anthrax toxin is produced by *Bacillus anthracis*, the causative agent of anthrax, and is responsible for the major symptoms of the disease. Clinical anthrax is rare, but there is growing concern over the potential use of *B. anthracis* in biological warfare and terrorism. Although a vaccine against anthrax exists, various factors make mass vaccination impractical. The bacteria can be eradicated from the host by treatment with antibiotics, but because of the continuing action of the toxin, such therapy is of little value once symptoms have become evident. Thus, a specific inhibitor of the toxin's action will prove a valuable adjunct to antibiotic therapy. The toxin consists of a single receptor-binding moiety, termed "protective antigen" (PA), and two enzymatic moieties, termed "edema factor" (EF) and "lethal factor" (LF). After release from the bacteria as nontoxic monomers, these three proteins diffuse to the surface of mammalian cells and assemble into toxic, cell-bound complexes.

Cleavage of PA into two fragments by a cell-surface protease enables the fragment that remains bound to the cell, PA63, to heptamerize and bind EF and LF with high affinity. After internalization by receptor-mediated endocytosis, the complexes are trafficked to the endosome. There, at low pH, the PA moiety inserts into the membrane and mediates translocation of EF and LF to the cytosol. EF is an adenylate cyclase that has an inhibitory effect on professional phagocytes, and LF is a protease that acts specifically on macrophages, causing their death and the death of the host.

Down-regulating TNF-alpha itself, and/or a receptor for TNF-alpha, as is herein also provided, is also beneficial in individuals with Chagas cardiomyopathy.

Also, use of a signaling molecule according to the invention for the preparation of a pharmaceutical composition for modulation of vascularization or angiogenesis in wound repair, in particular of burns, is herein provided. Also, use of a pharmaceutical composition as provided herein is provided in cases of post-operative physiological stress, whereby not only vascularization will benefit from treatment, but the general well-being of the patient is improved as well.

Another use of a signaling molecule according to the invention comprises its use for the preparation of another pharmaceutical composition for the treatment of cancer. Such a pharmaceutical composition preferably acts via modulating and up-regulating apoptotic responses that are classically down-regulated by NF-κB activity. Inhibiting the activity with a signaling molecule according to the invention allows for increased cell death of tumorous cells. Another anti-cancerous activity of a signaling molecule as provided herein comprises down-regulation of c-myb, in particular, in the case of hematopoietic tumors in humans. In this context, down-regulation of 14.3.3 protein is also provided.

A further use of a signaling molecule according to the invention comprises its use for the preparation of a further pharmaceutical composition for the treatment of cancer. Such a pharmaceutical composition preferably acts via modulating and down-regulating transferrin receptor availability, in particular, on tumorous cells. Transferrin receptors are classically up-regulated by NF-κB activity. Inhibiting the activity with a signaling molecule according to the invention allows for reduced iron up-take and increased death of tumorous cells. In particular, erythroid and thromboid cells are susceptible to the treatment.

Yet a further use of a signaling molecule according to the invention comprises its use for the preparation of yet another pharmaceutical composition for the treatment of cancer, in particular of cancers that are caused by viruses, such as is the case with retroviral-induced malignancies and other viral-induced malignancies. Such a pharmaceutical composition preferably acts via modulating and down-regulating cell-proliferative responses that are classically up-regulated by virus-induced transcriptional or NF-κB activity. Inhibiting the activity with a signaling molecule according to the invention allows for decreased proliferation and increased cell death of tumorous cells. Such a pharmaceutical composition may also act via modulating angiogenic responses induced by IL-8, whereby, for example, inhibition of IL-8 expression via inhibition of transcription factor AP-1 or NF-κB expression results in the inhibition of vascularization-dependent tumor growth.

Furthermore, the invention provides the use of a signaling molecule for the preparation of a pharmaceutical composition for optimizing human or animal fertility and embryo survival, and a method for optimizing fertility and embryo survival. In particular, the invention provides for a method and composition allowing the down-regulation of TNF-alpha in the fertilized individual, optimally in combination with a composition and method for up-regulating IL-10 in the individual. Such a composition and method find immediate use in both human and veterinary medicine.

Also, the invention provides the use of a signaling molecule for the preparation of a pharmaceutical composition for modulating the body weight of an individual, in particular, by modulating gene expression of a gene under influence of peroxisome proliferator-activated receptor gamma (PPARgamma) activation and lipid metabolism by applying a signaling molecule according to the invention, and a method for modulating body weight comprising providing an individual with a signaling molecule according to the invention.

A further use of a signaling molecule as provided herein lies in the modulation of expression of a gene in a cultured cell. Such a method as provided herein comprises subjecting a signaling molecule according to the invention to the cultured cell. Proliferation and/or differentiation of cultured cells (cells having been or being under conditions of in vitro cell culture known in the art) can be modulated by subjecting the cultured cell to a signaling molecule according to the invention. It is contemplated that, for example, research into proliferation or differentiation of cells, such as stem-cell research, will benefit greatly from the understanding that a third major way of effecting gene modulation exists, and considering the ease of application of synthetic peptides and analogues or derivatives thereof.

Furthermore, it is contemplated that a signaling molecule as provided herein finds an advantageous use as a co-stimulatory substance in a vaccine, accompanying modern day adjuvants or replacing the classically used mycobacterial adjuvants, especially considering that certain mycobacteria express hCG-like proteins, of which it is now postulated that these bacteria have already made use of this third pathway found in gene modulation as provided herein by providing the host with breakdown products mimicking the signaling molecules identified herein. Treatment and use of the compositions as provided herein is not restricted to animals only; plants and other organisms are also subject to this third pathway as provided herein. Furthermore, now that the existence of such a pathway has been demonstrated, it is herein provided to make it the subject of diagnosis as well, for example, to determine the gene modulatory state of a cell in a method comprising determining the presence or absence of a signaling molecule as provided herein or determining the presence or absence of a protease capable of generating such a signaling molecule from a (preferable endogenous) protein.

BRIEF DESCRIPTION OF FIGURES

FIGS. 20–30 show the effect of NMPF on vessel branches. FIGS. 29–30 show the effect of NMPF on vessel thickness.

DETAILED DESCRIPTION OF THE INVENTION

Figure 1:
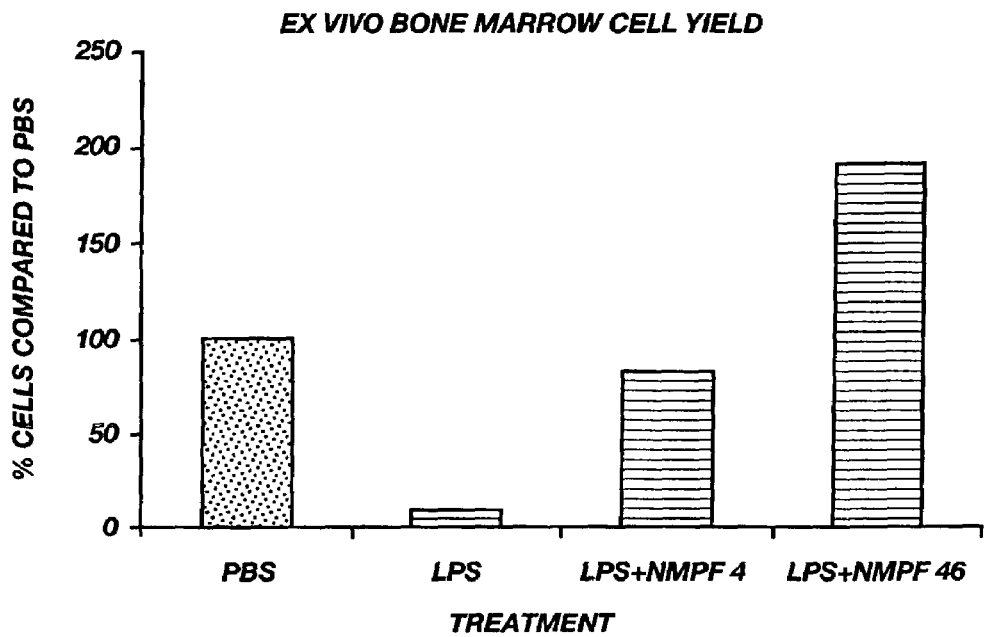
FIGS. 1–2. Bone marrow (BM) cell yield of treated BALB/c mice (n=6). BM cells were isolated from treated mice and cultured in vitro in the presence of rmGM-CSF for nine days. These figures show cell yield after nine days of culture of BM cells isolated from mice treated with PBS, LPS or LPS in combination with NMPF peptides 4, 46, 7 and 60. In these figures, cell yield is expressed in relative percentage of cells compared to PBS. Each condition consists of 6 Petri dishes and results shown in these figures are representative of 6 dishes. Differences of ≧20% were considered significant and line bars represent significant data as compared to the LPS control group. A representative experiment is shown. Findings involving all experimental conditions were entirely reproduced in 3 additional experiments.

Cells react to environmental and intrinsic changes, which they perceive through extracellular and inter- as well as intracellular signals. The nature of these signals can be either, for example, physical or chemical. Moreover, different classes of molecules present in blood react to each other and induce a cascade of reactions that have direct effect on other molecules and/or eventually lead to cellular responses, for example, complement system and blood coagulation proteins.

Many genes are regulated not by a signaling molecule that enters the cells but by molecules that bind to specific receptors on the surface of cells, for example, receptors with enzymatic activity (receptor tyrosine kinases, receptor-like protein tyrosine phosphatases, receptor serine/threonine kinases, histidine kinases, guanylyl cyclases) and receptors without enzymatic activity (cytokine receptors, integrins, and G-protein-coupled receptors). Interaction between cell-surface receptors and their ligands can be followed by a cascade of intracellular events that modulate one or more intracellular transducing proteins, including variations in the intracellular levels of so-called second messengers (diacylglycerol, $Ca^{2+}$, cyclic nucleotides, inositol(1,4,5) trisphosphate, phosphatidylinositol(3,4,5) trisphosphate, and phosphatidylinositol transfer protein (PITP)). This leads to the activation or inhibition of a so-called "effector protein." The second messengers in turn lead to changes in protein, for example, protein phosphorylation through the action of cyclic AMP, cyclic GMP, calcium-activated protein kinases, or protein kinases (for example, AGC group serine/threonine protein kinases, CAMK group serine/threonine protein kinases, CMGC group serine/threonine kinases, protein tyrosine kinase group, or others like MEK/Ste7p). Phosphorylation by protein kinases is one of the regulatory mechanisms in signal transmission that modulate different cellular pathways such as Ras/MAPK pathway, MAP kinase pathway, JAK-STAT pathway, or wnt-pathway. In many instances, this all results in altered gene expression (for example, genes for the regulation of other genes, cell survival, growth, differentiation, maturation, and functional activity).

Many of the responses to binding of ligands to cell-surface receptors are cytoplasmatic and do not involve immediate gene activation in the nucleus. In some instances, a pre-existing inactive transcription factor following a cell-surface interaction is activated, which leads to immediate gene activation. For example, the protein NF-κB, which can be activated within minutes by a variety of stimuli, including membrane receptors (for example, pattern recognition receptors like Toll-like receptor binding to pathogen-associated molecular patterns), inflammatory cytokines such as TNF-α, IL-1, T-cell activation signals, growth factors and stress inducers.

Our genomic experiment with NMPF peptide LQGV (SEQ ID NO:1) showed very immediate effects on signal transduction and gene regulation since the cells were treated with the peptide for only four hours. In this short period of time, LQGV (SEQ ID NO:1) down-regulated at least 120 genes and up-regulated at least 6 genes in the presence of a strong stimulator (PHA/IL-2 stimulated T-cell line (PM1)), demonstrating the profound effect on a signaling molecule according to the invention and modulatory effect on gene expression. The genes affected by LQGV (SEQ ID NO:1) include onco-genes, genes for transcription factors, intracellular enzymes, membrane receptors, intracellular receptors, signal-transducing proteins (for example, kinases) and some genes for unkown molecules. This shows that LQGV (SEQ ID NO:1) as an example of the synthetic signaling molecule (oligopeptide or functional analogue or derivative thereof), as described here, has a broad spectrum of effects at different extracellular and intracellular levels. In addition, our HPLC/MS data have shown the presence of LQGV (SEQ ID NO:1) in the nucleus of a macrophage cell line (RAW267.4) within a half hour and also indicates the direct effects on DNA level as well as at an intracellular level, which is further supported by NF-κB experiments. The ultimate modulatory effect of LQGV (SEQ ID NO:1) is dependent on, for example, type of the cell, differentiation and maturation status of the cell, the functional status and the presence of other regulatory molecules. This was evident by a shock experiment in which different NMPF peptides had similar or different effects on the disease. The same results were obtained with DC, fertilized chicken egg experiments, and CAO experiments; NMPF effects were dependent on type of co-stimulation (GM-CSF alone or in combination with LPS or VEGF) and time of the treatment. Due to this, NMPF have the ability to modulate cellular responses at different levels.

EXAMPLES

Material and Methods

Peptide Synthesis

The peptides as mentioned in this document such as LQG, AQG, LQGV (SEQ ID NO:1), AQGV (SEQ ID NO:2), LQGA (SEQ ID NO:19), VLPALP (SEQ ID NO:3), ALPALP (SEQ ID NO:21), VAPALP (SEQ ID NO:22), ALPALPQ (SEQ ID NO:23), VLPAAPQ (SEQ ID NO:24), VLPALAQ (SEQ ID NO:25), LAGV (SEQ ID NO:26), VLAALP (SEQ ID NO:27), VLPALA (SEQ ID NO:28), VLPALPQ (SEQ ID NO:29), VLAALPQ (SEQ ID NO:30), VLPALPA (SEQ ID NO:31), GVLPALP (SEQ ID NO:32), VVCNYRDVRFESIRLPGCPRGVNPV-VSYAVALSCQCAL (SEQ ID NO:35), RPRCRPINAT-LAVEKEGCPVCITVNTTICAGYCPT (SEQ ID NO:45), SKAPPPSLPSPSRLPGPS (SEQ ID NO:38), LQGVL-PALPQVVC (SEQ ID NO:34), SIRLPGCPRGVNPVVS (SEQ ID NO:39), LPGCPRGVNPVVS (SEQ ID NO:40), LPGC (SEQ ID NO:41), MTRV (SEQ ID NO:42), MTR, and VVC were prepared by solid-phase synthesis (Merrifield, 1963) using the fluorenylmethoxycarbonyl (Fmoc)/tert-butyl-based methodology (Atherton, 1985) with 2-chlorotrityl chloride resin (Barlos, 1991) as the solid support. The side-chain of glutamine was protected with a trityl function. The peptides were synthesized manually. Each coupling consisted of the following steps: (i) removal of the alpha-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP), and (iii) capping of the remaining amino functions with acetic anhydride/diisopropylethylamine (DIEA) in DMF/NMP. Upon completion of the synthesis, the peptide resin was treated with a mixture of trifluoroacetic acid (TFA)/$H_2O$/triisopropylsilane (TIS) 95:2.5:2.5. After 30 minutes, TIS was added until decoloration. The solution was evaporated in vacuo and the peptide precipitated with diethylether. The crude peptides were dissolved in water (50–100 mg/ml) and purified by reverse-phase high-performance liquid chromatography (RP-HPLC). HPLC conditions were: column: Vydac TP21810C18 (10×250 mm); elution system: gradient system of 0.1% TFA in water v/v (A) and 0.1% TFA in acetonitrile (ACN) v/v (B); flow rate 6 ml/min; absorbance was detected from 190–370 nm. There were different gradient systems used. For example, for peptides LQG and LQGV: 10 minutes 100% A followed by linear gradient 0–10% B in 50 minutes. For example, for peptides VLPALP (SEQ ID NO:3) and VLPALPQ (SEQ ID NO:29): 5 minutes 5% B followed by linear gradient 1% B/minute. The collected fractions were concentrated to about 5 ml by rotation film evaporation under reduced pressure at 40° C. The remaining TFA was exchanged against acetate by eluting two times over a column with anion exchange resin (Merck II) in acetate form. The elute was concentrated and lyophilized in 28 hours. Peptides later were prepared for use by dissolving them in PBS.

Transcription Factor Experiment

Macrophage cell line. The RAW 264.7 macrophages, obtained from American Type Culture Collection (Manassas, Va.), were cultured at 37° C. in 5% $CO_2$ using DMEM containing 10% FBS and antibiotics (100 U/ml of penicillin and 100 µg/ml streptomycin). Cells ($1\times10^6$/ml) were incubated with peptide (10 µg/ml) in a volume of 2 ml. After 8 h of cultures; cells were washed and prepared for nuclear extracts.

Nuclear extracts. Nuclear extracts and EMSA were prepared according to Schreiber et al. methods (Schriber et al. 1989, Nucleic Acids Research 17). Briefly, nuclear extracts from peptide-stimulated or nonstimulated macrophages were prepared by cell lysis followed by nuclear lysis. Cells were then suspended in 400 µl of buffer (10 mM HEPES (pH 7.9), 10 mM KCl, 0.1 mM KCL, 0.1 mM EDTA, 0.1 mM EGTA, 1 mM DTT, 0.5 mM PMSF and protease inhibitors), vigorously vortexed for 15 s, left standing at 4° C. for 15 min, and centrifuged at 15,000 rpm for 2 min. The pelleted nuclei were resuspended in buffer (20 mM HEPES (pH 7.9), 10% glycerol, 400 mM NaCl, 1 mM EDTA, 1 mM EGTA, 1 mM DTT, 0.5 mM PMSF and protease inhibitors) for 30 min on ice, then the lysates were centrifuged at 15,000 rpm for 2 min. The supernatants containing the solubilized nuclear proteins were stored at −70° C. until used for the Electrophoretic Mobility Shift Assays (EMSA).

EMSA. Electrophoretic mobility shift assays were performed by incubating nuclear extracts prepared from control (RAW 264.7) and peptide-treated RAW 264.7 cells with a 32P-labeled double-stranded probe (5' AGCTCA-GAGGGGGACTTTCCGAGAG 3' (SEQ ID NO:51)) synthesized to represent the NF-κB binding sequence. Shortly, the probe was end-labeled with T4 polynucleotide kinase according to manufacturer's instructions (Promega, Madison, Wis.). The annealed probe was incubated with nuclear extract as follows: in EMSA, binding reaction mixtures (20 µl) contained 0.25 µg of poly(dI-dC) (Amersham Pharmacia Biotech) and 20,000 rpm of 32P-labeled DNA probe in binding buffer consisting of 5 mM EDTA, 20% Ficoll, 5 mM DTT, 300 mM KCl and 50 mM HEPES. The binding reaction was started by the addition of cell extracts (10 µg) and was continued for 30 min at room temperature. The DNA-protein complex was resolved from free oligonucleotide by electrophoresis in a 6% polyacrylamide gel. The gels were dried and exposed to x-ray films.

ApoE Experiments

Apolipoprotein E (apoE) deficiency is associated with a series of pathological conditions including dyslipidemia, atherosclerosis, Alzheimer's disease, increased body weight and shorter life span. Inheritance of different alleles of the polymorphic apoE gene is responsible for 10% of the variation in plasma cholesterol in most populations. Individuals homozygous for one variant, apoE2, can develop type II dysbetalipoproteinaemia if an additional genetic or environmental factor is present. Some much rarer alleles of apoE produce dominant expression of this disorder in heterozygous individuals. ApoE is a ligand for the LDL receptor and its effects on plasma cholesterol are mediated by differences in the affinity of the LDL receptor for lipoproteins carrying variant apoE proteins. The factors that regulate apoE gene transcription have been investigated extensively by the expression of gene constructs in transgenic mice and involve complex interactions between factors that bind elements in the 5' promoter region, in the first intron and in 3' regions many kilobases distant from the structural gene. Deletion of the apoE gene is associated with changes in lipoprotein metabolism (plasma total cholesterol), HDL cholesterol, HDL/TC, and HDL/LDL ratios, esterification rate in apo B-depleted plasma, plasma triglyceride, hepatic HMG-CoA reductase activity, hepatic cholesterol content, decreased plasma homocyst(e)ine and glucose levels, and severe atherosclerosis and cutaneous xanthomatosis.

Results

NF-kB Experiments

Figure 31:
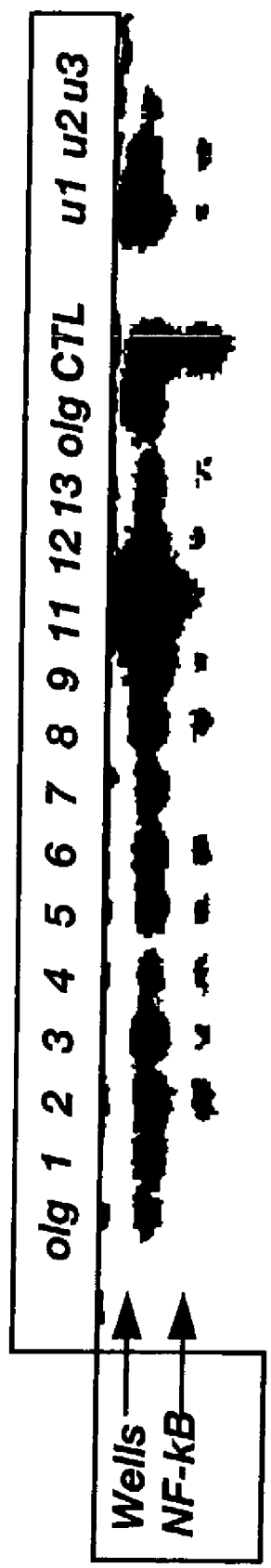
FIG. 31. Detection of NF-kB via EMSA. This figure shows the presence of NF-KB in the nuclear extracts of RAW264.7 cells treated with LPS or NMPF in combination with LPS for 4 hours. Numbers 1–13 correspond to nuclear extracts from cells treated with NMPF and LPS. CTL corresponds to nuclear extracts from cells treated with LPS only. Specificity of the radioactively labeled NF-kB probe is shown by competition with the unlabeled oligonucleotide (u1,u2,u3) in three different concentrations (1×, 10×, 100×) with nuclear extracts of CTL and olg corresponding to samples containing only labeled oligonucleotide (without nuclear extract). Description: (NMPF-1)VLPALPQVVC (SEQ ID NO:20), (NMPF-2)LQGVLPALPQ (SEQ ID NO:49), (NMPF-3)LQG, (NMPF-4)LQGV (SEQ ID NO:1), (NMPF-5)GVLPALPQ (SEQ ID NO:33), (NMPF-6)VLPALP (SEQ ID NO:3), (NMPF-7)VLPALPQ (SEQ ID NO:29), (NMPF-8)GVLPALP (SEQ ID NO:32), (NMPF-9) VVC, (NMPF-11)MTRV (SEQ ID NO:42), (NMPF-12) MTR.

The transcription factor NF-kB participates in the transcriptional regulation of a variety of genes. Nuclear protein extracts were prepared from LPS and peptide treated RAW264.7 cells or from LPS-treated RAW264.7 cells. In order to determine whether the peptide modulates the translocation of NF-kB into the nucleus, on these extracts EMSA was performed. FIG. 31 shows the amount of NF-kB present in the nuclear extracts of RAW264.7 cells treated with LPS or LPS in combination with peptide for 4 hours. Here we see that indeed some peptides are able to modulate the translocation of NF-kB since the amount of labeled oligonucleotide for NF-KB is reduced. In this experiment, peptides that show the modulation of translocation of NF-kB are: (NMPF-1)VLPALPQVVC (SEQ ID NO:20), (NMPF-2)LQGVL-PALPQ (SEQ ID NO:49), (NMPF-3)LQG, (NMPF-4) LQGV (SEQ ID NO:1), (NMPF-5)GVLPALPQ (SEQ ID NO:33), (NMPF-6)VLPALP (SEQ ID NO:3), (NMPF-7) VLPALPQ (SEQ ID NO:29), (NMPF-8)GVLPALP (SEQ ID NO:32), (NMPF-9)VVC, (NMPF-11)MTRV (SEQ ID NO:42), (NMPF-12)MTR.

Nuclear Location of Peptide Experiment

A reverse-phase high-performance liquid chromatography (RP-HPLC) method was used to prove the presence of synthetic oligopeptide in the nuclear extracts. We used a Shimadzu HPLC system equipped with a Vydac monomeric C18 column (column218MS54, LC/MS C18 reversed phase, 300A, 5 µm, 4.6 mm ID×250 mm L); elution system: gradient system of 0.01% TFA and 5% acetonitrile (CAN) in water v/v (A) and 0.01% TFA in 80% acetonitrile (ACN) v/v (B); flow rate 0.5 ml/min; absorbance was detected from 190–370 nm. The gradient time program was as follows:

| Time (min) | Buffer B concentration |
| --- | --- |
| 0.01 | 0 |
| 5.0 | 0 |
| 30.0 | 80 |
| 40.0 | 100 |
| 60.0 | 100 |
| 65.0 | 0 |
| 70.0 | 0 |

The elution time of peptide LQGV (SEQ ID NO:1) was determined by injecting 2 µg of the peptide in a separate run. Mass spectrometry (MS) analysis of fraction which contained possible NMPF-4 (LQGV (SEQ ID NO:1)) (elution time was determined by injecting the peptide in the same or separate run) was performed on LCQ Deca XP (Thermo Finnigan).

Results

Nuclear Location of Peptide Experiment

Figure 32:
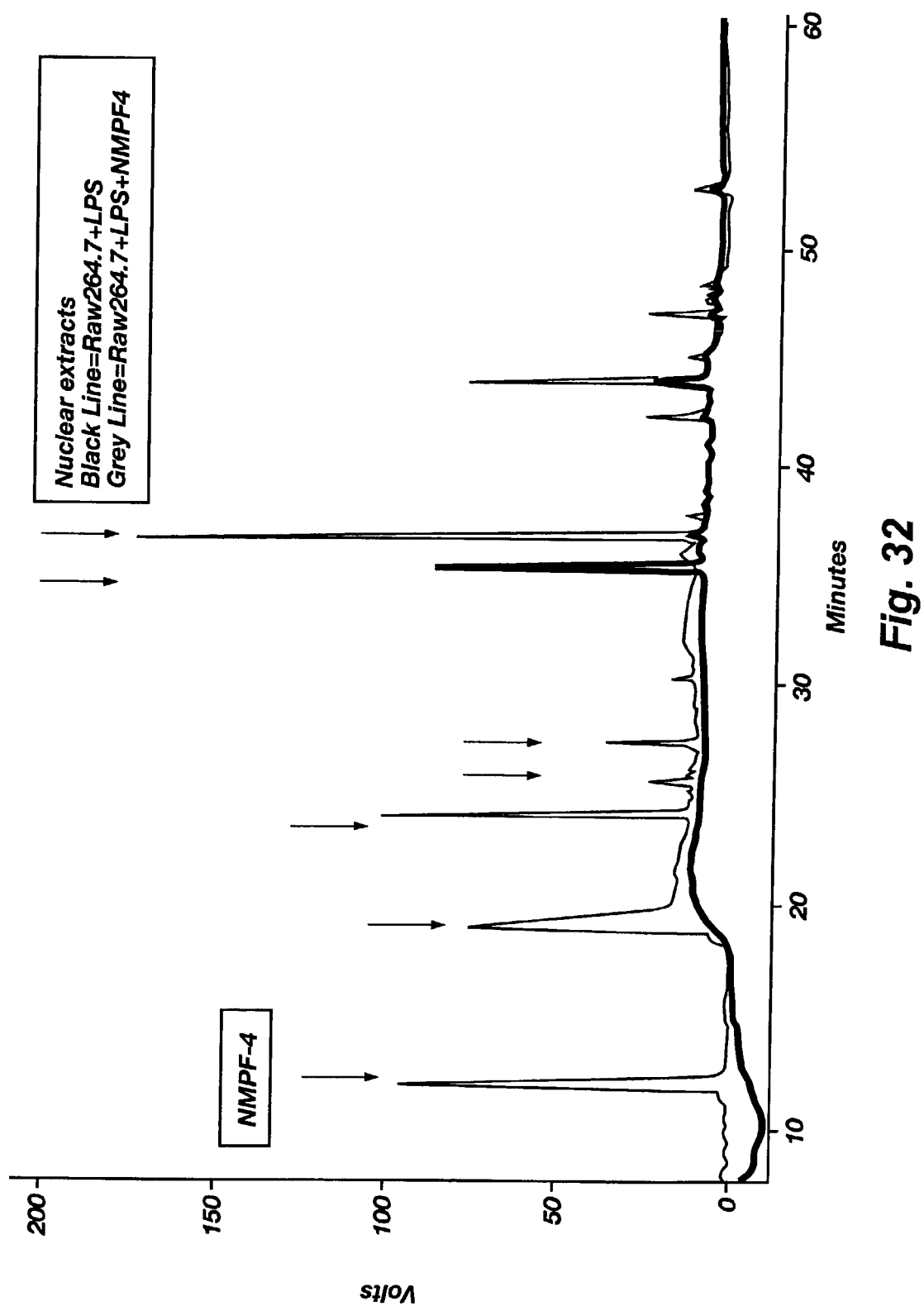
FIG. 32. HPLC chromatograph (wavelength 206) in which data profiles obtained from the nuclear protein extracts of LPS and LPS in combination with NMPF-stimulated RAW264.7 cells are overlayed.
Figure 33:
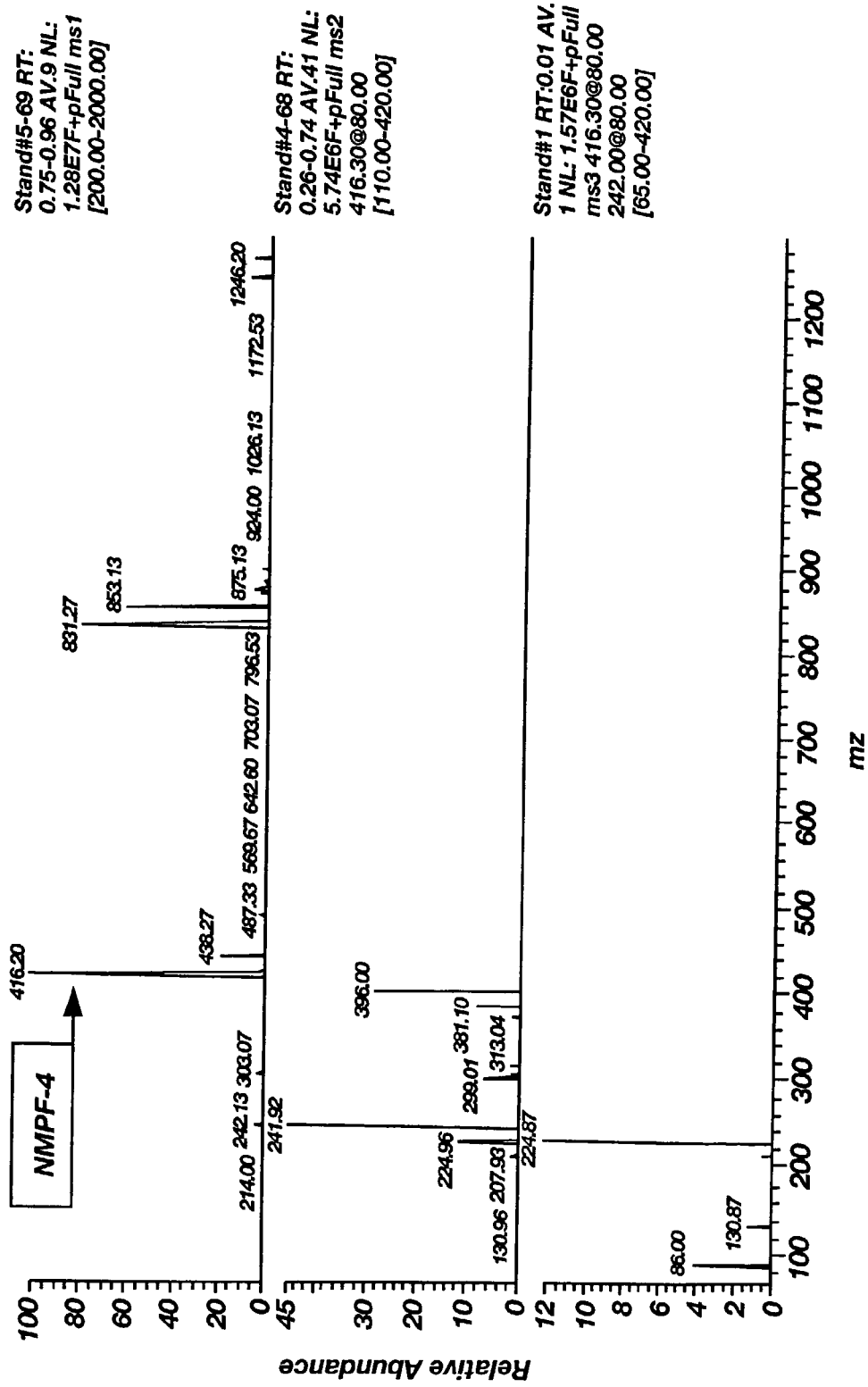
FIG. 33. MSn analysis of NMPF-4 peptide.
Figure 34:
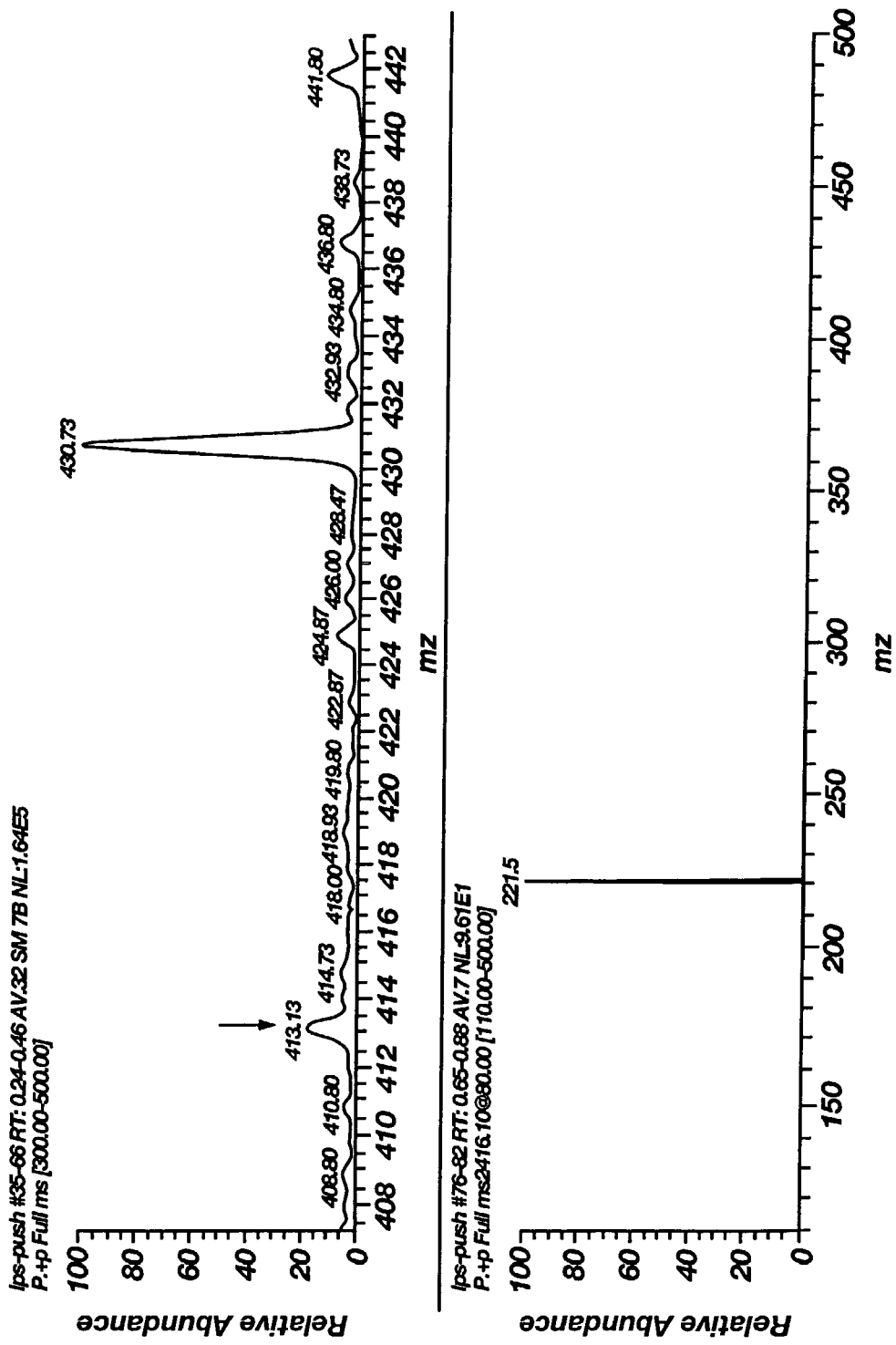
FIG. 34. MSn analysis of fraction from nuclear extract of LPS-stimulated RAW264.7 cells. Upper panel shows full spectrum of the fraction and lower panel shows the MS/MS spectrum of mass 413.13.

The nuclear protein extracts used in EMSA experiments were also checked for the presence of LQGV (SEQ ID NO:1) by means of HPLC and MS. FIG. 32 shows HPLC chromatograph (wavelength 206) in which data profiles obtained from the nuclear protein extracts of LPS and LPS in combination with NMPF-4 (LQGV (SEQ ID NO:1))-stimulated RAW264.7 cells are overlayed. This figure also shows the presence or absence of number of molecule signals in the nuclear extracts of oligopeptide+ LPS-treated cells as compared to nuclear extracts of LPS-treated cells. Since the HPLC profile of LQGV (SEQ ID NO:1) showed that the peptide elutes at around 12 minutes (data not shown), fraction corresponding to region 10–15 minutes was collected and analyzed for the presence of this peptide in MS.

Figure 35:
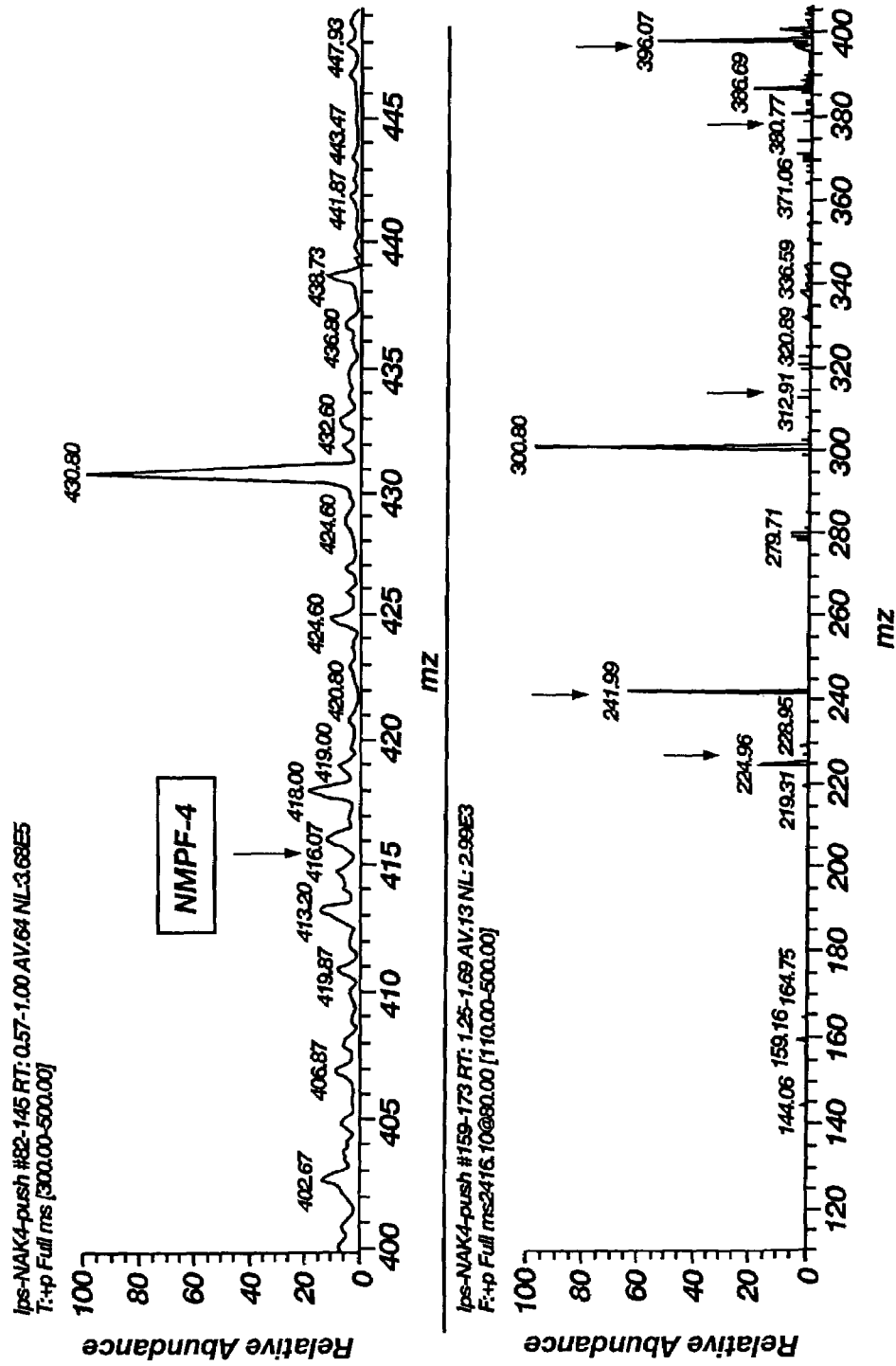
FIG. 35. MSn analysis of fraction from nuclear extract of LPS in combination with NMPF-4-stimulated RAW264.7 cells. Upper panel shows full spectrum of the fraction and lower panel shows the MS/MS spectrum of mass 416.07.
Figure 36:
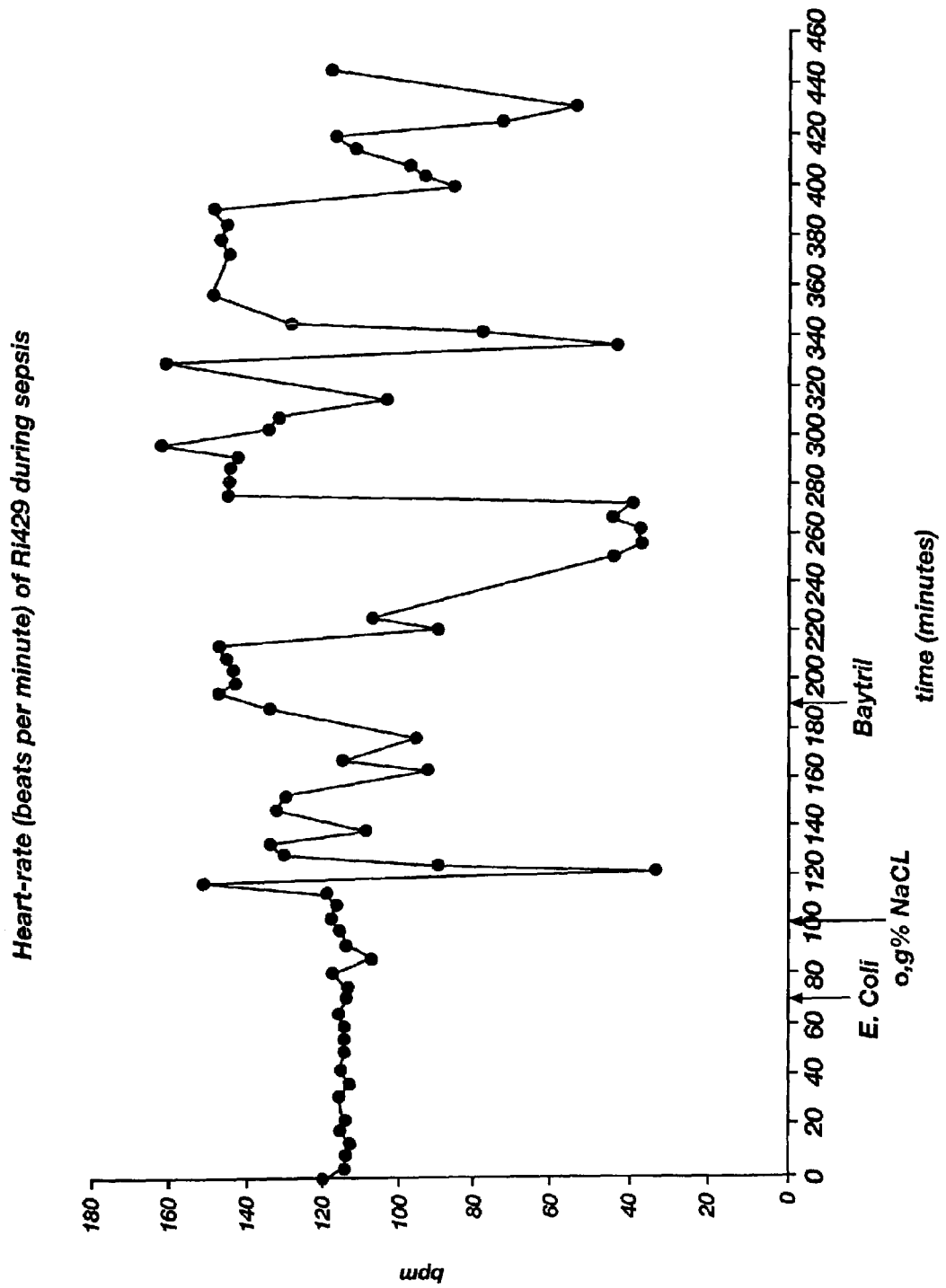
FIGS. 36–47. Effect of NMPF on septic shock syndrome in Rhesus monkeys. On the time point 70 minutes, *E. coli* was infused, and at the end of *E. coli* infusion (time point 190 minutes), the antibiotic Baytril was injected. The control monkey (monkey 429) was treated with 0.9% NaCl at the time point of 100 minutes, whereas the NMPF-treated monkeys (monkeys 459 and 427) received the NMPF treatment at the same time point as the control monkey. Heart rate (beats per minute), blood pressure (mmHg), difference between systolic and diastolic blood pressure and blood oxygen concentration (saturation in %) of the control monkey 429 (FIGS. 36–39), and NMPF-treated monkeys 459 (FIGS. 40–43) and 427 (FIGS. 44–47) in the time (minutes) during the experiment are shown.
Figure 37:
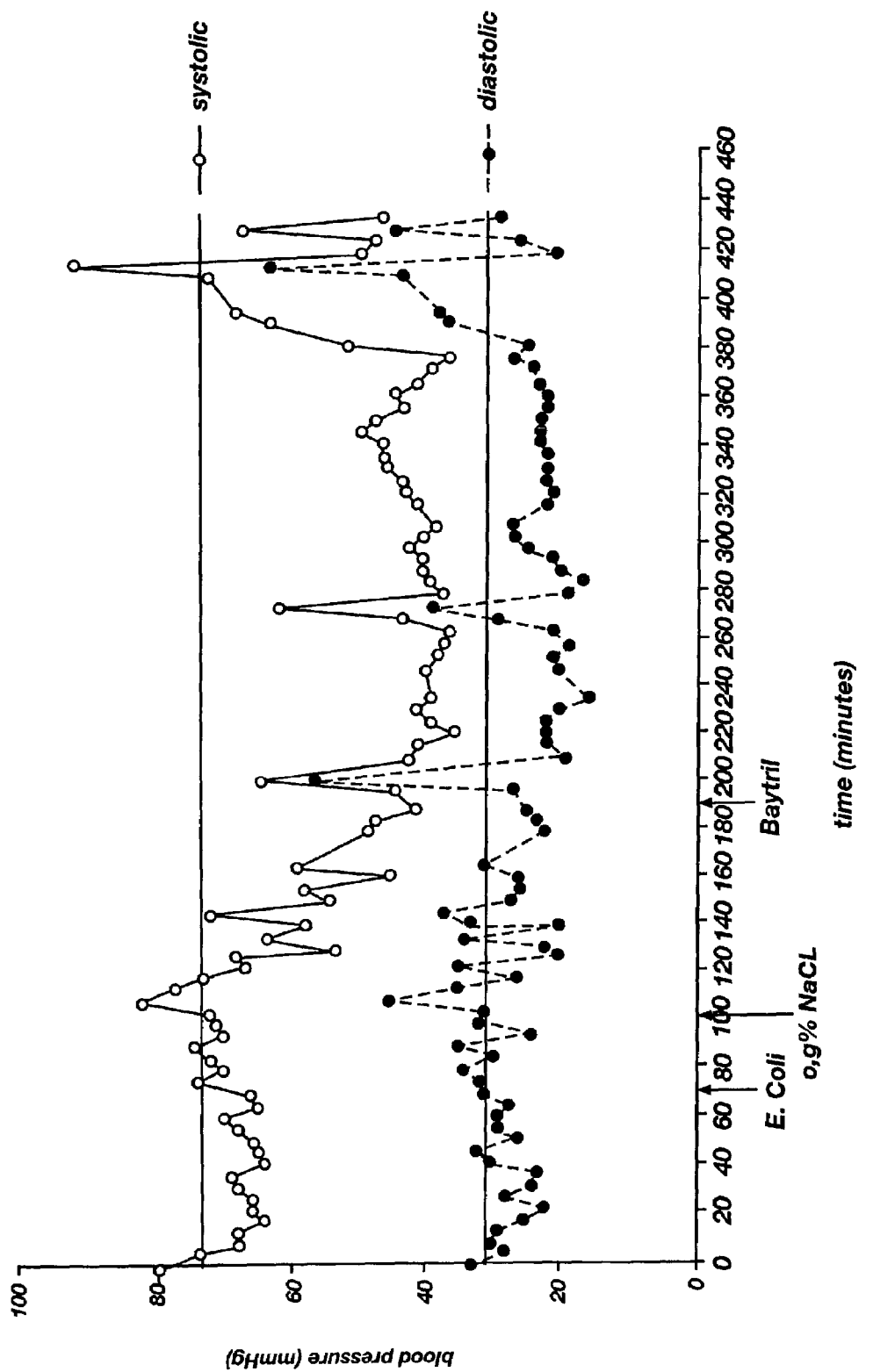
Figure 38:
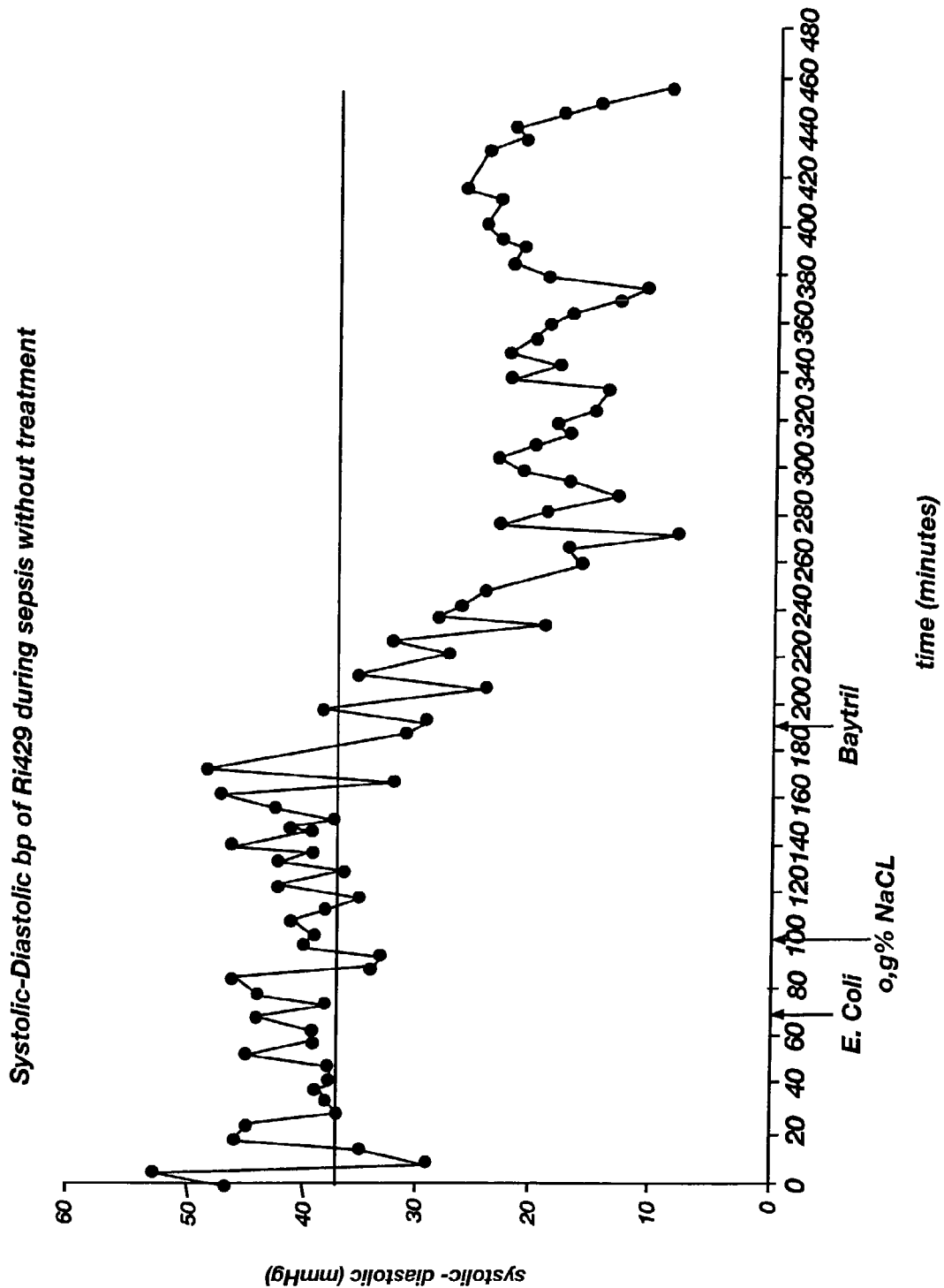
Figure 39:
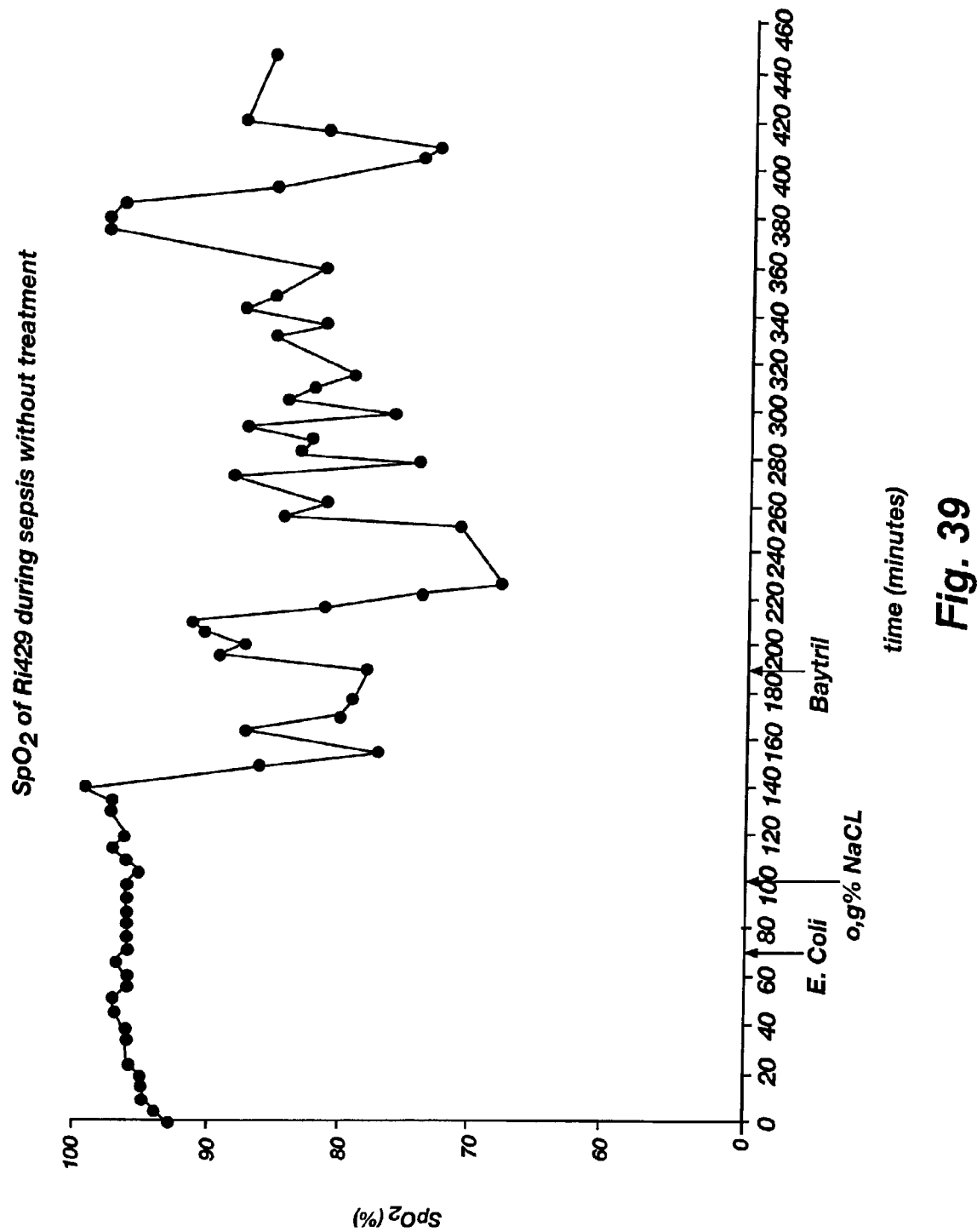
Figure 40:
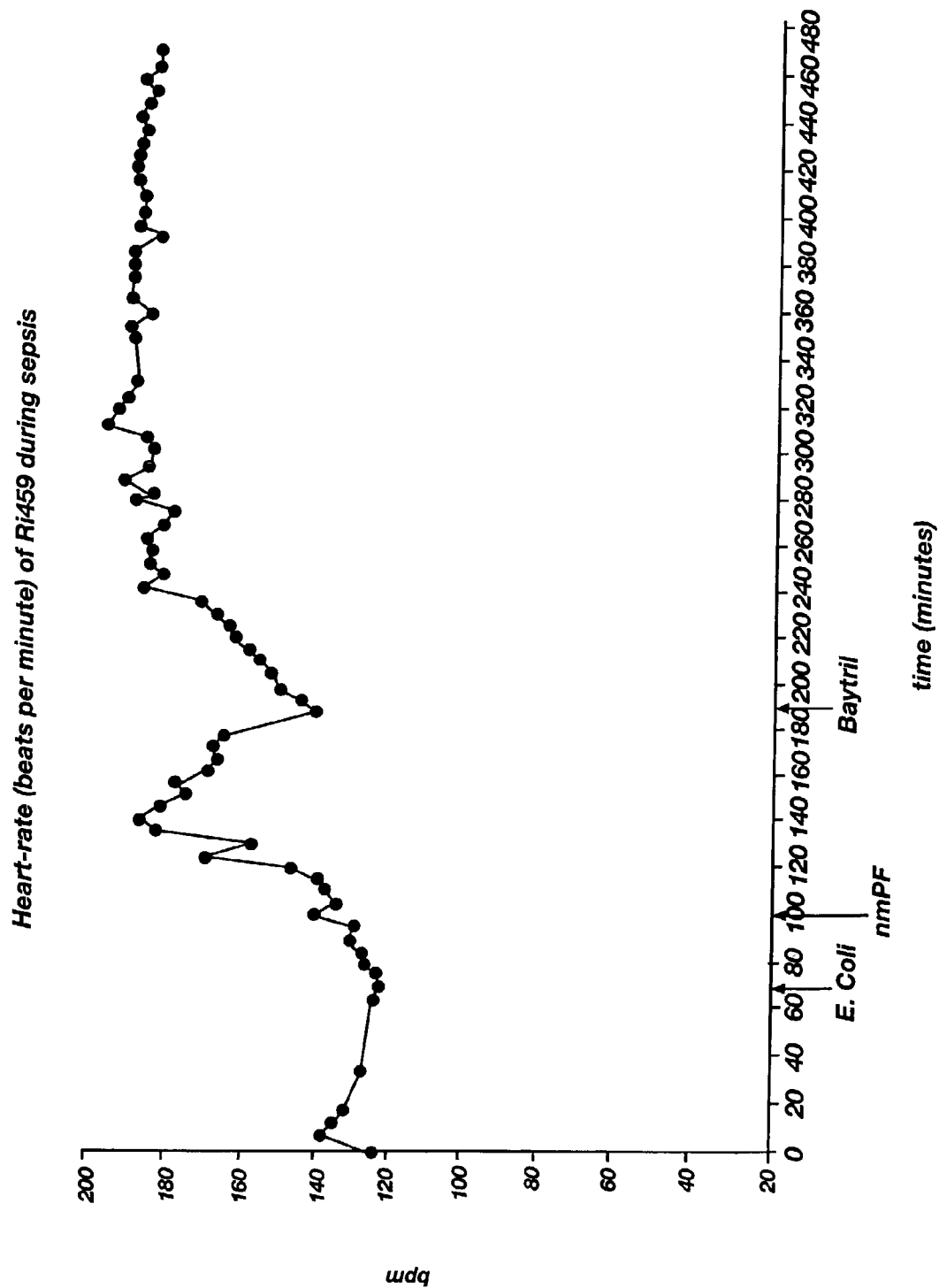
Figure 41:
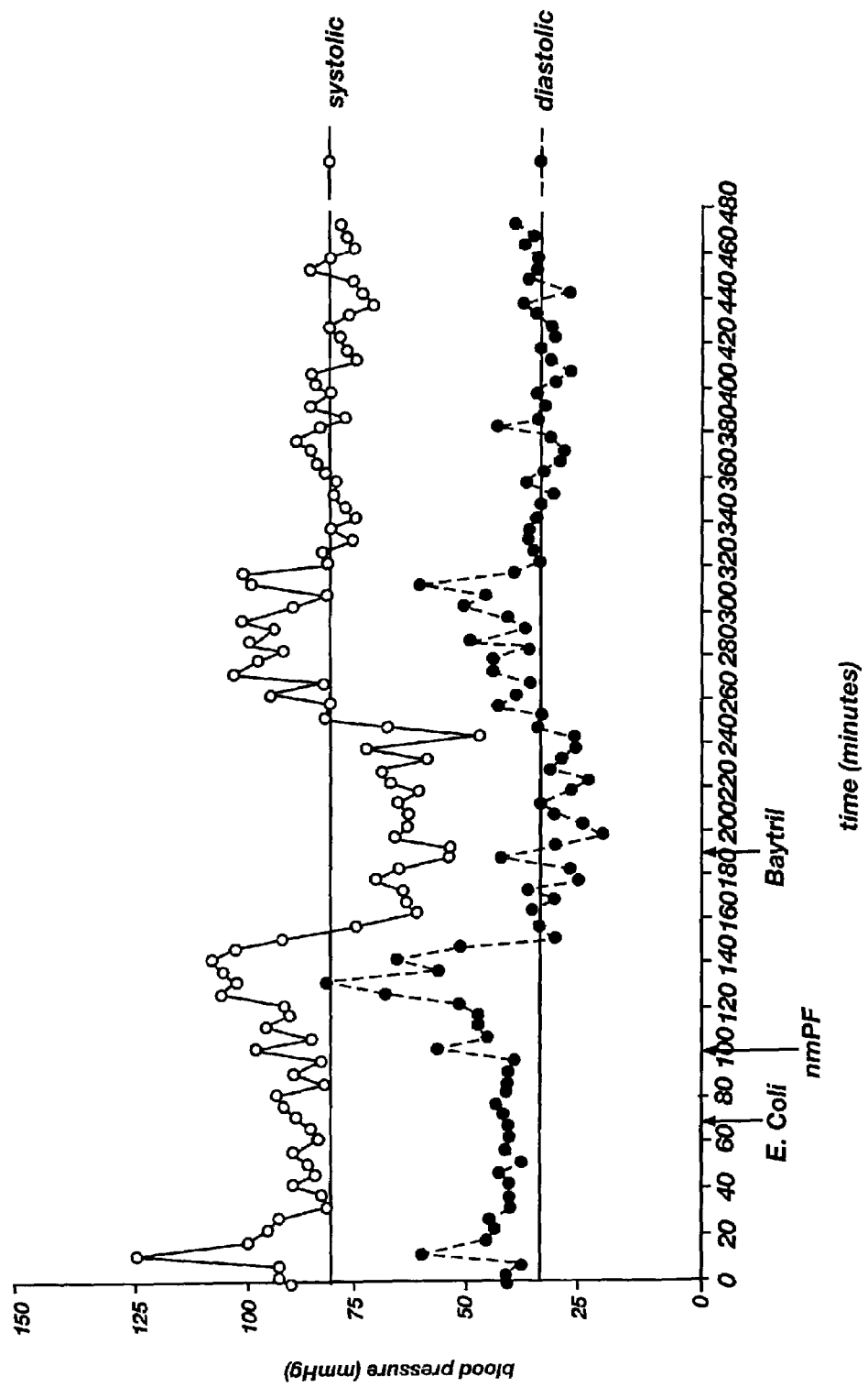
Figure 42:
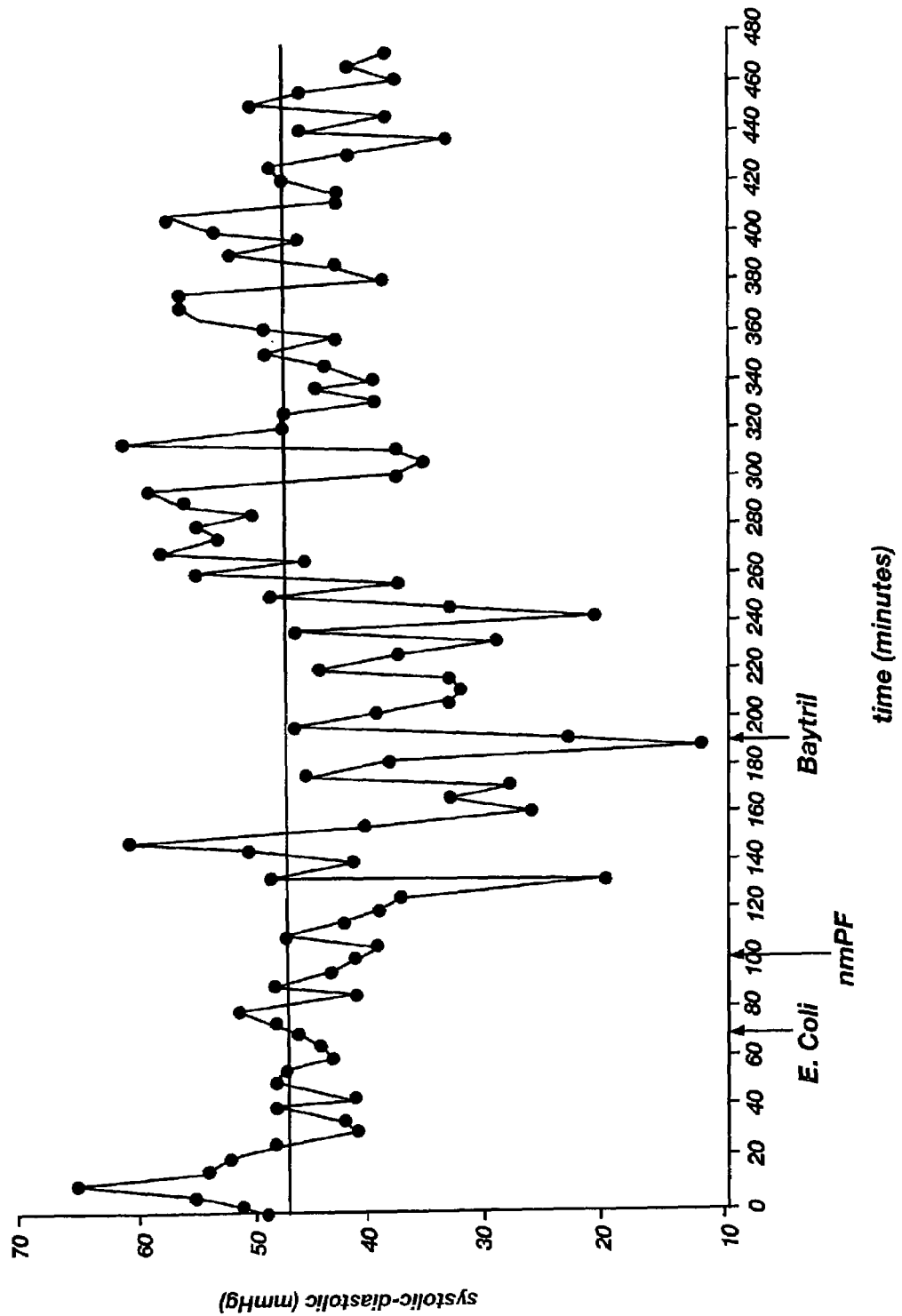
Figure 43:
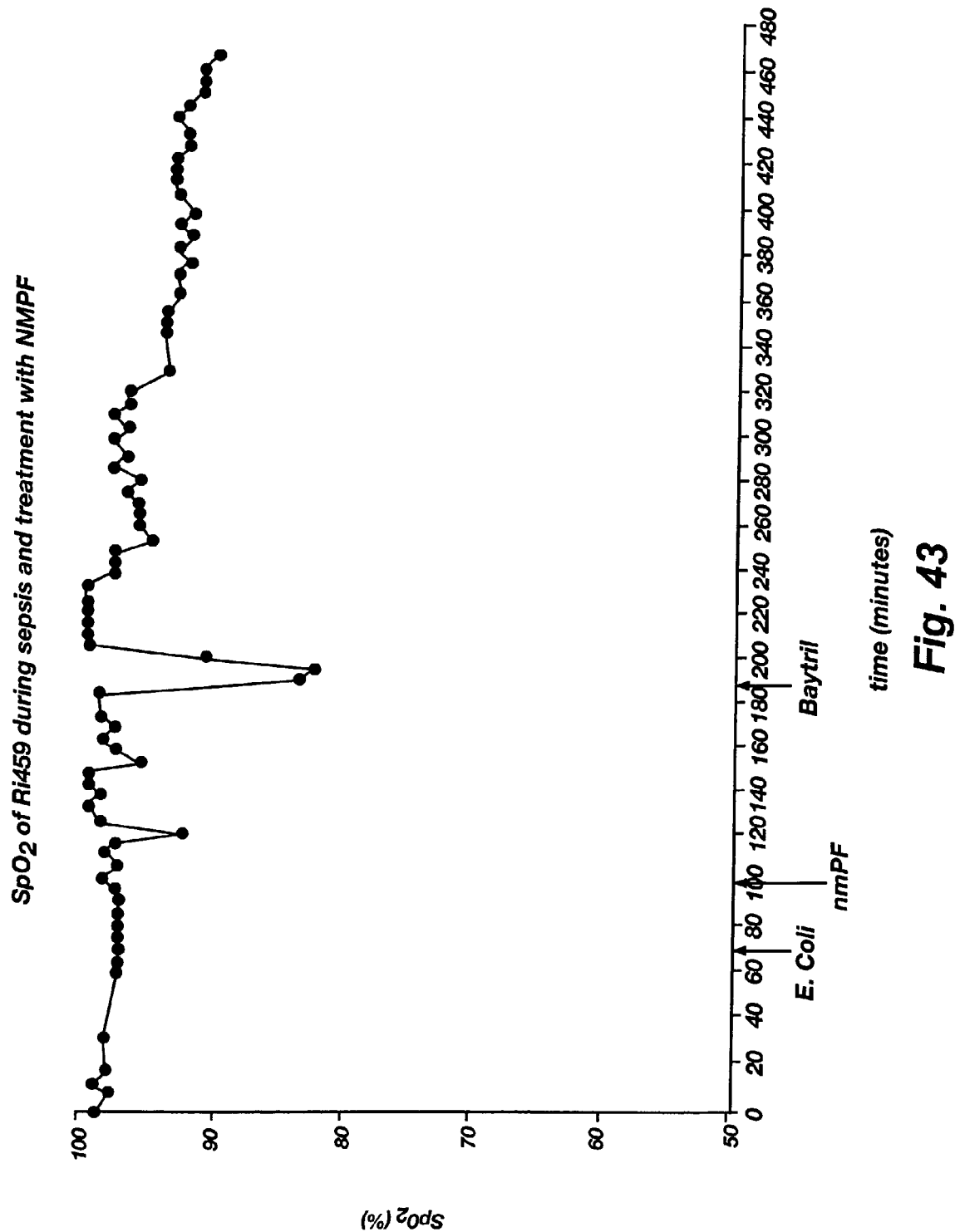
Figure 44:
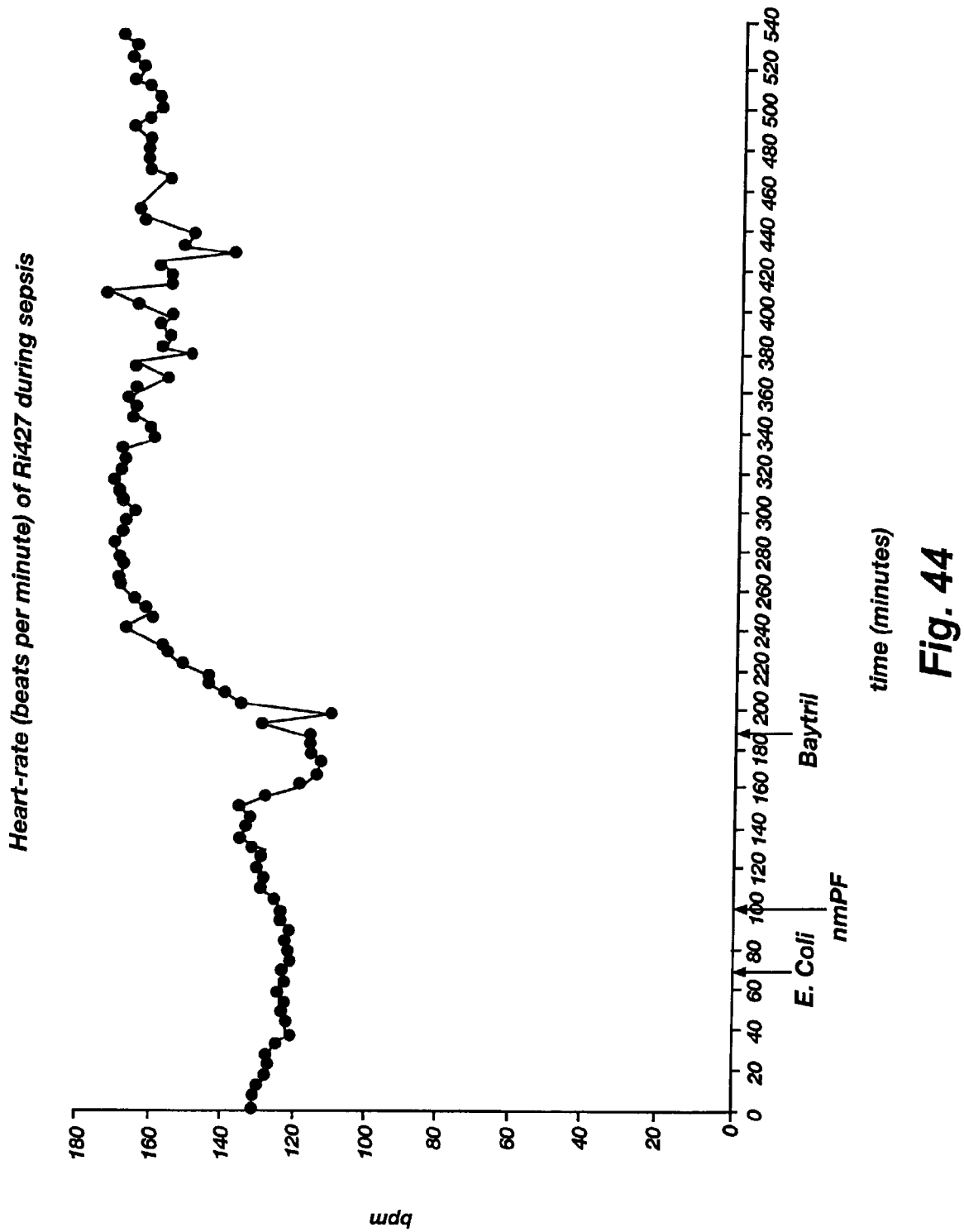
Figure 45:
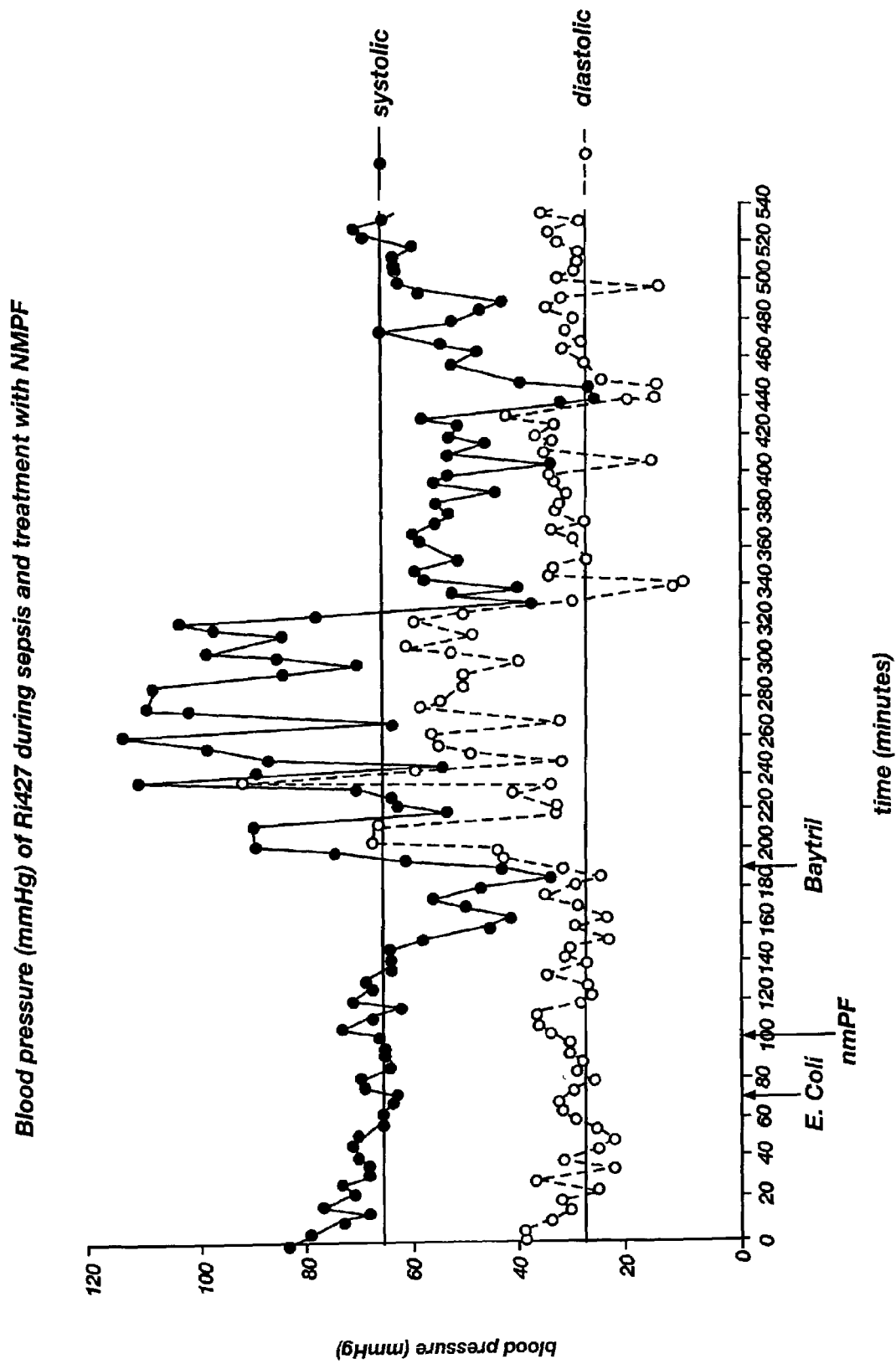
Figure 46:
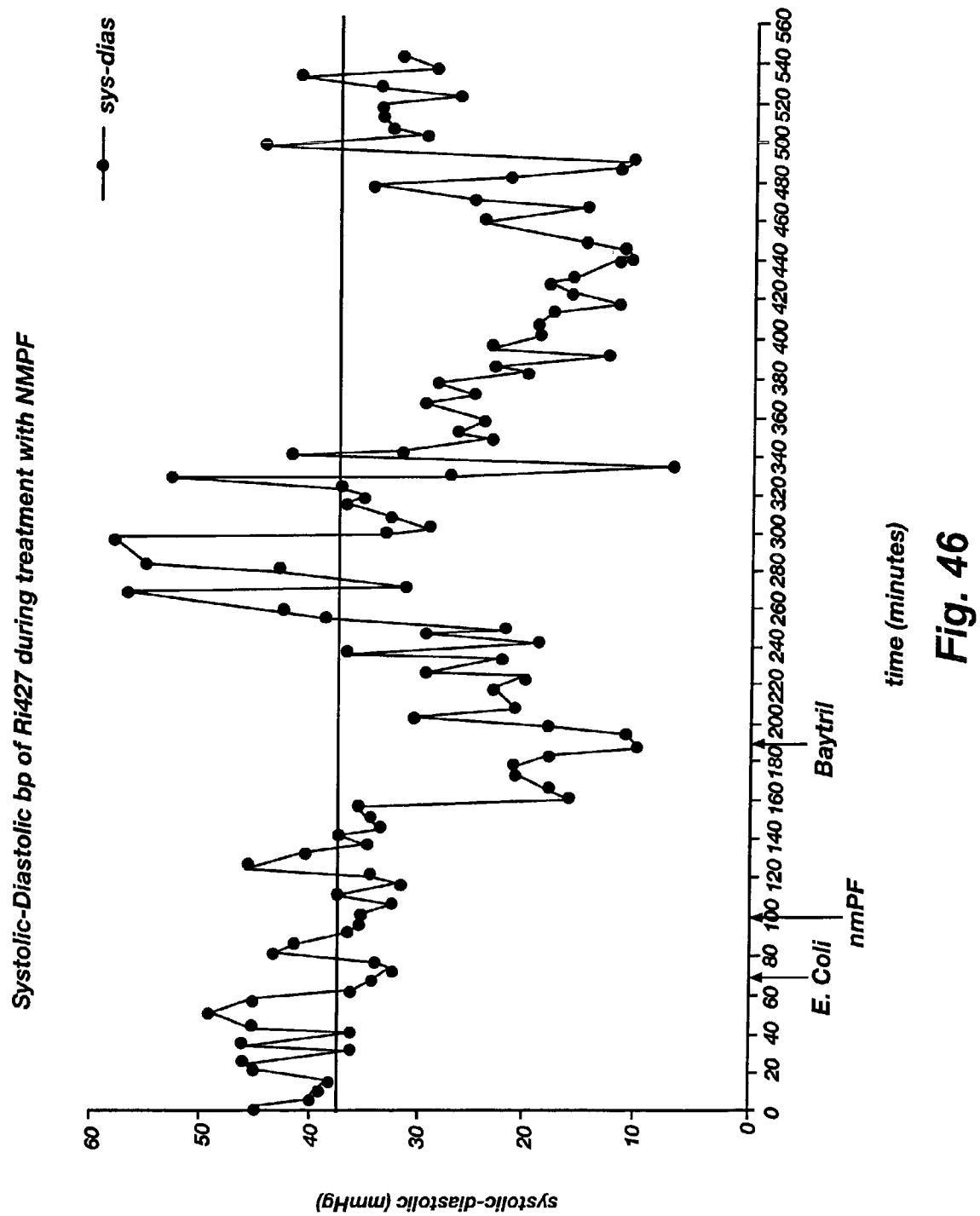
Figure 47:
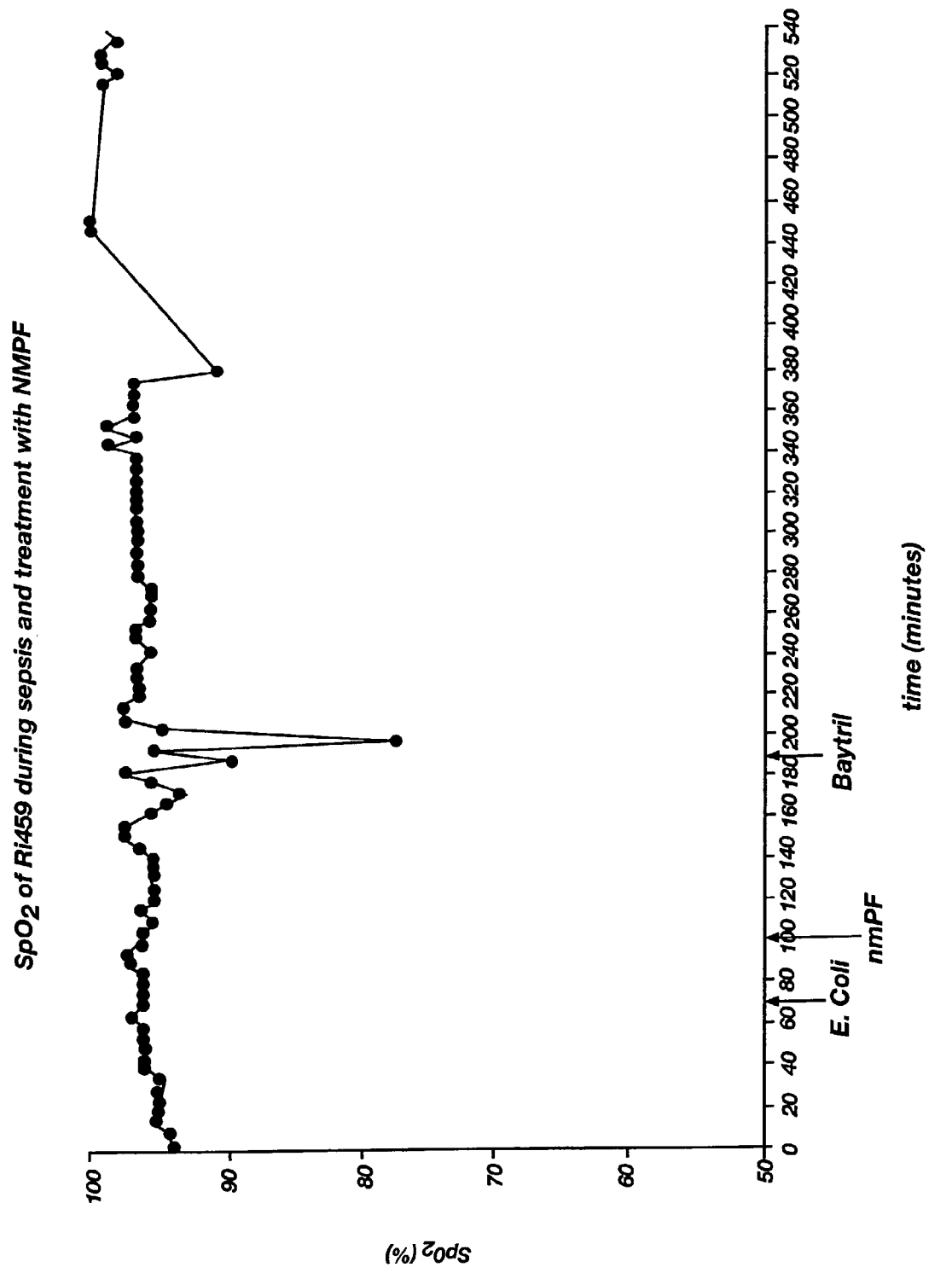
Figure 48A:
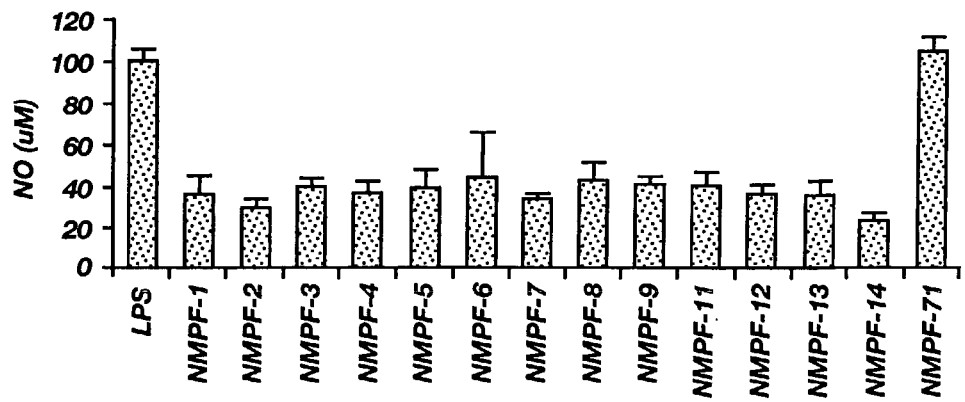
FIG. 48. This figure shows the NO production of LPS (10 μg/ml) stimulated RAW 264.7 macrophages co-stimulated with different NMPF peptides (1 μg/ml).
Figure 48B:
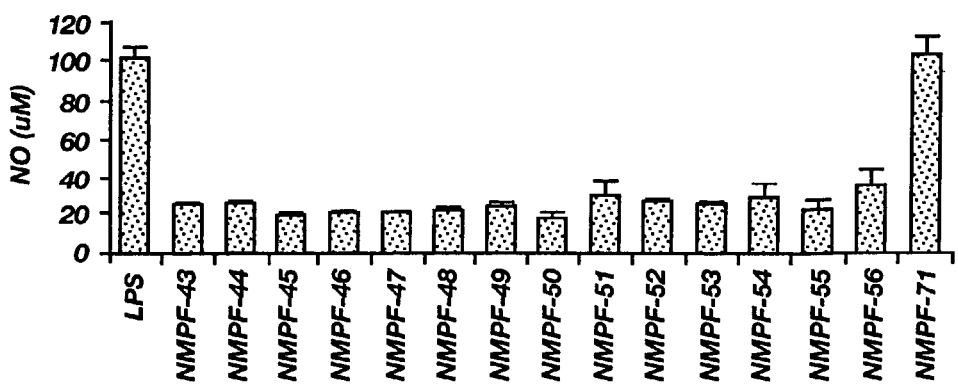
Figure 48C:
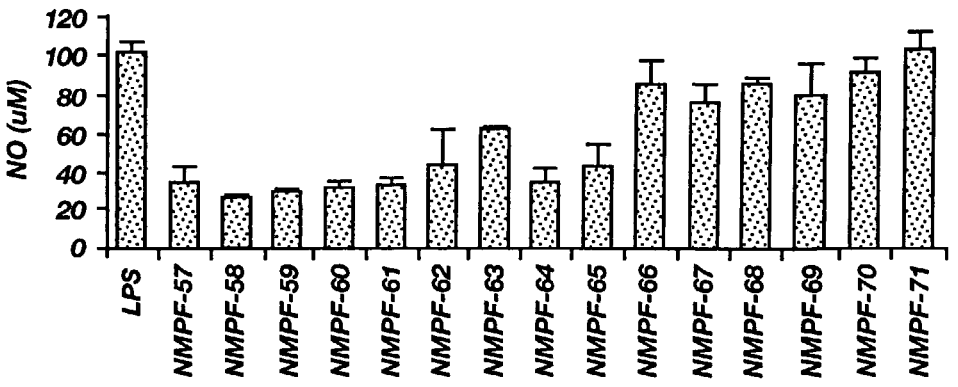
Figure 49A:
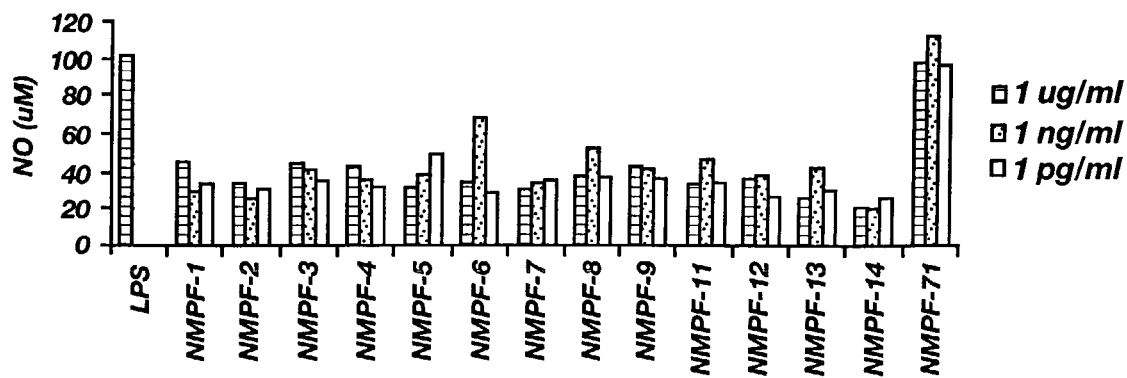
FIG. 49. The figure shows the NO production of LPS (10 μg/ml) stimulated RAW 264.7 macrophages co-stimulated with different NMPF peptides with three different concentrations.
Figure 49B:
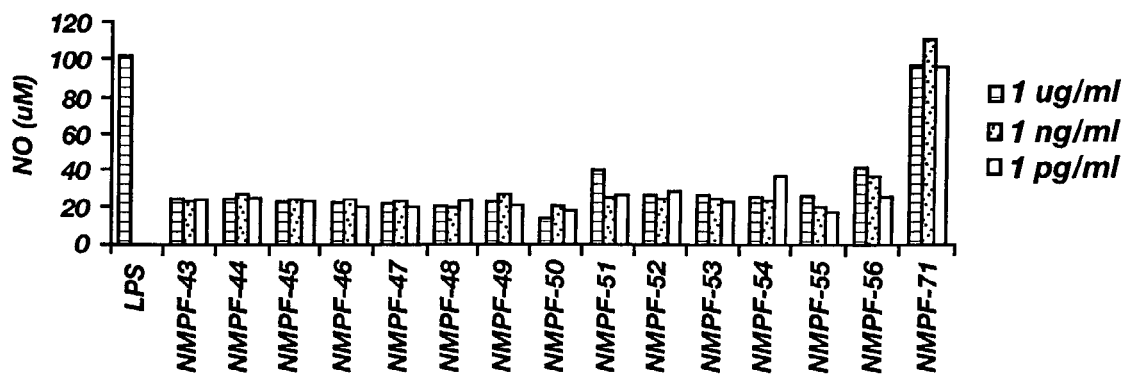
Figure 49C:
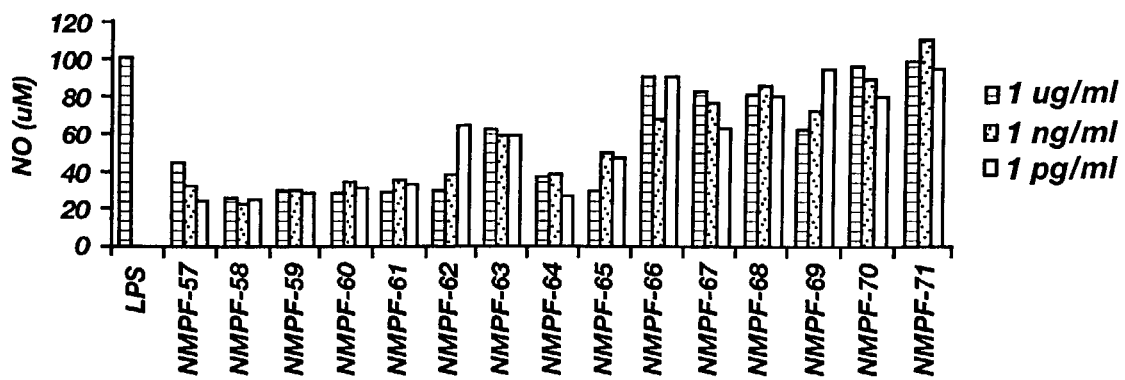
Figure 50:
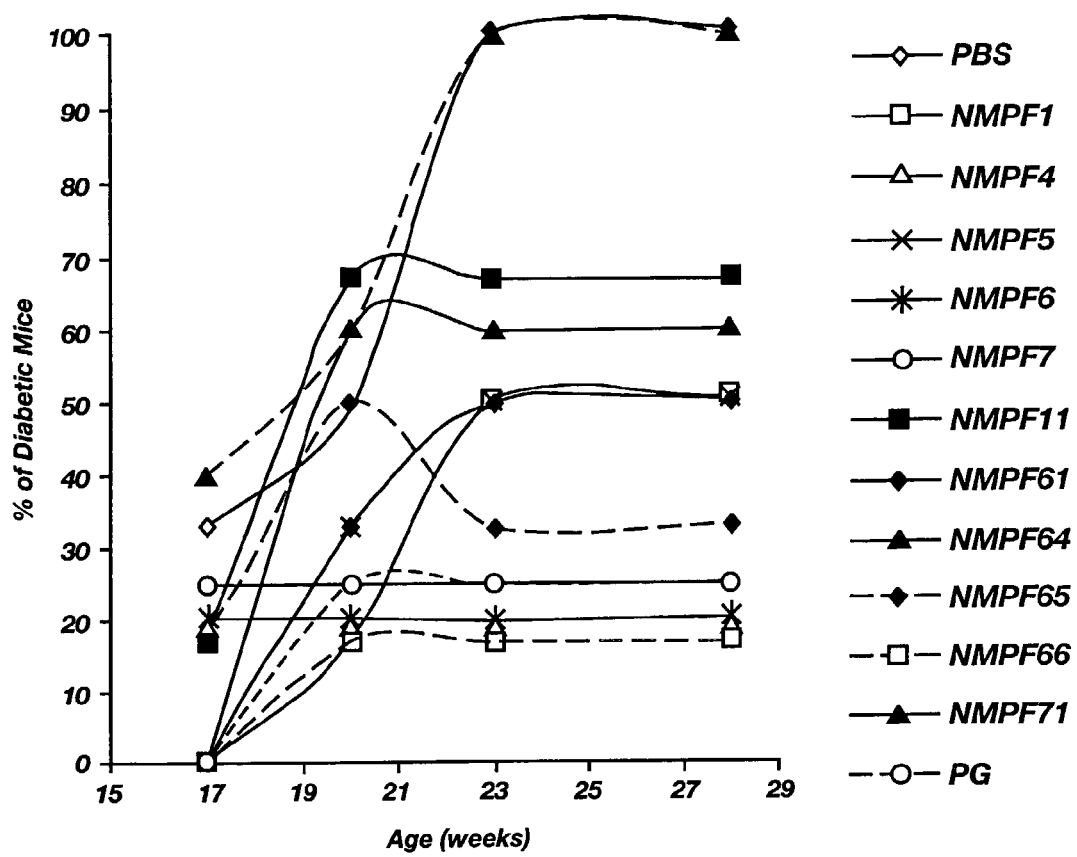
FIG. 50. This figure shows the percentage of diabetic NOD mice treated for 2 weeks with the various NMPF peptides FIG. 51. This figure shows the performed glucose tolerance test (GTT) in NOD mice treated with NMPF peptides (A), and fasting blood glucose levels (B).
Figure 51A:
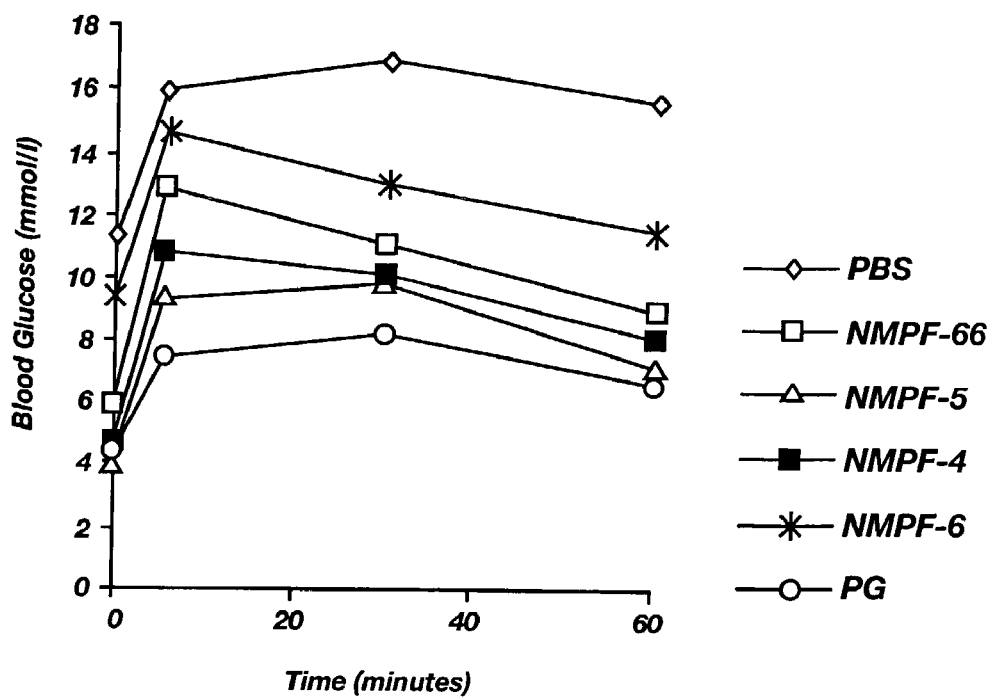
Figure 51B:
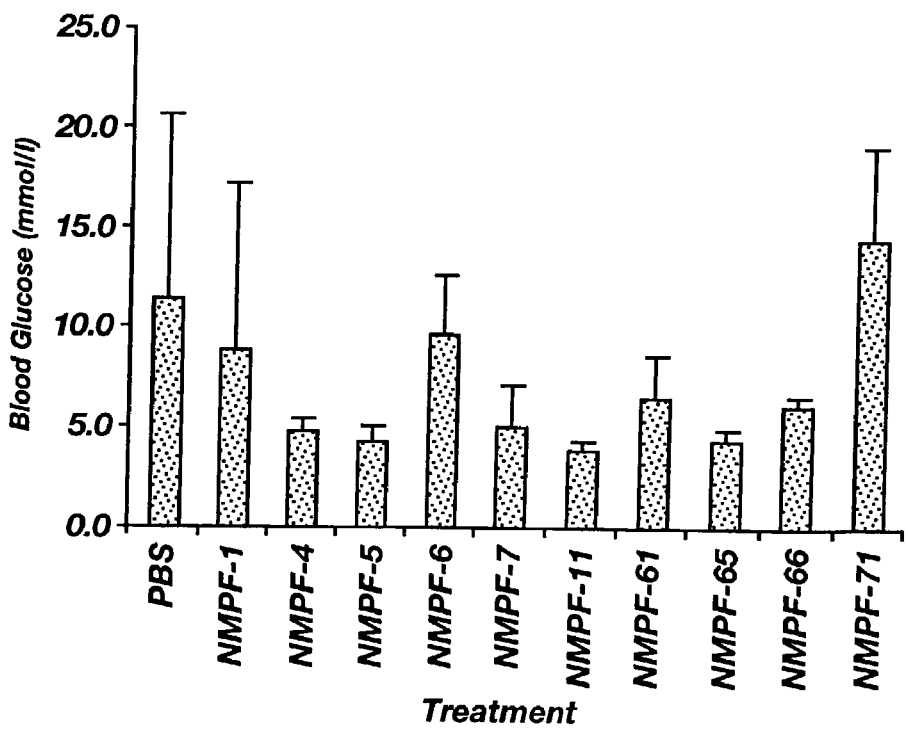

The molecular weight of this peptide is around 416 dalton. Besides 416 dalton mass, FIG. 35 shows some other molecular weights. This is to be explained by the high concentration of the peptide which induces the formation of dimers and sodium-adducts (m/z 416– [M+H]+, 438–[M+Na]+, 831–[2M+H]+, 853–[2M+Na]+, 1245–[3M+H]+, 1257–[3M+Na]+). FIG. 36 shows the MS results of 10–15 min. fraction of nuclear extract obtained from LPS stimulated cells. These results show the absence of 416 dalton mass, while FIG. 37 shows the presence of 416 dalton mass of which the MSn data (FIG. 37) and MS-sequence confirm the presence of LQGV (SEQ ID NO:1) peptide in the nuclear protein extract obtained from LQGV+LPS stimulated RAW264.7 cells.

Endotoxin Shock Model (Sepsis)

Sepsis. For the endotoxin model, BALB/c mice were injected i.p. with 8–9 mg/kg LPS (*E. coli* 026:B6; Difco Lab., Detroit, Mich., USA). Control groups (PBS) were treated with PBS i.p. only. To test the effect of NMPF from different sources (synthetic, commercial hCG preparation [c-hCG]), we treated BALB/c mice with a dose of 300–700 IU of different hCG preparations (PG23; Pregnyl batch no. 235863, PG25; Pregnyl batch no. 255957) and with synthetic peptides (5 mg/kg) after two hours of LPS injection. In other experiments, BALB/c mice were injected i.p. either with 10 mg/kg or with 11 mg/kg LPS (*E. coli* 026:B6; Difco Lab., Detroit, Mich., USA). Subsequently, mice were treated after 2 hours and 24 hours of LPS treatment with NMPF peptides.

Semi-quantitative sickness measurements. Mice were scored for sickness severity using the following measurement scheme:

1 Percolated fur, but no detectable behavior differences compared to normal mice.
2 Percolated fur, huddle reflex, responds to stimuli (such as tap on cage), just as active during handling as healthy mouse.
3 Slower response to tap on cage, passive or docile when handled, but still curious when alone in a new setting.
4 Lack of curiosity, little or no response to stimuli, quite immobile.
5 Labored breathing, inability or slow to self-right after being rolled onto back (moribund)
6 Sacrificed Results Endotoxin Shock Model (Sepsis)

Sepsis experiments. To determine the effect of synthetic peptides (NMPF) in high-dose LPS shock model, BALB/c mice were injected intraperitoneally with different doses of LPS and survival was assessed daily for 5 days. In this experiment (for the LPS endotoxin model), BALB/c mice were injected i.p. with 8–9 mg/kg LPS (*E. coli* 026:B6; Difco Lab., Detroit, Mich., USA). Control groups (PBS) were treated with PBS i.p. only. We treated BALB/c mice with a dose of 300–700 IU of different hCG preparations (PG23; Pregnyl batch no. 235863, PG25; Pregnyl batch no. 255957) or with peptides (5 mg/kg) after two hours of LPS injection.

These experiments showed (Table 1) that NMPF peptides 4, 6, 66 and PG23 inhibited shock completely (all mice had in first 24 hours sickness scores not higher than 2; shortly thereafter they recovered completely and had sickness scores of 0), while peptides 2, 3 and 7 accelerated shock (all mice had in first 24 hours sickness scores of 5 and most of them died, while the control mice treated with LPS+PBS had sickness scores of 3–4 in first 24 hours and most of them died after 48 hours with sickness scores of 5 (17% survival rate at 72 hours). In addition, peptides 1, 5, 8, 9, 11, 12, 13, 14 and 64 showed in a number of different experiments variability in effectiveness as well as in the kind (inhibitory vs. accelerating) of activity. This variability is likely attributable to the rate of breakdown of the various peptides and the different effects the various peptides and their breakdown products have in vivo. In addition, these experiments also showed the variability in anti-shock activity in c-hCG preparations that is likely attributable to the variation in the presence of anti-shock and shock-accelerating NMPF. Visible signs of sickness were apparent in all of the experimental animals, but the kinetics and obviously the severity of this sickness were significantly different. These data are representative of at least 10 separate experiments.

In Table 2 we see the effect of ALA-replacement (PEP-SCAN) in peptides LQG, LQGV (SEQ ID NO:1), VLPALP (SEQ ID NO:3), and VLPALPQ (SEQ ID NO:29) in septic shock experiments. We conclude that the change in even one amino acid by a neutral amino acid can lead to different activity. So, genomic differences as well as polymorphism in these peptides can regulate the immune response very precisely. Derivatives of these peptides, for example (but not limited to), by the addition of classical and non-classical amino acids or derivatives that are differentially modified during or after synthesis; for example, benzylation, amidation, glycosylation, proteolytic cleavage, linkage to an antibody molecule or other cellular ligand etc. could also lead to a better effectiveness of the activity.

To determine whether treatment of BALB/c mice with NMPF inhibits septic shock at different stages of disease, synthetic peptides (NMPF) were injected i.p. at 2 and 24 hours after the induction of septic shock with high dose LPS (10 mg/kg).

As shown in Tables 3 and 4, control mice treated with PBS after the shock induction reached a sickness score of 5 at 14 and 24 hours, and remained so after the second injection with PBS. The survival rate in control group mice was 0% at 48 hours. In contrast to control mice, mice treated with NMPF-9, 11, 12, 43, 46, 50 and 60 reached a maximum sickness score of 2–3 at 24 hours after the induction of septic shock and further reached a maximum sickness score of 1–2 at 48 hours after the second injection of NMPF. In addition, mice treated with NMPF-5, 7, 8, 45, 53 and 58 reached a sickness score of 5 and after the second injection with NMPF all mice returned to a sickness score of 1–2 and survival rates in NMPF groups were 100%. Mice treated with NMPF-3 reached sickness scores of 3–4 and the second NMPF injection did save these mice. These experiments show that NMPF peptides have anti-shock activity at different stages of the disease and NMPF have anti-shock activity even at a disease stage when otherwise irreversible damage had been done. This indicates that NMPF have effects on different cellular levels and also have repairing and regenerating capacity.

Dendritic Cells Experiments

Mice. The mouse strain used in this study was BALB/c (Harlan, Bicester, Oxon, GB). All mice used in experiments were females between 8 and 12 weeks of age. Mice were housed in a specific-pathogen-free facility. The Animal Use Committee at the Erasmus University Rotterdam, The Netherlands approved all studies.

In vivo treatment. At least six mice per group were injected intraperitoneally (i.p) with LPS (10 mg/kg; Sigma). After 2 and 24 hrs of LPS induction, mice were injected i.p. with either NMPF (5 mg/kg) or Phosphate Buffered Saline (PBS), in a volume of 100 µl. LPS-induced shock in this model had more than 90% mortality at 48 hrs.

Bone marrow cell culture. From treated mice, bone-marrow cells were isolated and cultured as follows. BALB/c mice were killed by suffocation with $CO_2$. The femurs and tibiae were removed and freed of muscles and tendons under aseptic conditions. The bones were placed in R10 medium (RPMI 1640, supplemented with 50 U/ml penicillin, 50 µg/ml streptomycin, 0.2 M Na-pyruvate, 2 mM glutamine, 50 µM 2-mercaptoethanol and 10% fetal calf serum (Bio Whittaker, Europe)).

The bones were then cleaned more thoroughly by using an aseptic tissue and were transferred to an ice cold mortier with 2 ml of R10 medium. The bones were crushed with a mortel to get the cells out of the bones. Cells were filtered through a sterile 100 µM filter (Beckton Dickinson Labware) and collected in a 50 ml tube (FALCON). This procedure was repeated until bone parts appeared translucent.

The isolated cells were resuspended in 10 ml of R10 and 30 ml of Geys medium was added. The cell suspension was kept on ice for 30 minutes to lyse the red blood cells. Thereafter, the cells were washed twice in R10 medium. Upon initiation of the culture, the cell concentration was adjusted to $2 \times 10^5$ cells per ml in R10 medium supplemented with 20 ng/ml recombinant mouse Granulocyte Monocyte-Colony Stimulating Factor (rmGM-CSF; BioSource International, Inc., USA) and seeded in 100 mm non-adherent bacteriological Petri dishes (Falcon). For each condition, six Petri dishes were used and for further analysis, cells were pooled and analyzed as described ahead. The cultures were placed in a 5% $CO_2$-incubator at 37° C. Every three days after culture initiation, 10 ml fresh R10 medium supplemented with rmGM-CSF at 20 ng/ml was added to each dish.

Nine days after culture initiation, non-adherent cells were collected and counted with a Coulter Counter (Coulter).

Alternatively, BM cells from untreated mice were isolated and cultured as described above and were in vitro treated with the following conditions: NMPF-4, NMPF-46, NMPF-7, NMPF-60 (20 µg/ml) were added to the culture either at day 0 or day 6 after culture initiation, or LPS (1 µg/ml) was added to the culture at day 6 with or without the NMPF.

Immunofluorescence staining. Cells ($2 \times 10^5$) were washed with FACS-buffer (PBS with 1% BSA and 0.02% sodium azide) and transferred to a round-bottomed 96-well plate (NUNC). The antibodies used for staining were against MHC-II (I-A/I-E) PE and CD11c/CD18 FITC (PharMingen/ Becton Dickinson, Franklin Lakes, N.J., USA).

Cells were resuspended in 200 µl FACS-buffer containing both of the antibodies at a concentration of 2.5 ng/µl per antibody. Cells were then incubated for 30 min at 4° C. Thereafter, cells were washed 3 times and finally resuspended in 200 µl FACS-buffer for flow-cytometric analysis in a FACSCalibur flow cytometer (Becton Dickinson, Heidelberg, Germany). All FACS-data were analyzed with CellQuest software (Becton Dickinson, Heidelberg, Del.). Statistical analysis All differences greater than 20% are considered to be significant.

Results

Dendritic Cell Experiments

Figure 2:
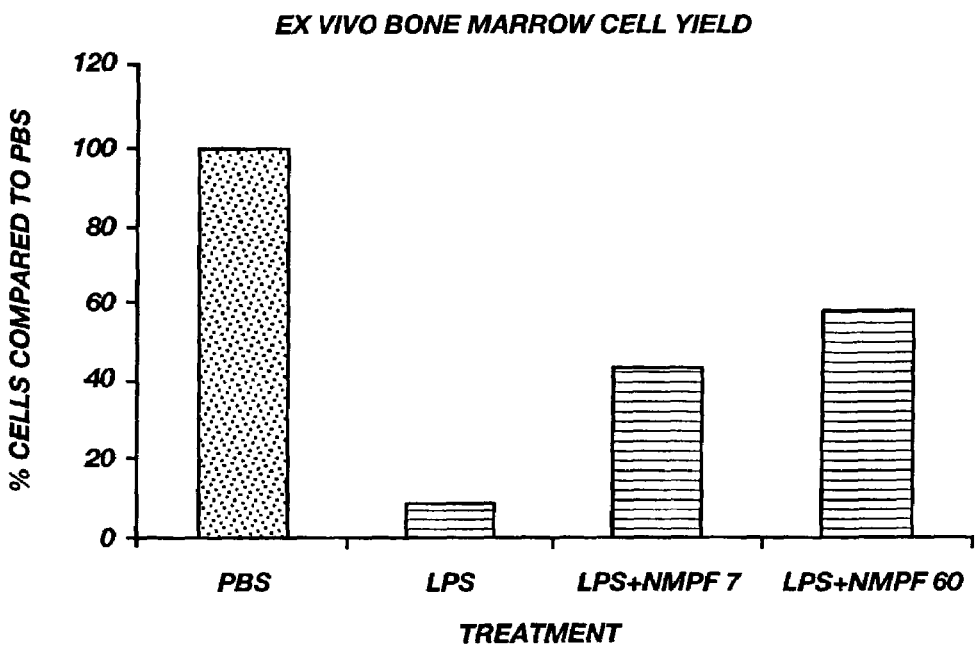

Cell yield of ex vivo bone-marrow cell cultures. To determine the ex vivo effect of LPS and NMPF treatment on the cell yield obtained from a nine-day culture of bone-marrow with rmGM-CSF, cells were isolated from the BM of treated mice and cultured, harvested and counted as described. As shown in FIGS. 1 and 2, the cell yield of the bone-marrow cultures of LPS (10 mg/kg) treated mice is significantly decreased compared to PBS treated mice. Mice treated with NMPF-4, NMPF-7, NMPF-46 and NMPF-60 after LPS shock induction had a significantly increased cell yield compared to LPS in the presence of rmGM-CSF. In addition, BM cultures from NMPF-46 treated mice gave a significantly increased cell yield even compared to the PBS group.

Immunofluorescence staining of in vivo-treated bone-marrow-derived DC. Culture of BM cells in the presence of rmGM-CSF gave rise to an increased population of cells that are positive for CD1 c and MHC-II. Cells positive for these cell membrane markers are bone-marrow-derived dendritic cells (DC). DC are potent antigen presenting cells (APC) and modulate immune responses. In order to determine the maturation state of myeloid-derived DC, cells were stained with CD11c and MHC-II.

Figure 3:
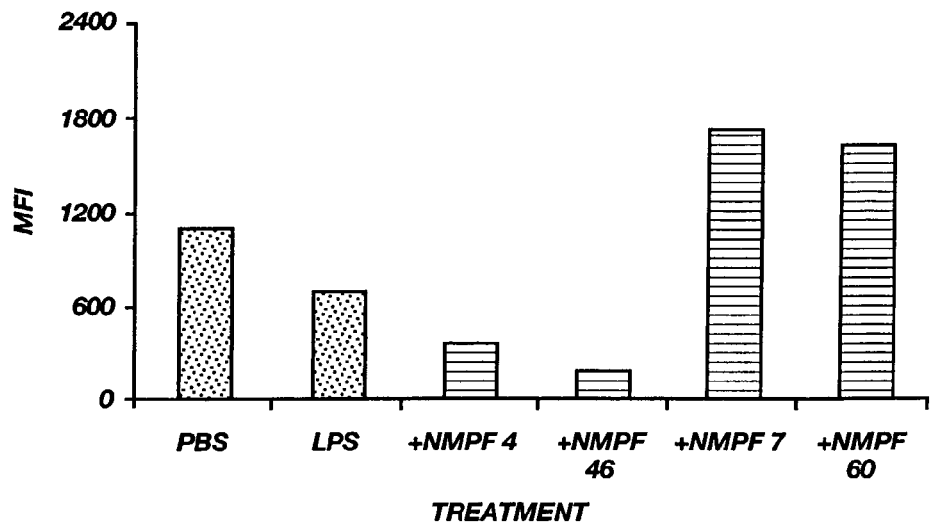
FIG. 3. Effect of ex vivo treatment on MHC-II expression on CD11c$^+$ cells. Bone marrow (BM) cells were isolated from treated BALB/c mice (n=6) and cultured ex vivo in the presence of rmGM-CSF for nine days. This figure shows MHC-II expression expressed in mean fluorescence intensity (MFI) after nine days of culturing of BM cells isolated from PBS, LPS or LPS in combination with NMPF. Each condition consists of 6 Petri dishes and results shown in these figures are representative of 6 dishes. Differences of ≧20% were considered significant and line bars represent significant data as compared to LPS control group. A representative experiment is shown. Findings involving all experimental conditions were entirely reproduced in 3 additional experiments.

As shown in FIG. 3, the expression of the MHC-II molecule was significantly decreased on CD11c-positive cells from LPS-treated mice as compared to the PBS group. This decrease in MHC-II expression was further potentiated by the in vivo treatment with NMPF-4 and NMPF-46. However, treatment of mice with NMPF-7 and NMPF-60 significantly increased the expression of the MHC-II molecule even as compared to the PBS group.

Cell yields of in vitro bone-marrow cell cultures. To determine the effect of LPS and NMPF in vitro on the cell yield of a nine-day culture of bone-marrow cells, we isolated the BM cells from untreated BALB/c mice and cultured them in the presence of rmGM-CSF. In addition to rmGM-CSF, cultures were supplemented with NMPF at either day 0 or day 6 with or without the addition of LPS at day 6.

Figure 4:
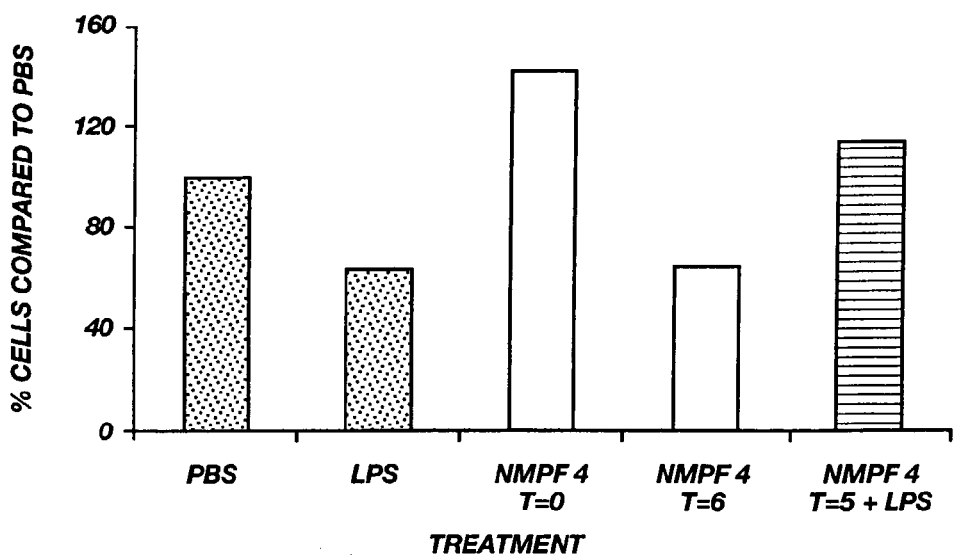
FIGS. 4–7. Bone marrow (BM) cell yield of in vitro-treated BM cultures. BM cells from BALB/c mice (n=3) were cultured in vitro and treated with either PBS, LPS (t=6), NMPF-4, 7, 46, 60 (t=0 or t=6) or combination of NMPF with LPS (t=6), in the presence of rmGM-CSF for nine days. These figures show cell yield expressed in relative percentage of cells compared to PBS after nine days of culture of BM cells. Each condition consists of 6 Petri dishes and results shown in these figures are representative of 6 dishes. Differences of ≧20% were considered significant. Line bars represent significant data as compared to LPS control group and dotted bars represent significant data as compared to PBS group. A representative experiment is shown. Findings involving all experimental conditions were entirely reproduced in 3 additional experiments.
Figure 5:
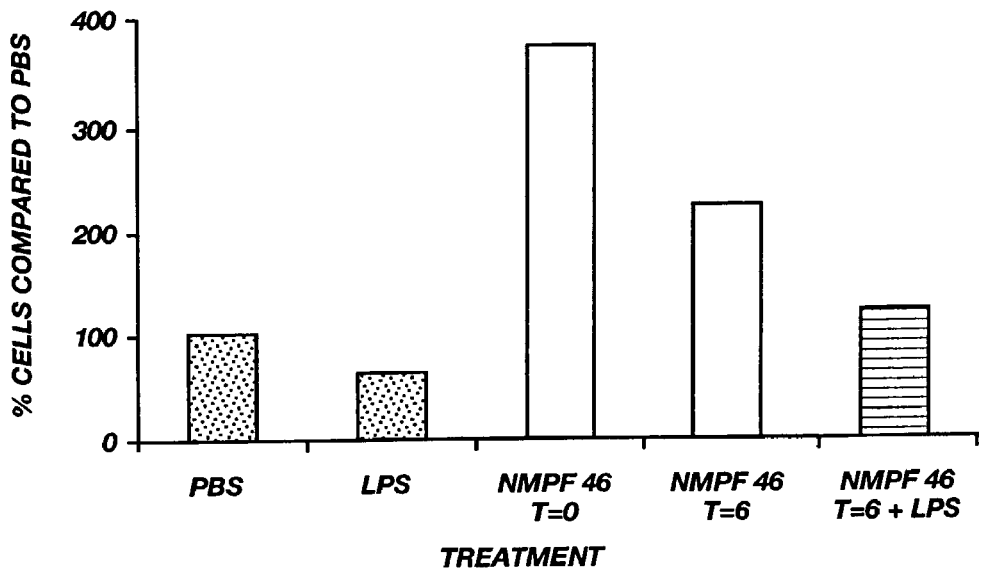
Figure 6:
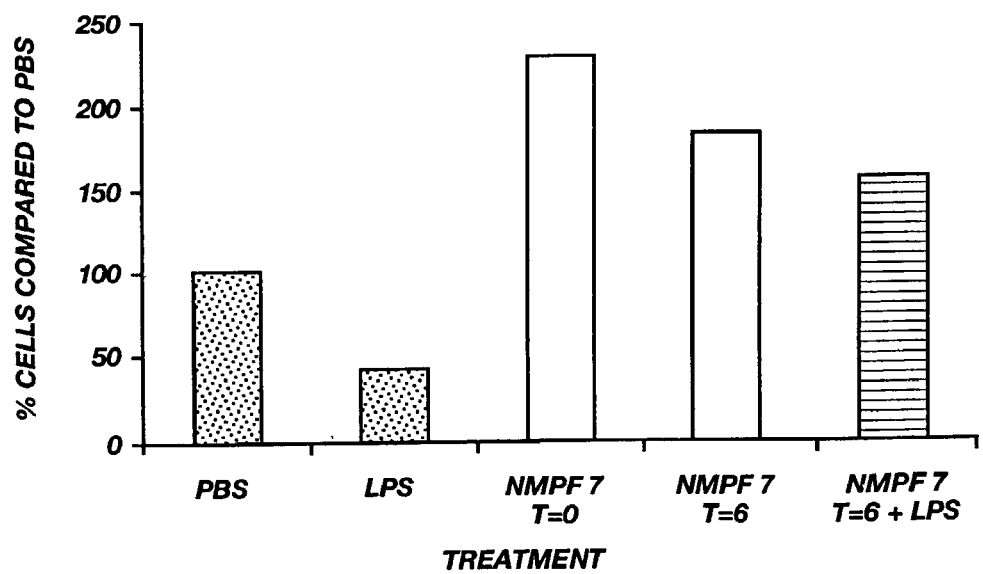
Figure 7:
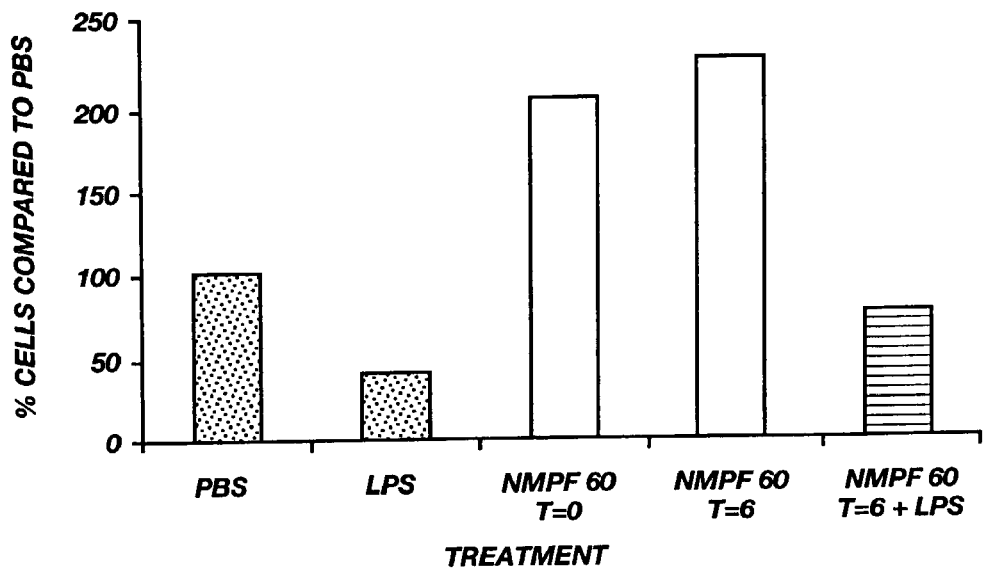
Figure 8:
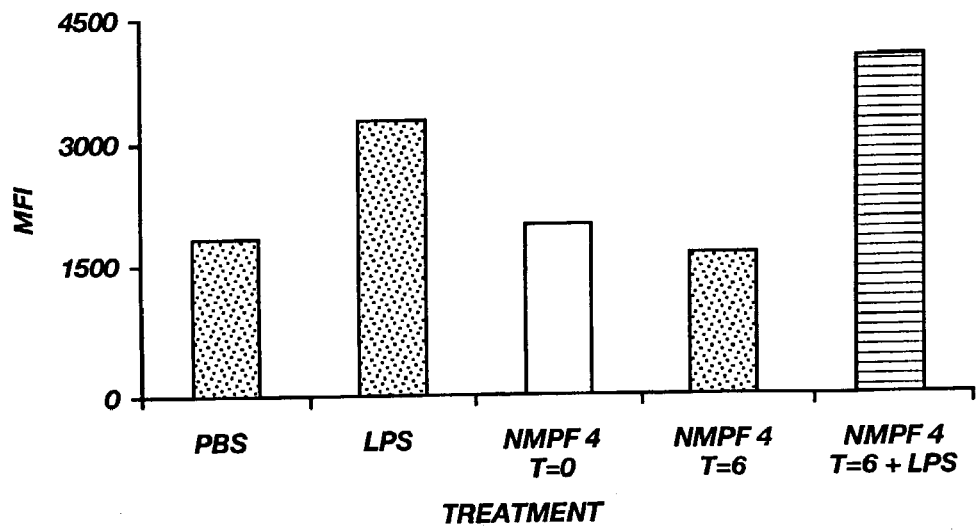
FIGS. 8–11. Effect of in vitro treatment on MHC-II expression on CD11c+ cells. BM cells from BALB/c mice (n=3) were cultured in vitro and treated with either PBS, LPS (t=6), NMPF-4, 7, 46, 60 (t=0 or t=6 days) or a combination of NMPF with LPS (t=6 days), in the presence of rmGM-CSF for nine days. These figures show MHC-II expression expressed in mean fluorescence intensity (MFI) of CD11c positive cells after nine days of culturing of BM cells. Each condition consists of 6 Petri dishes, and results shown in these figures are representative of 6 dishes. Differences of ≧20% were considered significant. Line bars represent significant data as compared to LPS control group and dotted bars represent significant data as compared to PBS group. A representative experiment is shown. Findings involving all experimental conditions were entirely reproduced in 3 additional experiments.
Figure 9:
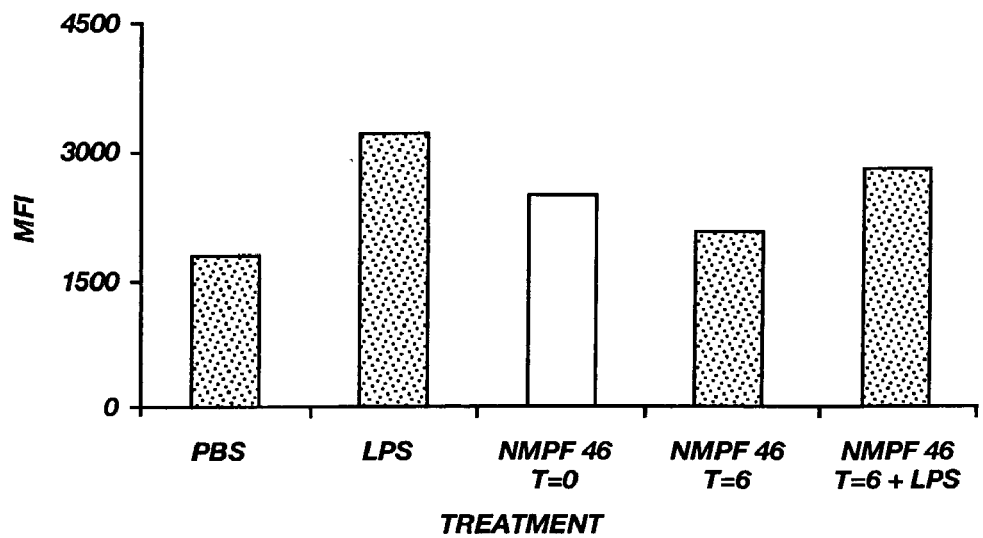
Figure 10:
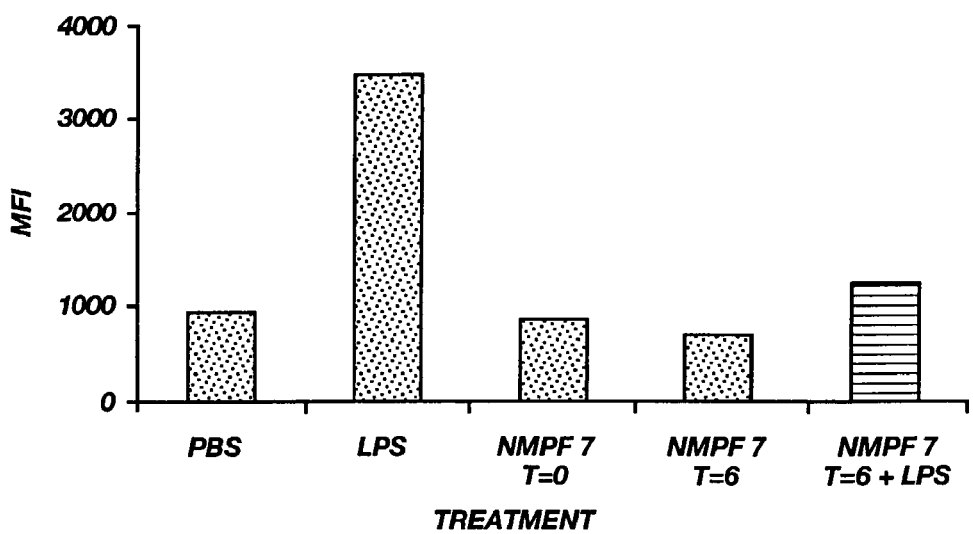
Figure 11:
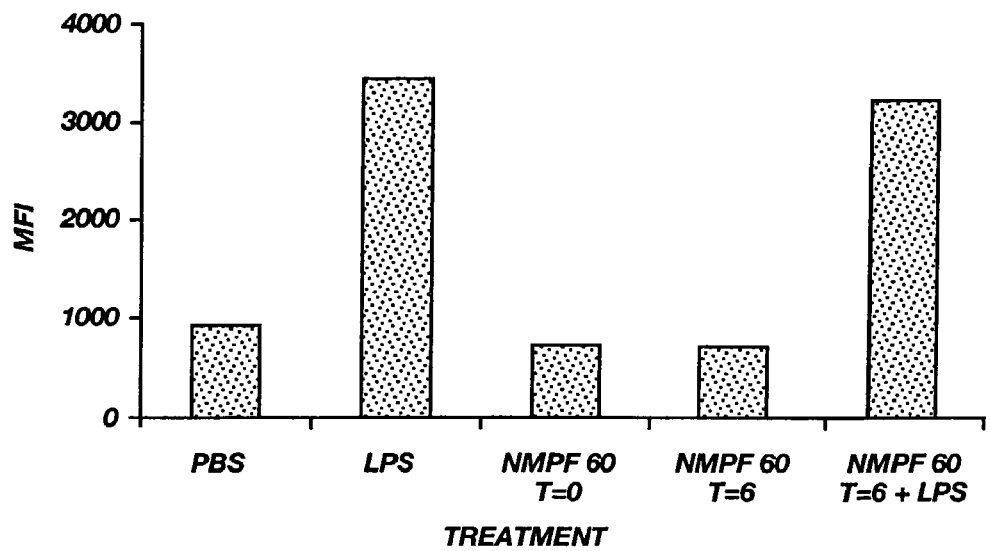

As shown in FIGS. 4–7, there is a significant decrease in cell yield in LPS-treated BM cells as compared to PBS. BM cells treated with NMPF-4, 7, 46 or 60 at time point t=0 or t=6 without LPS showed a significant increase in cell yield as compared to the PBS group. However, BM cell cultures treated with NMPF-4 at time point t=6 showed significant decrease in cell yield as compared to the PBS group and this effect is comparable with the effect of LPS (FIG. 4). In addition, BM cells treated with NMPF-4, 7, 46 or 60 at time point t=6 in combination with LPS showed a significant increase in cell yield as compared to the LPS group, and even in the group of NMPF-7, the cell yield was significantly increased as compared to the PBS group.

Immunofluorescence staining of in vitro-treated bone-marrow derived DC. To determine the maturation state of DC, CD1 c positive cells were stained for MHC-II antibody. FIGS. 8–11 show that there is an opposite effect of LPS on MHC-II expression as compared to in vivo experiments, namely, MHC-II expression is significantly increased with LPS treatment in vitro as compared to PBS. NMPF-4 with LPS further potentiated the effect of LPS, while NMPF-7 with or without LPS (t=6) significantly inhibited the expression of MHC-II as compared to LPS and PBS, respectively. However, cells treated with NMPF-46 without LPS (t=0) showed significantly increased expression of MHC-II on CD11c positive cells. Furthermore, no significant differences were found in the group treated with NMPF-60 with or without LPS on MHC-II expression as compared to LPS- and PBS-treated cells.

Figure 12:
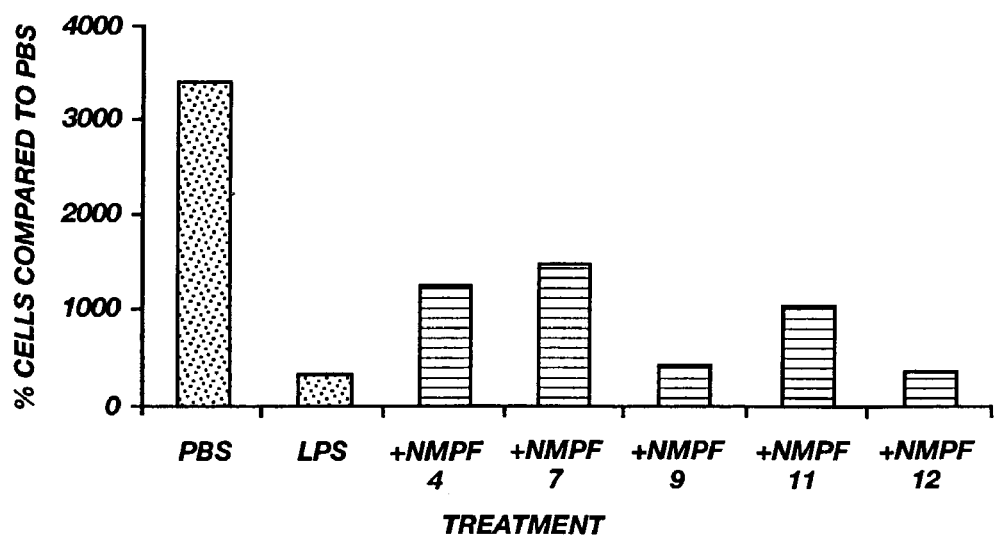
FIGS. 12–15. Bone marrow (BM) cell yield of ex vivo-treated BALB/c mice (n=6). BM cells were isolated from treated mice and cultured ex vivo in the presence of rmGM-CSF for nine days. These figures show cell yield after nine days of culture of BM cells in suspension (unattached) and attached to Petri dish (attached). BM cells were isolated from mice treated with PBS, LPS or LPS in combination with different NMPF peptides. In these figures cell yield is expressed in relative percentage of cells compared to PBS. Each condition consists of 6 Petri dishes and results shown here are representative of 6 dishes. Differences of ≧20% were considered significant and line bars represent significant data as compared to LPS control group. A representative experiment is shown. Findings involving all experimental conditions were entirely reproduced in 3 additional experiments.
Figure 13:
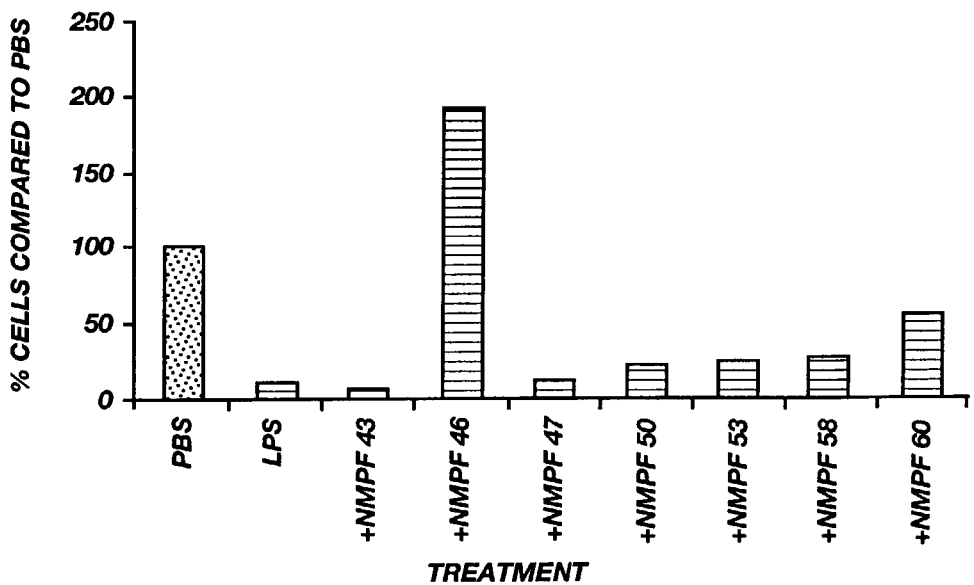
Figure 14:
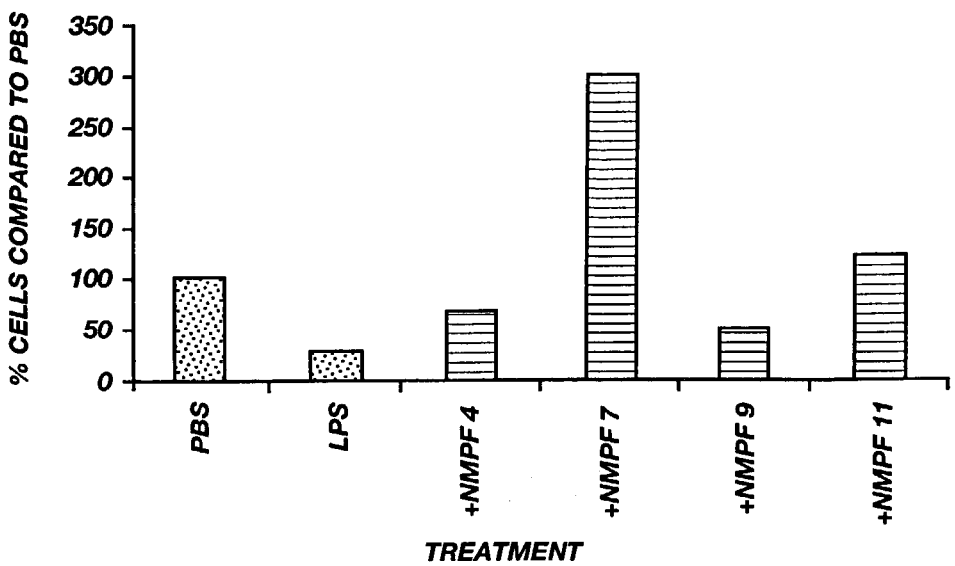
Figure 15:
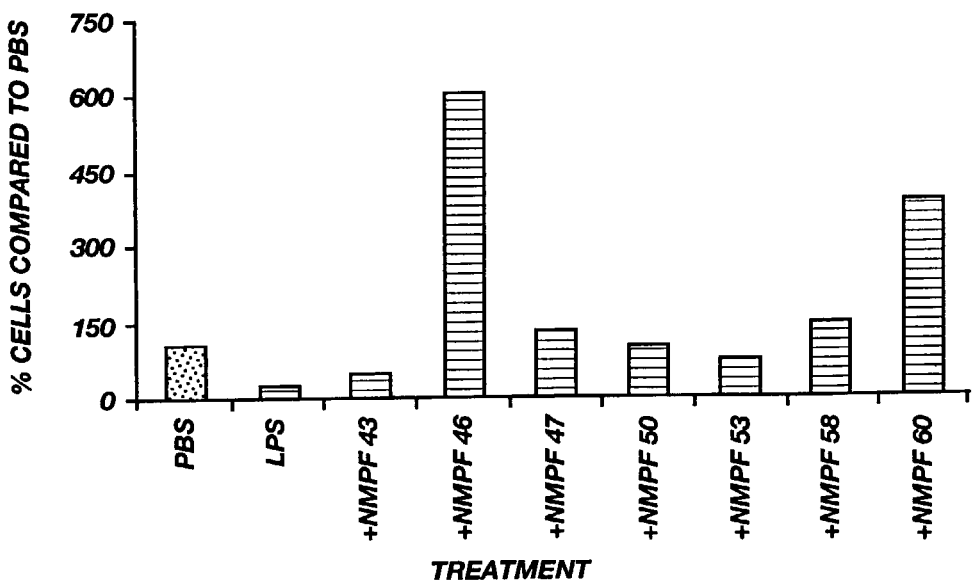

To determine the in vivo effect of LPS and NMPF treatment on the cell yield obtained from a nine-day culture of bone-marrow with rmGM-CSF, cells were isolated from the BM of treated mice and cultured, harvested and counted as described. The cell yield of "attached" cells was significantly increased with NMPF-4, 7, 9, 11, 43, 46, 47, 50, 53, 58 60 and even in the group of NMPF-7, 46 and 60, the cell yield was significant increased as compared to the PBS group (FIGS. 14–15). In addition, cell yield of "unattached" cells was significantly increased with NMPF-4, 7, 9, 11, 46, 50, 53, 58 60, and again in the group of NMPF-46, the cell yield was significant increased as compared to the PBS group (FIGS. 12–13).

Figure 16:
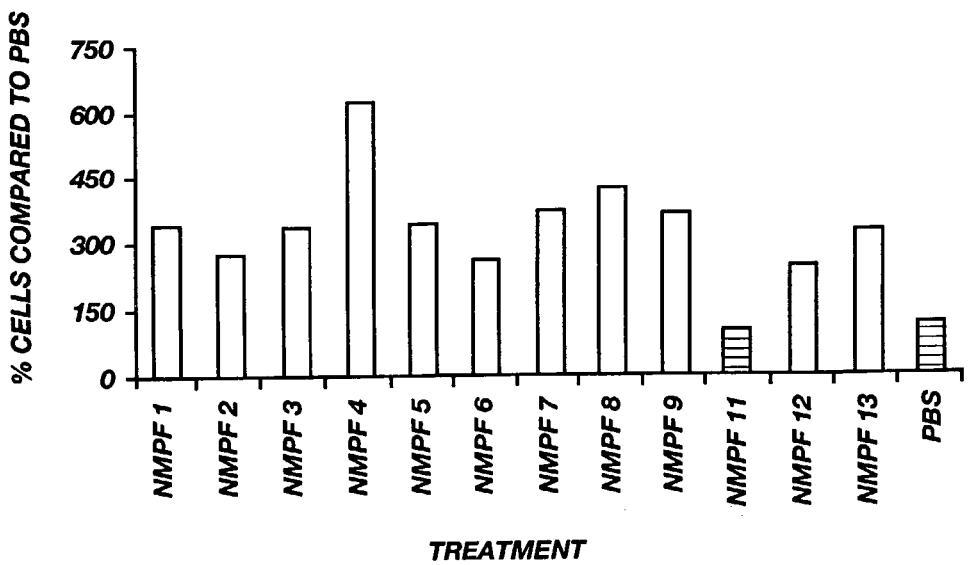
FIGS. 16–17. Bone marrow (BM) cell yield of in vitro treated BM cultures from NOD mice. BM cells from 15-week-old female NOD mice (n=3) were cultured in vitro and treated with either PBS or NMPF in the presence of rmGM-CSF for nine days. These figures show cell yield after nine days of culture of BM cells in suspension (unattached) and attached to Petri dishes (attached). In these figures cell yield is expressed in relative percentage of cells compared to PBS. Each condition consists of 6 Petri dishes and results shown here are representative of 6 dishes. Differences of ≧20% were considered significant and dotted bars represent significant data as compared to PBS control group. A representative experiment is shown. Findings involving all experimental conditions were entirely reproduced in 3 additional experiments.
Figure 17:
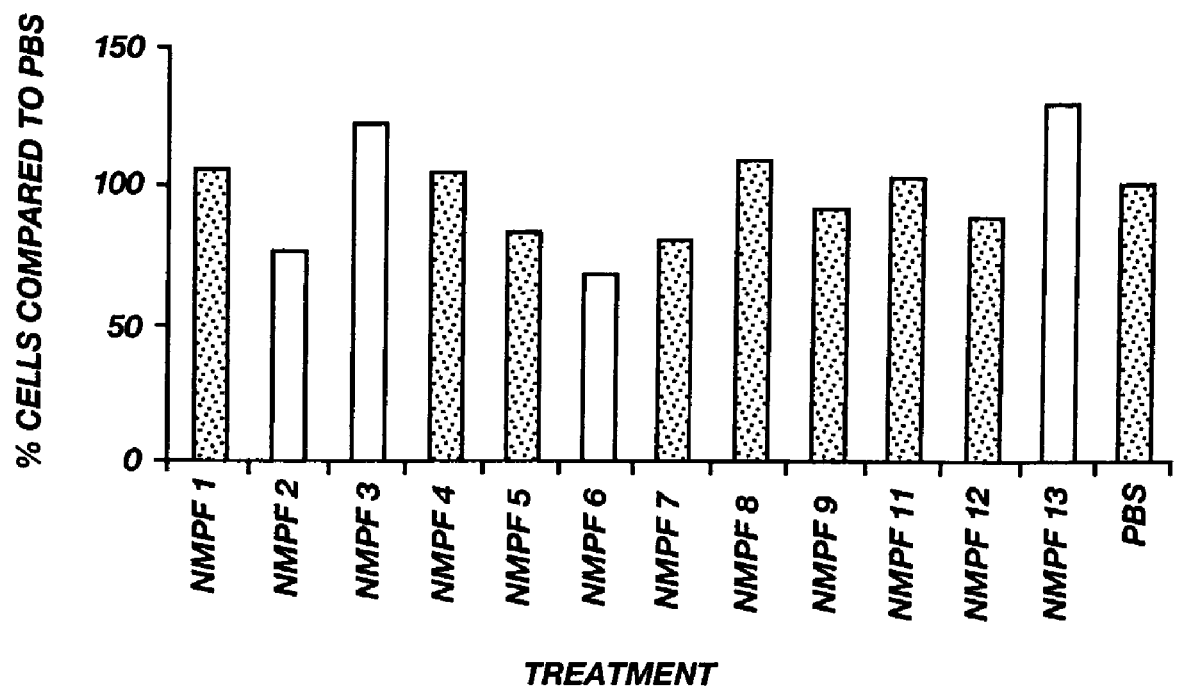
Figure 19:
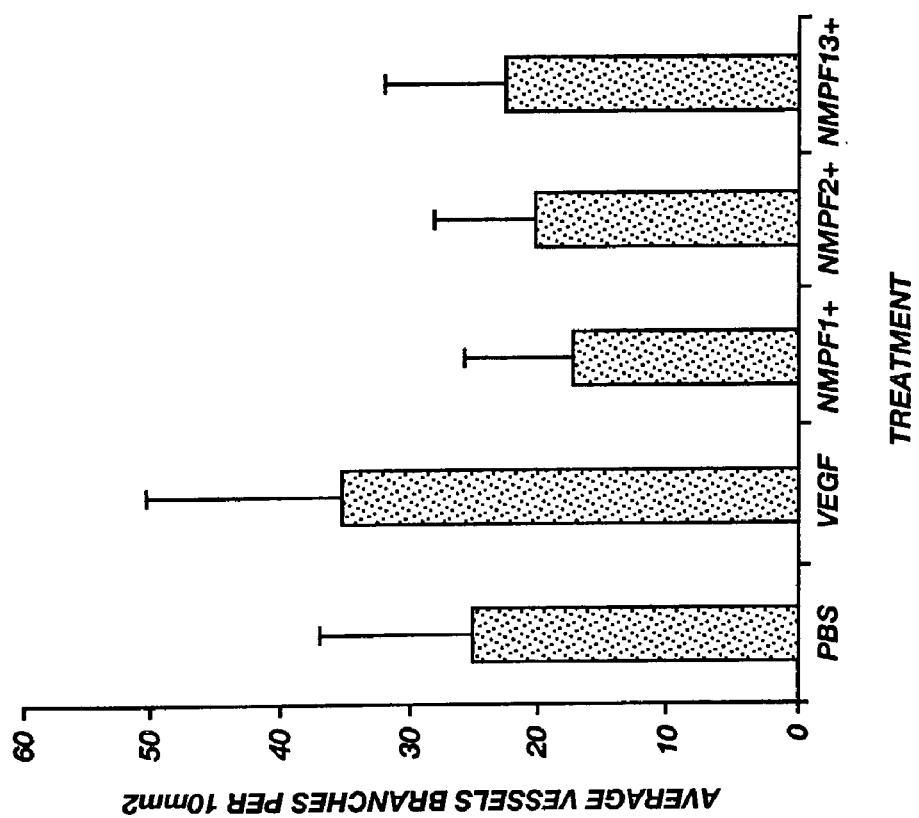
FIGS. 18–30. In vivo treatment of fertilised chicken eggs with NMPF and the effect of NMPF on angiogenesis. Fertile chicken eggs (day 0) were treated with either PBS, NMPF, VEGF or VEGF in combination with NMPF. Ten eggs were injected for every condition. On day 8 of incubation, the embryos were removed from the eggs and were placed in a 100-mm Petri dish. The embryo and the blood vessels were photographed in vivo with the use of a microscope. Of each egg one overview picture was taken and 4 detail pictures of the blood vessels were taken. Quantification of angiogenesis (vessel branches) was accomplished by counting the number of blood vessel branches. Quantification of this vasculogenesis was accomplished by measuring the blood vessel thickness. The number of blood vessel branches and vessel thickness were measured in the pictures and were correlated to a raster (in the pictures) of 10 mm² for comparison. The mean number of branches and the mean blood vessel thickness of each condition (N=10) were calculated and compared to either the PBS or VEGF controls using a Student's T-test. Line bars represent significant ($p<0.05$) data as compared to PBS control group and dotted bars represent significant ($p<0.05$) data as compared to VEGF group.
Figure 18:
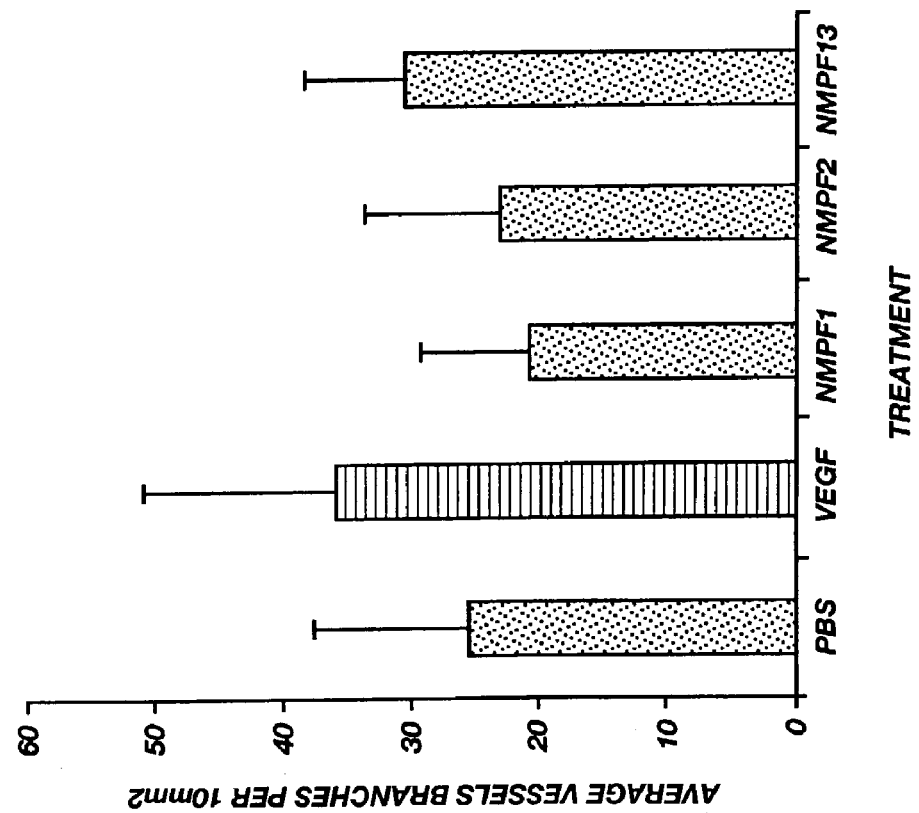
Figure 21:
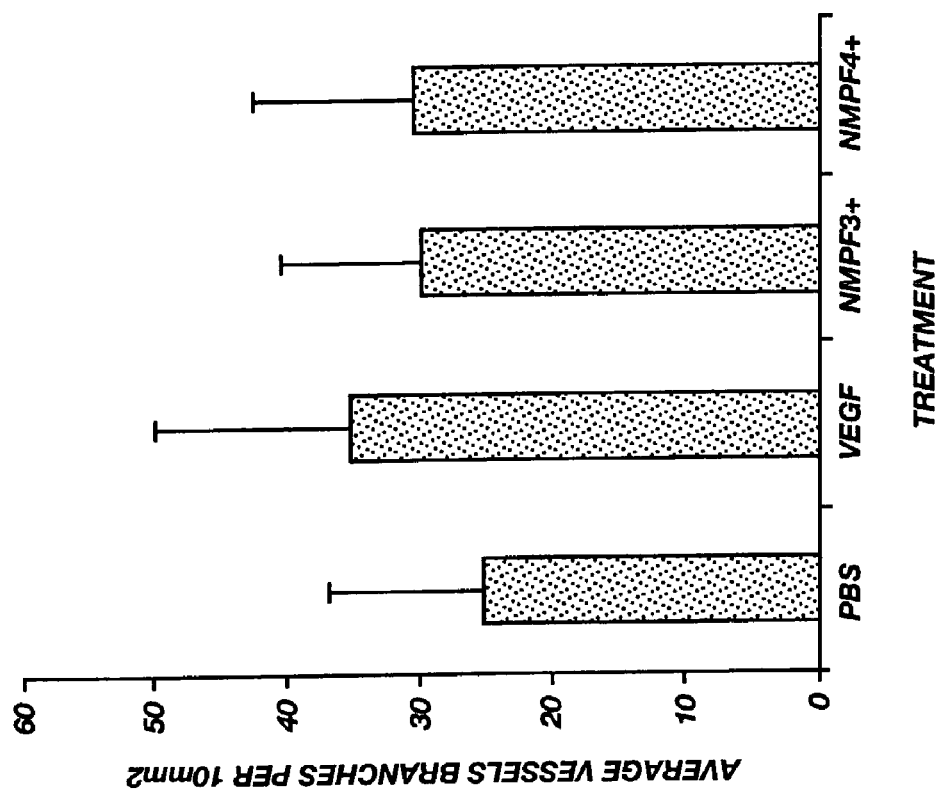
Figure 20:
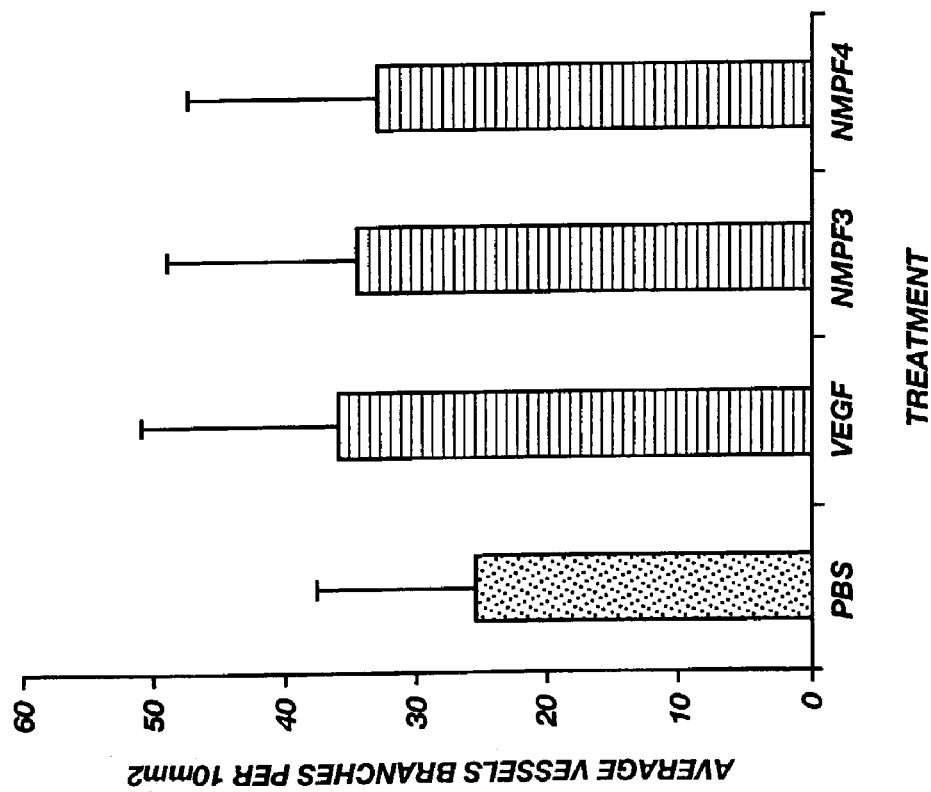
Figure 23:
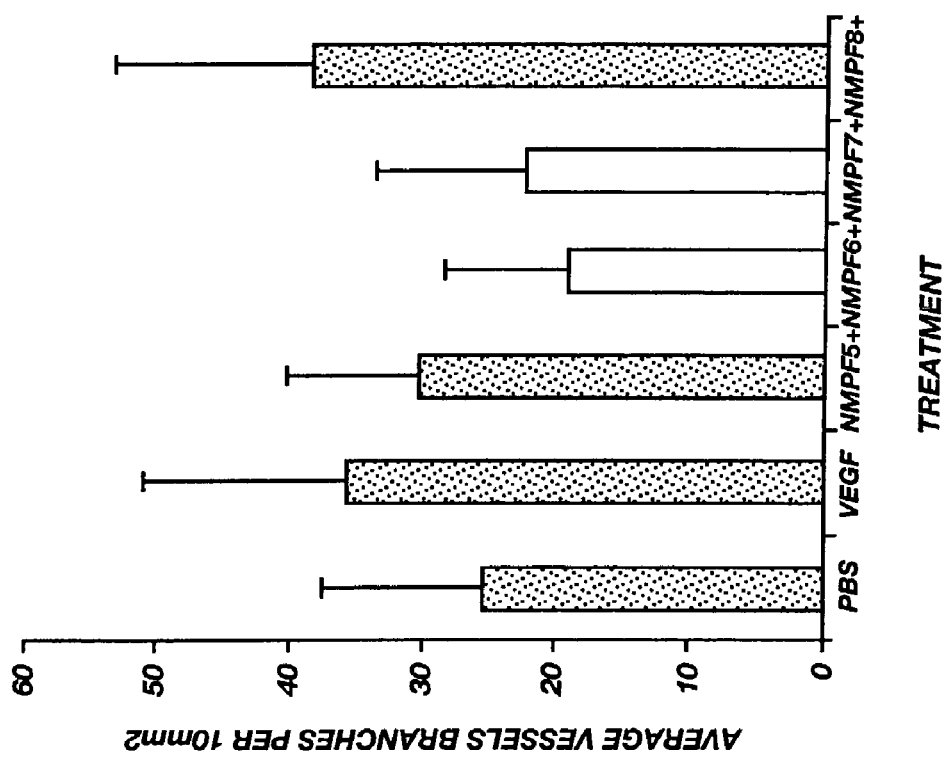
Figure 22:
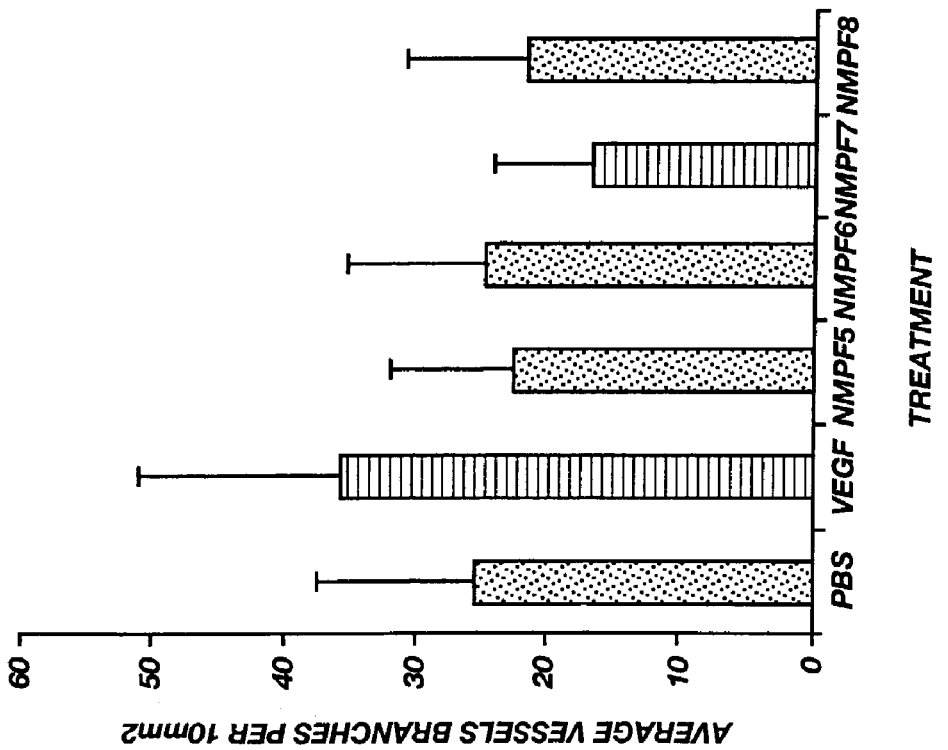
Figure 25:
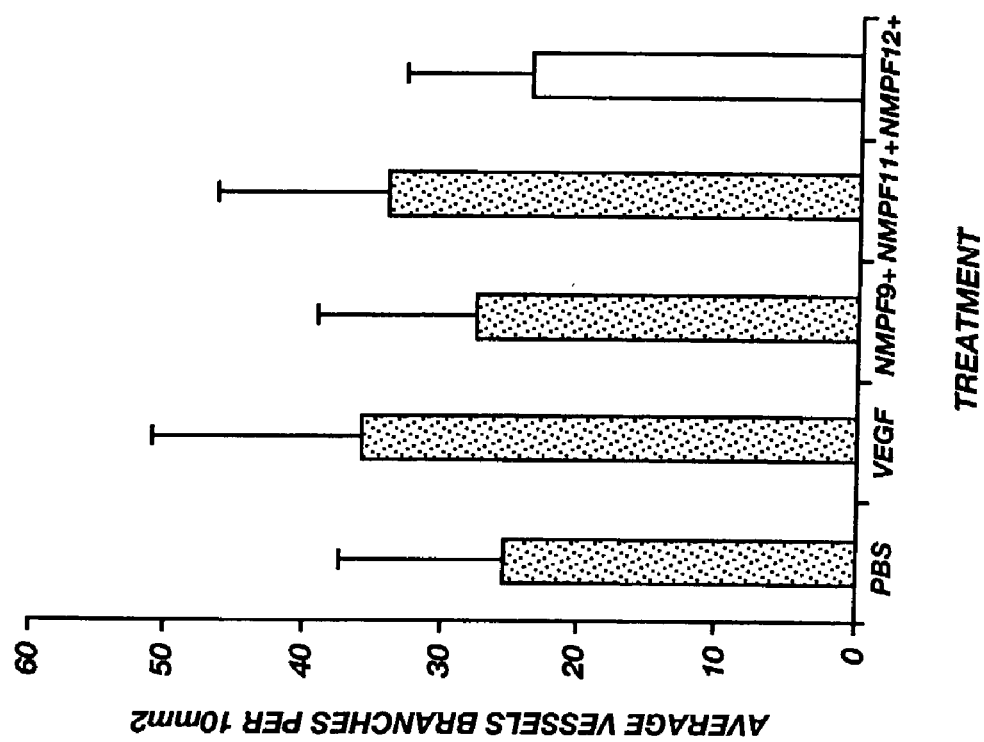
Figure 24:
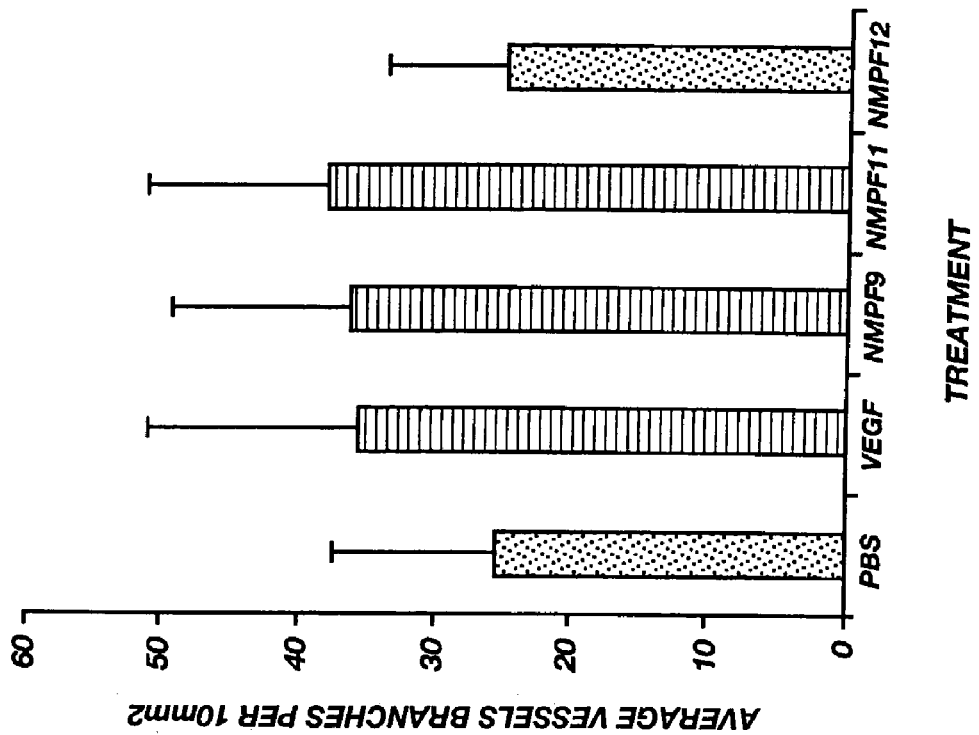
Figure 26:
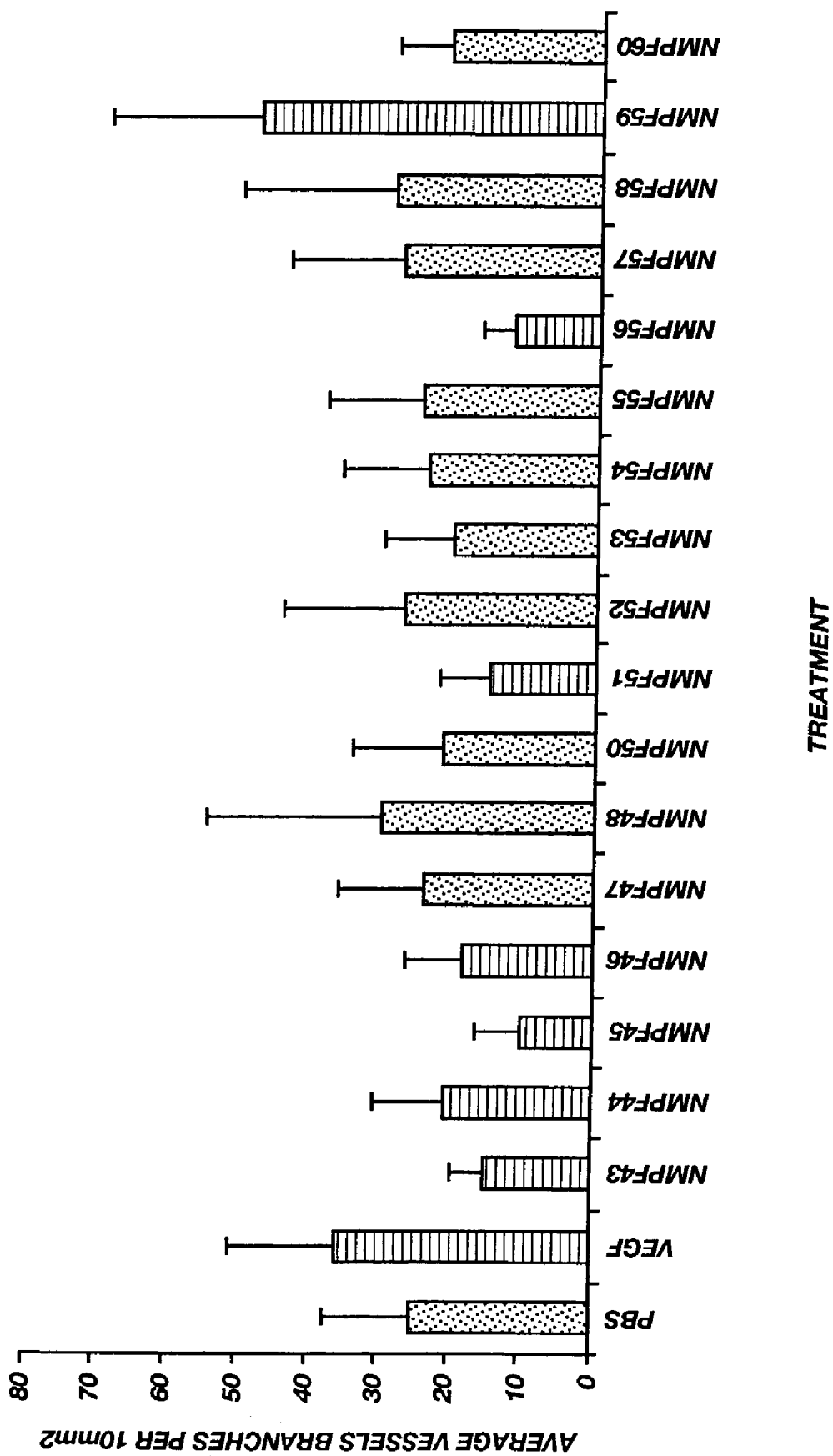
Figure 27:
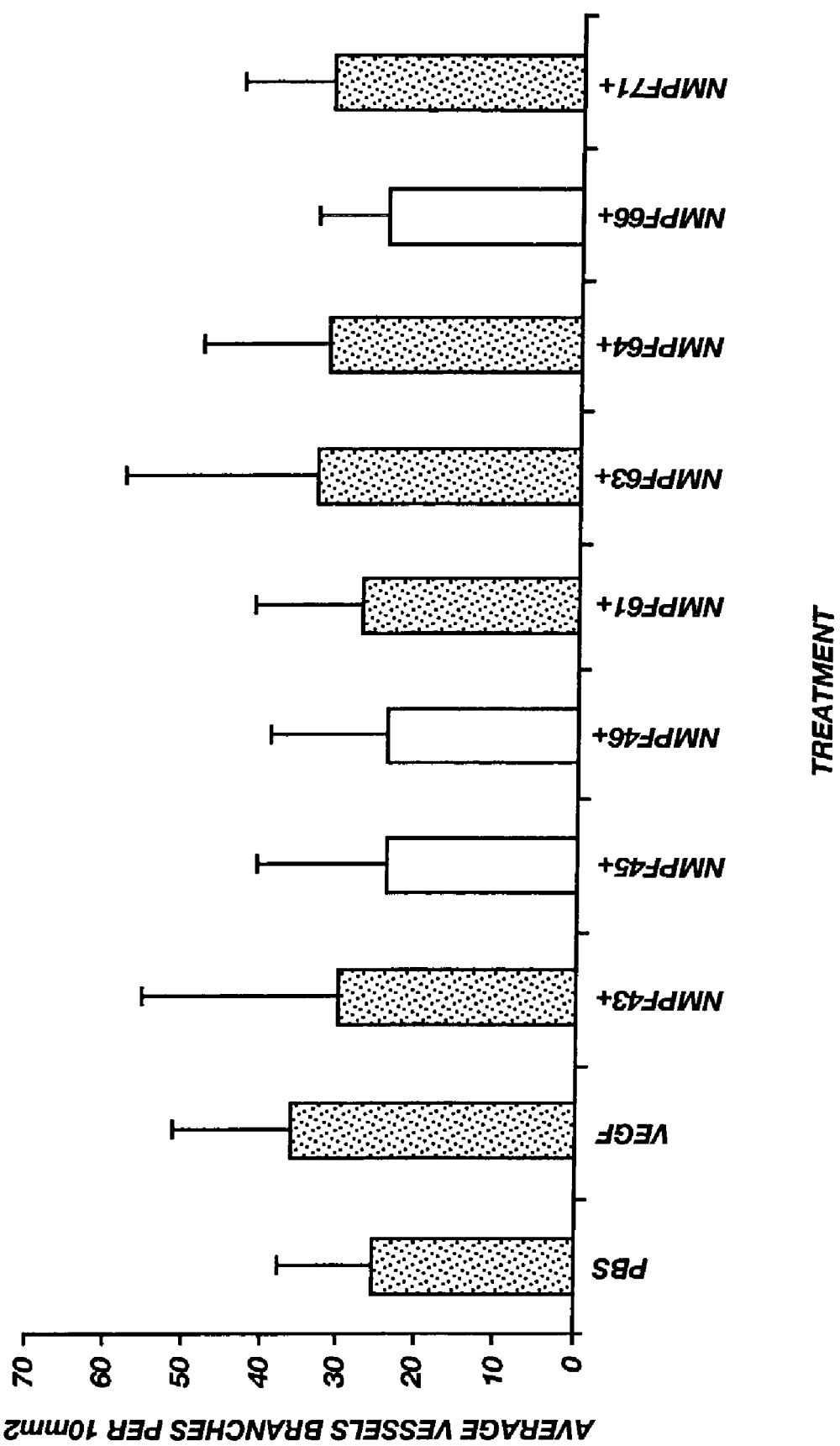
Figure 28:
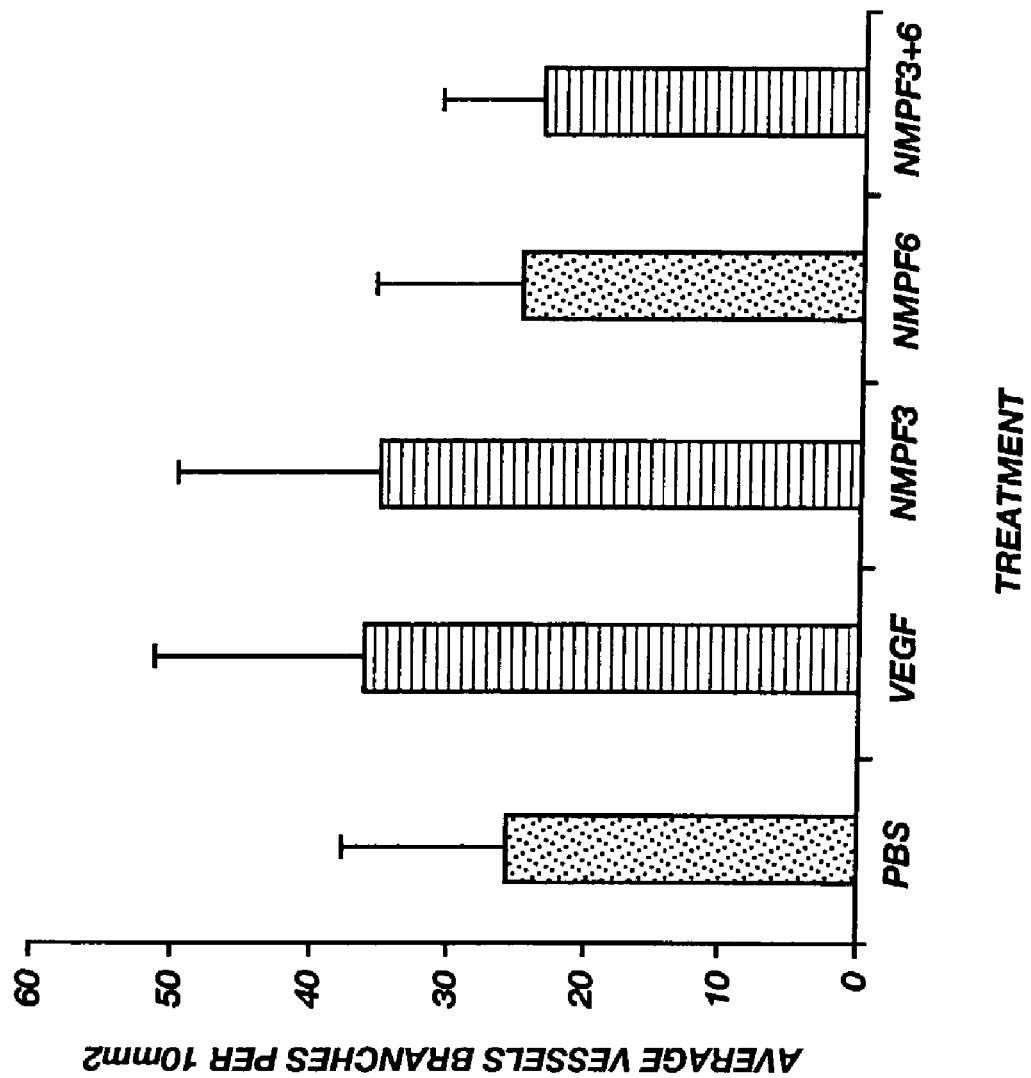

To determine the effect of LPS and NMPF in vitro on the cell yield of a nine-day culture of bone-marrow cells of female NOD mice, we isolated the BM cells from untreated NOD mice and cultured them in the presence of rmGM-CSF. In addition to rmGM-CSF, cultures were supplemented with NMPF. In these experiments, the bone-marrow cell yield of "unattached" cells was significantly increased with NMPF-1, 2, 3, 4, 5, 6, 7, 8, 9, 12 and 13 as compared to the PBS group, and no effect was observed with NMPF-11 (FIG. 16). The 'attached' bone-marrow cells of these experiments showed different yield than the 'un-attached' cells, namely, there was a significant increase in cell yield in cultures treated with NMPF-3 and 13, while cultures treated with NMPF-2 and 6 showed significant decrease in the cell yield as compared to PBS (FIG. 17) (additional results are summarized in Table 5).

Coronary Artery Occlusion (CAO) Experiments

CAO induction and treatment. NMPF have immunoregulatory effects in chronic inflammatory as well as acute inflammatory mice models. Since certain cytokines like TGF-beta1, TNF-alpha, IL-1 and ROS (reactive oxygen species) have been implicated in irreversible myocardial damage produced by prolonged episodes of coronary artery occlusion and reperfusion in vivo that leads to ischemia and myocardial infarct, we tested the cardio-protective properties of peptides in ad libitum fed male Wistar rats (300 g). The experiments were performed in accordance with the Guiding Principles in the Care and Use of Animals as approved by the Council of the American Physiological Society and under the regulations of the Animal Care Committee of the Erasmus University Rotterdam. Shortly, rats (n=3) were stabilized for 30 minutes followed by i.v. with 1 ml of peptide treatment (0.5 mg/ml) in 10 minutes. Five minutes after completion of treatment, rats were subjected to a 60-min coronary artery occlusion (CAO). In the last 5 minutes of CAO, rats were again treated over 10 minutes by i.v. with 1 ml of peptide (0.5 mg/ml) followed by 120 minutes of reperfusion (IP). Experimental and surgical procedures are described in detail in Cardiovascular Research 37(1998) 76–81. At the end of each experiment, the coronary artery was re-occluded and was perfused with 10 ml Trypan Blue (0.4%, Sigma Chemical Co.) to stain the normally perfused myocardium dark blue and delineate the nonstained area at risk (AR). The heart was then quickly excised and cut into slices of 1 mm from apex to base. From each slice, the right ventricle was removed and the left ventricle was divided into the AR and the remaining left ventricle, using micro-surgical scissors. The AR was then incubated for 10 min in 37° C. Nitro-Blue-Tetrazolium (Sigma Chemical Co.; 1 mg per 1 ml Sorensen buffer, pH 7.4), which stains vital tissue purple but leaves infarcted tissue unstained. After the infarcted area (IA) was isolated from the noninfarcted area, the different areas of the LV were dried and weighed separately. Infarct size was expressed as percentage of the AR. Control rats were treated with PBS.

Results

Coronary Artery Occlusion (CAO) Experiments

Our CAO data showed that 15 rats in the control group treated with only PBS had an infarcted area of 70±2% (average±standard error) after 60-minutes of CAO followed by 2 hours of reperfusion, while rats treated with peptides VLPALP (SEQ ID NO:3), LQGV (SEQ ID NO:1), VLPALPQVVC (SEQ ID NO:20), LQGVLPALPQ (SEQ ID NO:49), LAGV (SEQ ID NO:26), LQAV (SEQ ID NO:52) and MTRV (SEQ ID NO:42) showed an infarcted area of 62±6%, 55±6%, 55±5%, 67±2%, 51±4%, 62±6% and 68±2%, respectively. Here, we see that certain peptides (such as VLPALP (SEQ ID NO:3), LQGV (SEQ ID NO:1), VLPALPQVVC (SEQ ID NO:20), LAGV (SEQ ID NO:26)) have a protective effect on the area at risk for infarction. In addition, peptide LQAV (SEQ ID NO:52) showed a smaller infarcted area but, in some instances, the area was hemorrhagic infarcted. In addition NMPF-64 (LPGCPRGVNPVVS (SEQ ID NO:40)) had also a protective effect (35%) in CAO experiments. It is important to note that mice treated with certain above-mentioned peptides showed less viscosity of blood. Apart from immunological effect, these peptides may have also an effect on the blood coagulation system directly or indirectly since there is certain homology with blood coagulation factors (for additional results of NMPF peptides see table 5.) So, in both models, the circulatory system plays an important role in the pathogenesis of the disease.

Chicken Egg Experiments

In vivo treatment of fertilized chicken eggs with NMPF. Fertile chicken eggs (Drost Loosdrecht BV, the Netherlands) were incubated in a diagonal position in an incubator (Pas Reform BV, the Netherlands) at 37° C. and 32% relative humidity.

Solutions of NMPF peptides (1 mg/ml) and VEGF were made in PBS. At least ten eggs were injected for every condition. The treatment was performed as follows: on day 0 of incubation, a hole was drilled into the eggshell to open the air cell. A second hole was drilled 10 mm lower and right from the first hole for injection. The holes in the eggshell were disinfected with jodium. The NMPF peptides (100 μg/egg) and/or VEGF (100 ng/ml) were injected in a volume of 100 μl. The holes in the eggshell were sealed with tape (Scotch Magic™ Tape, 3M) and the eggs were placed into the incubator.

Quantification of angiogenesis. On day 7 of incubation, the eggs were viewed under a UV lamp to check if the embryos were developing in a normal way and the dead embryos were counted. On day 8 of incubation, the embryos were removed from the eggs by opening the shell at the bottom of the eggs. The shell membrane was carefully dissected and removed. The embryos were placed in a 100-mm Petri dish. The embryo and the blood vessels were photographed (Nikon E990, Japan) in vivo with the use of a microscope (Zeiss Stemi SV6, Germany). One overview picture was taken and 4 detail pictures of the blood vessels were taken. Only eggs with vital embryos were evaluated.

Data analysis. Quantification of angiogenesis was accomplished by counting the number of blood vessel branches. Quantification of vasculogenesis was accomplished by measuring the blood vessel thickness. The number of blood vessel branches and the blood vessel thickness were counted in the pictures (4 pictures/egg) using Corel Draw 7. Thereafter, the number of blood vessel branches and the thickness of the blood vessels were correlated to a raster of microscope (10 mm$^2$) for comparison.

The mean number of branches and the mean blood vessel thickness of each condition (n=10) were calculated and compared to the PBS control eggs using a Student's T-test.

Results

Chicken Egg Experiments

In order to determined the effect of NMPF on angiogenesis and vasculogenesis, we treated fertilized chicken eggs with NMPF or NMPF in combination with VEGF as described in materials and methods section. FIGS. 18–28 show that NMPF-3, 4, 9 and 11 promoted angiogenesis (p<0.05), while NMPF VEGF 7, 43, 44, 45, 46, 51 and 56 inhibited angiogenesis (p<0.05). NMPF-6, 7, 12, 45, 46 and 66 were able to inhibit angiogenesis induced by VEGF. Moreover, NMPF-6 itself did not show any effect on angiogensis, but it inhibited (p<0.05) NMPF-3-induced angiogenesis.

Figure 29:
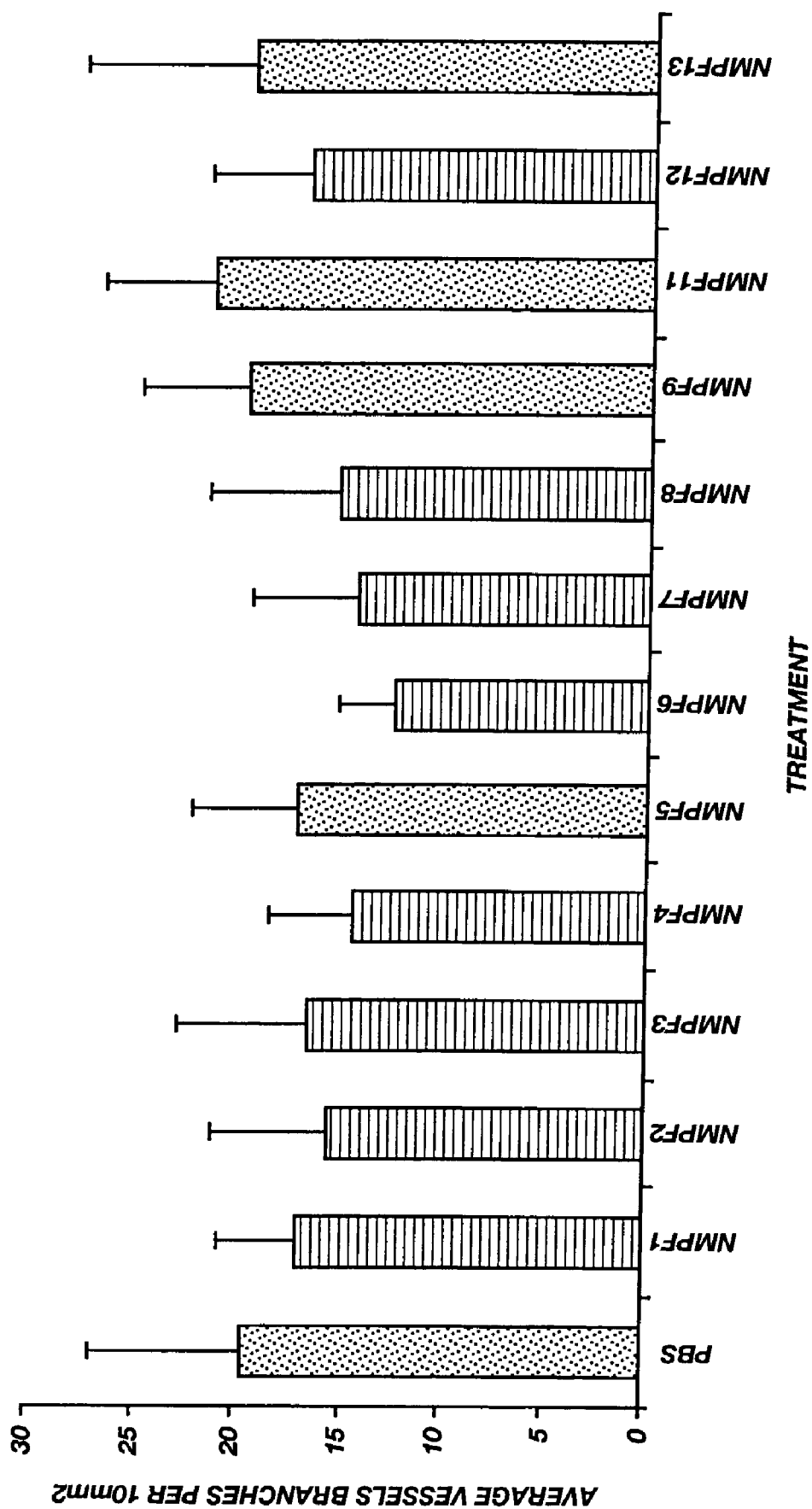
Figure 30:
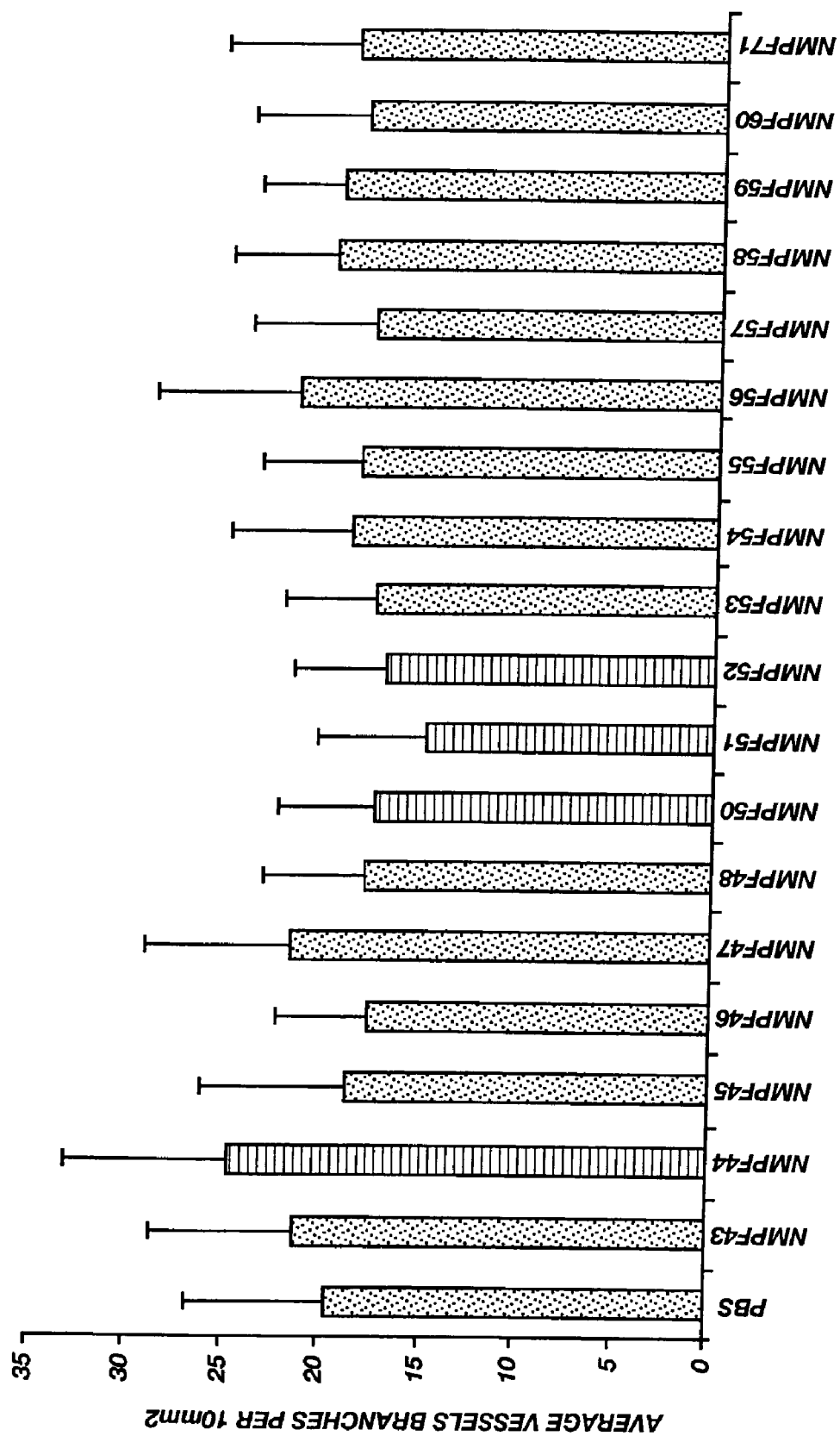

FIGS. 29–30 show that NMPF-1, 2, 3, 4, 6, 7, 8, 12, 50, 51, and 52 had vasculogenesis-inhibiting (p<0.05) effect, while only NMPF-44 promoted (p<0.05) vasculogenesis.

NOD Experiment

Mice. Female NOD mice at the age of 13–14 weeks were treated i.p. with PBS (n=6) or NMPF peptides (VLPALPQVVC (SEQ ID NO:20), LQGV (SEQ ID NO:1), GVLPALPQ (SEQ ID NO:33), VLPALP (SEQ ID NO:3), VLPALPQ (SEQ ID NO:29), MTRV (SEQ ID NO:42), LPGCPRGVNPVVS (SEQ ID NO:40), CPRGVNPVVS (SEQ ID NO:50), LPGC (SEQ ID NO:41), MTRVLQGVLPALPQVVC (SEQ ID NO:44), VVCNYRDVRFESIRLPGCPRGVNPVVSYAVALSCQCAL (SEQ ID NO:35)) (5 mg/kg, n=6) three times a week for 2 weeks. Every four days urine, was checked for the presence of glucose (Gluketur Test; Boehringer Mannheim, Mannheim, Germany). All mice used in these studies were maintained in a pathogen-free facility. They were given free access to food and water. The experiments were approved by the Animal Experiments Committee of the Erasmus University Rotterdam. Diabetes was assessed by measurement of the venous blood glucose level using an Abbott Medisense Precision glucometer. Mice were considered diabetic after two consecutive glucose measurements ≧11 mmol/l (200 mg/dl). Onset of diabetes was dated from the first consecutive reading.

A glucose tolerance test (GTT) was performed at 28 weeks of age in fasted mice (n=5) by injecting 1 g/kg D-glucose intraperitoneally (i.p.). At 0 (fasting), 5, 30 and 60 minutes, blood samples were collected from the tail and tested for glucose content.

NO Experiment

Cell culture. The RAW 264.7 murine macrophage cell line, obtained from American Type Culture Collection (Manassas, Va., USA), was cultured at 37° C. in 5% $CO_2$ using DMEM containing 10% fetal calf serum (FCS), 50 U/ml penicillin, 50 μg/ml streptomycin, 0.2 M Na-pyruvate, 2 mM glutamine and 50 μM 2-mercaptoethanol (Bio Whittaker, Europe). The medium was changed every 2 days.

Nitrite measurements. Nitrite production was measured in the RAW 264.7 macrophage supernatants. The cells (7.5× 10$^5$/ml) were cultured in 48-well plates in 500 μl of culture medium. The cells were stimulated with LPS (10 microg/ml) and/or NMPF (1 pg/ml, 1 ng/ml, 1 μg/ml) for 24 hours, then the culture media were collected. Nitrite was measured by adding 100 microl of Griess reagent (Sigma) to 100 microl samples of culture medium. The $OD_{540}$ was measured using a microplate reader, and the nitrite concentration was calculated by comparison with the $OD_{540}$ produced using standard solutions of sodium nitrite in the culture medium.

Results

NOD Experiment

In order to determine whether NMPF has an effect on the disease development in NOD mice, we tested NMPF on pre-diabetic female NOD mice at the age of 13–14 weeks. After only two weeks of treatment (injection of NMPF (5 mg/kg) every other day), glucosuria data of all NOD mice was analyzed. At the end of 17 weeks, profound anti-diabetic effect (mice negative for glucosuria) was observed in different NMPF groups as compared to the PBS group, especially in NMPF groups treated with peptides VLPALPQVVC (SEQ ID NO:20), VLPALP (SEQ ID NO:3), MTRV (SEQ ID NO:42), LPGCPRGVNPVVS (SEQ ID NO:40) and LPGC (SEQ ID NO:41). In addition, impairment of the glucose tolerance test was positively correlated to insulitis but negatively correlated to the number of functional beta cells; also this test showed that NOD mice successfully treated with NMPF were tolerant for glucose as compared to the PBS group. Our results show that PBS-treated NOD mice were all diabetic at the age of 23 weeks. Whereas, NOD mice treated three times a week for two weeks with NMPF showed profound inhibition of diabetes development. The strongest anti-diabetic effects were seen with NMPF-1, 4, 5, 6, 7, 65, 66 and commercial hCG preparation (Pregnyl, Organon, Oss, The Netherlands, batch no. 235863). These mice had a low fasting blood glucose level and were tolerant for glucose (data partially shown). However, NMPF-71 showed no effect on the incidence of diabetes, while NMPF-64 and NMPF-11 had a moderate anti-diabetic effect.

NO Experiment

NO production is a central mediator of the vascular and inflammatory response. Our results show that macrophages (RAW 264.7) stimulated with LPS produce large amounts of NO. However, these cells co-stimulated with most of the NMPF peptides (NMPF peptide 1 to 14, 43 to 66 and 69) even in a very low dose (1 pg/ml) inhibited the production of NO.

Results

ApoE Experiment

The invention provides a method and a signaling molecule for the treatment of conditions that are associated with dysfunctional LDL receptors such as apoE and other members of the apolipoprotein family. In particular, use of a signaling molecule comprising GVLPALPQ (SEQ ID NO:33) (NMPF-5) and/or VLPALP (SEQ ID NO:3) (NMPF-6) or a functional analogue or derivative thereof is preferred. Groups of apoE-deficient mice (n=6 per group) were fed a high cholesterol food and given PBS or NMPF every other day intraperitoneally. After 2.5 weeks, body weight was determined as shown in the Table below.

| | Average Weight (g) | SD (g) | p-value |
|---|---|---|---|
| ApoE-/- PBS | 31.667 | 1.007 | |
| ApoE-/- NMPF-4 | 31.256 | 1.496 | 0.536 |
| ApoE-/- NMPF-5 | 29.743 | 1.160 | 0.019 |
| Background/PBS | 26.760 | 1.582 | $10^{-6}$ |
| ApoE-/- NMPF-6 | 29.614 | 1.064 | 0.004 |

Analysis of Different Peptides in Databases

Examples of different databases in which peptides were analyzed are:

Proteomics tools: Similarity searches
BLAST data base (ExPasy, NCBI)
SMART (EMBL)
PATTINPROT (PBIL)
Post-translational modification prediction
SignalP (CBS)
Primary structure analysis
HLA Peptide Binding Predictions (BIMAS)
Prediction of MHC type I and II peptide binding
(SYFPEITHI)
Amino acid scale representation (Hydrophobicity, other
conformational parameters, etc.) (PROTSCALE)
Representations of a protein fragment as a helical wheel(Helix Wheel / HelixDraw)
RESULTS
A non-extensive l,ist of relevant oligopeptides useful for application in a method to
identify signaling molecules according to the invention derivable from protein data bases
pdb|1DE7|1DE7-A INTERACTION OF FACTOR XIII ACTIVATION PEPTIDE WITH
ALPHA-THROMBIN
LQGV, LQGVV, LQGVVP
pdb|1DL6|1DL6-A SOLUTION STRUCTURE OF HUMAN TFIIB N-TERMINAL
DOMAIN
LDALP
pdb|1QMH|1QMH-A CRYSTAL STRUCTURE OF RNA 3'-TERMINAL PHOSPHATE
CYCLASE, AN UBIQUITOUS ENZYME
LQTV, VLPAL, LVLQTVLPAL
pdb|1LYP|1LYP CAP18 (RESIDUES 106–137)
IQG, IQGL, LPKL, LLPKL
pdb|1B9O|1B9O-A HUMAN ALPHA-LACTALBUMIN
LPEL
pdb|1GLU|1GLU-A GLUCOCORTICOID RECEPTOR (DNA-BINDING DOMAIN)
PARP
pdb|2KIN|2KIN-B KINESIN (MONOMERIC) FROM *RATTUS NORVEGICUS*
MTRI
pdb|1SMP|1SMP-I MOL_ID: 1; MOLECULE: *SERRATIA METALLO* PROTEINASE;
CHAIN: A
LQKL, LQKLL, PEAP, LQKLLPEAP
pdb|1ES7|1ES7-B COMPLEX BETWEEN BMP-2 AND TWO BMP RECEPTOR IA
ECTODOMAINS
LPQ, PTLP, LQPTL
pdb|1BHX|1BHX-F X-RAY STRUCTURE OF THE COMPLEX OF HUMAN ALPHA
THROMBIN WITH THE INHIBITOR SDZ 229–357
LQV, LQVV
pdb|1VCB|1VCB-A THE VHL-ELONGINC-ELONGINB STRUCTURE
PELP
pdb|1CQK|1CQK-A CRYSTAL STRUCTURE OF THE CH3 DOMAIN FROM THE
MAK33 ANTIBODY
PAAP, PAAPQ, PAAPQV
pdb|1FCB|1FCB-A FLAVOCYTOCHROME
LQG,
pdb|1LDC|1LDC-A L-LACTATE DEHYDROGENASE: CYTOCHROME C
OXIDOREDUCTASE (FLAVOCYTOCHROME B = 2 =) (E.C.1.1.2.3) MUTANT WITH
TYR 143 REPLACED BY PHE (Y143F) COMPLEXED WITH PYRUVATE
LQG
pdb|1BFB|1BFB BASIC FIBROBLAST GROWTH FACTOR COMPLEXED WITH
HEPARIN TETRAMER FRAGMENT
LPAL, PALP, PALPE
pdb|1MBF|1MBF MOUSE C-MYB DNA-BINDING DOMAIN REPEAT 1
LPN
pdb|1R2A|1R2A-A THE MOLECULAR BASIS FOR PROTEIN KINASE A
LQG, LTELL -continued pdb|1CKA|1CKA-B C-CRK (N-TERMINAL SH3 DOMAIN) (C-CRKSH3-N)
COMPLEXED WITH C3G PEPTIDE (PRO-PRO-PRO-ALA-LEU-PRO-PRO-LYS-LYS-
ARG)
PALP
pdb|1RLQ|1RLQ-R C-SRC (SH3 DOMAIN) COMPLEXED WITH THE PROLINE-
RICH LIGAND RLP2 (RALPPLPRY) (NMR, MINIMIZED AVERAGE STRUCTURE)
LPPL, PPLP
pdb|1TNT|1TNT MU TRANSPOSASE (DNA-BINDING DOMAIN) (NMR, 33
STRUCTURES)
LPG, LPGL, EPK
pdb|1GJS|1GJS-A SOLUTION STRUCTURE OF THE ALBUMIN BINDING DOMAIN
OF STREPTOCOCCAL PROTEIN G
LAAL, LAALP
pdb|1GBR|1GBR-B GROWTH FACTOR RECEPTOR-BOUND PROTEIN 2 (GRB2, N-
TERMINAL SH3 DOMAIN) COMPLEXED WITH SOS-A PEPTIDE (NMR, 29
STRUCTURES)
LPKL, PKLP
pdb|1A78|1A78-A COMPLEX OF TOAD OVARY GALECTIN WITH THIO-
DIGALACTOSE
VLPSIP
pdb|1ISA|1ISA-A IRON(II) SUPEROXIDE DISMUTASE (E.C.1.15.1.1)
LPAL, PALP
pdb|1FZV|1FZV-A THE CRYSTAL STRUCTURE OF HUMAN PLACENTA GROWTH
FACTOR-1 (PLGF-1), AN ANGIOGENIC PROTEIN AT 2.0A RESOLUTION
PAVP, MLPAVP
pdb|1JLI|1JLI HUMAN INTERLEUKIN 3 (IL-3) MUTANT WITH TRUNCATION AT
BOTH N- AND C-TERMINI AND 14 RESIDUE CHANGES, NMR, MINIMIZED
AVERAGE
LPC, LPCL, PCLP
pdb|1HSS|1HSS-A 0.19 ALPHA-AMYLASE INHIBITOR FROM WHEAT
VPALP
pdb|3CRX|3CRX-A CRE RECOMBINASE/DNA COMPLEX INTERMEDIATE I
LPA, LPAL, PALP
pdb|1PRX|1PRX-A HORF6 A NOVEL HUMAN PEROXIDASE ENZYME
PTIP, VLPTIP
pdb|1RCY|1RCY RUSTICYANIN (RC) FROM *THIOBACILLUS FERROOXIDANS*
VLPGFP
pdb|1A3Z|1A3Z REDUCED RUSTICYANIN AT 1.9 ANGSTROMS
PGFP, VLPGFP
pdb|1GER|1GER-A GLUTATHIONE REDUCTASE (E.C.1.6.4.2) COMPLEXED WITH
FAD
LPALP, PALP
pdb|1PBW|1PBW-A STRUCTURE OF BCR-HOMOLOGY (BH) DOMAIN
PALP
pdb|1BBS|1BBS RENIN (E.C.3.4.23.15)
MPALP
AI188872 11.3 366 327 18 382 [*Homo sapiens*]qd27c01.x1
Soares_placenta_8to9weeks_2NbHP8to9W
*Homo sapiens* cDNA clone IMAGE:1724928 3' similar to
gb:J00117 CHORIOGONADOTROPIN BETA CHAIN PRECURSOR
(HUMAN);, mRNA sequence.; minus strand; translated
MXRVLQGVLPALPQVVC, MXRV, MXR,
AI126906 19.8 418 343 1 418 [*Homo sapiens*]qb95f01.x1 Soares_fetal_heart_NbHH19W
*Homo sapiens* cDNA clone IMAGE:1707865 3' similar to gb:J00117
CHORIOGONADOTROPIN BETA CHAIN PRECURSOR
(HUMAN);, mRNA sequence.; minus strand; translated
ITRVMQGVIPALPQVVC
AI221581 29.1 456 341 23 510 [*Homo sapiens*]qg20a03.x1
Soares_placenta_8to9weeks_2NbHP8to9W *Homo sapiens* cDNA clone IMAGE:1760044
3' similar to gb:J00117 CHORIOGONADOTROPIN BETA CHAIN PRECURSOR
(HUMAN);, mRNA sequence.; minus strand; translated
MTRVLQVVLLALPQLV
Mm.42246.3 Mm.42246 101.3 837 304 28 768 GENE = Pck1 PROTSIM = pir:T24168
phosphoenolpyruvate carboxykinase 1,
cytosolic; translated
KVIQGSLDSLPQAV, LDSL, LPQ
Mm.22430.1 Mm.22430 209.4 1275 157 75 1535 GENE = Ask-pending
PROTSIM = pir:T02633 activator of S phase kinase; translated
VLQAILPSAPQ, LQA, LQAIL, PSAP, LPS
Hs.63758.4 Hs.63758 93.8 3092 1210 51 2719 GENE = TFR2
PROTSIM = pir:T30154 transferrin receptor 2; translated KVLQGRLPAVAQAV, LQG,
LPA, LPAV
Mm.129320.2 Mm.129320 173.0 3220 571 55 2769 GENE = PROTSIM = pir:T 16409
Sequence 8 from Patent WO9950284; translated
LVQKVVPMLPRLLC, LVQ, LPRL, PMLP
Mm.22430.1 Mm.22430 209.4 1275 157 75 1535 GENE = Ask-pending
PROTSIM = pir:T02633 activator of S phase kinase; translated
VLQAILPSAPQ, LQA, LQAIL, PSAP, PSAPQ -continued P20155 IAC2_HUMAN Acrosin-trypsin inhibitor II precursor (HUSI-II) [SPINK2] [*Homo sapiens*]
LPGCPRHFNPV, LPG, LPGC
Rn.2337.1 Rn.2337 113.0 322 104 1 327 GENE = PROTSIM = PRF:1402234A Rat pancreatic secretory trypsin inhibitor type II (PSTI-II) mRNA, complete cds; minus strand; translated
LVGCPRDYDPV, LVG, LVGC
Hs.297775.1 Hs.297775 43.8 1167 753 31 1291 GENE = PROTSIM = sp:O00268 ESTs, Weakly similar to T2D3_HUMAN TRANSCRIPTION INITIATION FACTOR TFIID 135 KDA SUBUNIT [*H.sapiens*]; minus strand; translated
PGCPRG, PGCP
Mm.1359.1 Mm.1359 PROTSTM = pir.A39743 urokinase plasmiogen activator receptor
LPGCP, PGCP, LPG, LPGC
sptrembl|O56177|O56177 ENVELOPE GLYCOPROTEIN
VLPAAP, PAAP
sptrembl|Q9W234|Q9W234 CG13509 PROTEIN.//:trembl|AE003458|AE003458_7 gene: "CG13509" *Drosophila melanogaster* genomic scaffold
LAGTIPATP, LAG, PATP
swiss|P81272|NS2B HUMAN NITRIC-OXIDE SYNTHASE IIB (EC 1.14.13.39) (NOS, TYPE II B) (NOSIIB) (FRAGMENTS)
GVLPAVP, LPA, VLPAVP, PAVP
sptrembl|O30137|O30137 HYPOTHETICAL 17.2 KDA
GVLPALP, PALP, LPAL
sptrembl|Q9IYZ3|Q9IYZ3 DNA POLYMERASE
GLLPCLP, LPC, LPCL, PCLP
sptrembl|Q9PVW5|Q9PVW5 NUCLEAR PROTEIN NP220
PGAP, LPQRPRGPNP, LPQ, PROP, PNP
Hs.303116.2 PROTSIM = pir;T33097 stromal cell-derived factor 2-like1; translated
GCPR
pdb|1DU3|1DU3-A CRYSTAL STRUCTURE OF TRAIL-SDR5
GCPRGM
pdb|1D0G|1D0G-R CRYSTAL STRUCTURE OF DEATH RECEPTOR 5 (DR5) BOUND TO APO2L/TRAIL
GCPRGM
pdb|1BIO|1BIO HUMAN COMPLEMENT FACTOR D IN COMPLEX WITH ISATOIC ANHYDRIDE INHIBITOR
LQHV
pdb|4NOS|4NOS-A HUMAN INDUCIBLE NITRIC OXIDE SYNTHASE WITH INHIBITOR
FPGC, PGCP
pdb|1FL7|1FL7-B HUMAN FOLLICLE STIMULATING HORMONE
PARP, VPGC
pdb|1HR6|1HR6-A YEAST MITOCHONDRIAL PROCESSING PEPTIDASE
CPRG, LKGC
pdb|1BFA|1BFA RECOMBINANT BIFUNCTIONAL HAGEMAN FACTOR/AMYLASE INHIBITOR FROM
PPGP, LPGCPREV, LPGC, PGCP, CPRE
swissnew|P01229|1SHB HUMAN Lutropin beta chain precursor
MMRVLQAVLPPLPQVVC, MMR, MMRV, LQA, LQAV, VLPPLP, PPLP, QVVC, VVC, VLPPLPQ, AVLPPLP, AVLPPLPQ
swissnew|P07434|CGHB PAPAN Choriogonadotropin beta chain precursor
MMRVLQAVLPPVPQVVC, MMR, MMRV, LQA, LQAG, VLPPVP, VLPPVPQ, QVVC, VVC, AVLPPVP, AVLPPVPQ
swissnew|Q28376|TSHB HORSE Thyrotropin beta chain precursor
MTRD, LPK, QDVC, DVC, IPGC, PGCP
swissnew|P95180|NUOB MYCTU NADH dehydrogenase I chain B
LPGC, PGCP
sptrembl|Q9Z284|Q9Z284 NEUTROPHIL ELASTASE
PALP, PALPS
sptrembl|Q9UCG8|Q9UCG8 URINARY GONADOTROPHIN PEPTIDE (FRAGMENT)
LPGGPR, LPG, LPGG, GGPR
XP_028754 growth hormone releasing hormone [*Homo sapiens*]
LQRG, LQRGV, LGQL
SignalP (CBS)
SignalP predictions: (for example)
MTRVLQGVLPALP
QVVC

| HLA Peptide Binding Predictions (BIMAS) (For example) | |
|---|---|
| HLA molecule type I (A_0201): | Half time of dissociation |
| VLQGVLPAL | (84) |
| GVLPALPQV | (51) |
| VLPALPQVV | (48) |
| RLPGCPRGV | (14) |
| TMTRVLQGV | (115) |

-continued

|  | | scores |
|---|---|---|
| MHC II (H2-Ak 15-mers) | C P T M T R V L Q G V L P A L | 14 |
|  | P G C P R G V N P V V S Y A V | 14 |
| HLA-DRB1*0101 15-mers | P R G V N P V V S Y A V A L S | 29 |
|  | T R V L Q G V L P A L P Q V V | 28 |
|  | L Q G V L P A L P Q V V C N Y | 22 |
| HLA-DRB1*0301 (DR17) 15-mers | C P T M T R V L Q G V L P A L | 26 |
|  | M T R V L Q G V L P A L P Q V | 21 |
|  | S I R L P G C P R G V N P V V | 17 |

TABLE 1

Results of shock experiments in mice

| | SEQUENCE | % SURVIVAL IN TIME (HRS) | | | |
|---|---|---|---|---|---|
| | | 0 | 16 | 40 | 72 |
| TEST SUBSTANCE | | | | | |
| PBS | | 100 | 100 | 67 | 17 |
| PG23 | | 100 | 100 | 100 | 100 |
| PG25 | | 100 | 83 | 83 | 83 |
| PEPTIDE NMPF | | | | | |
| 1 | VLPALPQVVC | 100 | 100 | 50 | 17 |
| 2 | LQGVLPALPQ | 100 | 67 | 0 | 0 |
| 3 | LQG | 100 | 83 | 20 | 17 |
| 4 | LQGV | 100 | 100 | 100 | 100 |
| 5 | GVLPALPQ | 100 | 100 | 80 | 17 |
| 6 | VLPALP | 100 | 100 | 100 | 100 |
| 7 | VLPALPQ | 100 | 83 | 0 | 0 |
| 8 | GVLPALP | 100 | 100 | 83 | 67 |
| 9 | VVC | 100 | 100 | 50 | 50 |
| 11 | MTRV | 100 | 100 | 67 | 50 |
| 12 | MTR | 100 | 100 | 67 | 50 |
| 13 | LQGVLPALPQVVC | 100 | 100 | 100 | 100 |
| 14 | (CYCLIC) LQGVLPALPQVVC | 100 | 83 | 83 | 83 |
| 64 | LPGCPRGVNPVVS | 100 | 100 | 100 | 100 |
| 66 | LPGC | 100 | 100 | 100 | 100 |

TABLE 2

Additional results of shock experiments

NMPF SEQUENCE ID:

| | ANTI-SHOCK EFFECT |
|---|---|
| LQGV | +++ |
| AQGV | +++ |
| LQGA | +++ |
| VLPALP | +++ |
| ALPALP | ++ |
| VAPALP | ++ |
| ALPALPQ | ++ |
| VLPAAPQ | ++ |
| VLPALAQ | +++ |
| | SHOCK ACCELERATING EFFECT |
| LAGV | +++ |
| LQAV | +++ |
| VLAALP | +++ |
| VLPAAP | +++ |
| VLPALA | +++ |
| VLPALPQ | +++ |
| VLAALPQ | +++ |
| VLPALPA | +++ |

TABLE 3

Further additional results of shock experiments

| | % SURVIVAL IN TIME (HRS) | | | |
|---|---|---|---|---|
| NMPF PEPTIDES | Tx 0 | 14 | 24 | 48 |
| PBS | 100 | 100 | 100 | 0 |
| NMPF-3 | 100 | 100 | 100 | 0 |
| NMPF-5 | 100 | 100 | 100 | 100 |
| NMPF-7 | 100 | 100 | 100 | 67 |
| NMPF-8 | 100 | 100 | 100 | 100 |
| NMPF-9 | 100 | 100 | 100 | 100 |
| NMPF-11 | 100 | 100 | 100 | 100 |
| NMPF-12 | 100 | 100 | 100 | 100 |
| NMPF-43 | 100 | 100 | 100 | 100 |
| NMPF-45 | 100 | 100 | 100 | 100 |
| NMPF-46 | 100 | 100 | 100 | 100 |
| NMPF-50 | 100 | 100 | 100 | 100 |
| NMPF-53 | 100 | 100 | 100 | 100 |
| NMPF-58 | 100 | 100 | 100 | 100 |
| NMPF-60 | 100 | 100 | 100 | 100 |

TABLE 4

Further additional results

| | SICKNESS SCORES | | | |
|---|---|---|---|---|
| NMPF PEPTIDES | Tx 0 | 14 | 24 | 48 |
| PBS | 0,0,0,0,0 | 5,5,5,5,4,4 | 5,5,5,5,5,5 | †††††† |
| NMPF-3 | 0,0,0,0,0 | 3,3,3,3,3,4 | 4,4,4,4,4,4 | ††††† |
| NMPF-5 | 0,0,0,0,0 | 5,5,5,5,5,5 | 5,5,5,5,5,5 | 2,2,2,2,2,2 |
| NMPF-7 | 0,0,0,0,0 | 1,1,4,4,4,4 | 5,5,5,5,5,5 | 2,2,2,2,†† |
| NMPF-8 | 0,0,0,0,0 | 3,3,5,5,5,5 | 5,5,5,5,5,5 | 2,2,4,4,4,5 |
| NMPF-9 | 0,0,0,0,0 | 3,3,4,4,5,5 | 2,2,2,2,2,2 | 1,1,2,2,2,2 |
| NMPF-11 | 0,0,0,0,0 | 1,1,3,3,4,4 | 2,2,2,2,4,4 | 1,1,1,1,1,1 |
| NMPF-12 | 0,0,0,0,0 | 1,1,1,1,3,3 | 1,1,1,1,1,1 | 1,1,1,1,1,1 |
| NMPF-43 | 0,0,0,0,0 | 1,1,4,4,4,4 | 1,1,1,1,3,3 | 2,2,2,2,2,2 |
| NMPF-45 | 0,0,0,0,0 | 5,5,5,5,4,4 | 3,3,4,4,5,5 | 2,2,4,4,5,5 |
| NMPF-46 | 0,0,0,0,0 | 1,1,2,2,2,2 | 1,1,1,1,1,1 | 1,1,1,1,1,1 |
| NMPF-50 | 0,0,0,0,0 | 1,1,1,1,3,3 | 2,2,2,2,3,3 | 1,1,1,1,1,1 |
| NMPF-53 | 0,0,0,0,0 | 5,5,5,5,5,5 | 5,5,5,5,5,5 | 1,1,2,2,2,2 |
| NMPF-58 | 0,0,0,0,0 | 5,5,5,5,3,3 | 5,5,5,5,3,3 | 1,1,1,1,1,1 |
| NMPF-60 | 0,0,0,0,0 | 1,1,4,4,2,2 | 2,2,2,2,4,4 | 1,1,1,1,1,1 |

TABLE 5

Summary of results of the various peptides in the various experiments.

| ID | SEQUENCE | SEPSIS | ANGIOGENSIS | CAO | DC | NOD |
|---|---|---|---|---|---|---|
| NMPF-1 | VLPALPQVVC | −+ | | + | + | |
| NMPF-2 | LQGVLPALPQ | −+ | | | + | |
| NMPF-3 | LQG | −+ | | + | + | |
| NMPF-4 | LQGV | + | + | + | + | |
| NWPF-5 | GVLPALPQ | −+ | | | + | |
| NMPF-6 | VLPALP | + | + | + | + | |
| NMPF-7 | VLPALPQ | + | + | | + | |
| NMPF-8 | GVLPALP | −+ | | | + | |
| NMPF-9 | VVC | + | + | | + | |
| NMPF-10 | QVVC | | | | | |
| NMPF-11 | MTRV | + | + | | + | + |
| NMPF-12 | MTR | −+ | + | | + | |
| NMPF-13 | LQGVLPALPQVVC | + | | | + | |
| NMPF-14 | cyclic-LQGVLPALPQVVC | + | | | | |
| NMPF-43 | AQG | + | + | | + | |
| NMPF-44 | LAG | | + | | | |
| NMPF-45 | LQA | + | + | | | |
| NMPF-46 | AQGV | + | + | | + | |
| NMPF-47 | LAGV | −+ | | + | + | |
| NMPF-48 | LQAV | | | | | |
| NMPF-49 | LQGA | + | | | | |
| NMPF-50 | ALPALP | + | | | + | |
| NMPF-51 | VAPALP | + | + | | | |
| NMPF-52 | VLAALP | | | | | |
| NMPF-53 | VLPAAP | + | | | + | |
| NMPF-54 | VLPALA | | | | | |
| NMPF-55 | ALPALPQ | + | | | | |
| NMPF-56 | VAPALPQ | | + | | | |
| NMPF-57 | VLAALPQ | | | | | |
| NMPF-58 | VLPAAPQ | + | | | + | |
| NMPF-59 | VLPALAQ | + | + | | | |
| NMPF-60 | VLPALPA | + | | | + | |
| NMPF-61 | VVCNYRDVRFESIRLPGCPRGVNPVVSYAVALSCQCAL | −+ | | + | | |
| NMPF-62 | VVCNYRDVRFESIRLPGCPRGVNPVVSYAVALSCQ | | | | | |
| NMPF-63 | SIRLPGCPRGVNPVVS | −+ | | | | |
| NMPF-64 | LPGCPRGVNPVVS | | | | + | |
| NMPF-65 | CPRGVNPVVS | | | | | |
| NMPF-66 | LPGC | + | + | | + | |
| NMPF-67 | CPRGVNP | | | | | |
| NMPF-68 | PGCP | −+ | | | | |
| NMPF-69 | RPRCRPINATLAVEKEGCPVCITVNTTICAGYCPT | | | | | |
| NMPF-70 | MTRVLQGVLPALPQ | −+ | | | | |
| NMPF-71 | MTRVLPGVLPALPQVVC | −+ | | | | |
| NMPF-74 | CALCRRSTTDCGGPKDHPLTC | | | | | |
| NMPF-75 | SKAPPPSLPSPSRLPGPC | | | | | |
| NMPF-76 | TCDDPRFQDSSSSKAPPPSLPSPSRLPGPSDTPILPQ | | | | | |

+ = effects; −+ = variable effect; no entry is no effect or not yet tested when table was assembled

TABLE 6

MODULATION OF NO AND/OR TNF-ALPHA

| ID | SEQUENCE | TNF-A | NO | TNF-A and NO |
|---|---|---|---|---|
| NMPF-1 | VLPALPQVVC | ++ | ++++ | ++++ |
| NMPF-2 | LQGVLPALPQ | −+ | ++++ | ++++ |
| NMPF-3 | LQG | + | ++++ | ++++ |
| NMPF-4 | LQGV | ++++ | ++++ | +++++++ |
| NMPF-5 | GVLPALPQ | ++++ | ++++ | +++++++ |
| NMPF-6 | VLPALP | ++++ | ++++ | +++++++ |
| NMPF-7 | VLPALPQ | ++++ | ++++ | +++++++ |
| NMPF-8 | GVLPALP | ++++ | ++++ | +++++++ |
| NMPF-9 | VVC | ++++ | ++++ | +++++++ |
| NMPF-10 | QVVC | ++++ | +++ | ++++ |
| NMPF-11 | MTRV | ++++ | ++++ | ++++ |
| NMPF-12 | MTR | ++++ | ++++ | ++++ |
| NMPF-13 | LQGVLPALPQVVC | ++ | ++++ | ++++ |
| NMPF-14 | cyclic-LQGVLPALPQVVC | ++ | ++++ | ++++ |
| NMPF-43 | AQG | ++++ | ++++ | +++++++ |
| NMPF-44 | LAG | −+ | ++++ | ++++ |
| NMPF-45 | LQA | ++++ | ++++ | +++++++ |
| NMPF-46 | AQGV | ++++ | ++++ | +++++++ |
| NMPF-47 | LAGV | ++ | ++++ | ++++ |

TABLE 6-continued

MODULATION OF NO AND/OR TNF-ALPHA

| ID | SEQUENCE | TNF-A | NO | TNF-A and NO |
|---|---|---|---|---|
| NMPF-48 | LQAV | ++ | ++++ | ++++ |
| NMPF-49 | LQGA | ++ | ++++ | ++++ |
| NMPF-50 | ALPALP | ++++ | ++++ | +++++++ |
| NMPF-51 | VAPALP | + | +++ | ++++ |
| NMPF-52 | VLAALP | ++ | ++++ | ++++ |
| NMPF-53 | VLPAAP | ++++ | ++++ | +++++++ |
| NMPF-54 | VLPALA | + | ++++ | +++++ |
| NMPF-55 | ALPALPQ | + | ++++ | ++++ |
| NMPF-56 | VAPALPQ | −+ | ++++ | ++++ |
| NMPF-57 | VLAALPQ | + | ++++ | ++++ |
| NMPF-58 | VLPAAPQ | ++++ | ++++ | +++++++ |
| NMPF-59 | VLPALAQ | ++ | ++++ | ++++ |
| NMPF-60 | VLPALPA | ++++ | ++++ | +++++++ |
| NMPF-61 | VVCNYRDVRFESIRLP GCPRGVNPVVSYAVAL SCQCAL | −+ | ++++ | ++++ |
| NMPF-62 | VVCNYRDVRFESIRLP GCPRGVNPVVSYAVAL SCQ | −+ | ++++ | ++++ |
| NMPF-63 | SIRLPGCPRGVNPVVS | −+ | ++ | ++ |
| NMPF-64 | LPGCPRGVNPVVS | ++ | ++++ | ++++ |
| NMPF-65 | CPRGVNPVVS | ++ | +++ | +++ |
| NMPF-66 | LPGC | +++ | ++ | +++ |
| NMPF-67 | CPRGVNP | −+ | + | + |
| NMPF-68 | PGCP | + | + | +++ |
| NMPF-69 | RPRCRPINATLAVEKE GCPVCITVNTTICAGY CPT | −+ | ++ | ++ |
| NMPF-70 | MTRVLQGVLPALPQ | −+ | + | + |
| NMPF-71 | MTRVLPGVLPALPQVV C | −+ | −+ | −+ |
| NMPF-74 | CALCRRSTTDCGGPKD HPLTC | −+ | ++ | + |
| NMPF-75 | SKAPPPSLPSPSRLPG PS | + | ++ | ++ |
| NMPF-76 | TCDDPRFQDSSSSKAP PPSLPSPSRLPGPSDT PILPQ | + | + | + |
| NMPF-78 | CRRSTTDCGGPKDHPL TC | + | + | + | from −+ to +++++++ indicates from barely active to very active in modulating

Monkey Experiment

Efficacy of NMPF

Here, a mixture 1:1:1 of LQGV (SEQ ID NO:1), AQGV (SEQ ID NO:2) and VLPALP (SEQ ID NO:3), administered in a gram-negative induced rhesus monkey sepsis model for prevention of septic shock.

Overwhelming inflammatory and immune responses are essential features of septic shock and play a central part in the pathogenesis of tissue damage, multiple organ failure, and death induced by sepsis. Cytokines, especially tumor necrosis factor (TNF)-• interleukin (IL)-1•, and macrophage migration inhibitory factor (MIF), have been shown to be critical mediators of septic shock. Yet, traditional anti-TNF and anti-IL-1 therapies have not demonstrated much benefit for patients with severe sepsis. We have designed peptides that block completely LPS induced septic shock in mice, even when treatment with these peptides is started up to 24 hours after LPS injection. These peptides are also able to inhibit the production of MIF. This finding provides the possibility of therapeutic use of these peptides for the treatment of patients suffering from septic shock. Since primates are evolutionary more closer to humans, we tested these peptides for their safety and effectiveness in a primate system.

EXPERIMENTAL DESIGN

| GROUP | EXPERIMENTAL TREATMENT (independent variable, e.g., placebo treated control group) | BIOTECHNIQUES | NUMBER |
|---|---|---|---|
| animal I | i.v. infusion of a lethal dose of live Escherichia.coli (10E10 CFU/kg) + antibiotics + placebo treated | Live E. coli infusion Blood sampling No recovery (section) | N = 1 |
| animal II | i.v. infusion of a lethal dose of live Escherichia.coli (10E10 CFU/kg) + antibiotics + oligopeptide (5mg/kg of each of 3 peptides) | Live E. coli infusion Blood sampling No recovery (section) | N = 1 |

Only naive monkeys were used in this pre-clinical study to exclude any interaction with previous treatments. The animals were sedated with ketamine hydrochloride. Animals were intubated orally and allowed to breathe freely. The animals were kept anesthetized with $O_2/N_2O$/isofluorane. The animals received atropin as pre-medication for $O_2/N_2O$/isofluorane anesthesia. A level of surgical anesthesia was maintained during the 2 h infusion of E. coli and for 6 h following E. coli challenge, after which the endotracheal tubes were removed and the animals were euthanized. Before bacteria were induced, a 1 hour pre-infusion monitoring of heart-rate and blood pressure was performed.

Two rhesus monkeys were infused with a $10^{10}$ CFU per kg of the Gram negative bacterium E. coli to induce a fatal septic shock. One monkey received placebo-treatment and was sacrificed within 7 hours after infusion of the bacteria without recovery from the anesthesia. The second monkey received treatment with test compound and was sacrificed at the same time point.

In a limited dose-titration experiment performed with the same bacterium strain in 1991, the used dose proved to induce fatal shock within 8 hours. In recent experiments, a 3-fold lower dose was used inducing clear clinical and pathomorphological signs of septic shock without fatal outcome.

The monkeys were kept anaesthetized throughout the observation period and sacrificed 7 hours after the start of the bacterium infusion for pathological examination. The animals underwent a gross necropsy in which the abdominal and thoracic cavities were opened and internal organs examined in situ.

Full Description of the Experiment with Three Rhesus Monkeys

The study was conducted in rhesus monkeys (Maccaca mulatta). Only experimentally naive monkeys were used in the study to exclude any interaction with previous treatments. Prior to the experiment, the state of health of the animals was assessed physically by a veterinarian. All animals had been declared to be in good health and were free of pathogenic ecto- and endoparasites and common bacteriological infections: *Yersinia pestis, Yersinia enterocolitica, Yersinia pseudotuberculosis, Shigella, Aeromonas hydrophilia*, pathogenic *Campylobacter* species and *Salmonella*.

Reagents. The *Escherichia coli* strain was purchased from ATCC (E. coli; 086a: K61 serotype, ATCC 33985). In a control experiment, the strain proved equally susceptible to bactericidal factors in human and rhesus monkey serum. Prior to the experiment, a fresh culture was set-up; the E. coli strain was cultured for one day, harvested and washed thoroughly to remove free endotoxin. Prior to infusion into the animal, the number and viability of the bacteria were assessed. Serial dilutions of the E. coli stock were plated on BHI agar and cultured overnight at 37° C. The colonies on each plate were counted and the number of colony-forming units per ml was calculated. The body weight measurement of the day of the experiment was used to calculate the E coli dose and E. coli stock was suspended in isotonic saline (N.P.B.I., Emmer-Compascuum, The Netherlands) at the concentration needed for infusion (total dose volume for infusion approximately 10 ml/kg.). The E. coli suspension was kept on ice until infusion. Antibiotic was used to synchronize the shock induction in the monkeys. Baytril (Baytril 2.5%, Bayer, Germany) was used instead of gentamycin, as the strain proved only marginally susceptible to the latter antibiotic. Individual animals were identified by a number or letter combination tattooed on the chest.

Experimental design.

used to support body temperature. The monkeys were continuously monitored during E. coli challenge and for the 6 hr period following E. coli administration. After 7 hrs, 2 animals (the control animal and one treated with NMPF) were sacrificed to compare the direct effect of the compound at the level of histology. The $3^{rd}$ animal, treated with NMPF, was allowed to recover from anaesthesia and was intensively observed during the first 12 hours after recovery, followed by frequent daily observation. The decision to allow the $3^{rd}$ animal to recover was made after consulting with the veterinarian.

Induction of septic shock. Before the infusion of E. coli, a 1 hr pre-infusion monitoring of heart-rate and blood pressure was performed. All three animals received an i.v. injection of E. coli 086 (k61 serotype; ATCC 33985) at a lethal dose of 10×109 CFU/kg bodyweight. In a dose titration study with this batch performed in 1991, this bacterial dose induced lethal shock within 8 hrs after the start of the infusion. The infusion period was 2 hrs.

Antibiotics. Baytril was administered intravenously immediately after completion of the 2 h. E. coli infusion (i.v.; dose 9 mg/kg).

| GROUP (number/ letter or other identification) | EXPERIMENTAL TREATMENT (independent variable, e.g., placebo treated control group) | | NUMBER | SEX |
|---|---|---|---|---|
| Animal I | i.v. infusion of a lethal dose of live Escherichia.coli (10E10 CFU/kg) + antibiotic + placebo treated | Live E. coli infusion Blood sampling No recovery | N = 1 | F |
| Animal II | i.v. infusion of a lethal dose of live Escherichia.coli (10E10 CFU/kg) + antibiotic + NMPF-4, 6, 46; each 5 mg/kg | Live E. coli infusion Blood sampling No recovery (section) | N = 1 | F |
| Animal III | i.v. infusion of a lethal dose of live Escherichia.coli (10E10 CFU/kg) + antibioti + NMPF-4, 6, 46; each 5 mg/kg | Live E. coli infusion Blood sampling Recovery and survival | N = 1 | F |

Anesthesia. All animals were fasted overnight prior to the experiment. On the morning of the experiment, the animals were sedated with ketamine hydrochloride (Tesink, The Netherlands) and transported to the surgery. The animal was placed on its side on a temperature-controlled heating pad to support body temperature. Rectal temperature was monitored using a Vet-OX 5700. The animals were intubated orally and were allowed to breathe freely. The animals were kept anesthetized using $O_2/N_2O$ isofluorane inhalation anesthesia during the E. coli infusion and the 7 hour observation period following E. coli challenge, after which the endothracheal tubes were removed and the animals were euthanized or allowed to recover from anesthesia. The femoral or the cephalic vein was cannulated and used for infusing isotonic saline, live E. coli and antibiotic administration. Insensible fluid loss was compensated for by infusing isotonic saline containing 2.5% glucose (Fresenius, 's Hertogenbosch, NL) at a rate of 3.3 ml/kg/hr.

Preparative actions. During anesthesia, the animals were instrumented for measurement of blood pressure (with an automatic cuff), heart rate and body temperature. Isotonic saline was infused at 3.3 ml/kg/hr to compensate for fluid loss. Femoral vessels were cannulated for infusion of E. coli and antibiotics. Temperature-controlled heating pads were Treatment with NMPF. 30 minutes post-onset of E. coli infusion, the animals were administered a single intravenous bolus injection of a mixer of NMPF oligopeptides. The oligopeptide mixer contained the following NMPF peptides: LQGV (5 mg/kg), AQGV (5 mg/kg) and VLPALP (5 mg/kg). These NMPF peptides were dissolved in 0.9% sodium chloride for injection (N.P.B.I., Emmer Compascuum, The Netherlands).

Results

Preliminary Monkey Results

An anti-shock effect of the test compound on sepsis in the monkey treated with the oligopeptide mixture, namely the inhibition of the effect of the sepsis in this early 7-hour trajectory of this primate model, was observed. Immunomodulatory effects with these peptides have been observed in vitro/ex vivo, such as in T-cell assays, the inhibition of pathological Th1 immune responses, suppression of inflammatory cytokines (MIF), increase in production of anti-inflammatory cytokines (IL-10, TGF-beta) and immunomodulatory effects on antigen presenting cells (APC) like dendritic cells and macrophages.

The following organs were weighed and a bacterial count was performed: kidneys, liver, lungs, lymph nodes, and gross lesions.

Tissues of all organs were preserved in neutral aqueous phosphate buffered 4% solution of formaldehyde. Lymphoid organs were cryopreserved. All tissues will be processed for histopathological examination.

Further Results Obtained in the Three-Monkey Experiment

Monkey 429(control). Female monkey (5.66 kg) received an i.v. injection of E. coli 086 (10E10 CFU/kg). In a dose titration study with this batch performed in 1991, this bacterial dose induced lethal shock within 8 hrs after the start of the infusion. The infusion period was 2 hrs. Baytril was administered intravenously immediately after completion of the 2 h. E. coli infusion (i.v.; dose 9 mg/kg). After the E. coli injection, the monkey was observed by the authorized veterinarian without knowing which of the monkeys received NMPF treatment. The clinical observations were as follows: vomiting, undetectable pulse, heart arythmia, abnormalities in ECG: signs of ventricle dilatation/heart decompensation (prolonged QRS complex, extra systoles), decreased blood clotting and forced respiration. In addition, there was big fluctuation in heart rate (30–150 beats per minute), collapse of both systolic and diastolic blood pressure (35/20 mmHg) and decrease in blood oxygen concentration (80–70%). Seven hours after the start of the E. coli infusion, the monkey began to vomit blood and feces and have convulsions. After final examination, the veterinarian did not give permission to let this monkey awake. At this time point, the control monkey was euthanized. Hereafter, post-mortem examination was conducted and internal organs were examined in situ. A number of internal bleedings were found by the pathologist.

Monkey 459(NMPF). Female monkey (5.44 kg) received an i.v. injection of E. coli 086 (10E10 CFU/kg). In a dose titration study with this batch performed in 1991, this bacterial dose induced lethal shock within 8 hrs after the start of the infusion. The infusion period was 2 hrs. 30 minutes after the initiation of E. coli infusion; NMPF was i.v. injected in a single bolus injection. Baytril was administered intravenously immediately after completion of the 2 h. E. coli infusion (i.v.; dose 9 mg/kg). After the E. coli injection, this monkey was also observed by the authorized veterinarian without knowing which of the monkeys received NMPF treatment. The clinical observations were as follows: normal pulse, heart sounds normal, normal ECG, higher heart-rate but otherwise stable (180 beats per minute), no hypotension (75/30 mmHg), normal blood oxygen concentration (95–85%), lungs sound normal, normal turgor. Seven hours after the start of the E. coli infusion, the clinical condition of the monkey was stable. After final examination, the veterinarian did give permission to let this monkey awake due to her stable condition. In order to compare the hematological and immunological parameters between the control and NMPF-treated monkey, at this time point NMPF-treated monkey 459 was euthanized. Hereafter, post-mortem examination was conducted and internal organs were examined in situ. No macroscopic internal bleedings were found by the pathologist.

Monkey 427(NMPF). Female monkey (4.84 kg) received an i.v. injection of E. coli 086 (10E10 CFU/kg). In a dose titration study with this batch performed in 1991, this bacterial dose induced lethal shock within 8 hrs after the start of the infusion. The infusion period was 2 hrs. 30 minutes after the initiation of E. coli infusion, NMPF was i.v. injected. Baytril was administered intravenously immediately after completion of the 2 h. E. coli infusion (i.v.; dose 9 mg/kg). After the E. coli injection, this monkey was also observed by the authorized veterinarian without knowing which of the monkeys received NMPF treatment. The clinical observations were as follows: normal pulse, heart sounds normal, normal ECG, moderately higher heart-rate but otherwise stable (160 beats per minute), no hypotension (70/30 mmHg), normal blood oxygen concentration (95–90%), lungs sound normal, normal turgor. Seven hours after the start of the E. coli infusion, the clinical condition of the monkey was stable. After final examination, the veterinarian did give permission to let this monkey wake up due to her stable condition. Monkey woke up quickly, she was alert and there was a slow disappearance of oedema.

Genomic Experiment

PM1 T-cell line was obtained from American Type Culture Collection (Manassas, Va.) and was cultured at 37° C. in 5% $CO_2$. These cells were maintained and cultured in RPMI 1640, 10% fetal bovine serum, 2 mM L-glutamine, and antibiotics penicillin and streptomycin. For genomic experiments, cells ($2\times10^6$/ml) were incubated with phyto-hemagglutinin (PHA, 10 µg/ml) and IL-2 (200 IU/ml) or PHA, IL-2 and peptide LQGV (10 mg/ml) in a volume of 2 ml in 6-well plates. After 4 h of cultures, $10\times10^6$ cells were washed and prepared for genechip probe arrays experiment. The genechip expression analysis was performed according to the manufacturer's instructions (Expression Analysis, Technical Manual, Affymetrix Genechip). The following major steps outline Genechip Expression Analysis: 1) Target preparation, 2) Target hybridization, 3) Experiment and fluidics station setup, 4) Probe Array washing and staining, 5) Probe array scan and 6) Data analysis.

Results

Genomic Experiment

The gene-chip expression analysis revealed that LQGV treatment of PM1 (T-cell line) cells for 4 hours in the presence of PHA/IL-2 down-regulated at least 120 genes more than 2 fold as compared to control PM1 cells (stimulated with PHA/IL-2) only. Moreover, at least 6 genes were up-regulated more than 2 fold in peptide-treated cells as compared to control cells.

| Fold Change/Descriptions |
|---|
| Down regulated genes due to treatment with LQGV in genomics experiment |
| 21.2 M11507 Human transferrin receptor mRNA, complete cds<br>(_5, _M, _3 represent<br>transcript regions 5 prime, Middle, and 3 prime respectively)<br>10.1 Human (c-myb) gene, complete primary cds, and five complete alternatively spliced cds<br>(U22376 /FEATURE = cds#5 /DEFINITION = HSU22376) |

-continued

| Fold Change/Descriptions |
| --- |

9.7 Cluster Incl. X68836:*H.sapiens* mRNA for S-adenosylmethionine
synthetase (cds = (65,1252)
/gb = X68836 /gi = 36326 /ug = Hs.77502 /len = 1283)
9.3 M97935 *Homo sapiens* transcription factor ISGF-3 mRNA, complete cds
(_5, _MA, MB, _3 represent
transcript regions 5 prime, MiddleA, MiddleB, and 3 prime respectively)
8.7 Human mRNA for phosphatidylinositol transfer protein (PI-TPbeta),
complete cds (D30037 /FEATURE =
/DEFINITION = HUMPITPB)
7.5 Cluster Incl. U28964:*Homo sapiens* 14-3-3 protein mRNA, complete cds
(cds = (126,863) /gb = U28964
/gi = 899458 /ug = Hs.75103 /len = 1030)
6.7 Human CDK tyrosine 15-kinase WEE1Hu (Wee1Hu) mRNA, complete cds
(U10564 /FEATURE =
/DEFINITION = HSU10564)
6.7 *Homo sapiens* E2F-related transcription factor (DP-1) mRNA, complete cds
(L23959 /FEATURE =
/DEFINITION = HUMDP1A)
6.5 Cluster Incl. W29030:55c4 *Homo sapiens* cDNA
(gb = W29030 /gi = 1308987
/ug = Hs.4963 /len = 758)
6.1 Cluster Incl. U08997:Human glutamate dehydrogenase gene, complete cds
(cds = (0,1676) /gb = U08997 /gi = 478987 /ug = Hs.239377 /len = 1677)
5.7 M97935 *Homo sapiens* transcription factor ISGF-3 mRNA, complete cds
(_5, _MA, MB, _3 represent
transcript regions 5 prime, MiddleA, MiddleB, and 3 prime respectively)
5.6 Cluster Incl. Y00638:Human mRNA for leukocyte common antigen (T200)
(cds = (86,4000) /gb = Y00638 /gi = 34280 /ug = Hs.170121 /len = 4315)
5.3 Ras-Like Protein Tc21
5.3 *H.sapiens* mRNA for Fas/Apo-1 (clone pCRTM11-Fasdelta(4,7))
(X83492
/FEATURE = exons#1–2 /DEFINITION = HSFAS47)
4.8 Cluster Incl. AJ002428:*Homo sapiens* VDAC1 pseudogene
(cds = (0,853) /gb = AJ002428 /gi = 3183956 /ug = Hs.201553 /len = 854)
4.7 Ras-Related Protein Rap1b
4.6 Cluster Incl. AL080119:*Homo sapiens* mRNA; cDNA DKFZp564M2423
(from clone DKFZp564M2423) (cds = (85,1248) /gb = AL080119
/gi = 5262550 /ug = Hs.165998 /len = 2183)
4.5 Cluster Incl. AF047448:*Homo sapiens* TLS-associated protein TASR
mRNA, complete cds
(cds = (29,580) /gb = AF047448 /gi = 2961148 /ug = Hs.239041 /len = 620)
4.5 Cluster Incl. D14710:Human mRNA for ATP synthase alpha subunit,
complete cds
(cds = (63,1724) /gb = D14710 /gi = 559324 /ug = Hs.155101 /len = 1857)
4.5 Cluster Incl. X59618:*H.sapiens* RR2 mRNA for small subunit
ribonucleotide reductase
(cds = (194,1363) /gb = X59618 /gi = 36154 /ug = Hs.75319 /len = 2475)
4.5 Human mRNA for annexin II, 5 UTR (sequence from the 5 cap to the start
codon)
(D28364 /FEATURE = /DEFINITION = HUMAI23)
4.5 Cluster Incl. AA477898:zu34f08.r1 *Homo sapiens* cDNA, 5 end
/clone = IMAGE-739911 /clone_end = 5
(gb = AA477898 /gi = 2206532 /ug = Hs.239414 /len = 449)
4.4 Cluster Incl. L19161:Human translation initiation factor eIF-2 gamma
subunit mRNA, complete cds (cds = (0,1418) /gb = L19161
/gi = 306899 /ug = Hs.211539 /len = 1440gb = AA477898
/gi = 2206532 /ug = Hs.239414 /len = 449)
4.4 Human serine/threonine-protein kinase PRP4h (PRP4h) mRNA, complete
cds
(U48736 /FEATURE = /DEFINITION = HSU48736)
4.4 Cluster Incl. L43821:*Homo sapiens* enhancer of filamentation (HEF1)
mRNA, complete cds
(cds = (163,2667) /gb = L43821 /gi = 1294780 /ug = Hs.80261 /len = 3817)
4.4 Ras-Like Protein Tc21
4.4 Human (c-myb) gene, complete primary cds, and five complete alternatively
spliced cds (U22376 /FEATURE = cds#3
/DEFINITION = HSU22376)
4.3 Cluster Incl. U18271:Human thymopoietin (TMPO) gene
(cds = (313,2397) /gb = U18271
/gi = 2182141 /ug = Hs.170225 /len = 2796)
4.2 Fk506-Binding Protein, Alt. Splice 2
4.2 Human proliferating cell nuclear antigen (PCNA) gene, promoter region
(J05614 /FEATURE = mRNA
/DEFINITION = HUMPCNAPRM)
4.1 Human insulin-stimulated protein kinase 1 (ISPK-1) mRNA, complete cds
(U08316 /FEATURE =
/DEFINITION = HSU08316)

-continued

Fold Change/Descriptions 4.1 Cluster Incl. W28732:50h7 *Homo sapiens* cDNA
(gb = W28732 /gi = 1308680
/ug = Hs.177496 /len = 818)
4.1 Cluster Incl. Y00638:Human mRNA for leukocyte common antigen (T200)
(cds = (86,4000) /gb = Y00638
/gi = 34280/ug = Hs.170121 /len = 4315)
4 *Homo sapiens* putative purinergic receptor P2Y10 gene, complete cds
(AF000545 /FEATURE = cds
/DEFINITION = HSAF000545)
3.8 Cluster Incl. U08997:Human glutamate dehydrogenase gene, complete cds
(cds = (0,1676) /gb = U08997
/gi = 478987 /ug = Hs.239377 /len = 1677)
3.6 Human mRNA for raf oncogene
(X03484 /FEATURE = cds /DEFINITION = HSRAFR)
3.6 Cluster Incl. M32886:Human sorcin CP-22 mRNA, complete cds
(cds = (12,608) /gb = M32886
/gi = 338481 /ug = Hs.117816/len = 952)
3.6 *Homo sapiens* GTP-binding protein (RAB1) mRNA, complete cds
(M28209 /FEATURE = /DEFINITION = HUMRAB1A)
3.5 Human FKBP-rapamycin associated protein (FRAP) mRNA, complete cds
(L34075 /FEATURE = /DEFINITION = HUMFRAPX)
3.5 Human DNA topoisomerase II (top2) mRNA, complete cds
(J04088 /FEATURE = /DEFINITION = HUMTOPII)
3.4 Human translation initiation factor eIF-2 gamma subunit mRNA, complete
cds
(L19161 /FEATURE = /DEFINITION = HUMIEF2G)
3.4 Human mRNA for pre-mRNA splicing factor SRp20, 5 UTR (sequence
from the 5 cap to the start codon)
(D28423 /FEATURE = /DEFINITION = HUMPSF82)
3.4 Cluster Incl. AA442560:zv75g07.r1 *Homo sapiens* cDNA, 5 end
/clone = IMAGE-759516 /clone_end = 5
(gb = AA442560 /gi = 2154438 /ug = Hs.135198 /len = 566)
3.4 Cluster Incl. X98248:*H.sapiens* mRNA for sortilin /cds = (21,2522)
(gb = X98248 /gi = 1834494 /ug = Hs.104247 /len = 3723)
3.3 Cluster Incl. AB020670:*Homo sapiens* mRNA for KIAA0863 protein,
complete cds
(cds = (185,3580) /gb = AB020670 /gi = 4240214 /ug = Hs.131915 /len = 4313)
3.3 Cluster Incl. W28869:53h2 *Homo sapiens* cDNA
(gb = W28869
/gi = 1308880 /ug = Hs.74637 /len = 975)
3.3 Cluster Incl. Z12830:*H.sapiens* mRNA for SSR alpha subunit /cds = (29,889)
(gb = Z12830 /gi = 551637 /ug = Hs.76152 /len = 974)
3.3 Cluster Incl. AL021546:Human DNA sequence from BAC 15E1 on
chromosome 12.
Contains Cytochrome C Oxidase Polypeptide VIa-liver precursor gene,
60S ribosomal protein L31 pseudogene, pre-mRNA splicing factor SRp30c
gene,
two putative genes, ESTs, STSs and putative CpG islands
(cds = (0,230) /gb = AL021546
/gi = 2826890 /ug = Hs.234768 /len = 547)
3.2 Cluster Incl. U78082:Human RNA polymerase transcriptional regulation
mediator (h-MED6) mRNA, complete cds
(cds = (50,523) /gb = U78082 /gi = 2618737 /ug = Hs.167738 /len = 885)
3.2 *H.sapiens* RbAp48 mRNA encoding retinoblastoma binding protein
(X74262 /FEATURE = cds /DEFINITION = HSRBAP48)
3.1 Cluster Incl. M64174:Human protein-tyrosine kinase (JAK1) mRNA,
complete cds
(cds = (75,3503) /gb = M64174 /gi = 190734 /ug = Hs.50651 /len = 3541)
3.1 Cluster Incl. AI862521:wj15a06.x1 *Homo sapiens* cDNA, 3 end
/clone = IMAGE-2402866 /clone_end = 3
(gb = AI862521 /gi = 5526628 /ug = Hs.146861 /len = 606)
3.1 Cluster Incl. W27517:31h6 *Homo sapiens* cDNA
(gb = W27517 /gi = 1307321 /ug = Hs.13662 /len = 732)
3 Human rab GDI mRNA, complete cds
(D13988 /FEATURE = /DEFINiTION = HUMRABGDI)
3 Cluster Incl. AL080119:*Homo sapiens* mRNA; cDNA DKFZp564M2423
(from clone DKFZp564M2423)
(cds = (85,1248) /gb = AL080119 /gi = 5262550 Aig = Hs.165998 /len = 2183)
3 Human cAMP-dependent protein kinase type I-alpha subunit (PRKAR1A)
mRNA, complete cds
( M33336 /FEATURE = /DEFINITION = HUMCAMPPK)
3 Cluster Incl. L75847:Human zinc finger protein 45 (ZNF45) mRNA,
complete cds (cds = (103,2151) /gb = L75847
/gi = 1480436 /ug = Hs.41728 /len = 2409)
3 Cluster Incl. M21154:Human S-adenosylmethionine decarboxylase mRNA,
complete cds
(cds = (248,1252) /gb = M21154 /gi = 178517 /ug = Hs.75744 /len = 1805)

-continued

Fold Change/Descriptions

3 Cluster Incl. AA675900:g02504r *Homo sapiens* cDNA, 5 end
/clone = g02504 /clone_end = 5
(gb = AA675900 /gi = 2775247 /ug = Hs.119325 /len = 647)
3 Cluster Incl. M97936:Human transcription factor ISGF-3 mRNA sequence
(cds = UNKNOWN /gb = M97936 /gi = 475254 /ug = Hs.21486 /len = 2607)
2 M33336 /DEFINITION = HUMCAMPPK Human cAMP-dependent protein kinase
type I-alpha subunit (PRKAR1A)
mRNA, complete cds
2 U16720 /FEATURE = mRNA /DEFINITION = HSU16720 Human interleukin 10
(IL10) gene, complete cds
2 M33336 HUMCAMPPK Human cAMP-dependent protein kinase type I-alpha
subunit (PRKAR1A) mRNA
2 U50079 /FEATURE = /DEFINITION = HSU50079 Human histone deacetylase HD1
mRNA, complete cds
2 U16720 /FEATURE = mRNA /DEFINITION = HSU16720 Human interleukin 10
(IL10) gene, complete cds
2 X87212 /FEATURE = cds /DEFINITION = HSCATHCGE *H.sapiens* mRNA for
cathepsin C
2 Cluster Incl. AI740522:wg16b07.x1 *Homo sapiens* cDNA, 3 end /clone = IMAGE-
2365237 /clone_end = 3 /gb = AI740522
2 M21154 /FEATURE = mRNA /DEFINITION = HUMAMD Human S-
adenosylmethionine decarboxylase mRNA, complete cds
2 X00737 /FEATURE = cds /DEFINITION = HSPNP Human mRNA for purine
nucleoside phosphorylase (PNP; EC 2.4.2.1)
2.1 Cluster Incl. AF034956:*Homo sapiens* RAD51D mRNA, complete cds
/cds = (124,993) /gb = AF034956 /gi = 2920581
2.1 Ras Inhibitor Inf
2.1 Cluster Incl. M27749:Human immunoglobulin-related 14.1 protein mRNA,
complete cds /cds = (118,759) /gb = M27749
2.1 Ras-Like Protein Tc4
2.1 X92106 /FEATURE = cds /DEFINITION = HSBLEO *H.sapiens* mRNA for
bleomycin hydrolase
2.1 D88674 /FEATURE = /DEFINITION = D88674 *Homo sapiens* mRNA for antizyme
inhibitor, complete cds
2.1 Cluster Incl. H15872:ym22b12.r1 *Homo sapiens* cDNA, 5 end /clone = IMAGE-
48838 /clone_end = 5 /gb = H15872
2.1 Cluster Incl. L07541:Human replication factor C, 38-kDa subunit mRNA, complete
cds /cds = (9,1079) /gb = L07541
2.1 V01512 /FEATURE = mRNA#1 /DEFINITION = HSCFOS Human cellular
oncogene c-fos (complete sequence)
2.1 Cluster Incl. L23959:*Homo sapiens* E2F-related transcription factor (DP-1) mRNA,
complete cds /cds = (37,1269)
2.1 Stimulatory Gdp/Gtp Exchange Protein For C-Ki-Ras P21 And Smg P21
2.1 Cluster Incl. L13943:Human glycerol kinase (GK) mRNA exons 1–4, complete cds
/cds = (66,1640) /gb = L13943 /gi = 348166
2.1 Cluster Incl. X78925:*H.sapiens* HZF2 mRNA for zinc finger protein /cds = (0,2198)
/gb = X78925 /gi = 498722 /ug = Hs.2480
2.1 X74794 /FEATURE = cds /DEFINITION = HSP1CDC21 *H.sapiens* P1-Cdc21
mRNA
2.1 U78733 /FEATURE = mRNA#1 /DEFINITION = HSSMAD2S8 *Homo sapiens* mad
protein homolog Smad2 gene, exon 11
2.2 Cluster Incl. L07540:Human replication factor C, 36-kDa subunit mRNA, complete
cds /cds = (9,1031) /gb = L07540
2.2 Cluster Incl. AF040958:*Homo sapiens* lysosomal neuraminidase precursor, mRNA,
complete cds /cds = (129,1376)
2.2 D00596 /FEATURE = cds /DEFINITION = HUMTS1 *Homo sapiens* gene for
thymidylate synthase, exons 1, 2, 3, 4, 5, 6, 7,
2.2 Cluster Incl. AI659108:tu08c09.x1 *Homo sapiens* cDNA, 3 end /clone = IMAGE-
2250448 /clone_end = 3 /gb = AI659108
2.2 Cluster Incl. AF042083:*Homo sapiens* BH3 interacting domain death agonist (BID)
mRNA, complete cds /cds = (140,727)
2.2 Cluster Incl. W28907:53e12 *Homo sapiens* cDNA /gb = W28907 /gi = 1308855
/ug = Hs.111429/len = 989
2.3 Cluster Incl. AF073362:*Homo sapiens* endo/exonuclease Mre11 (MRE11A)
mRNA, complete cds /cds = (0,2126)
2.3 *Escherichia coli* /REF = J04423 /DEF = *E coli* bioD gene dethiobiotin synthetase
/LEN = 676 (-5 and -3 represent transcript
2.3 Cluster Incl. D59253:Human mRNA for NCBP interacting protein 1, complete cds
/cds = (36,506) /gb = D59253
2.3 M21154 /FEATURE = mRNA /DEFINITION = HUMAMD Human S-
adenosylmethionine decarboxylase mRNA, complete cds
2.3 Proto-Oncogene C-Myc, Alt. Splice 3, Orf 114
2.3 Cluster Incl. W26787:15d8 *Homo sapiens* cDNA /gb = W26787 /gi = 1306078
/ug = Hs.195188 /len = 768
2.4 L12002 /FEATURE = /DEFINITION = HUMITGA4A Human integrin alpha 4
subunit mRNA, complete cds
2.4 Cluster Incl. M55536:Human glucose transporter pseudogene /cds = UNKNOWN -continued

| Fold Change/Descriptions |
|---|
| /gb = M55536/gi = 183299/ug = Hs.121583 2.4 X98743 /FEATURE = cds /DEFINITION = HSRNAHELC *H.sapiens* mRNA for RNA helicase (Myc-regulated dead box protein) |
| 2.4 S75881 /FEATURE = /DEFINITION = S75881 A-myb = DNA-binding transactivator {3 region} [human, CCRF-CEM T leukemia line, mRNA Partial, 831 nt] |
| 2.4 Cluster Incl. AF050110:*Homo sapiens* TGFb inducible early protein and early growth response protein alpha genes, complete cds /cds = (123,1565) /gb = AF050110 /gi = 3523144 /ug = Hs.82173 /len = 2899 |
| 2.5 Cluster Incl. M86667:*H.sapiens* NAP (nucleosome assembly protein) mRNA, complete cds /cds = (75,1250) /gb = M86667 /gi = 189066 /ug = Hs.179662 /len = 1560 |
| 2.5 U17743 /FEATURE = /DEFINITION = HSU 17743 Human JNK activating kinase (JNKK1) mRNA, complete cds |
| 2.5 Cluster Incl. U90549:Human non-histone chromosomal protein (NHC) mRNA, complete cds /cds = (691,963) /gb = U90549 /gi = 2062699 /ug = Hs.63272 /len = 1981 |
| 2.5 Cluster Incl. U31382:Human G protein gamma-4 subunit mRNA, complete cds /cds = (98,325) /gb = U31382 /gi = 995916 /ug = Hs.32976 /len = 670 |
| 2.5 Cluster Incl. S81916:phosphoglycerate kinase {alternatively spliced} [human, phosphoglycerate kinase deficient patient with episodes of muscl, mRNA Partial Mutant, 307 nt] /cds = (0,143) /gb = S81916 /gi = 1470308 /ug = Hs.169313 /len = 307 |
| 2.5 Cluster Incl. M64595:Human small G protein (Gx) mRNA, 3 end /cds = (0,542) /gb = M64595 /gi = 183708 /ug = Hs.173466 /len = 757 |
| 2.5 Serine Hydroxymethyltransferase, Cytosolic, Alt. Splice 3 |
| 2.5 U88629 /FEATURE = cds /DEFINITION = HSU88629 Human RNA polymerase II elongation factor ELL2, complete cds |
| 2.5 Cluster Incl. U72518:Human destrin-2 pseudogene mRNA, complete cds /cds = (268,798) /gb = U72518 /gi = 1673523 /ug = Hs.199299 /len = 1057 |
| 2.5 Cluster Incl. L14595:Human alanine/serine/cysteine/threonine transporter (ASCT1) mRNA, complete cds |
| 2.5 Cluster Incl. AB014584:*Homo sapiens* mRNA for KIAA0684 protein, partial cds /cds = (0,2711) /gb = AB014584 /gi = 3327181 /ug = Hs.24594 /len = 4124 |
| 2.5 Cluster Incl. AI924594:wn57a11.x1 *Homo sapiens* cDNA, 3 end /clone = IMAGE-2449532 /clone_end = 3 /gb = AI924594 /gi = 5660558 /ug = Hs. 122540 /len = 685 |
| 2.5 U68111 /FEATURE = mRNA /DEFINITION = HSPPP1R2E6 Human protein phosphatase inhibitor 2 (PPP1R2) gene, exon 6 |
| 2.5 Cluster Incl. AL009179:dJ97D16.4 (Histone H2B) /cds = (25,405) /gb = AL009179 /gi = 3217024 /ug = Hs.137594 /len = 488 |
| 2.6 Cluster Incl. AF091077:*Homo sapiens* clone 558 unknown mRNA, complete sequence /cds = (1,300) /gb = AF091077 /gi = 3859991 /ug = Hs.40368 /len = 947 |
| 2.7 Cluster Incl. M28211:*Homo sapiens* GTP-binding protein (RAB4) mRNA, complete cds /cds = (70,711) /gb = M28211 /gi = 550067 /ug = Hs.234038 /len = 735 |
| 2.6 X69549 /FEATURE = cds /DEFINITION = HSRHO2 *H.sapiens* mRNA for rho GDP-dissociation Inhibitor 2 |
| 2.6 Cluster Incl. Z85986:Human DNA sequence from clone 108K11 on chromosome 6p21 Contains SRP20 (SR protein family member), Ndr protein kinasegene similar to yeast suppressor protein SRP40, EST and GSS /cds = (0,932) /gb = Z85986 gi = 4034056 /ug = Hs.152400 /len = 933 |
| 2.6 Zinc Finger Protein, Kruppel-Like |
| 2.7 D10656 /FEATURE = /DEFINITION = HUMCRK Human mRNA for CRK-II, complete cds |
| 2.7 M28211 /FEATURE = /DEFINITION = HUMRAB4A *Homo sapiens* GTP-binding protein (RAB4) mRNA, complete cds |
| 2.7 Cluster Incl. AB019435:*Homo sapiens* mRNA for putative phospholipase, complete cds /cds = (72,3074) /gb = AB019435 /gi = 4760646 /ug = Hs.125670 /len = 3088 |
| 2.8 U39318 /FEATURE = /DEFINITION = HSU39318 Human E2 ubiquitin conjugating enzyme UbcHSC (UBCH5C) mRNA, complete cds |
| 2.9 Cluster Incl. X78711:*H.sapiens* mRNA for glycerol kinase testis specific 1 /cds = (26,1687) /gb = X78711 /gi = 515028 /ug = Hs.1466 /len = 1838 |
| 2.8 Cluster Incl. W27594:34h4 *Homo sapiens* cDNA /gb = W27594 /gi = 1307542 /ug = Hs.8258 /len = 702 |
| 2.8 X05360 /FEATURE = cds /DEFINITION = HSCDC2 Human CDC2 gene involved in cell cycle control |

-continued

Fold Change/Descriptions 2.8 V00568 /FEATURE = cds /DEFINITION = HSMYC1 Human mRNA encoding the c-myc oncogene
2.8 Cluster Incl. L24804:Human (p23) mRNA, complete cds /cds = (232,714) /gb = L24804 /gi = 438651 /ug = Hs.75839 /len = 782
2.10 Cluster Incl. Y09443:*H.sapiens* mRNA for alkyl-dihydroxyacetonephosphate synthase precursor /cds = (15,1991) /gb = Y09443 /gi = 1922284 /ug = Hs.22580 /len = 2074
2.8 Cluster Incl. Z82200:Human DNA sequence from clone 333E23 on chromosome Xq21.1 Contains putative purinergic receptor P2Y10 /cds = (0,1019) /gb = Z82200 /gi = 2370075 /ug = Hs.166137 /len = 1020
2.9 L05624 /FEATURE = /DEFINITION = HUMMKK *Homo sapiens* MAP kinase kinase mRNA, complete cds
2.9 Cluster Incl. D88357:*Homo sapiens* mRNA for CDC2 delta T, complete cds /cds = (27,749) /gb = D88357 /gi = 3126638 /ug = Hs.184572 /len = 780

Up regulated genes due to LQGV treatment 4.9 Cluster Incl. AF043324:*Homo sapiens* N-myristoyltransferase 1 mRNA, complete cds (cds = (10,1500) /gb = AF043324 /gi = 3005062 /ug = Hs.111039 /len = 4378)
3.3 Cluster Incl. L08096:Human CD27 ligand mRNA, complete cds /cds = (150,731) (gb = L08096 /gi = 307127 /ug = Hs.99899 /len = 926)
2 Cluster Incl. AF043325:*Homo sapiens* N-myristoyltransferase 2 mRNA, complete cds /cds = (46,1542) /gb = AF043325 /gi = 3005064 /ug = Hs.122647 /len = 2838
2.1 Cluster Incl. AL031681:dJ862K6.2.2 (splicing factor, argmine/serine-rich 6 (SRP55-2)(isoform 2)) /cds = (106,513)
2.1 Cluster Incl. X87838:*H.sapiens* mRNA for beta-catenin /cds = (214,2559) /gb = X87838 /gi = 1154853 /ug = Hs.171271
2.2 Cluster Incl. AW024285:wt69d06.x1 *Homo sapiens* cDNA, 3 end /clone = IMAGE-2512715 /clone_end = 3 /gb = AW024285
2.2 Cluster Incl. D38524:Human mRNA for 5-nucleotidase /cds = (83,1768) /gb = D38524 /gi = 633070 /ug = Hs.138593
2.2 Cluster Incl. L38935:*Homo sapiens* GT212 mRNA /cds = UNKNOWN /gb = L38935 /gi = 1008845 /ug = Hs.83086 /len = 1165
2.5 Cluster Incl. L12711:*Homo sapiens* transketolase (tk) mRNA, complete cds /cds = (98,1969) /gb = L12711 /gi = 388890
2.6 Cluster Incl. AF026029:*Homo sapiens* poly(A) binding protein II (PABP2) gene, complete cds /cds = (1282,2202)
2.8 Cluster Incl. X70683:*H.sapiens* mRNA for SOX-4 protein /cds = (350,1774) /gb = X70683 /gi = 36552 /ug = Hs.83484

Further Examples of Use

Examples of different receptor-intracellular signaling pathways involved in different disease pathogenesis where signaling molecules according to the invention find their use are:

LPS stimulation of antigen presenting cells (like DC, macrophages, monocytes) through different Toll-like receptors activates different signaling pathways, including MAPK pathways, ERK, JNK and p38 pathways. These pathways directly or indirectly phosphorylate and activate various transcription factors, including Elk-1, c-Jun, c-Fos, ATF-1, ATF-2, SRF, and CREB. In addition, LPS activates the IKK pathway of MyD88, IRAK, and TRAF6. TAK1-TAB2 and MEKK1-ECSIT complexes phosphorylate IKKb, which in turn phosphorylates IkBs. Subsequent degradation of IkBs permits nuclear translocation of NFkB/Rel complexes, such as p50/p65. Moreover, the P13K-Akt pathway phosphorylates and activates p65 via an unknown kinase. Some of these pathways could also be regulated by other receptor signaling molecules such as hormones/growth factor receptor tyrosine kinases (PKC/Ras/IRS pathway) and cytokine receptors (JAK/STAT pathway). In the genomic experiment with the T-cell line, several of these genes appeared to be down-regulated or up-regulated by the peptide used (LQGV (SEQ ID NO:1)). It is now clear that other peptides in T-cells and the same and other peptides in other cell types similarly down-regulate or up-regulate several of these transcription factors and signaling molecules. In DC and fertilized egg experiments, NMPF had the ability to modulate growth factor (GM-CSF, VEGF) and LPS signaling. Some diseases associated with dysregulation of NF-kB and related transcription factors are: Atherosclerosis, asthma, arthritis, anthrax, cachexia, cancer, diabetes, euthyroid sick syndrome, AIDS, inflammatory bowel disease, stroke, (sepsis) septic shock, inflammation, neuropathological diseases, autoimmunity, thrombosis, cardiovascular disease, psychological disease, post-surgical depression, wound healing, burn-wounds healing and neurodegenerative disorders.

PKC plays an essential role in T-cell activation via stimulation of, for example, AP-1 and NF-kB that selectively translocate to the T-cell synapse via the Vav/Rac pathway. PKC is involved in a variety of immunological and non-immunological diseases as is clear from standard text books of internal medicine (examples are metabolic diseases, cancer, angiogenesis, immune-mediated disorders, diabetes etc.).

LPS and ceramide induce differential multimeric receptor complexes, including CD14, CD11b, Fc-gRIII, CD36, TAPA, DAF and TLR4. This signal transduction pathway explains the altered function of monocytes in hypercholesterolemia and lipid disorders.

Oxidized, low-density lipoproteins contribute to stages of the atherogenic process and certain concentrations of oxidized, low-density lipoproteins induce apoptosis in macrophages through signal transduction pathways. These pathways are involved in various vascular diseases such as atherosclerosis, thrombosis etc.

Bacterial DNA is recognized by cells of the innate immune system. This recognition requires endosomal maturation and leads to activation of NF-KB and the MAPK pathway. Recently, it has been shown that signaling requires the Toll-like receptor 9 (TLR9) and the signaling adaptor protein MyD88. Recognition of dsRNA during viral infection seems to be dependent on intracellular recognition by the dsRNA-dependent protein kinase PKR. TLRs play an essential role in the immune system and they are important in bridging and balancing innate immunity and adaptive immunity. Modulation of these receptors or their downstream signaling pathways is important for the treatment of various immunological conditions such as infections, cancer, immune-mediated diseases, autoimmunity, certain metabolic diseases with immunological component, vascular diseases, inflammatory diseases, etc.

Effect of growth factor PDGF-AA on NF-KB and proinflammatory cytokine expression in rheumatoid synoviocytes: PDGF-AA augmented NF-KB activity and mRNA expression of IL-1b, IL-8 and MIP-1a. Therefore, PDGF-AA may play an important role in progression of inflammation as well as proliferation of synoviocytes in RA.

Dendritic cell (DC) activation is a critical event for the induction of immune responses. DC activation induced by LPS can be separated into two distinct processes: first, maturation, leading to up-regulation of MHC and costimulatory molecules, and second, rescue from immediate apoptosis after withdrawal of growth factors (survival). LPS induces NF-KB transcription factor. Inhibition of NF-KB activation blocked maturation of DCs in terms of up-regulation of MHC and co-stimulatory molecules. In addition, LPS activates the extracellular signal-regulated kinases (ERK), and specific inhibition of MEK1, the kinase which activates ERK, abrogates the ability of LPS to prevent apoptosis but does not inhibit DC maturation or NF-kB nuclear translocation. This shows that ERK and NF-kB regulate different aspects of LPS-induced DC activation. Our DC data and NF-kB data also show the various effects of NMPF peptides on DC maturation and proliferation in the presence or absence of LPS. NMPF peptides modulate these pathways and are novel tools for the regulation of DC function and immunoregulation. This opens new ways for the treatment of immune diseases, particularly those in which the immune system is in disbalance (DC1-DC2, Th1-Th2, regulatory cell, etc.).

DC mediate NK cell activation which can result in tumor growth inhibition. DC and other antigen-presenting cells (like macrophages, B-cells) play an essential role in the immune system and they are also important in bridging and balancing innate immunity and adaptive immunity. Modulation of these cells or their downstream signaling pathways is important for the treatment of various immunological conditions such as infections, cancer, immune-mediated diseases, autoimmunity, certain metabolic diseases with immunological component, vascular diseases, inflammatory diseases, etc. There is also evidence in the literature that mast cells play important roles in exerting the innate immunity by releasing inflammatory cytokines and recruitment of neutrophils after recognition of infectious agents through TLRs on mast cells.

In murine macrophages infected with *Mycobacterium tuberculosis* through the JAK pathway activate STAT1 and activation of STAT1 may be the main transcription factor involved in IFN-g-induced MHC class II inhibition.

Recognition of mannose-binding lectin (MBL) through TLRs influences multiple immune mechanisms in response to infection and is involved in innate immunity. Balance between innate and adaptive immunity is crucial for a balanced immune system and dysregulation in the immune system leads to a different spectrum of diseases such as inflammatory diseases, autoimmunity, infectious diseases, pregnancy-associated diseases (like miscarriage and pre-eclampsia), diabetes, atherosclerosis and other metabolic diseases.

Nuclear factor-κB (NFκB) is critical for the transcription of multiple genes involved in myocardial ischemia-reperfusion injury. Clinical and experimental studies have shown that myocardial ischemia-reperfusion injury results in activation of the TLRs and the complement system through both the classical and the alternative pathway in myocardial infarction, atherosclerosis, intestinal ischemia, hemorrhagic shock pulmonary injury, and cerebral infarction, etc.

Peroxisome proliferator-activated receptors (PPARs) are ligand-activated transcription factors which function as regulators of lipid and lipoprotein metabolism, glucose homeostasis, influence cellular proliferation, differentiation and apoptosis and modulation of inflammatory responses. PPAR alpha is highly expressed in liver, muscle, kidney and heart, where it stimulates the beta-oxidative degradation of fatty acids. PPAR gamma is predominantly expressed in intestine and adipose tissue, where it triggers adipocyte differentiation and promotes lipid storage. Recently, the expression of PPAR alpha and PPAR gamma was also reported in cells of the vascular wall, such as monocyte/macrophages, endothelial and smooth muscle cells. The hypolipidemic fibrates and the antidiabetic glitazones are synthetic ligands for PPAR alpha and PPAR gamma, respectively. Furthermore, fatty acid-derivatives and eicosanoids are natural PPAR ligands: PPAR alpha is activated by leukotriene B4, whereas prostaglandin J2 is a PPAR gamma ligand, as well as of some components of oxidized LDL, such as 9- and 13-HODE. These observations suggested a potential role for PPARs not only in metabolic but also in inflammation control and, by consequence, in related diseases such as atherosclerosis. More recently, PPAR activators were shown to inhibit the activation of inflammatory response genes (such as IL-2, IL-6, IL-8, TNF alpha and metalloproteases) by negatively interfering with the NFκB, STAT and AP-1 signaling pathways in cells of the vascular wall. Furthermore, PPARs may also control lipid metabolism in the cells of the atherosclerotic plaque. PPARs are also involved in a variety of immunological and non-immunological diseases as is clear from standard text books of internal medicine (examples are metabolic diseases, cancer, angiogenesis, immune-mediated disorders, diabetes, etc.).

As mentioned above, the nuclear receptor PPARg is important in adipogenesis and lipid storage and is involved in atherosclerosis. While expressed in adipose tissue, this receptor is also expressed in macrophages and in the colon. In addition, PPARg is implicated in a number of processes such as cancer and inflammation. Moreover, microbes, via its cognate receptors, typified by the TLRs, possess the capacity to regulate PPARg-dependent metabolic functions and as such illustrates the intricate interplay between the microbial flora and metabolic control in the alimentary tract.

Cyclo-oxygenase 2 (COX2), an inducible isoform of prostaglandin H synthase, which mediates prostaglandin synthesis during inflammation and which is selectively overexpressed in colon tumors, is thought to play an important role in colon carcinogenesis. Induction of COX2 by inflammatory cytokines or hypoxia-induced oxidative stress can be mediated by nuclear factor κ B (NFκB). So, inhibition of NF-KB modulates the COX pathway and this inhibition of NFκB can be therapeutically useful in diseases in which COXs are involved, such as inflammation, pain, cancer (especially colorectal cancer), inflammatory bowel disease and others.

Neuronal subsets in normal brains constitutively express functionally competent C5a receptors. The functional role of C5a receptors revealed that C5a triggered rapid activation of protein kinase C and activation and nuclear translocation of the NF-κB transcription factor. In addition, C5a was found to be mitogenic for undifferentiated human neuroblastoma cells, a novel action for the C5aR. In contrast, C5a protects terminally differentiated human neuroblastoma cells from toxicity mediated by the amyloid A beta peptide. This shows that normal hippocampal neurons as well as undifferentiated and differentiated human neuroblastoma cells express functional C5a receptors. These results show the role of neuronal C5aR receptors in normal neuronal development, neuronal homeostasis, and neuroinflammatory conditions such as Alzheimer's disease.

Activation of the complement system plays also an important role in the pathogenesis of atherosclerosis. The proinflammatory cytokine interleukin (IL)-6 is potentially involved in the progression of the disease. Here, the complement system induces IL-6 release from human vascular smooth-muscle cells (VSMC) by a Gi-dependent pathway involving the generation of oxidative stress and the activation of the redox sensitive transcription factors NF-kB and AP-1. Modulation of the complement system is important for broad ranges of disorders such as blood disorders, infections, some metabolic diseases (diabetes), vascular diseases, transplant rejection and related disorders, autoimmune diseases, and other immunological diseases.

Different transcription factors like NF-κB and intracellular signaling molecules such as different kinases are also involved in multiple drug resistance. So, it is reasonable to believe that NMPF peptides will be effective against multiple drug resistance. Moreover, our genomic data shows that a number of genes and signaling molecules involved in tumorogenesis and metastasis are modulated. In addition, since oligopeptides also have an effect on angiogenesis, these peptides will also be used for the treatment of cancer and related diseases whereby angiogenesis requires modulation.

Proliferative diabetic retinopathy (PDR) is one of the major causes of acquired blindness. The hallmark of PDR is neovascularization (NV), abnormal angiogenesis that may ultimately cause severe vitreous cavity bleeding and/or retinal detachment. Since NMPF peptides have angiogenesis stimulatory as well as inhibitory effects and have the ability to modulate intracellular signaling involved in growth factors (like insulin), pharmacologic therapy with certain NMPF peptides can improve metabolic control (like glucose) or blunt the biochemical consequences of hyperglycemia (through mechanisms such as in which aldose reductase, protein kinase C (PKC), or PPARs are involved). For this metabolic control or diabetes (type 2), NMPF (LQGV (SEQ ID NO:1), VLPALP (SEQ ID NO:3), VLPALPQ (SEQ ID NO:29), GVLPALPQ (SEQ ID NO:33), AQG, LAG, LQA, AQGV (SEQ ID NO:2), VAPALP (SEQ ID NO:22), VAPALPQ (SEQ ID NO:173), VLPALPA (SEQ ID NO:31), LPGC (SEQ ID NO:41), MTR, MTRV (SEQ ID NO:48), LQG, CRGVNPVVS (SEQ ID NO:175)) are recommended. The angiogenesis in PDR could be also treated with the above-mentioned oligopeptides.

What is claimed is:

1. A method for treating an NFkappaB regulated inflammatory condition comprising administering to a subject in need of such treatment a molecule consisting of an oligopeptide selected from Table 6, said molecule capable of reducing production of NO by a cell.

2. A method for treating an NFkappaB regulated inflammatory condition comprising administering to a subject in need of such treatment a molecule consisting of an oligopeptide selected from Table 6 wherein said molecule is capable of modulating translocation and/or activity of a gene transcription factor present in a cell.

3. The method according to claim 1 wherein said molecule additionally is capable of modulating translocation and/or activity of a gene transcription factor present in said cell.

4. The method according to claim 2 wherein said gene transcription factor comprises a NF-kappaB/Rel protein.

5. The method according to claim 3 wherein said modulating translocation and/or activity of a gene transcription factor allows modulation of TNF-alpha production by said cell.

6. The method according to claim 5 wherein said TNF-alpha production is reduced.

7. The method according to claim 1 wherein said inflammatory condition comprises an acute inflammatory condition.

8. The method according to claim 1 wherein said treatment comprises administering to said subject a pharmaceutical composition comprising the molecule capable of reducing production of NO by a cell.

9. The method according to claim 8 wherein said pharmaceutical composition comprises at least two oligopeptides or functional analogues thereof capable of reducing production of NO by a cell.

10. The method according to claim 9 wherein said at least two oligopeptides are selected from the group consisting of LQGV (SEQ ID NO:1), AQGV (SEQ ID NO:2) and VLPALP (SEQ ID NO:3).

11. A method of treating an NFkappaB regulated inflammatory condition in a subject by reducing NO production by the subject's macrophages, the method comprising administering to the subject an oligopeptide selected from Table 6 capable of reducing production of NO by a cell.

12. The method according to claim 3 wherein said gene transcription factor comprises a NF-kappaB/Rel protein.

13. The method according to claim 2 wherein said inflammatory condition comprises an acute inflammatory condition.

14. The method according to claim 2 wherein said treatment comprises administering to said subject a pharmaceutical composition comprising the molecule capable of reducing production of NO by a cell.

15. The method according to claim 1, wherein the oligopeptide is selected from the group consisting of LQGV (SEQ ID NO:1), AQGV (SEQ ID NO:2), MTRV (SEQ ID NO: 42) and QVVC (SEQ ID NO: 43).

16. The method according to claim 2, wherein the oligopeptide is selected from the group consisting of LQGV (SEQ ID NO:1), AQGV (SEQ ID NO:2), MTRV (SEQ ID NO: 42) and QVVC (SEQ ID NO: 43).

17. The method according to claim 16, wherein the oligopeptide is selected from the group consisting of LQGV (SEQ ID NO:1), AQGV (SEQ ID NO:2), MTRV (SEQ ID NO: 42) and QVVC (SEQ ID NO: 43).

* * * * *

UNITED STATES PATENT AND TRADEMARK OFFICE
CERTIFICATE OF CORRECTION

PATENT NO. : 7,175,679 B2
APPLICATION NO. : 10/029206
DATED : February 13, 2007
INVENTOR(S) : Nisar Asmed Khan and Robert Benner It is certified that error appears in the above-identified patent and that said Letters Patent is hereby corrected as shown below:

In the specification:

| | | |
|---|---|---|
| COLUMN 5, | LINE 37, | change "KB" to --κB-- |
| COLUMN 11, | LINE 52, | change "CALCRRSTFDCGGPKDH" to --CALCRRSTTDCGGPKDH-- |
| COLUMN 12, | LINE 15, | change "KB" to --κB-- |
| COLUMN 12, | LINE 67, | change "KB" to --κB-- |
| COLUMN 13, | LINE 4, | change "KB" to --κB-- |
| COLUMN 13, | LINE 9, | change "KB" to --κB-- |
| COLUMN 17, | LINE 15, | change "KB" to --κB-- |
| COLUMN 17, | LINE 31, | change "KB" to --κB-- |
| COLUMN 17, | LINE 65, | change "KB" to --κB-- |
| COLUMN 28, | LINE 6, | change "KB" to --κB-- |
| COLUMN 36, | LINE 39, | change "CD1 c" to --CD11c-- |
| COLUMN 37, | LINE 8, | change "CD1 c" to --CD11c-- |
| COLUMN 42, | LINE 35, | In the TABLE, under the heading "RESULTS" change "l,ist" to --list-- |
| COLUMN 42, | LINE 36, | In the TABLE, under the heading "RESULTS" change "data bases" to --databases-- |
| COLUMN 42, | LINE 39, | In the TABLE, under the heading "RESULTS" after "LQGV" insert --(SEQ ID NO:1)--; after "LQGVV" insert --(SEQ ID NO:53)--; and after "LQGVVP" insert --(SEQ ID NO:54)-- |
| COLUMN 42, | LINE 39, | In the TABLE, under the heading "RESULTS" after "LDALP" insert --(SEQ ID NO:55)-- |
| COLUMN 42, | LINE 41, | In the TABLE, under the heading "RESULTS" change "AN UBIQUITOUS" to --A UBIQUITOUS-- |
| COLUMN 42, | LINE 42, | In the TABLE, under the heading "RESULTS" after "LQTV" insert --(SEQ ID NO:56)--; after "VLPAL" insert --(SEQ ID NO:8)--; and after "LVLQTVLPAL" insert --(SEQ ID NO:57)-- |
| COLUMN 42, | LINE 44, | In the TABLE, under the heading "RESULTS" after "IQGL" insert --(SEQ ID NO:58)--; after "LPKL" insert --(SEQ ID NO:59)--; and after "LLPKL" insert --(SEQ ID NO:60)-- |
| COLUMN 42, | LINE 46, | In the TABLE, under the heading "RESULTS" after "LPEL" insert --(SEQ ID NO:61)-- |

UNITED STATES PATENT AND TRADEMARK OFFICE
CERTIFICATE OF CORRECTION

| | | |
|---|---|---|
| PATENT NO. | : 7,175,679 B2 | Page 2 of 14 |
| APPLICATION NO. | : 10/029206 | |
| DATED | : February 13, 2007 | |
| INVENTOR(S) | : Nisar Asmed Khan and Robert Benner | |

It is certified that error appears in the above-identified patent and that said Letters Patent is hereby corrected as shown below:

In the specification (continued):

| | |
|---|---|
| COLUMN 42, LINE 48, | In the TABLE, under the heading "RESULTS" after "PAPRP" insert --(SEQ ID NO:62)-- |
| COLUMN 42, LINE 50, | In the TABLE, under the heading "RESULTS" after "MTRI" insert --(SEQ ID NO:63)-- |
| COLUMN 42, LINE 53, | In the TABLE, under the heading "RESULTS" after "LQKL" insert --(SEQ ID NO:64)--; after "LQKLL" insert --(SEQ ID NO:65)--; after "PEAP" insert --(SEQ ID NO:66)--; and after "LQKLLPEAP" insert --(SEQ ID NO:67)-- |
| COLUMN 42, LINE 56, | In the TABLE, under the heading "RESULTS" after "PTLP" insert --(SEQ ID NO:68)-- and after "LQPTL" insert --(SEQ ID NO:69)-- |
| COLUMN 42, LINE 59, | In the TABLE, under the heading "RESULTS" after "LQVV" insert --(SEQ ID NO:70)-- |
| COLUMN 42, LINE 61, | In the TABLE, under the heading "RESULTS" after "PELP" insert --(SEQ ID NO:71)-- |
| COLUMN 42, LINE 64, | In the TABLE, under the heading "RESULTS" after "PAAP" insert --(SEQ ID NO:72)--; after "PAAPQ" insert --(SEQ ID NO:73)--; and after "PAAPQV" insert --(SEQ ID NO:74)-- |
| COLUMN 42, LINE 73, | In the TABLE, under the heading "RESULTS" after "LPAL" insert --(SEQ ID NO:75)--; after "PALP" insert --(SEQ ID NO:76)--; and after "PALPE" insert --(SEQ ID NO:77)-- |
| COLUMN 42, LINE 77, | In the TABLE, under the heading "RESULTS" after "LTELL" insert --(SEQ ID NO:78)-- |
| COLUMN 43, LINE 4, | after "ARG" and before ")" insert --(SEQ ID NO:79)-- |
| COLUMN 43, LINE 5, | after "PALP" insert --(SEQ ID NO:76)-- |
| COLUMN 43, LINE 8, | after "LPPL" insert --(SEQ ID NO:80)-- and after "PPLP" insert --(SEQ ID NO:81)-- |
| COLUMN 43, LINE 11, | after "LPGL" insert --(SEQ ID NO:82)-- and change "EPK" to --LPK-- |
| COLUMN 43, LINE 14, | after "LAAL" insert --(SEQ ID NO:83)-- and after "LAALP" insert --(SEQ ID NO:84)-- |

UNITED STATES PATENT AND TRADEMARK OFFICE
CERTIFICATE OF CORRECTION

PATENT NO. : 7,175,679 B2
APPLICATION NO. : 10/029206
DATED : February 13, 2007
INVENTOR(S) : Nisar Asmed Khan and Robert Benner It is certified that error appears in the above-identified patent and that said Letters Patent is hereby corrected as shown below:

In the specification (continued):

| | | |
|---|---|---|
| COLUMN 43, | LINE 18, | after "LPKL" insert --(SEQ ID NO:59)-- and after "PKLP" insert --(SEQ ID NO:85)-- |
| COLUMN 43, | LINE 21, | after "VLPSIP" insert --(SEQ ID NO:86)-- |
| COLUMN 43, | LINE 23, | after "LPAL" insert --(SEQ ID NO:75)-- and after "PALP" insert --(SEQ ID NO:76)-- |
| COLUMN 43, | LINE 26, | after "PAVP" insert --(SEQ ID NO:13)-- and after "MLPAVP" insert --(SEQ ID NO:87)-- |
| COLUMN 43, | LINE 30, | after "LPCL" insert --(SEQ ID NO:88)-- and after "PCLP" insert --(SEQ ID NO:89)-- |
| COLUMN 43, | LINE 32, | after "VPALP" insert --(SEQ ID NO:90)-- |
| COLUMN 43, | LINE 34, | after "LPAL" insert --(SEQ ID NO:75)-- and after "PALP" insert --(SEQ ID NO:76)-- |
| COLUMN 43, | LINE 36, | after "PTIP" insert --(SEQ ID NO:91)-- and after "VLPTIP" insert --(SEQ ID NO:92)-- |
| COLUMN 43, | LINE 38, | after "VLPGFP" insert --(SEQ ID NO:93)-- |
| COLUMN 43, | LINE 40, | after "PGFP" insert --(SEQ ID NO:94)-- and after "VLPGFP" insert --(SEQ ID NO:93)-- |
| COLUMN 43, | LINE 43, | after "LPALP" insert --(SEQ ID NO:95)-- and after "PALP" insert --(SEQ ID NO:76)-- |
| COLUMN 43, | LINE 45, | after "PALP" insert --(SEQ ID NO:76)-- |
| COLUMN 43, | LINE 47, | after "MPALP" insert --(SEQ ID NO:96)-- |
| COLUMN 43, | LINE 52, | delete the comma after "(HUMAN);" |
| COLUMN 43, | LINE 53, | after "MXRVLQGVLPALPQVVC" insert --(SEQ ID NO:97)-- and after "MXRV" insert --(SEQ ID NO:98)-- |
| COLUMN 43, | LINE 57, | delete the comma after "(HUMAN);" and delete the period after "sequence" |
| COLUMN 43, | LINE 58, | after "ITRVMQGVIPALPQVVC" insert --(SEQ ID NO:99)-- |
| COLUMN 43, | LINE 61, | delete the comma after "(HUMAN);" and delete the period after "sequence" |
| COLUMN 43, | LINE 62, | after "MTRVLQVVLLALPQLV" insert --(SEQ ID NO:100)-- |
| COLUMN 43, | LINE 66, | after "KVIQGSLDSLPQAV" insert --(SEQ ID NO:101)-- and after "LDSL" insert --(SEQ ID NO:102)-- |

UNITED STATES PATENT AND TRADEMARK OFFICE
CERTIFICATE OF CORRECTION

PATENT NO.         : 7,175,679 B2
APPLICATION NO. : 10/029206
DATED                : February 13, 2007
INVENTOR(S)       : Nisar Asmed Khan and Robert Benner It is certified that error appears in the above-identified patent and that said Letters Patent is hereby corrected as shown below:

In the specification (continued):

| | |
|---|---|
| COLUMN 43, LINE 69, | after "VLQAILPSAPQ" insert --(SEQ ID NO:103)--; after "LQAIL" insert --(SEQ ID NO:104)--; and after "PSAP" insert --(SEQ ID NO:105)-- |
| COLUMN 43, LINE 71, | after "KVLQGRLPAVAQAV" insert --(SEQ ID NO:106)-- |
| COLUMN 43, LINE 72, | after "LPAV" insert --(SEQ ID NO:107)-- |
| COLUMN 43, LINE 75, | after "LVQKVVPMLPRLLC" insert --(SEQ ID NO:108)--; after "LPRL" insert --(SEQ ID NO:109)--; and after "PMLP" insert --(SEQ ID NO:110)-- |
| COLUMN 43, LINE 78, | after "VLQAILPSAPQ" insert --(SEQ ID NO:103)--; after "LQAIL" insert --(SEQ ID NO:104)--; after "PSAP" insert --(SEQ ID NO:105)--; and after "PSAPQ" insert --(SEQ ID NO:111)-- |
| COLUMN 45, LINE 4, | after "LPGCPRHFNPV" insert --(SEQ ID NO:112)-- and after "LPGC" insert --(SEQ ID NO:41)-- |
| COLUMN 45, LINE 8, | after "LVGCPRDYDPV" insert --(SEQ ID NO:113)-- and after "LVGC" insert --(SEQ ID NO:114)-- |
| COLUMN 45, LINE 12, | after "PGCPRG" insert --(SEQ ID NO:115)-- and after "PGCP" insert --(SEQ ID NO:10)-- |
| COLUMN 45, LINE 14, | after "LPGCP" insert --(SEQ ID NO:116)--; after "PGCP" insert --(SEQ ID NO:10)--; and after "LPGC" insert --(SEQ ID NO:40)-- |
| COLUMN 45, LINE 16, | after "VLPAAP" insert --(SEQ ID NO:117)-- and after "PAAP" insert --(SEQ ID NO:72)-- |
| COLUMN 45, LINE 19, | after "LAGTIPATP" insert --(SEQ ID NO:118)-- and after "PATP" insert --(SEQ ID NO:119)-- |
| COLUMN 45, LINE 22, | after "GVLPAVP" insert --(SEQ ID NO:11)--; after "VLPAVP" insert --(SEQ ID NO:12)--; and after "PAVP" insert --(SEQ ID NO:13)-- |

UNITED STATES PATENT AND TRADEMARK OFFICE
CERTIFICATE OF CORRECTION

PATENT NO. : 7,175,679 B2
APPLICATION NO. : 10/029206
DATED : February 13, 2007
INVENTOR(S) : Nisar Asmed Khan and Robert Benner It is certified that error appears in the above-identified patent and that said Letters Patent is hereby corrected as shown below:

In the specification (continued):

| | |
|---|---|
| COLUMN 45, LINE 24, | after "GVLPALP" insert --(SEQ ID NO:32)--; after "PALP" insert --(SEQ ID NO:76)--; and after "LPAL" insert --(SEQ ID NO:75)-- |
| COLUMN 45, LINE 26, | after "GLLPCLP" insert --(SEQ ID NO:120)--; after "LPCL" insert --(SEQ ID NO:88)--; and after "PCLP" insert --(SEQ ID NO:89)-- |
| COLUMN 45, LINE 28, | after "PGAP" insert --(SEQ ID NO:121)--; after "LPQRPRGPNP" insert --(SEQ ID NO:122)--; and change "PROP" to --PRGP-- and insert --(SEQ ID NO:123)-- thereafter |
| COLUMN 45, LINE 30, | after "GCPR" insert --(SEQ ID NO:124)-- |
| COLUMN 45, LINE 32, | after "GCPRGM" insert --(SEQ ID NO:125)-- |
| COLUMN 45, LINE 35, | after "GCPRGM" insert --(SEQ ID NO:125)-- |
| COLUMN 45, LINE 38, | after "LQHV" insert --(SEQ ID NO:126)-- |
| COLUMN 45, LINE 41, | after "FPGC" insert --(SEQ ID NO:9)-- and after "PGCP" insert --(SEQ ID NO:10)-- |
| COLUMN 45, LINE 43, | after "PARP" insert --(SEQ ID NO:62)-- and after "VPGC" insert --(SEQ ID NO:127)-- |
| COLUMN 45, LINE 45, | after "CPRG" insert --(SEQ ID NO:128)-- and after "LKGC" insert --(SEQ ID NO:129)-- |
| COLUMN 45, LINE 48, | after "PPGP" insert --(SEQ ID NO:130)--; after "LPGCPREV" insert --(SEQ ID NO:131)--; after "LPGC" insert --(SEQ ID NO:41)--; after "PGCP" insert --(SEQ ID NO:10)--; and after "CPRE" insert --(SEQ ID NO:132)-- |
| COLUMN 45, LINE 50, | after "MMRVLQAVLPPLPQVVC" insert --(SEQ ID NO:133)--; after "MMRV" insert --(SEQ ID NO:52)--; after "VLPPLP" insert --(SEQ ID NO:135)--; and after "PPLP" insert --(SEQ ID NO:81)-- |
| COLUMN 45, LINE 51, | after "QVVC" insert --(SEQ ID NO:43)--; after "VLPPLPQ" insert --(SEQ ID NO:136)--; after "AVLPPLP" insert --(SEQ ID NO:137)--; and after "AVLPPLPQ" insert --(SEQ ID NO:138)-- |

UNITED STATES PATENT AND TRADEMARK OFFICE
CERTIFICATE OF CORRECTION

| | | |
|---|---|---|
| PATENT NO. | : 7,175,679 B2 | |
| APPLICATION NO. | : 10/029206 | |
| DATED | : February 13, 2007 | |
| INVENTOR(S) | : Nisar Asmed Khan and Robert Benner | |

It is certified that error appears in the above-identified patent and that said Letters Patent is hereby corrected as shown below:

In the specification (continued):

| | |
|---|---|
| COLUMN 45, LINE 53, | after "MMRVLQAVLPPVPQVVC" insert --(SEQ ID NO:139)--; after "MMRV" insert --(SEQ ID NO:134)--; after "LQAG" insert --(SEQ ID NO:140)--; after "VLPPVP" insert --(SEQ ID NO:141)--; and after "VLPPVPQ" insert --(SEQ ID NO:142)-- |
| COLUMN 45, LINE 54, | after "QVVC" insert --(SEQ ID NO:43)--; after "AVLPPVP" insert --(SEQ ID NO:143)--; and after "AVLPPVPQ" insert --(SEQ ID NO:144)-- |
| COLUMN 45, LINE 56, | after "MTRD" insert --(SEQ ID NO:145)--; after "QDVC" insert --(SEQ ID NO:146)--; after "IPGC" insert --(SEQ ID NO:147)--; and after "PGCP" insert --(SEQ ID NO:10)-- |
| COLUMN 45, LINE 58, | after "LPGC" insert --(SEQ ID NO:41)-- and after "PGCP" insert --(SEQ ID NO:10)-- |
| COLUMN 45, LINE 60, | after "PALP" insert --(SEQ ID NO:76)-- and after "PALPS" insert --(SEQ ID NO:148)-- |
| COLUMN 45, LINE 62, | after "LPGGPR" insert --(SEQ ID NO:149)--; after "LPGG" insert --(SEQ ID NO:150)--; after "GGPR" insert --(SEQ ID NO:151)-- |
| COLUMN 45, LINE 64, | after "LQRG" insert --(SEQ ID NO:152)--; after "LQRGV" insert --(SEQ ID NO:153)--; after "LGQL" insert --(SEQ ID NO:154)-- |
| COLUMN 45, LINE 67, | after "MTRVLQGVLPALP" insert --(SEQ ID NO:155)-- |
| COLUMN 45, LINE 68, | after "QVVC" insert --(SEQ ID NO:43)-- |
| COLUMN 45, LINE 71, | after "VLQGVLPAL" insert --(SEQ ID NO:156)-- |
| COLUMN 45, LINE 72, | after "GVLPALPQV" insert --(SEQ ID NO:157)-- |
| COLUMN 45, LINE 73, | after "VLPALPQVV" insert --(SEQ ID NO:158)-- |
| COLUMN 45, LINE 74, | after "RLPGCPRGV" insert --(SEQ ID NO:159)-- |
| COLUMN 45, LINE 75, | after "TMTRVLQGV" insert --(SEQ ID NO:160)-- |

UNITED STATES PATENT AND TRADEMARK OFFICE
CERTIFICATE OF CORRECTION

PATENT NO. : 7,175,679 B2
APPLICATION NO. : 10/029206
DATED : February 13, 2007
INVENTOR(S) : Nisar Asmed Khan and Robert Benner It is certified that error appears in the above-identified patent and that said Letters Patent is hereby corrected as shown below:

In the specification (continued):

| | | |
|---|---|---|
| COLUMN 47, | LINE 3, | after "CPTMTRVLQGVLPAL" insert --(SEQ ID NO:161)-- |
| COLUMN 47, | LINE 4, | after "PGCPRGVNPVVSYAV" insert --(SEQ ID NO:162)-- |
| COLUMN 47, | LINE 5, | after "PRGVNPVVSYAVALS" insert --(SEQ ID NO:163)-- |
| COLUMN 47, | LINE 6, | after "TRVLQGVLPALPQVV" insert --(SEQ ID NO:164)-- |
| COLUMN 47, | LINE 7, | after "LQGVLPALPQVVCNY" insert --(SEQ ID NO:165)-- |
| COLUMN 47, | LINE 8, | after "CPTMTRVLQGVLPAL" insert --(SEQ ID NO:161)-- |
| COLUMN 47, | LINE 9, | after "MTRVLQGVLPALPQV" insert --(SEQ ID NO:166)-- |
| COLUMN 47, | LINE 10, | after "SIRLPGCPRGVNPVV" insert --(SEQ ID NO:167)-- |
| COLUMN 47, | LINE 29, | after "VLPALPQVVC" insert --(SEQ ID NO:28)-- |
| COLUMN 47, | LINE 30, | after "LQGVLPALPQ" insert --(SEQ ID NO:49)-- |
| COLUMN 47, | LINE 32, | after "LQGV" insert --(SEQ ID NO:1)-- |
| COLUMN 47, | LINE 33, | after "GVLPALPQ" insert --(SEQ ID NO:33)-- |
| COLUMN 47, | LINE 34, | after "VLPALP" insert --(SEQ ID NO:3)-- |
| COLUMN 47, | LINE 35, | after "VLPALPQ" insert --(SEQ ID NO:29)-- |
| COLUMN 47, | LINE 36, | after "GVLPALP" insert --(SEQ ID NO:32)-- |
| COLUMN 47, | LINE 38, | after "MTRV" insert --(SEQ ID NO:42)-- |
| COLUMN 47, | LINE 40, | after "LQGVLPALPOVVC" insert --(SEQ ID NO:34)-- |
| COLUMN 47, | LINE 42, | after "LQGVLPALPOVVC" insert --(SEQ ID NO:34)-- |
| COLUMN 47, | LINE 43, | after "LPGCPRGVNPVVS" insert --(SEQ ID NO:40)-- |
| COLUMN 47, | LINE 44, | after "LPGC" insert --(SEQ ID NO:41)-- |

UNITED STATES PATENT AND TRADEMARK OFFICE
CERTIFICATE OF CORRECTION

PATENT NO. : 7,175,679 B2
APPLICATION NO. : 10/029206
DATED : February 13, 2007
INVENTOR(S) : Nisar Asmed Khan and Robert Benner It is certified that error appears in the above-identified patent and that said Letters Patent is hereby corrected as shown below:

In the specification (continued):

| | | |
|---|---|---|
| COLUMN 47, | LINE 51, | after "LQGV" insert --(SEQ ID NO:1)-- |
| COLUMN 47, | LINE 52, | after "AQGV" insert --(SEQ ID NO:2)-- |
| COLUMN 47, | LINE 53, | after "LQGA" insert --(SEQ ID NO:19)-- |
| COLUMN 47, | LINE 54, | after "VLPALP" insert --(SEQ ID NO:3)-- |
| COLUMN 47, | LINE 55, | after "ALPALP" insert --(SEQ ID NO:21)-- |
| COLUMN 47, | LINE 56, | after "VAPALP" insert --(SEQ ID NO:23)-- |
| COLUMN 47, | LINE 57, | after "ALPALPQ" insert --(SEQ ID NO:23)-- |
| COLUMN 47, | LINE 58, | after "VLPAAPQ" insert --(SEQ ID NO:24)-- |
| COLUMN 47, | LINE 59, | after "VLPALAQ" insert --(SEQ ID NO:25)-- |
| COLUMN 47, | LINE 60, | after "LAGV" insert --(SEQ ID NO:26)-- |
| COLUMN 47, | LINE 61, | after "LQAV" insert --(SEQ ID NO:52)-- |
| COLUMN 47, | LINE 62, | after "VLAALP" insert --(SEQ ID NO:27)-- |
| COLUMN 47, | LINE 63, | after "VLPAAP" insert --(SEQ ID NO:117)-- |
| COLUMN 47, | LINE 64, | after "VLPALA" insert --(SEQ ID NO:28)-- |
| COLUMN 47, | LINE 65, | after "VLPALPQ" insert --(SEQ ID NO:29)-- |
| COLUMN 47, | LINE 66, | after "VLAALPQ" insert --(SEQ ID NO:30)-- |
| COLUMN 47, | LINE 67, | after "VLPALPA" insert --(SEQ ID NO:31)-- |
| COLUMN 49, | TABLE 5, | under the column heading "SEQUENCE" after "VLPALPQVVC" insert --(SEQ ID NO:20)-- |
| COLUMN 49, | TABLE 5, | under the column heading "SEQUENCE" after "LQGVLPALPQ" insert --(SEQ ID NO:49)-- |
| COLUMN 49, | TABLE 5, | under the column heading "SEQUENCE" after "LQGV" insert --(SEQ ID NO:1)-- |
| COLUMN 49, | TABLE 5, | under the column heading "SEQUENCE" after "GVLPALPQ" insert --(SEQ ID NO:33)-- |
| COLUMN 49, | TABLE 5, | under the column heading "SEQUENCE" after "VLPALP" insert --(SEQ ID NO:3)-- |
| COLUMN 49, | TABLE 5, | under the column heading "SEQUENCE" after "VALPQ" insert --(SEQ ID NO:29)-- |
| COLUMN 49, | TABLE 5, | under the column heading "SEQUENCE" after "GVLPALP" insert --(SEQ ID NO:32)-- |
| COLUMN 49, | TABLE 5, | under the column heading "SEQUENCE" after "QVVC" insert --(SEQ ID NO:43)-- |
| COLUMN 49, | TABLE 5, | under the column heading "SEQUENCE" after "MTRV" insert --(SEQ ID NO:42)-- |

UNITED STATES PATENT AND TRADEMARK OFFICE
CERTIFICATE OF CORRECTION

PATENT NO. : 7,175,679 B2
APPLICATION NO. : 10/029206
DATED : February 13, 2007
INVENTOR(S) : Nisar Asmed Khan and Robert Benner It is certified that error appears in the above-identified patent and that said Letters Patent is hereby corrected as shown below:

In the specification (continued):

| | | |
|---|---|---|
| COLUMN 49, | TABLE 5, | under the column heading "SEQUENCE" after "LQGVLPALPQVVC" insert --(SEQ ID NO:34)-- |
| COLUMN 49, | TABLE 5, | under the column heading "SEQUENCE" after "LQGVLPALPQVVC" insert --(SEQ ID NO:34)-- |
| COLUMN 49, | TABLE 5, | under the column heading "SEQUENCE" after "AQGV" insert --(SEQ ID NO:2)-- |
| COLUMN 49, | TABLE 5, | under the column heading "SEQUENCE" after "LAGV" insert --(SEQ ID NO:26)-- |
| COLUMN 49, | TABLE 5, | under the column heading "SEQUENCE" after "LQAV" insert --(SEQ ID NO:52)-- |
| COLUMN 49, | TABLE 5, | under the column heading "SEQUENCE" after "LQGA" insert --(SEQ ID NO:19)-- |
| COLUMN 49, | TABLE 5, | under the column heading "SEQUENCE" after "ALPALP" insert --(SEQ ID NO:21)-- |
| COLUMN 49, | TABLE 5, | under the column heading "SEQUENCE" after "VAPALP" insert --(SEQ ID NO:22)-- |
| COLUMN 49, | TABLE 5, | under the column heading "SEQUENCE" after "VLAALP" insert --(SEQ ID NO:27)-- |
| COLUMN 49, | TABLE 5, | under the column heading "SEQUENCE" after "VLPAAP" insert --(SEQ ID NO:117)-- |
| COLUMN 49, | TABLE 5, | under the column heading "SEQUENCE" after "VLPALA" insert --(SEQ ID NO:28)-- |
| COLUMN 49, | TABLE 5, | under the column heading "SEQUENCE" after "ALPALPQ" insert --(SEQ ID NO:23)-- |
| COLUMN 49, | TABLE 5, | under the column heading "SEQUENCE" after "VAPALPQ" insert --(SEQ ID NO:173)-- |
| COLUMN 49, | TABLE 5, | under the column heading "SEQUENCE" after "VLAALPQ" insert --(SEQ ID NO:30)-- |
| COLUMN 49, | TABLE 5, | under the column heading "SEQUENCE" after "VLPAAPQ" insert --(SEQ ID NO:24)-- |
| COLUMN 49, | TABLE 5, | under the column heading "SEQUENCE" after "VLPALAQ" insert --(SEQ ID NO:25)-- |

UNITED STATES PATENT AND TRADEMARK OFFICE
CERTIFICATE OF CORRECTION

PATENT NO. : 7,175,679 B2
APPLICATION NO. : 10/029206
DATED : February 13, 2007
INVENTOR(S) : Nisar Asmed Khan and Robert Benner It is certified that error appears in the above-identified patent and that said Letters Patent is hereby corrected as shown below:

In the specification (continued):

| | |
|---|---|
| COLUMN 49, TABLE 5, | under the column heading "SEQUENCE" after "VLPALPA" insert --(SEQ ID NO:31)-- |
| COLUMN 49, TABLE 5, | under the column heading "SEQUENCE" after "VVCNYRDVRFESIRLPGCPRGVNPVVSYAVALSCQCAL" insert --(SEQ ID NO:35)-- |
| COLUMN 49, TABLE 5, | under the column heading "SEQUENCE" after "VVCNYRDVRFESIRLPGCPRGVNPVVSYAVALSCQ" insert --(SEQ ID NO:169)-- |
| COLUMN 49, TABLE 5, | under the column heading "SEQUENCE" after "SIRLPGCPRGVNPVVS" insert --(SEQ ID NO:39)-- |
| COLUMN 49, TABLE 5, | under the column heading "SEQUENCE" after "LPGCPRGVNPVVS" insert --(SEQ ID NO:40)-- |
| COLUMN 49, TABLE 5, | under the column heading "SEQUENCE" after "CPRGVNPVVS" insert --(SEQ ID NO:50)-- |
| COLUMN 49, TABLE 5, | under the column heading "SEQUENCE" after "LPGC" insert --(SEQ ID NO:41)-- |
| COLUMN 49, TABLE 5, | under the column heading "SEQUENCE" after "CPRGVNP" insert --(SEQ ID NO:170)-- |
| COLUMN 49, TABLE 5, | under the column heading "SEQUENCE" after "PGCP" insert --(SEQ ID NO:10)-- |
| COLUMN 49, TABLE 5, | under the column heading "SEQUENCE" after "RPRCRPINATLAVEKEGCPVCITVNTTICAGYCPT" insert --(SEQ ID NO:45)-- |
| COLUMN 49, TABLE 5, | under the column heading "SEQUENCE" after "MTRVLQGVLPALPQ" insert --(SEQ ID NO:171)-- |
| COLUMN 49, TABLE 5, | under the column heading "SEQUENCE" after "MTRVLPGVLPALPQVVC" insert --(SEQ ID NO:174)-- |
| COLUMN 49, TABLE 5, | under the column heading "SEQUENCE" after "CALCRRSTTDCGGPKDHPLTC" insert --(SEQ ID NO:46)-- |
| COLUMN 49, TABLE 5, | under the column heading "SEQUENCE" after "SKAPPPSLPSPSRLPGPC" insert --(SEQ ID NO:172)-- |

UNITED STATES PATENT AND TRADEMARK OFFICE
CERTIFICATE OF CORRECTION

| | | |
|---|---|---|
| PATENT NO. | : 7,175,679 B2 | |
| APPLICATION NO. | : 10/029206 | |
| DATED | : February 13, 2007 | |
| INVENTOR(S) | : Nisar Asmed Khan and Robert Benner | |

It is certified that error appears in the above-identified patent and that said Letters Patent is hereby corrected as shown below:

In the specification (continued):

| | | |
|---|---|---|
| COLUMN 49, | TABLE 5, | under the column heading "SEQUENCE" after "TCDDPRFQDSSSSKAPPPSLPSPSRLPGPSDTPILPQ" insert --(SEQ ID NO:48)-- |
| COLUMN 49, | TABLE 6, | under the column heading "SEQUENCE" after "VLPALPQVVC" insert --(SEQ ID NO:20)-- |
| COLUMN 49, | TABLE 6, | under the column heading "SEQUENCE" after "LQGVLPALPQ" insert --(SEQ ID NO:49)-- |
| COLUMN 49, | TABLE 6, | under the column heading "SEQUENCE" after "LQGV" insert --(SEQ ID NO:1)-- |
| COLUMN 49, | TABLE 6, | under the column heading "SEQUENCE" after "GVLPALPQ" insert --(SEQ ID NO:33)-- |
| COLUMN 49, | TABLE 6, | under the column heading "SEQUENCE" after "VLPALP" insert --(SEQ ID NO:3)-- |
| COLUMN 49, | TABLE 6, | under the column heading "SEQUENCE" after "VALPQ" insert --(SEQ ID NO:29)-- |
| COLUMN 49, | TABLE 6, | under the column heading "SEQUENCE" after "GVLPALP" insert --(SEQ ID NO:32)-- |
| COLUMN 49, | TABLE 6, | under the column heading "SEQUENCE" after "QVVC" insert --(SEQ ID NO:43)-- |
| COLUMN 50, | TABLE 6, | under the column heading "SEQUENCE" after "MTRV" insert --(SEQ ID NO:42)-- |
| COLUMN 50, | TABLE 6, | under the column heading "SEQUENCE" after "LQGVLPALPQVVC" insert (SEQ ID NO:34)-- |
| COLUMN 50, | TABLE 6, | under the column heading "SEQUENCE" after "LQGVLPALPQVVC" insert --(SEQ ID NO:34)-- |
| COLUMN 50, | TABLE 6, | under the column heading "SEQUENCE" after "AQGV" insert --(SEQ ID NO:2)-- |
| COLUMN 50, | TABLE 6, | under the column heading "SEQUENCE" after "LAGV" insert --(SEQ ID NO:26)-- |
| COLUMN 51, | TABLE 6, | under the column heading "SEQUENCE" after "LAGV" insert --(SEQ ID NO:26) |
| COLUMN 51, | TABLE 6, | under the column heading "SEQUENCE" after "LQAV" insert --(SEQ ID NO:52)-- |

UNITED STATES PATENT AND TRADEMARK OFFICE
CERTIFICATE OF CORRECTION

| | | |
|---|---|---|
| PATENT NO. | : 7,175,679 B2 | |
| APPLICATION NO. | : 10/029206 | |
| DATED | : February 13, 2007 | |
| INVENTOR(S) | : Nisar Asmed Khan and Robert Benner | |

It is certified that error appears in the above-identified patent and that said Letters Patent is hereby corrected as shown below:

In the specification (continued):

| | | |
|---|---|---|
| COLUMN 51, | TABLE 6, | under the column heading "SEQUENCE" after "LQGA" insert --(SEQ ID NO:19)-- |
| COLUMN 51, | TABLE 6, | under the column heading "SEQUENCE" after "ALPALP" insert --(SEQ ID NO:21)-- |
| COLUMN 51, | TABLE 6, | under the column heading "SEQUENCE" after "VAPALP" insert --(SEQ ID NO:22)-- |
| COLUMN 51, | TABLE 6, | under the column heading "SEQUENCE" after "VLAALP" insert --(SEQ ID NO:27)-- |
| COLUMN 51, | TABLE 6, | under the column heading "SEQUENCE" after "VLPAAP" insert --(SEQ ID NO:117)-- |
| COLUMN 51, | TABLE 6, | under the column heading "SEQUENCE" after "VLPALA" insert --(SEQ ID NO:28)-- |
| COLUMN 51, | TABLE 6, | under the column heading "SEQUENCE" after "ALPALPQ" insert --(SEQ ID NO:23)-- |
| COLUMN 51, | TABLE 6, | under the column heading "SEQUENCE" after "VAPALPQ" insert --(SEQ ID NO:173)-- |
| COLUMN 51, | TABLE 6, | under the column heading "SEQUENCE" after "VLAALPQ" insert --(SEQ ID NO:30)-- |
| COLUMN 51, | TABLE 6, | under the column heading "SEQUENCE" after "VLPAAPQ" insert --(SEQ ID NO:24)-- |
| COLUMN 51, | TABLE 6, | under the column heading "SEQUENCE" after "VLPALAQ" insert --(SEQ ID NO:25)-- |
| COLUMN 51, | TABLE 6, | under the column heading "SEQUENCE" after "VLPALPA" insert --(SEQ ID NO:31)-- |
| COLUMN 51, | TABLE 6, | under the column heading "SEQUENCE" after "VVCNYRDVRFESIRLPGCPRGVNPVVSYAVALSCQCAL" insert --(SEQ ID NO:35)-- |
| COLUMN 51, | TABLE 6, | under the column heading "SEQUENCE" after "VVCNYRDVRFESIRLPGCPRGVNPVVSYAVALSCQ" insert --(SEQ ID NO:169)-- |
| COLUMN 51, | TABLE 6, | under the column heading "SEQUENCE" after "SIRLPGCPRGVNPVVS" insert --(SEQ ID NO:39)-- |
| COLUMN 51, | TABLE 6, | under the column heading "SEQUENCE" after "LPGCPRGVNPVVS" insert --(SEQ ID NO:40)-- |

UNITED STATES PATENT AND TRADEMARK OFFICE
CERTIFICATE OF CORRECTION

| | | |
|---|---|---|
| PATENT NO. | : 7,175,679 B2 | |
| APPLICATION NO. | : 10/029206 | |
| DATED | : February 13, 2007 | |
| INVENTOR(S) | : Nisar Asmed Khan and Robert Benner | |

It is certified that error appears in the above-identified patent and that said Letters Patent is hereby corrected as shown below:

In the specification (continued):

| | |
|---|---|
| COLUMN 51, TABLE 6, | under the column heading "SEQUENCE" after "CPRGVNPVVS" insert --(SEQ ID NO:50)-- |
| COLUMN 51, TABLE 6, | under the column heading "SEQUENCE" after "LPGC" insert --(SEQ ID NO:41)-- |
| COLUMN 51, TABLE 6, | under the column heading "SEQUENCE" after "CPRGVNP" insert --(SEQ ID NO:170)-- |
| COLUMN 51, TABLE 6, | under the column heading "SEQUENCE" after "PGCP" insert --(SEQ ID NO:10)-- |
| COLUMN 51, TABLE 6, | under the column heading "SEQUENCE" after "RPRCRPINATLAVEKEGCPVCITVNTTI CAGYCPT" insert --(SEQ ID NO:45)-- |
| COLUMN 51, TABLE 6, | under the column heading "SEQUENCE" after "MTRVLQGVLPALPQ" insert --(SEQ ID NO:171)-- |
| COLUMN 51, TABLE 6, | under the column heading "SEQUENCE" after "MTRVLPGVLPALPQVVC" insert --(SEQ ID NO:174)-- |
| COLUMN 51, TABLE 6, | under the column heading "SEQUENCE" after "CALCRRSTTDCGGPKDHPLTC" insert --(SEQ ID NO:46)-- |
| COLUMN 51, TABLE 6, | under the column heading "SEQUENCE" after "SKAPPPSLPSPSRLPGPC" insert --(SEQ ID NO:172)-- |
| COLUMN 51, TABLE 6, | under the column heading "SEQUENCE" after "TCDDPRFQDSSSSKAPPPSLPSPSRLPGPS DTPILPQ" insert --(SEQ ID NO:48)-- |
| COLUMN 51, TABLE 6, | under the column heading "SEQUENCE" after "CRRSTTDCGGPKDHPLTC" insert --(SEQ ID NO:47)-- |
| COLUMN 51, LINE 54, | change "·" (first occurrence) to --α-- and change "·" (second occurrence) to --ß-- |
| COLUMN 53, LINE 40, | In the Experimental Design Table, under the column named "EXPERIMENTAL TREATMENT" change "antibioti" to --antibiotic-- |

UNITED STATES PATENT AND TRADEMARK OFFICE
CERTIFICATE OF CORRECTION

PATENT NO. : 7,175,679 B2
APPLICATION NO. : 10/029206
DATED : February 13, 2007
INVENTOR(S) : Nisar Asmed Khan and Robert Benner It is certified that error appears in the above-identified patent and that said Letters Patent is hereby corrected as shown below:

In the specification (continued):
      COLUMN 54, LINE 62,     change "vitrolex" to --vitro/ex--
      COLUMN 67, LINE 6,      change "KB" to --κB--
      COLUMN 67, LINE 20,     change "KB" to --κB--
      COLUMN 67, LINE 22,     change "KB" to --κB--
      COLUMN 67, LINE 32,     change "KB" to --κB-- (both occurrences)
      COLUMN 69, LINE 3,      change "KB" to --κB--

Signed and Sealed this

Twenty-third Day of December, 2008

JON W. DUDAS
*Director of the United States Patent and Trademark Office*

SEQUENCE LISTING

```
<160> NUMBER OF SEQ ID NOS: 175

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 1

Leu Gln Gly Val
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 2

Ala Gln Gly Val
  1

<210> SEQ ID NO 3
```

-continued

```
<211> LENGTH: 6
<212> TYPE: PRT
<213> ORGANISM: Artificial Sequence
<220> FEATURE:
<223> OTHER INFORMATION: Description of Artificial Sequence:
      oligopeptide

<400> SEQUENCE: 3

Val Leu Pro Ala Leu Pro
  1               5

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: peptide

<400> SEQUENCE: 4

Met Leu Ala Arg Arg Lys Pro Val Leu Pro Ala Leu Thr Ile Asn Pro
  1               5                  10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: peptide

<400> SEQUENCE: 5

Met Leu Ala Arg Arg Lys Pro
  1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: peptide

<400> SEQUENCE: 6

Met Leu Ala Arg
  1

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: peptide

<400> SEQUENCE: 7

Val Leu Pro Ala Leu Thr
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:
      pdb/1QMH/1QMH-A

<400> SEQUENCE: 8

Val Leu Pro Ala Leu
  1               5
```

```
<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:
      pdb/4NOS/4NOS-A

<400> SEQUENCE: 9

Phe Pro Gly Cys
 1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:
      Hs.297775.1

<400> SEQUENCE: 10

Pro Gly Cys Pro
 1

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:
      swiss/P81272/NS2B HUMAN

<400> SEQUENCE: 11

Gly Val Leu Pro Ala Val Pro
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:
      swiss/P81272/NS2B HUMAN

<400> SEQUENCE: 12

Val Leu Pro Ala Val Pro
 1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:
      pdb/1FZV/1FZV-A

<400> SEQUENCE: 13

Pro Ala Val Pro
 1

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:
      oligopeptide

<400> SEQUENCE: 14
```

```
Leu Gln Gly Val Val Pro Arg Gly Val
  1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 15

Gly Val Val Pro
  1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:
      oligopeptide

<400> SEQUENCE: 16

Val Pro Arg Gly Val
  1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 17

Pro Arg Gly Val
  1

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: polypeptide

<400> SEQUENCE: 18

Met Ala Pro Lys Lys
  1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 19

Leu Gln Gly Ala
  1

<210> SEQ ID NO 20
<211> LENGTH: 10
<212> TYPE: PRT
<213> ORGANISM: Artificial Sequence
<220> FEATURE:
```

<223> OTHER INFORMATION: Description of Artificial Sequence:
       oligopeptide

<400> SEQUENCE: 20

Val Leu Pro Ala Leu Pro Gln Val Val Cys
 1               5                  10

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:
       oligopeptide

<400> SEQUENCE: 21

Ala Leu Pro Ala Leu Pro
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:
       oligopeptide

<400> SEQUENCE: 22

Val Ala Pro Ala Leu Pro
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:
       oligopeptide

<400> SEQUENCE: 23

Ala Leu Pro Ala Leu Pro Gln
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:
       oligopeptide

<400> SEQUENCE: 24

Val Leu Pro Ala Ala Pro Gln
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:
       oligopeptide

<400> SEQUENCE: 25

Val Leu Pro Ala Leu Ala Gln
 1               5

```
<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 26

Leu Ala Gly Val
 1

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:
      oligopeptide

<400> SEQUENCE: 27

Val Leu Ala Ala Leu Pro
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence:
      oligopeptide

<400> SEQUENCE: 28

Val Leu Pro Ala Leu Ala
 1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:
      oligopeptide

<400> SEQUENCE: 29

Val Leu Pro Ala Leu Pro Gln
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence:
      oligopeptide

<400> SEQUENCE: 30

Val Leu Ala Ala Leu Pro Gln
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence:
      oligopeptide

<400> SEQUENCE: 31
```

```
Val Leu Pro Ala Leu Pro Ala
 1               5
```

```
<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence:
      oligopeptide

<400> SEQUENCE: 32

Gly Val Leu Pro Ala Leu Pro
 1               5
```

```
<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:
      oligopeptide

<400> SEQUENCE: 33

Gly Val Leu Pro Ala Leu Pro Gln
 1               5
```

```
<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence:
      oligopeptide

<400> SEQUENCE: 34

Leu Gln Gly Val Leu Pro Ala Leu Pro Gln Val Val Cys
 1               5                  10
```

```
<210> SEQ ID NO 35
<211> LENGTH: 38
<212> TYPE: PRT
<213> ORGANISM: Artificial Sequence
<220> FEATURE:
<223> OTHER INFORMATION: Description of Artificial Sequence:
      oligopeptide

<400> SEQUENCE: 35

Val Val Cys Asn Tyr Arg Asp Val Arg Phe Glu Ser Ile Arg Leu Pro
 1               5                  10                  15

Gly Cys Pro Arg Gly Val Asn Pro Val Val Ser Tyr Ala Val Ala Leu
             20                  25                  30

Ser Cys Gln Cys Ala Leu
         35
```

```
<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence:
      oligopeptide

<400> SEQUENCE: 36

Arg Pro Arg Cys Arg Pro Ile Asn Ala Thr Leu Ala Val Glu Lys
 1               5                  10                  15
```

```
<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence:
      oligopeptide

<400> SEQUENCE: 37

Glu Gly Cys Pro Val Cys Ile Thr Val Asn Thr Thr Ile Cys Ala Gly
 1               5                  10                  15

Tyr Cys Pro Thr
            20

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence:
      oligopeptide

<400> SEQUENCE: 38

Ser Lys Ala Pro Pro Pro Ser Leu Pro Ser Pro Ser Arg Leu Pro Gly
 1               5                  10                  15

Pro Ser

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence:
      oligopeptide

<400> SEQUENCE: 39

Ser Ile Arg Leu Pro Gly Cys Pro Arg Gly Val Asn Pro Val Val Ser
 1               5                  10                  15

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence:
      oligopeptide

<400> SEQUENCE: 40

Leu Pro Gly Cys Pro Arg Gly Val Asn Pro Val Val Ser
 1               5                  10

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 41

Leu Pro Gly Cys
 1

<210> SEQ ID NO 42
<211> LENGTH: 4
```

```
<212> TYPE: PRT
<213> ORGANISM: Artificial Sequence
<220> FEATURE:
<223> OTHER INFORMATION: Description of Artificial Sequence:
      oligopeptide

<400> SEQUENCE: 42

Met Thr Arg Val
  1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence:
      oligopeptide

<400> SEQUENCE: 43

Gln Val Val Cys
  1

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 44

Met Thr Arg Val Leu Gln Gly Val Leu Pro Ala Leu Pro Gln Val Val
  1               5                  10                  15

Cys

<210> SEQ ID NO 45
<211> LENGTH: 35
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 45

Arg Pro Arg Cys Arg Pro Ile Asn Ala Thr Leu Ala Val Glu Lys Glu
  1               5                  10                  15

Gly Cys Pro Val Cys Ile Thr Val Asn Thr Thr Ile Cys Ala Gly Tyr
                 20                  25                  30

Cys Pro Thr
         35

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 46

Cys Ala Leu Cys Arg Arg Ser Thr Thr Asp Cys Gly Gly Pro Lys Asp
  1               5                  10                  15

His Pro Leu Thr Cys
                 20
```

```
<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 47

Cys Arg Arg Ser Thr Thr Asp Cys Gly Gly Pro Lys Asp His Pro Leu
 1               5                  10                  15

Thr Cys

<210> SEQ ID NO 48
<211> LENGTH: 37
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 48

Thr Cys Asp Asp Pro Arg Phe Gln Asp Ser Ser Ser Ser Lys Ala Pro
 1               5                  10                  15

Pro Pro Ser Leu Pro Ser Pro Ser Arg Leu Pro Gly Pro Ser Asp Thr
            20                  25                  30

Pro Ile Leu Pro Gln
        35

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: peptide
      signalling molecule

<400> SEQUENCE: 49

Leu Gln Gly Val Leu Pro Ala Leu Pro Gln
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: NMPF
      peptide

<400> SEQUENCE: 50

Cys Pro Arg Gly Val Asn Pro Val Val Ser
 1               5                  10

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: probe to
      represent the NF-kappaB binding sequence

<400> SEQUENCE: 51
agctcagagg gggactttcc gagag                                        25

<210> SEQ ID NO 52
<211> LENGTH: 4
```

```
<212> TYPE: PRT
<213> ORGANISM: Artificial Sequence
<220> FEATURE:
<223> OTHER INFORMATION: Description of Artificial Sequence: peptide
      LQAV showed smaller infarcted area

<400> SEQUENCE: 52

Leu Gln Ala Val
  1

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence:
      pdb/1DE7/1DE7-A

<400> SEQUENCE: 53

Leu Gln Gly Val Val
  1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence:
      pdb/1DE7/1DE7-A

<400> SEQUENCE: 54

Leu Gln Gly Val Val Pro
  1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence:
      pdb/1DL6/1DL6-A

<400> SEQUENCE: 55

Leu Asp Ala Leu Pro
  1               5

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence:
      pdb/1QMH/1QMH-A

<400> SEQUENCE: 56

Leu Gln Thr Val
  1

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence:
      pdb/1QMH/1QMH-A

<400> SEQUENCE: 57

Leu Val Leu Gln Thr Val Leu Pro Ala Leu
```

```
                1               5              10
```

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence:
      pdb/1LYP/1LYP

<400> SEQUENCE: 58

Ile Gln Gly Leu
  1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence:
      pdb/1LYP/1LYP

<400> SEQUENCE: 59

Leu Pro Lys Leu
  1

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence:
      pdb/1LYP/1LYP

<400> SEQUENCE: 60

Leu Leu Pro Lys Leu
  1               5

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence:
      pdb/1B9O/1B9O-A

<400> SEQUENCE: 61

Leu Pro Glu Leu
  1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence:
      pdb/1GLU/1GLU-A

<400> SEQUENCE: 62

Pro Ala Arg Pro
  1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence:

pdb/2KIN/2KIN-B

<400> SEQUENCE: 63

Met Thr Arg Ile
 1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence:
      pdb/1SMP/1SMP-I

<400> SEQUENCE: 64

Leu Gln Lys Leu
 1

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence:
      pdb/1SMP/1SMP-I

<400> SEQUENCE: 65

Leu Gln Lys Leu Leu
 1               5

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence:
      pdb/1SMP/1SMP-I

<400> SEQUENCE: 66

Pro Glu Ala Pro
 1

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence:
      pdb/1SMP/1SMP-I

<400> SEQUENCE: 67

Leu Gln Lys Leu Leu Pro Glu Ala Pro
 1               5

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence:
      pdb/1ES/1ES7-B

<400> SEQUENCE: 68

Pro Thr Leu Pro
 1

<210> SEQ ID NO 69

```
<211> LENGTH: 5
<212> TYPE: PRT
<213> ORGANISM: Artificial Sequence
<220> FEATURE:
<223> OTHER INFORMATION: Description of Artificial Sequence:
      pdb/1ES7/1ES7-B

<400> SEQUENCE: 69

Leu Gln Pro Thr Leu
 1               5

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence:
      pdb/1BHX/1BHX-F

<400> SEQUENCE: 70

Leu Gln Val Val
 1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence:
      pdb/1VCB/1VCB-A

<400> SEQUENCE: 71

Pro Glu Leu Pro
 1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence:
      pdb/1CQK/1CQK-A

<400> SEQUENCE: 72

Pro Ala Ala Pro
 1

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence:
      pdb/1CQK/1CQK-A

<400> SEQUENCE: 73

Pro Ala Ala Pro Gln
 1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence:
      pdb/1CQK/1CQK-A

<400> SEQUENCE: 74
```

```
Pro Ala Ala Pro Gln Val
  1               5

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence:
      pdb/1BFB/1BFB

<400> SEQUENCE: 75

Leu Pro Ala Leu
  1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence:
      pdb/1BFB/1BFB

<400> SEQUENCE: 76

Pro Ala Leu Pro
  1

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence:
      pdb/1BFB/1BFB

<400> SEQUENCE: 77

Pro Ala Leu Pro Glu
  1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence:
      pdb/1R2A/1R2A-A

<400> SEQUENCE: 78

Leu Thr Glu Leu Leu
  1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: C3G peptide

<400> SEQUENCE: 79

Pro Pro Pro Ala Leu Pro Pro Lys Lys Arg
  1               5                  10

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence:
```

```
        pdb/1RLQ/1RLQ-R

<400> SEQUENCE: 80

Leu Pro Pro Leu
  1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence:
      pdb/1RLQ/1RLQ-R; swissnew/P01229/LSHB HUMAN

<400> SEQUENCE: 81

Pro Pro Leu Pro
  1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence:
      pdb/1TNT/1TNT

<400> SEQUENCE: 82

Leu Pro Gly Leu
  1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence:
      pdb/1GJS/1GJS-A

<400> SEQUENCE: 83

Leu Ala Ala Leu
  1

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence:
      pdb/1GJS/1GJS-A

<400> SEQUENCE: 84

Leu Ala Ala Leu Pro
  1               5

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence:
      pdb/1GBR/1GBR-B

<400> SEQUENCE: 85

Pro Lys Leu Pro
  1

<210> SEQ ID NO 86
```

```
<211> LENGTH: 6
<212> TYPE: PRT
<213> ORGANISM: Artificial Sequence
<220> FEATURE:
<223> OTHER INFORMATION: Description of Artificial Sequence:
      pdb/1A78/1A78-A

<400> SEQUENCE: 86

Val Leu Pro Ser Ile Pro
  1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence:
      pdb/1FZV/1FZV-A

<400> SEQUENCE: 87

Met Leu Pro Ala Val Pro
  1               5

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence:
      pdb/1JLI/1JLI

<400> SEQUENCE: 88

Leu Pro Cys Leu
  1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence:
      pdb/1JLI/1JLI

<400> SEQUENCE: 89

Pro Cys Leu Pro
  1

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence:
      pdb/1HSS/1HSS-A

<400> SEQUENCE: 90

Val Pro Ala Leu Pro
  1               5

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence:
      pdb/1PRX/1PRX-A

<400> SEQUENCE: 91
```

```
Pro Thr Ile Pro
1

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence:
      pdb/1PRX/1PRX-A

<400> SEQUENCE: 92

Val Leu Pro Thr Ile Pro
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence:
      pdb/1RCY/1RCY

<400> SEQUENCE: 93

Val Leu Pro Gly Phe Pro
1               5

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence:
      pdb/1A3Z/1A3Z

<400> SEQUENCE: 94

Pro Gly Phe Pro
1

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence:
      pdb/1GER/1GER-A

<400> SEQUENCE: 95

Leu Pro Ala Leu Pro
1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence:
      pdb/1BBS/1BBS

<400> SEQUENCE: 96

Met Pro Ala Leu Pro
1               5

<210> SEQ ID NO 97
<211> LENGTH: 17
<212> TYPE: PRT
<213> ORGANISM: Artificial Sequence
<220> FEATURE:
```

```
<223> OTHER INFORMATION: Description of Artificial Sequence: AI188872
<220> FEATURE:
<221> NAME/KEY: MISC_FEATURE
<222> LOCATION: (2)
<223> OTHER INFORMATION: The (Xaa( at position 2 indicates an unknown
      amino acid

<400> SEQUENCE: 97

Met Xaa Arg Val Leu Gln Gly Val Leu Pro Ala Leu Pro Gln Val Val
  1               5                  10                  15

Cys

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: AI188872
<220> FEATURE:
<221> NAME/KEY: MISC_FEATURE
<222> LOCATION: (2)
<223> OTHER INFORMATION: The (Xaa( at position 2 indicates an unknown
      amino acid

<400> SEQUENCE: 98

Met Xaa Arg Val
  1

<210> SEQ ID NO 99
<211> LENGTH: 17
<212> TYPE: PRT
<213> ORGANISM: Artificial Sequence
<220> FEATURE:
<223> OTHER INFORMATION: Description of Artificial Sequence: AI126906

<400> SEQUENCE: 99

Ile Thr Arg Val Met Gln Gly Val Ile Pro Ala Leu Pro Gln Val Val
  1               5                  10                  15

Cys

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: AI221581

<400> SEQUENCE: 100

Met Thr Arg Val Leu Gln Val Val Leu Leu Ala Leu Pro Gln Leu Val
  1               5                  10                  15

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Mm.42246.3

<400> SEQUENCE: 101

Lys Val Ile Gln Gly Ser Leu Asp Ser Leu Pro Gln Ala Val
  1               5                  10

<210> SEQ ID NO 102
<211> LENGTH: 4
<212> TYPE: PRT
<213> ORGANISM: Artificial Sequence
<220> FEATURE:
```

<223> OTHER INFORMATION: Description of Artificial Sequence: Mm.42246.3

<400> SEQUENCE: 102

Leu Asp Ser Leu
 1

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Mm.22430.1

<400> SEQUENCE: 103

Val Leu Gln Ala Ile Leu Pro Ser Ala Pro Gln
 1               5                  10

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Mm.22430.1

<400> SEQUENCE: 104

Leu Gln Ala Ile Leu
 1               5

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Mm.22430.1

<400> SEQUENCE: 105

Pro Ser Ala Pro
 1

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Hs.63758.4

<400> SEQUENCE: 106

Lys Val Leu Gln Gly Arg Leu Pro Ala Val Ala Gln Ala Val
 1               5                  10

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Hs.63758.4

<400> SEQUENCE: 107

Leu Pro Ala Val
 1

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Mm.129320.2

```
<400> SEQUENCE: 108

Leu Val Gln Lys Val Val Pro Met Leu Pro Arg Leu Leu Cys
  1               5                  10

<210> SEQ ID NO 109
<211> LENGTH: 4
<212> TYPE: PRT
<213> ORGANISM: Artificial Sequence
<220> FEATURE:
<223> OTHER INFORMATION: Description of Artificial Sequence: Mm.129320.2

<400> SEQUENCE: 109

Leu Pro Arg Leu
  1

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence: Mm.129320.2

<400> SEQUENCE: 110

Pro Met Leu Pro
  1

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Mm.22430.1

<400> SEQUENCE: 111

Pro Ser Ala Pro Gln
  1               5

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: P20155

<400> SEQUENCE: 112

Leu Pro Gly Cys Pro Arg His Phe Asn Pro Val
  1               5                  10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Rn.2337.1

<400> SEQUENCE: 113

Leu Val Gly Cys Pro Arg Asp Tyr Asp Pro Val
  1               5                  10

<210> SEQ ID NO 114
<211> LENGTH: 4
<212> TYPE: PRT
<213> ORGANISM: Artificial Sequence
<220> FEATURE:
<223> OTHER INFORMATION: Description of Artificial Sequence: Rn.2337.1
```

```
<400> SEQUENCE: 114

Leu Val Gly Cys
  1

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Hs.297775.1

<400> SEQUENCE: 115

Pro Gly Cys Pro Arg Gly
  1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Mm.1359.1

<400> SEQUENCE: 116

Leu Pro Gly Cys Pro
  1               5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence:
      sptrembl/O56177/O56177

<400> SEQUENCE: 117

Val Leu Pro Ala Ala Pro
  1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence:
      sptrembl/Q9W234/Q9W234

<400> SEQUENCE: 118

Leu Ala Gly Thr Ile Pro Ala Thr Pro
  1               5

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence:
      sptrembl/Q9W234/Q9W234

<400> SEQUENCE: 119

Pro Ala Thr Pro
  1

<210> SEQ ID NO 120
<211> LENGTH: 7
<212> TYPE: PRT
<213> ORGANISM: Artificial Sequence
<220> FEATURE:
```

```
<223> OTHER INFORMATION: Description of Artificial Sequence:
      sptrembl/Q9IYZ3/Q9IYZ3

<400> SEQUENCE: 120

Gly Leu Leu Pro Cys Leu Pro
1               5

<210> SEQ ID NO 121
<211> LENGTH: 4
<212> TYPE: PRT
<213> ORGANISM: Artificial Sequence
<220> FEATURE:
<223> OTHER INFORMATION: Description of Artificial Sequence:
      sptrembl/Q9PVW5/Q9PVW5

<400> SEQUENCE: 121

Pro Gly Ala Pro
1

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence:
      sptrembl/Q9PVW5/Q9PVW5

<400> SEQUENCE: 122

Leu Pro Gln Arg Pro Arg Gly Pro Asn Pro
1               5                   10

<210> SEQ ID NO 123
<211> LENGTH: 4
<212> TYPE: PRT
<213> ORGANISM: Artificial Sequence
<220> FEATURE:
<223> OTHER INFORMATION: Description of Artificial Sequence:
      sptrembl/Q9PVW5/Q9PVW5

<400> SEQUENCE: 123

Pro Arg Gly Pro
1

<210> SEQ ID NO 124
<211> LENGTH: 4
<212> TYPE: PRT
<213> ORGANISM: Artificial Sequence
<220> FEATURE:
<223> OTHER INFORMATION: Description of Artificial Sequence: Hs.303116.2

<400> SEQUENCE: 124

Gly Cys Pro Arg
1

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence:
      pdb/1DU3/1DU3-A

<400> SEQUENCE: 125

Gly Cys Pro Arg Gly Met
1               5

<210> SEQ ID NO 126
```

```
<211> LENGTH: 4
<212> TYPE: PRT
<213> ORGANISM: Artificial Sequence
<220> FEATURE:
<223> OTHER INFORMATION: Description of Artificial Sequence:
      pdb/1BIO/1BIO

<400> SEQUENCE: 126

Leu Gln His Val
  1

<210> SEQ ID NO 127
<211> LENGTH: 4
<212> TYPE: PRT
<213> ORGANISM: Artificial Sequence
<220> FEATURE:
<223> OTHER INFORMATION: Description of Artificial Sequence:
      pdb/1FL7/1FL7-B

<400> SEQUENCE: 127

Val Pro Gly Cys
  1

<210> SEQ ID NO 128
<211> LENGTH: 4
<212> TYPE: PRT
<213> ORGANISM: Artificial Sequence
<220> FEATURE:
<223> OTHER INFORMATION: Description of Artificial Sequence:
      pdb/1HR6/1HR6-A

<400> SEQUENCE: 128

Cys Pro Arg Gly
  1

<210> SEQ ID NO 129
<211> LENGTH: 4
<212> TYPE: PRT
<213> ORGANISM: Artificial Sequence
<220> FEATURE:
<223> OTHER INFORMATION: Description of Artificial Sequence:
      pdb/1H6/1HR6-A

<400> SEQUENCE: 129

Leu Lys Gly Cys
  1

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence:
      pdb/1BFA/1BFA

<400> SEQUENCE: 130

Pro Pro Gly Pro
  1

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence:
      pdb/1BFA/1BFA

<400> SEQUENCE: 131
```

```
Leu Pro Gly Cys Pro Arg Glu Val
  1               5

<210> SEQ ID NO 132
<211> LENGTH: 4
<212> TYPE: PRT
<213> ORGANISM: Artificial Sequence
<220> FEATURE:
<223> OTHER INFORMATION: Description of Artificial Sequence:
      pdb/1BFA/1BFA

<400> SEQUENCE: 132

Cys Pro Arg Glu
  1

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 133

Met Met Arg Val Leu Gln Ala Val Leu Pro Pro Leu Pro Gln Val Val
  1               5                  10                  15

Cys

<210> SEQ ID NO 134
<211> LENGTH: 4
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 134

Met Met Arg Val
  1

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 135

Val Leu Pro Pro Leu Pro
  1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 136

Val Leu Pro Pro Leu Pro Gln
  1               5

<210> SEQ ID NO 137
<211> LENGTH: 7
<212> TYPE: PRT
```

```
<213> ORGANISM: Artificial Sequence
<220> FEATURE:
<223> OTHER INFORMATION: Description of Artificial Sequence:
      swissnew/P01229/LSHB HUMAN

<400> SEQUENCE: 137

Ala Val Leu Pro Pro Leu Pro
  1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence:
      swissnew/P01229/LSHB HUMAN

<400> SEQUENCE: 138

Ala Val Leu Pro Pro Leu Pro Gln
  1               5

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 139

Met Met Arg Val Leu Gln Ala Val Leu Pro Pro Val Pro Gln Val Val
  1               5                  10                  15

Cys

<210> SEQ ID NO 140
<211> LENGTH: 4
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 140

Leu Gln Ala Gly
  1

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 141

Val Leu Pro Pro Val Pro
  1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 142
```

```
Val Leu Pro Pro Val Pro Gln
  1               5
```

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 143

```
Ala Val Leu Pro Pro Val Pro
  1               5
```

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence:
      swissnew/P07434/CGHB PAPAN

<400> SEQUENCE: 144

```
Ala Val Leu Pro Pro Val Pro Gln
  1               5
```

<210> SEQ ID NO 145
<211> LENGTH: 4
<212> TYPE: PRT
<213> ORGANISM: Artificial Sequence
<220> FEATURE:
<223> OTHER INFORMATION: Description of Artificial Sequence:
      swissnew/Q28376/TSHB HORSE

<400> SEQUENCE: 145

```
Met Thr Arg Asp
  1
```

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence:
      swissnew/Q28376/TSHB HORSE

<400> SEQUENCE: 146

```
Gln Asp Val Cys
  1
```

<210> SEQ ID NO 147
<211> LENGTH: 4
<212> TYPE: PRT
<213> ORGANISM: Artificial Sequence
<220> FEATURE:
<223> OTHER INFORMATION: Description of Artificial Sequence:
      swissnew/Q28376/TSHB HORSE

<400> SEQUENCE: 147

```
Ile Pro Gly Cys
  1
```

<210> SEQ ID NO 148
<211> LENGTH: 5
<212> TYPE: PRT
<213> ORGANISM: Artificial Sequence
<220> FEATURE:

```
<223> OTHER INFORMATION: Description of Artificial Sequence:
      sptrembl/Q9Z284/Q9Z284

<400> SEQUENCE: 148

Pro Ala Leu Pro Ser
 1               5

<210> SEQ ID NO 149
<211> LENGTH: 6
<212> TYPE: PRT
<213> ORGANISM: Artificial Sequence
<220> FEATURE:
<223> OTHER INFORMATION: Description of Artificial Sequence:
      sptrembl/Q9UCG8/Q9UCG8

<400> SEQUENCE: 149

Leu Pro Gly Gly Pro Arg
 1               5

<210> SEQ ID NO 150
<211> LENGTH: 4
<212> TYPE: PRT
<213> ORGANISM: Artificial Sequence
<220> FEATURE:
<223> OTHER INFORMATION: Description of Artificial Sequence:
      sptrembl/Q9UCG8/Q9UCG8

<400> SEQUENCE: 150

Leu Pro Gly Gly
 1

<210> SEQ ID NO 151
<211> LENGTH: 4
<212> TYPE: PRT
<213> ORGANISM: Artificial Sequence
<220> FEATURE:
<223> OTHER INFORMATION: Description of Artificial Sequence:
      sptrembl/Q9UCG8/Q9UCG8

<400> SEQUENCE: 151

Gly Gly Pro Arg
 1

<210> SEQ ID NO 152
<211> LENGTH: 4
<212> TYPE: PRT
<213> ORGANISM: Artificial Sequence
<220> FEATURE:
<223> OTHER INFORMATION: Description of Artificial Sequence: XP_028754

<400> SEQUENCE: 152

Leu Gln Arg Gly
 1

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: XP_028754

<400> SEQUENCE: 153

Leu Gln Arg Gly Val
 1               5

<210> SEQ ID NO 154
<211> LENGTH: 4
```

```
<212> TYPE: PRT
<213> ORGANISM: Artificial Sequence
<220> FEATURE:
<223> OTHER INFORMATION: Description of Artificial Sequence: XP_028754

<400> SEQUENCE: 154

Leu Gly Gln Leu
 1

<210> SEQ ID NO 155
<211> LENGTH: 13
<212> TYPE: PRT
<213> ORGANISM: Artificial Sequence
<220> FEATURE:
<223> OTHER INFORMATION: Description of Artificial Sequence: SignalP
      (CBS)

<400> SEQUENCE: 155

Met Thr Arg Val Leu Gln Gly Val Leu Pro Ala Leu Pro
 1               5                  10

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: HLA
      molecule type I (A_0201)

<400> SEQUENCE: 156

Val Leu Gln Gly Val Leu Pro Ala Leu
 1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: HLA
      molecule type I (A_0201)

<400> SEQUENCE: 157

Gly Val Leu Pro Ala Leu Pro Gln Val
 1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: HLA
      molecule type I (A_0201)

<400> SEQUENCE: 158

Val Leu Pro Ala Leu Pro Gln Val Val
 1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: HLA
      molecule type I (A_0201)

<400> SEQUENCE: 159

Arg Leu Pro Gly Cys Pro Arg Gly Val
 1               5
```

```
<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: HLA
      molecule type I (A_0201)

<400> SEQUENCE: 160

Thr Met Thr Arg Val Leu Gln Gly Val
  1               5

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: MHC II
      (H2-Ak 15-mers)

<400> SEQUENCE: 161

Cys Pro Thr Met Thr Arg Val Leu Gln Gly Val Leu Pro Ala Leu
  1               5                  10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: MHC II
      (H2-Ak 15-mers)

<400> SEQUENCE: 162

Pro Gly Cys Pro Arg Gly Val Asn Pro Val Val Ser Tyr Ala Val
  1               5                  10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence:
      HLA-DRB1*0101 15-mers

<400> SEQUENCE: 163

Pro Arg Gly Val Asn Pro Val Val Ser Tyr Ala Val Ala Leu Ser
  1               5                  10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence:
      HLA-DRB1*0101 15-mers

<400> SEQUENCE: 164

Thr Arg Val Leu Gln Gly Val Leu Pro Ala Leu Pro Gln Val Val
  1               5                  10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence:
      HLA-DRB1*0101 15-mers
```

```
<400> SEQUENCE: 165

Leu Gln Gly Val Leu Pro Ala Leu Pro Gln Val Val Cys Asn Tyr
 1               5                  10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence:
      HLA-DRB1*0301 (DR17) 15-mers

<400> SEQUENCE: 166

Met Thr Arg Val Leu Gln Gly Val Leu Pro Ala Leu Pro Gln Val
 1               5                  10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence:
      HLA-DRB1*0301 (DR17) 15-mers

<400> SEQUENCE: 167

Ser Ile Arg Leu Pro Gly Cys Pro Arg Gly Val Asn Pro Val Val
 1               5                  10                  15

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: NMPF-56
      peptide

<400> SEQUENCE: 168

Val Ala Pro Ala Leu Pro Gln
 1               5

<210> SEQ ID NO 169
<211> LENGTH: 35
<212> TYPE: PRT
<213> ORGANISM: Artificial Sequence
<220> FEATURE:
<223> OTHER INFORMATION: Description of Artificial Sequence: NMPF-62
      peptide

<400> SEQUENCE: 169

Val Val Cys Asn Tyr Arg Asp Val Arg Phe Glu Ser Ile Arg Leu Pro
 1               5                  10                  15

Gly Cys Pro Arg Gly Val Asn Pro Val Val Ser Tyr Ala Val Ala Leu
                20                  25                  30

Ser Cys Gln
         35

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: NMPF-67
      peptide

<400> SEQUENCE: 170
```

```
Cys Pro Arg Gly Val Asn Pro
  1               5

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: NMPF-70
      peptide

<400> SEQUENCE: 171

Met Thr Arg Val Leu Gln Gly Val Leu Pro Ala Leu Pro Gln
  1               5                  10

<210> SEQ ID NO 172
<211> LENGTH: 18
<212> TYPE: PRT
<213> ORGANISM: Artificial Sequence
<220> FEATURE:
<223> OTHER INFORMATION: Description of Artificial Sequence: NMPF-75
      peptide

<400> SEQUENCE: 172

Ser Lys Ala Pro Pro Pro Ser Leu Pro Ser Pro Ser Arg Leu Pro Gly
  1               5                  10                  15

Pro Cys

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: NMPF-56
      peptide

<400> SEQUENCE: 173

Val Ala Pro Ala Leu Pro Gln
  1               5

<210> SEQ ID NO 174
<211> LENGTH: 17
<212> TYPE: PRT
<213> ORGANISM: Artificial Sequence
<220> FEATURE:
<223> OTHER INFORMATION: Description of Artificial Sequence: NMPF-71
      peptide

<400> SEQUENCE: 174

Met Thr Arg Val Leu Pro Gly Val Leu Pro Ala Leu Pro Gln Val Val
  1               5                  10                  15

Cys

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: NMPF
      peptide

<400> SEQUENCE: 175

Cys Arg Gly Val Asn Pro Val Val Ser
  1               5
```